(12) United States Patent
Peterson et al.

(10) Patent No.: US 11,234,746 B2
(45) Date of Patent: *Feb. 1, 2022

(54) ACTIVE COMPRESSION APPARATUS, METHODS OF ASSEMBLY AND METHODS OF USE

(71) Applicant: ActivOrtho, Inc., Plymouth, MN (US)

(72) Inventors: Alex Peterson, Maple Grove, MN (US); Daniel S. Savage, Brecksville, OH (US); Paul J. Hindrichs, Plymouth, MN (US); Andrew K. Palmer, Eastham, MA (US); Michael P. Brenzel, St. Paul, MN (US); William F. Ogilvie, Austin, TX (US)

(73) Assignee: ActivOrtho, Inc., Plymouth, MN (US)

( * ) Notice: Subject to any disclaimer, the term of this patent is extended or adjusted under 35 U.S.C. 154(b) by 519 days.

This patent is subject to a terminal disclaimer.

(21) Appl. No.: 15/831,212

(22) Filed: Dec. 4, 2017

(65) Prior Publication Data
US 2018/0092677 A1    Apr. 5, 2018

Related U.S. Application Data

(63) Continuation-in-part of application No. PCT/US2017/019530, filed on Feb. 24, 2017.

(60) Provisional application No. 62/300,336, filed on Feb. 26, 2016.

(51) Int. Cl.
| | |
|---|---|
| *A61B 17/86* | (2006.01) |
| *A61B 17/72* | (2006.01) |
| *A61B 17/84* | (2006.01) |
| *A61B 17/88* | (2006.01) |

(52) U.S. Cl.
CPC ........ *A61B 17/863* (2013.01); *A61B 17/7225* (2013.01); *A61B 17/844* (2013.01); *A61B 17/866* (2013.01); *A61B 17/869* (2013.01); *A61B 17/8685* (2013.01); *A61B 17/8894* (2013.01)

(58) Field of Classification Search
CPC ... A61B 17/84; A61B 17/844; A61B 17/8625; A61B 17/863; A61B 17/864; A61B 17/866; A61B 17/869; A61B 17/7225; A61B 17/7216
See application file for complete search history.

(56) References Cited

U.S. PATENT DOCUMENTS

| | | | |
|---|---|---|---|
| 972,787 | A | 10/1910 | Huyck |
| 2,382,019 | A | 8/1945 | Miller |
| 2,397,545 | A | 4/1946 | Hardinge |

(Continued)

FOREIGN PATENT DOCUMENTS

| | | |
|---|---|---|
| AU | 648723 B2 | 10/1992 |
| CN | 103099667 A | 5/2013 |

(Continued)

OTHER PUBLICATIONS

WIPO, U.S. International Search Authority, International Search Report and Written Opinion dated Jun. 9, 2017 in International Patent Application No. PCT/US2017/019530, 13 pages.

(Continued)

*Primary Examiner* — Si Ming Ku
(74) *Attorney, Agent, or Firm* — Inskeep IP Group, Inc.

(57) ABSTRACT

Compression devices for joining tissue and methods for using and fabricating the same.

14 Claims, 67 Drawing Sheets

(56) References Cited

U.S. PATENT DOCUMENTS

| | | |
|---|---|---|
| 2,414,882 A | 1/1947 | Longfellow |
| 2,526,959 A | 10/1950 | Lorenzo |
| 2,563,976 A | 8/1951 | Torosian |
| 2,612,159 A | 9/1952 | Collison |
| 2,621,653 A | 12/1952 | Briggs |
| 2,699,774 A | 1/1955 | Livingston |
| 2,801,631 A | 8/1957 | Charnley |
| 2,952,254 A | 9/1960 | Keating |
| 2,985,168 A | 5/1961 | Jonas et al. |
| 3,051,169 A | 8/1962 | Grath |
| 3,076,453 A | 2/1963 | Tronzo |
| 3,435,526 A | 4/1969 | Brancato |
| 3,441,017 A | 4/1969 | Kaessmann |
| 3,678,925 A | 7/1972 | Fischer et al. |
| 3,716,051 A | 2/1973 | Fischer |
| 3,760,802 A | 9/1973 | Fischer et al. |
| 3,915,162 A | 10/1975 | Miller |
| 3,990,438 A | 11/1976 | Pritchard |
| 4,095,591 A | 6/1978 | Graham, Jr. et al. |
| 4,175,555 A | 11/1979 | Herbert |
| 4,463,753 A | 8/1984 | Gustilo |
| 4,621,629 A | 11/1986 | Koeneman |
| 4,653,486 A | 3/1987 | Coker |
| 4,711,232 A | 12/1987 | Fischer et al. |
| 4,799,841 A | 1/1989 | Ramsbro |
| 4,858,601 A | 8/1989 | Glisson |
| 4,940,467 A | 7/1990 | Tronzo |
| RE33,348 E | 9/1990 | Lower |
| 4,959,064 A | 9/1990 | Engelhardt |
| 5,019,079 A | 5/1991 | Ross |
| 5,041,116 A | 8/1991 | Wilson |
| 5,098,434 A | 3/1992 | Serbousek |
| 5,100,405 A | 3/1992 | McLaren |
| 5,209,753 A | 5/1993 | Biedermann et al. |
| 5,217,462 A | 6/1993 | Asnis et al. |
| 5,334,204 A | 8/1994 | Clewett et al. |
| 5,397,328 A | 3/1995 | Behrens et al. |
| 5,593,410 A | 1/1997 | Vrespa |
| 5,919,193 A | 7/1999 | Slavitt |
| 5,944,302 A | 8/1999 | Loc et al. |
| 6,001,101 A | 12/1999 | Augagneur et al. |
| 6,048,344 A | 4/2000 | Schenk |
| 6,053,922 A | 4/2000 | Krause et al. |
| 6,258,093 B1 | 7/2001 | Edwards et al. |
| 6,319,254 B1 | 11/2001 | Giet et al. |
| 6,447,518 B1 | 9/2002 | Krause et al. |
| 6,458,134 B1 | 10/2002 | Songer et al. |
| 6,656,184 B1 | 12/2003 | White et al. |
| 6,743,233 B1 | 6/2004 | Baldwin et al. |
| 6,949,101 B2 | 9/2005 | McCleary et al. |
| 6,955,513 B2 | 10/2005 | Niku |
| 7,122,037 B2 | 10/2006 | Happonen et al. |
| 7,135,023 B2 | 11/2006 | Watkins et al. |
| 7,175,626 B2 | 2/2007 | Neff |
| 7,329,258 B2 | 2/2008 | Studer |
| 7,569,055 B2 | 8/2009 | Zander et al. |
| 7,578,836 B2 | 8/2009 | Justin et al. |
| 7,582,107 B2 | 9/2009 | Trail et al. |
| 7,608,097 B2 | 10/2009 | Kyle |
| 7,611,521 B2 | 11/2009 | Lubbers et al. |
| 7,686,807 B2 | 3/2010 | Padget et al. |
| 7,833,256 B2 | 11/2010 | Biedermann et al. |
| 7,951,198 B2 | 5/2011 | Sucec et al. |
| 8,029,524 B1 | 10/2011 | Mitusina et al. |
| 8,043,333 B2 | 10/2011 | Frigg et al. |
| 8,048,134 B2 | 11/2011 | Partin |
| 8,052,706 B2 | 11/2011 | Mitusina |
| 8,057,500 B2 | 11/2011 | Mitusina |
| 8,118,952 B2 | 2/2012 | Gall et al. |
| 8,142,464 B2 | 3/2012 | Mitusina |
| 8,298,273 B2 | 10/2012 | Pathak |
| 8,308,783 B2 | 11/2012 | Morris et al. |
| 8,323,272 B2 | 12/2012 | Rusly et al. |
| 8,343,197 B2 | 1/2013 | Gonzalez-Hernandez |
| 8,366,559 B2 | 2/2013 | Papenfuss et al. |
| 8,394,127 B2 | 3/2013 | Winslow et al. |
| 8,398,690 B2 | 3/2013 | Bottlang et al. |
| 8,414,585 B2 | 4/2013 | Meneghini et al. |
| 8,518,044 B2 | 8/2013 | Sidebotham et al. |
| 8,529,611 B2 | 9/2013 | Champagne et al. |
| 8,591,579 B2 | 11/2013 | Pellegrino et al. |
| 8,685,067 B2 | 4/2014 | King et al. |
| 8,715,326 B2 | 5/2014 | Champagne et al. |
| 8,845,649 B2 | 9/2014 | Jackson |
| 8,852,239 B2 | 10/2014 | Jackson et al. |
| 8,956,356 B2 | 2/2015 | Zurschmiede |
| 8,961,516 B2 | 2/2015 | Nelson et al. |
| 8,968,415 B2 | 3/2015 | Meridew et al. |
| 8,998,925 B2 | 4/2015 | Schwappach |
| 9,078,716 B2 | 7/2015 | Pech |
| 9,161,793 B2 | 10/2015 | Huebner |
| 9,168,076 B2 | 10/2015 | Patty et al. |
| 9,173,693 B2 | 11/2015 | McDaniel et al. |
| 9,204,886 B2 | 12/2015 | May et al. |
| 9,204,910 B2 | 12/2015 | Epperly |
| 9,283,006 B2 | 3/2016 | Fonte |
| 9,314,286 B2 | 4/2016 | Bottlang et al. |
| 9,345,520 B2 | 5/2016 | Biedermann et al. |
| 9,381,052 B2 | 7/2016 | Ziran |
| 9,408,648 B2 | 8/2016 | Culbert |
| 9,421,051 B2 | 8/2016 | Finley |
| 9,445,850 B2 | 9/2016 | Kinmon |
| 9,456,857 B2 | 10/2016 | Labitzke |
| 9,482,260 B1 | 11/2016 | Krause |
| 9,492,202 B2 | 11/2016 | Matthis et al. |
| 9,526,542 B2 | 12/2016 | Ehmke |
| 9,700,361 B2 | 7/2017 | Bottlang et al. |
| 9,763,712 B2 | 9/2017 | Appenzeller et al. |
| 9,788,868 B2 | 10/2017 | Jackson |
| 9,801,663 B2 | 10/2017 | Krause |
| 9,808,867 B2 | 11/2017 | Krause et al. |
| 9,820,788 B2 | 11/2017 | Vrionis et al. |
| 9,827,029 B2 | 11/2017 | Hulliger |
| 9,848,930 B2 | 12/2017 | Huebner et al. |
| 9,861,413 B2 | 1/2018 | Palmer et al. |
| 9,980,762 B2 | 5/2018 | Anapliotis |
| 2002/0055740 A1 | 5/2002 | Lieberman |
| 2002/0095154 A1 | 7/2002 | Atkinson et al. |
| 2005/0152770 A1 | 7/2005 | Tschakaloff et al. |
| 2005/0165402 A1 | 7/2005 | Taras |
| 2005/0177167 A1 | 8/2005 | Muckter |
| 2005/0197660 A1 | 9/2005 | Haid, Jr. et al. |
| 2005/0277940 A1 | 12/2005 | Neff |
| 2006/0264954 A1 | 11/2006 | Sweeney, II et al. |
| 2007/0016204 A1 | 1/2007 | Martinez et al. |
| 2007/0270855 A1 | 11/2007 | Partin |
| 2007/0282342 A1 | 12/2007 | Niederberger et al. |
| 2008/0177333 A1 | 7/2008 | Ferguson |
| 2008/0188854 A1 | 8/2008 | Moser |
| 2008/0236601 A1 | 10/2008 | Jacobus |
| 2008/0262497 A1 | 10/2008 | Nijenbanning et al. |
| 2009/0062868 A1 | 3/2009 | Casutt |
| 2009/0264937 A1 | 10/2009 | Parrott |
| 2009/0275966 A1 | 11/2009 | Mitusina |
| 2010/0139182 A1 | 6/2010 | Wernersson et al. |
| 2010/0152786 A1 | 6/2010 | Behrbalk |
| 2010/0256690 A1 | 10/2010 | Appenzeller et al. |
| 2010/0318130 A1 | 12/2010 | Parlato et al. |
| 2011/0092992 A1 | 4/2011 | Darois et al. |
| 2011/0144703 A1* | 6/2011 | Krause ............... A61B 17/8625 606/309 |
| 2012/0053639 A1 | 3/2012 | Grant |
| 2012/0239038 A1 | 9/2012 | Saravia et al. |
| 2013/0012942 A1 | 1/2013 | Nelson et al. |
| 2013/0041469 A1 | 2/2013 | Phelps |
| 2013/0079879 A1 | 3/2013 | Suh |
| 2014/0005669 A1 | 1/2014 | Graham |
| 2014/0050550 A1 | 2/2014 | Stempniewski et al. |
| 2014/0081338 A1 | 3/2014 | Biedermann et al. |
| 2014/0094860 A1 | 4/2014 | Reimels |
| 2015/0012048 A1 | 1/2015 | Huebner et al. |
| 2015/0223843 A1 | 8/2015 | Tipirneni et al. |
| 2015/0230843 A1 | 8/2015 | Palmer et al. |
| 2015/0238232 A1 | 8/2015 | Biedermann et al. |

(56) References Cited

U.S. PATENT DOCUMENTS

| | | |
|---|---|---|
| 2015/0250604 A1 | 9/2015 | Fonte |
| 2015/0305819 A1 | 10/2015 | Krause |
| 2015/0313720 A1 | 11/2015 | Lorio |
| 2015/0374387 A1 | 12/2015 | Courtney, Jr. et al. |
| 2016/0213368 A1 | 7/2016 | Stecco et al. |
| 2016/0310190 A1 | 10/2016 | Gonzalez Blohm et al. |
| 2017/0020585 A1 | 1/2017 | Harshman et al. |
| 2017/0056979 A1 | 3/2017 | Krause et al. |
| 2017/0100171 A1 | 4/2017 | Palmer et al. |
| 2017/0189085 A1 | 7/2017 | Krause |
| 2017/0202563 A1 | 7/2017 | Leroy et al. |
| 2017/0245905 A1 | 8/2017 | Reimels |
| 2017/0311984 A1 | 11/2017 | Stecco et al. |
| 2017/0360489 A1 | 12/2017 | Palmer et al. |
| 2018/0092677 A1 | 4/2018 | Peterson et al. |
| 2018/0263669 A1 | 9/2018 | Peterson et al. |

FOREIGN PATENT DOCUMENTS

| | | |
|---|---|---|
| DE | 2906068 A1 | 6/1980 |
| DE | 3936703 A1 | 5/1991 |
| EP | 1967151 A1 | 9/2008 |
| EP | 1430845 B1 | 7/2009 |
| EP | 1753355 B1 | 11/2011 |
| EP | 1937172 B1 | 3/2014 |
| EP | 2858585 B1 | 5/2017 |
| JP | 1995049082 A | 2/1995 |
| JP | 2012504027 A | 2/2016 |
| JP | 2018502694 A | 2/2018 |
| NL | 1030218 C2 | 4/2007 |
| SU | 923533 A1 | 4/1982 |
| SU | 1061807 A1 | 12/1983 |
| WO | WO 1991/009572 A1 | 7/1991 |
| WO | WO 1997/003611 A1 | 2/1997 |
| WO | WO 2001/054598 A1 | 8/2001 |
| WO | WO 2003/047442 A1 | 6/2003 |
| WO | WO 2009/152270 A1 | 12/2009 |
| WO | WO 2010/017631 A1 | 2/2010 |
| WO | WO 2010/099239 A2 | 9/2010 |
| WO | WO 2012/154119 A1 | 11/2012 |
| WO | WO 2013/018062 A1 | 2/2013 |
| WO | WO2015/095353 A1 | 6/2015 |
| WO | WO 2015/168311 A1 | 11/2015 |
| WO | WO 2016/081528 A1 | 5/2016 |
| WO | WO 2017/117092 A1 | 7/2017 |
| WO | WO 2017/147537 A1 | 8/2017 |

OTHER PUBLICATIONS

European Patent Office, Examination Report dated Sep. 9, 2019 in European Patent Application No. 17757388.8, 7 pages.

Japanese Patent Office, Office Action dated Mar. 11, 2021 with English translation in Japanese Patent Application No. 2018-563764, 7 pages.

United States Patent and Trademark Office, Final Office Action dated Feb. 23, 2021 in U.S. Appl. No. 15/945,683, 21 pages.

WIPO, U.S. International Search Authority, International Search Report and Written Opinion dated Feb. 14, 2019 in International Patent Application No. PCT/US2018/063915, 9 pages.

European Patent Office, Extended European Search Report dated Jul. 6, 2021 in European Patent Application No. 18886087.1, 9 pages.

* cited by examiner

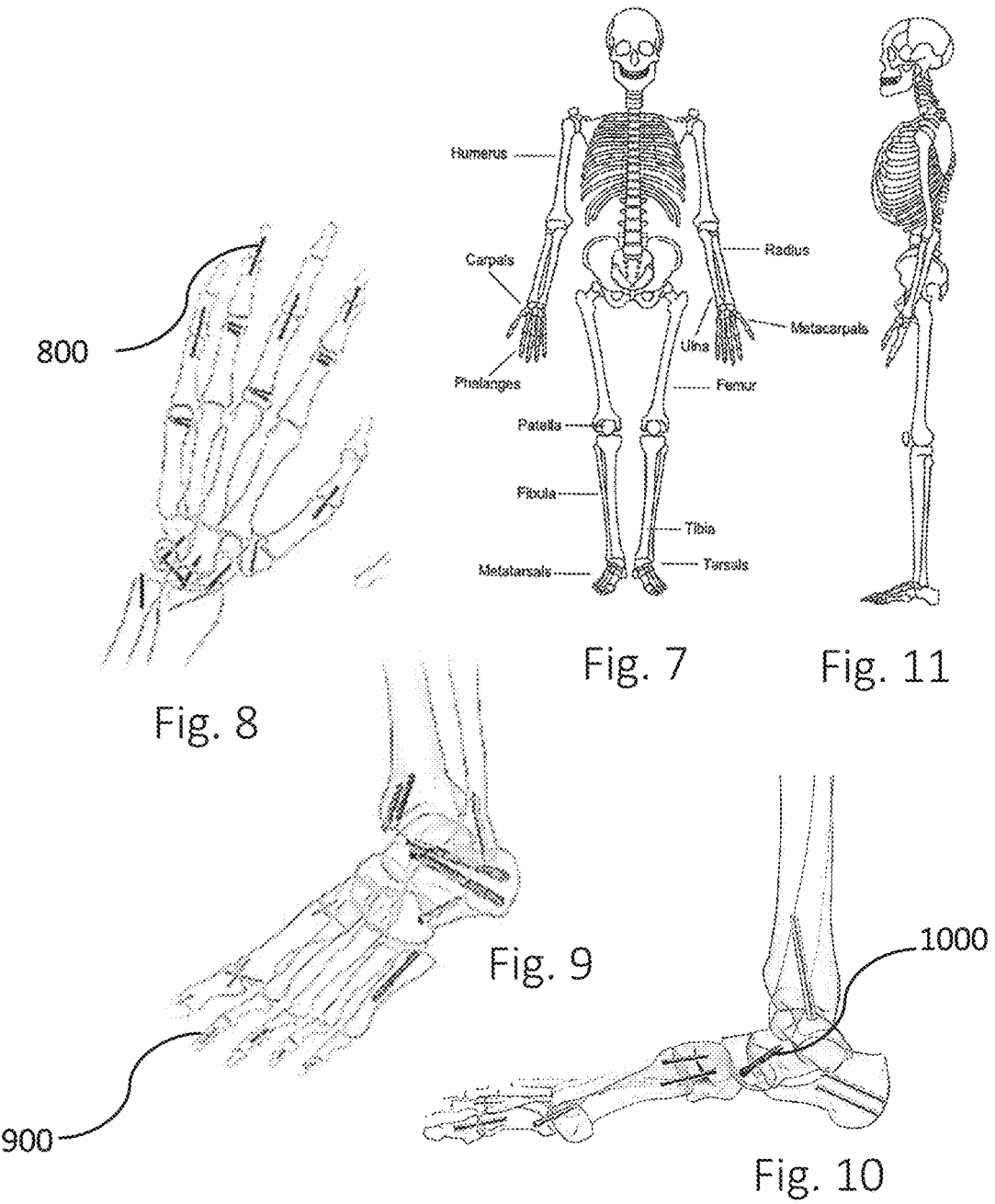

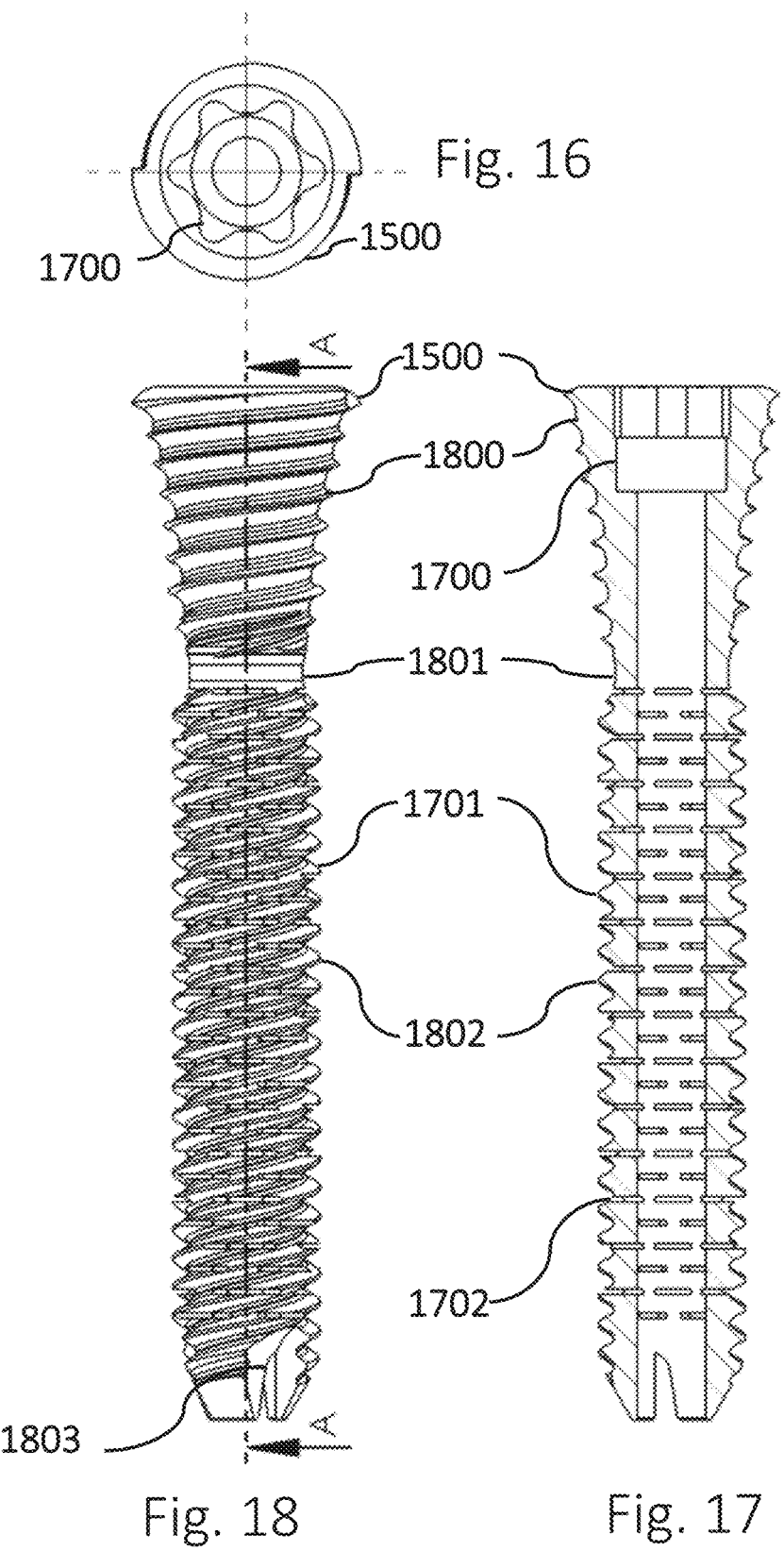

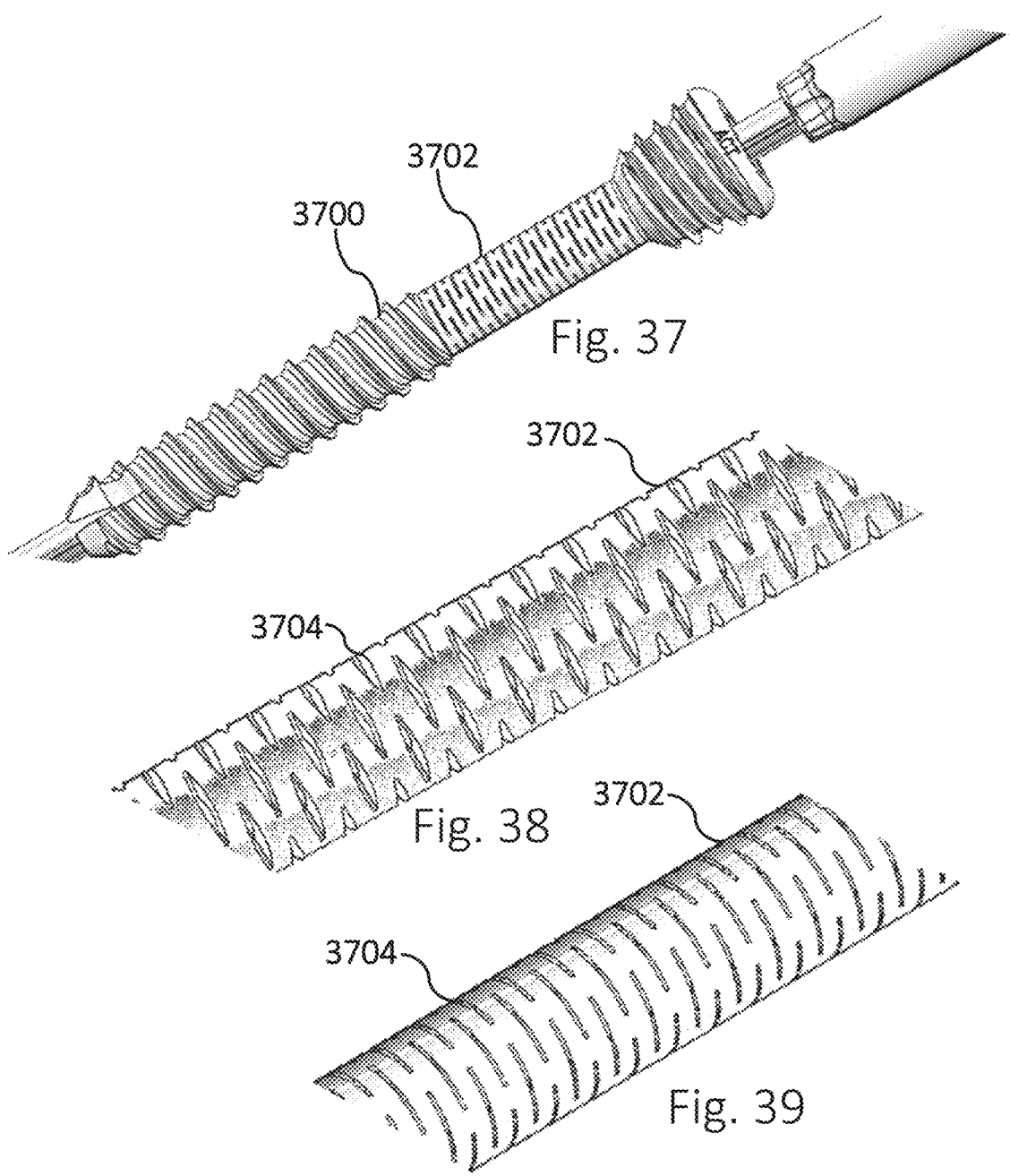

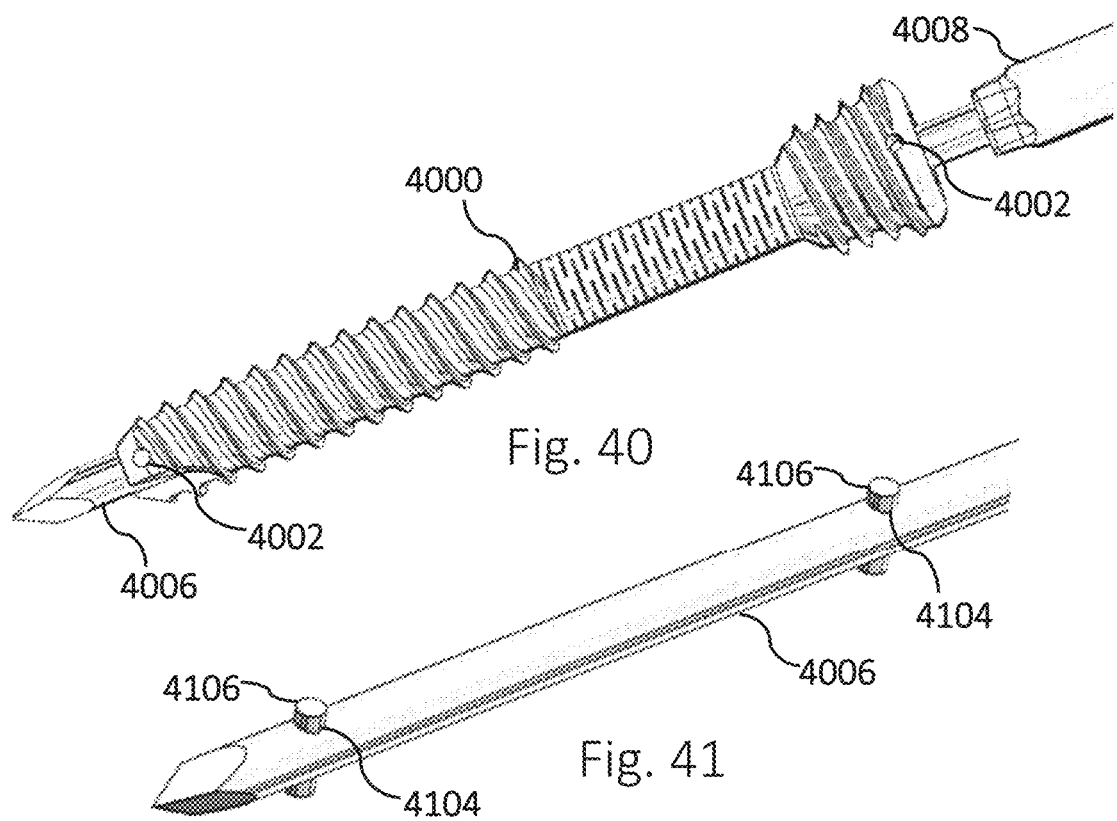
Fig. 40
Fig. 41
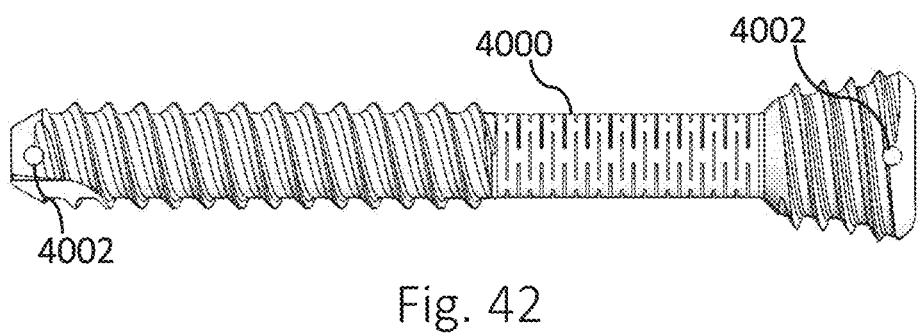
Fig. 42

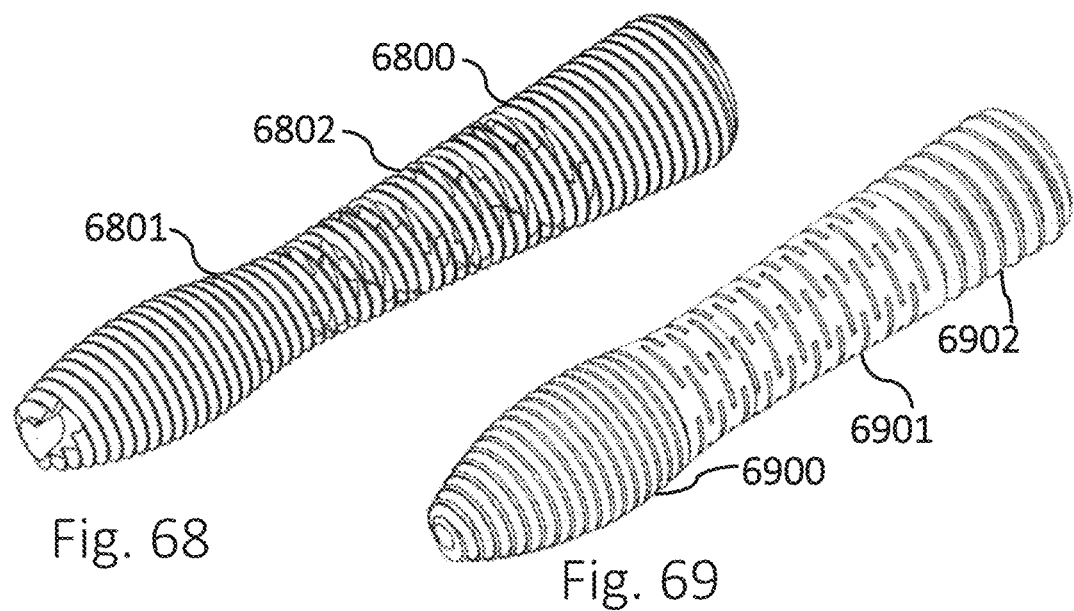
Fig. 68
Fig. 69
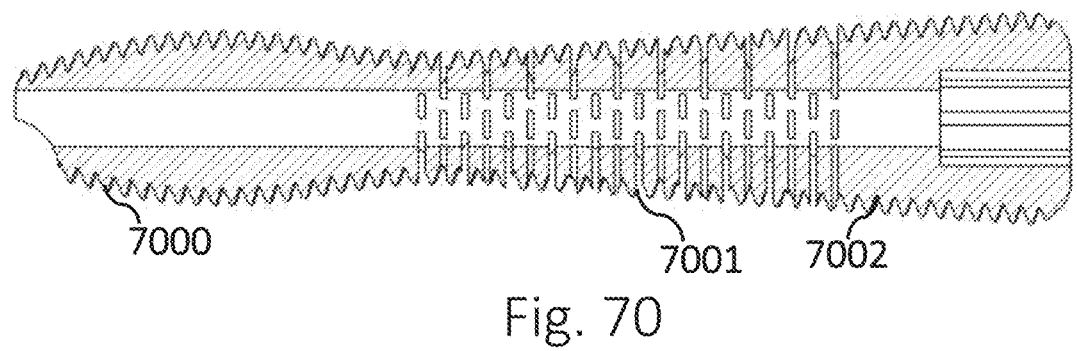
Fig. 70
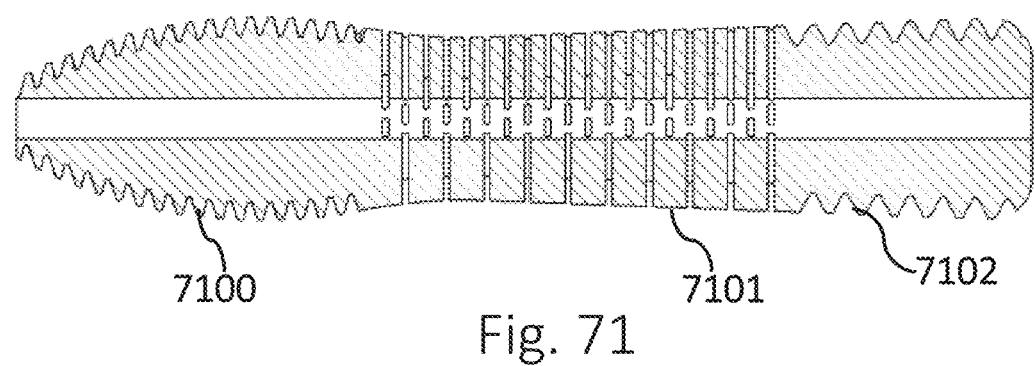
Fig. 71

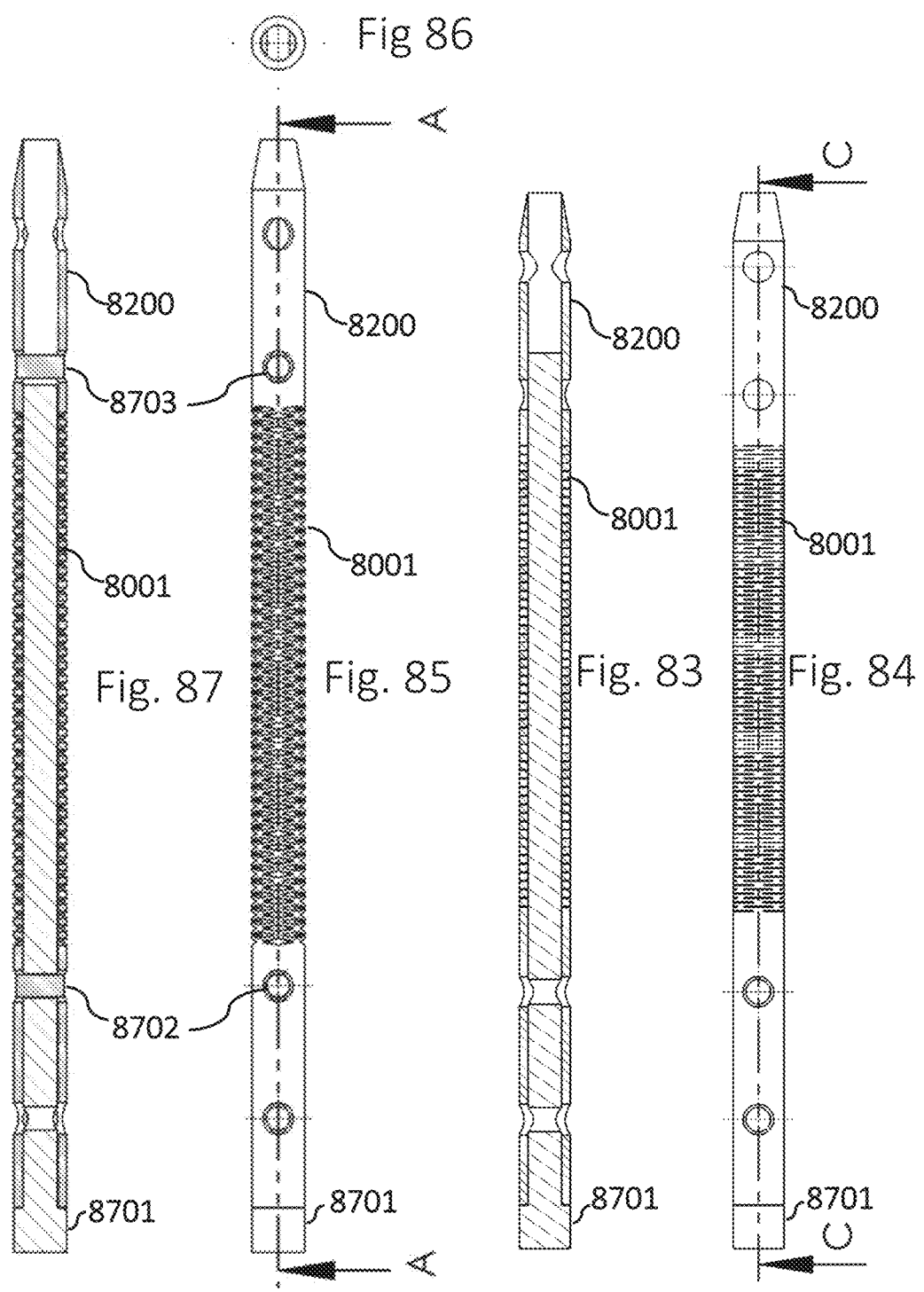

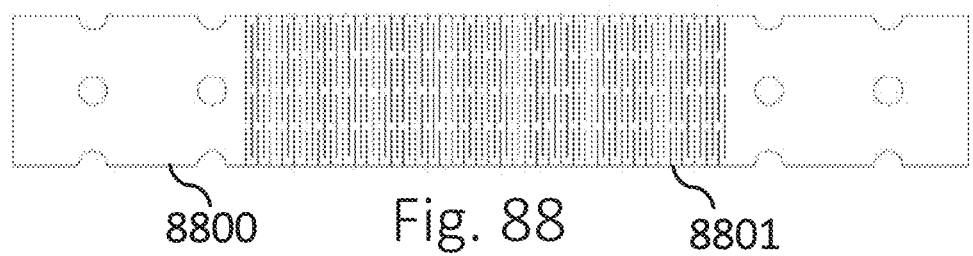
Fig. 88    8800    8801
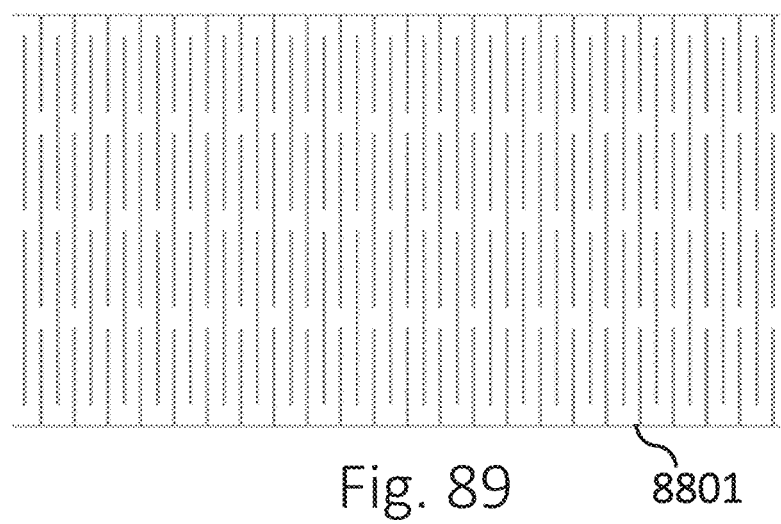
Fig. 89    8801
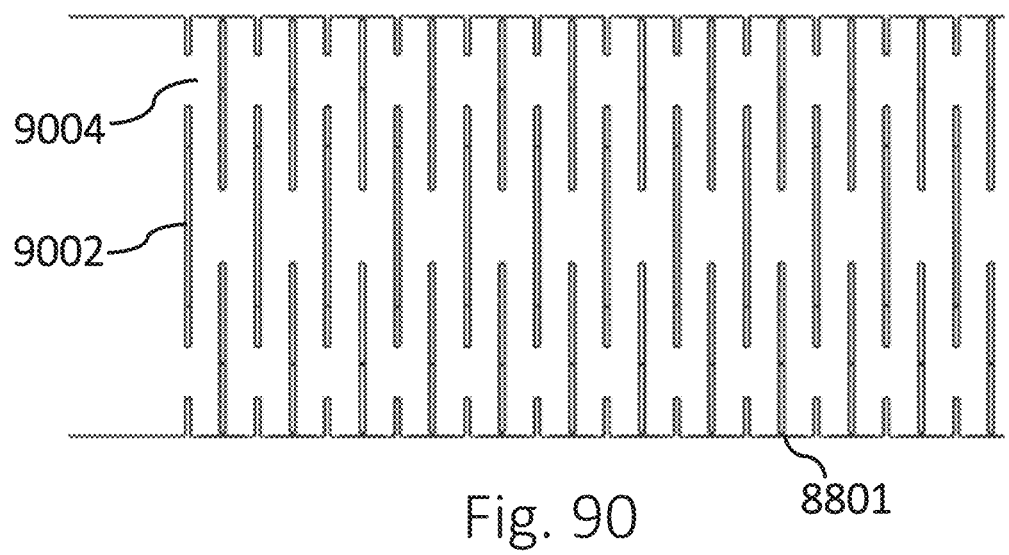
9004
9002
Fig. 90    8801

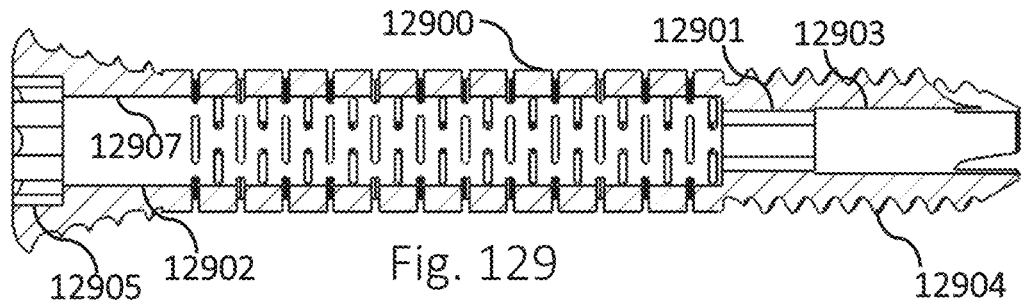
Fig. 129
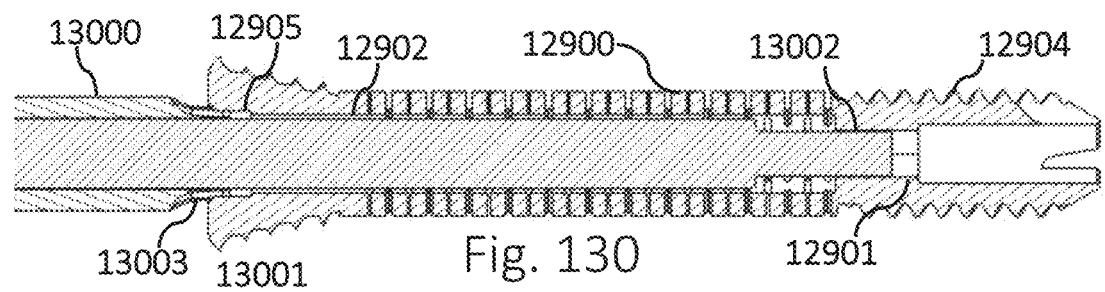
Fig. 130
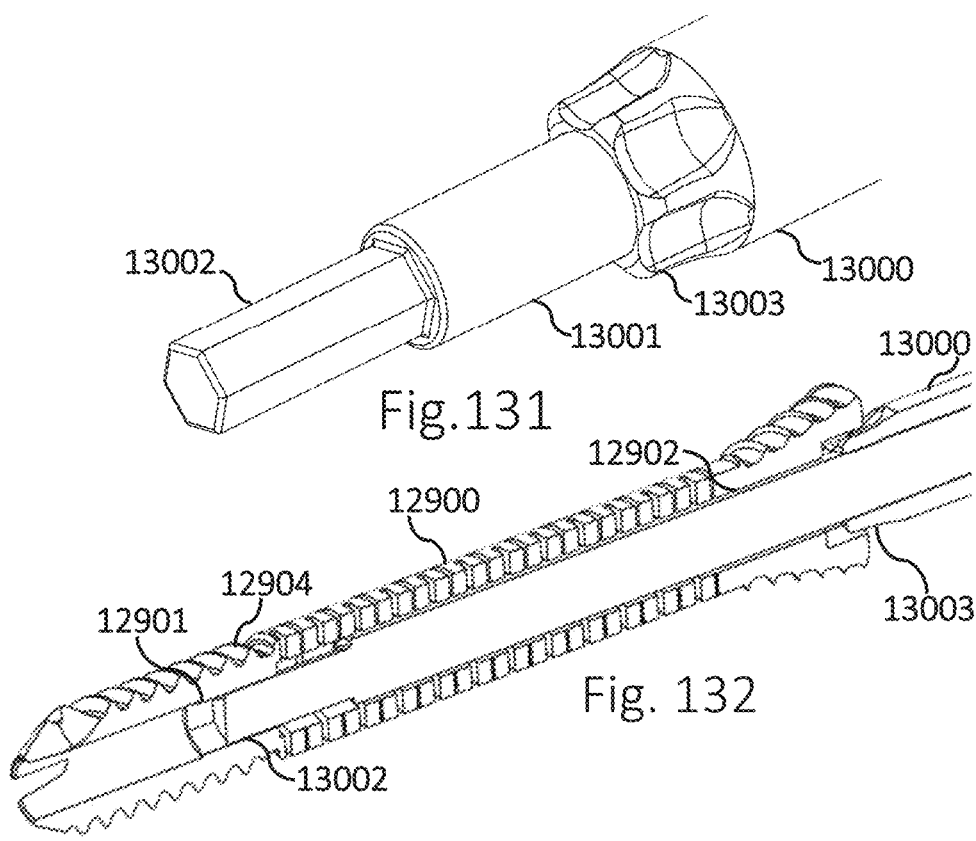
Fig. 131
Fig. 132

DETAIL A

ACTIVE COMPRESSION APPARATUS, METHODS OF ASSEMBLY AND METHODS OF USE

RELATED APPLICATIONS

This application is a continuation-in-part application of International Application No. PCT/US2017/019530 filed Feb. 24, 2017 entitled Active Compression Apparatus, Methods of Assembly and Methods of Use, which claims priority to and benefit of U.S. Provisional Application Ser. No. 62/300,336 filed Feb. 26, 2016 entitled Active Compression Apparatus, Methods of Assembly and Methods of Use, which are hereby incorporated herein by reference in their entireties.

FIELD OF THE INVENTION

The present invention relates generally to general surgery and orthopedic implants, and more specifically, but not exclusively, relates to devices implanted to aide bone fusion and repair. The invention relates to compression devices for joining two bone fragments, and associated devices for implanting such devices, to methods for compressing and/or fixing bone fragments for extended periods of time, and to the manufacturing of such devices.

BACKGROUND OF THE INVENTION

Bone fractures and other bone disorders are regularly treated by fusion. Bones are currently fused with the assistance of implants, such as, pins, rods, plates and screws which are designed to hold the bones or bone fragments in place while healing occurs and the bones or bone pieces are fused together. Compression can be used to join or stabilize two bone fragments and assists in the healing of the bone fragments. Examples of compression bone screws are known in the art, each having varying degrees of efficacy.

The goal of joint arthrodesis is to create a stable union between the intended fusion surfaces. Although a compressive force from a standard screw placement is dynamic during its application, once the screw is tightened down, it functions as a static device unable to maintain the compressive load as the bone remodels. A compressive load maintained across the fusion surface and a decrease in the stress shielding could aide healing. The stability from screw compression may also be affected by several factors such as bone density, bone resorption, and fixation orientation. It may be desirable to have a device that delivers an active or dynamic compression across the desired fusion site for an extended period of time to promote healing. Details of such benefits are further described by Bottlang, Michael PhD; Tsai, Stanley MS; Bliven, Emily K. BS; von Rechenberg, Brigitte DVM; Kindt, Philipp DVM; Augat, Peter PhD; Henschel, Julia BS; Fitzpatrick, Daniel C. MD; Madey, Steven M. MD, Journal of Orthopaedic Trauma: February 2017—Volume 31—Issue 2—p 71-77, which is hereby incorporated herein by reference in its entirety.

There exist active compression screw concepts. The term "active" being defined as having some axial tension capability over a change in length of the member. However, these concepts have complicated surgical procedures. The current active compression screw concepts are limited in their ability to change length per the ratio of screw length, and they are limited in the amount of axial force per the ratio of screw length. The current active compression screw concepts do not have the ability to adjust compression or have adjustable compression over time. The current active compression screws concepts do not have simple construction, making manufacturing complicated and expensive, and finally the current platforms cannot scale down to a therapeutic diameter for small bones. Therefore, improved devices and methods for fusing bones together are needed.

OBJECTS AND SUMMARY OF THE INVENTION

The present invention is directed to methods and apparatus for matter herein surrounding novel compression apparatuses, systems and methods for compressing suitable materials. In certain embodiments, the present invention is directed to apparatuses and methods that provide active compression to bone segments constructed with a unitary contiguous structure. The phrase "unitary contiguous structure" being defined as a structure formed from one piece of material and only material was removed to create the final construct, no joining of independent components or elements is needed to create the final construct.

The phrase "active compression" being defined as a continuous axial tension over a given length change of a member, such as an axial spring. This ability to change in length can be in a range of 1%-20% of the length of the member. In contrast a standard screw cannot provide axial tension or compression when the change in length exceeds the elastic limit of the construct which is typically a small deformation of 1%, herein defined as "passive compression".

In certain embodiments of the present invention, a device that provides active compression to bone segments constructed from two or more members. In certain embodiments, these devices have screw like features. In certain embodiments, a method of deployment or the surgical procedure for inserting the inventive device is similar to that of driving a screw like body into bone segments, similar to that of a common, non-active compression screw. Because the entire inventive device could potentially change in length, the effective therapeutic range or distance that the device could potentially provide an active compressive force is, in certain embodiments, over 6 mm so as to account for different levels of bone absorption. The amount of force needed to facilitate a union will differ depending on the anatomic features being fused. The inventive method and apparatus can be scaled to accommodate a range of compressive axial force of 0-200N and potentially larger, depending on a diameter of the apparatus.

It is known that the time period of application of the desired applied force is until the bone is fused. In certain embodiments of the present invention, an apparatus and method are provided in which the apparatus provides active compression to bone segments for a time exceeding current compression screws and up to the time for the bones to heal or fuse. The amount of force needed to facilitate bone healing over time may change. However, the present invention allows for structural variables to be adjusted such that the inventive apparatus delivers a compressive axial force in different amounts over time and stretched lengths. Additionally, such structural variables can be adjusted to deliver a consistent amount of force over a given distance or time. The devices of the present invention have the ability to be scaled down to an effective diameter for use in the small bones of the hand and feet having diameters potentially less than 2 mm.

An activation of an axial tension force according to the present invention can be before, during, or after deployment of the device into the desired anatomy, thus allowing for different surgical procedures to be developed and optimized for clinical benefit. To facilitate a common surgical procedural approach of first deploying a guide pin or K-wire and then performing the delivery of the device over that member, the apparatuses of the present invention can be cannulated. Alternatively, the apparatuses of the present invention can be non-cannulated or solid. The current invention can incorporate all other known existing features that facilitate tissue interaction and compression generation.

The axial tension force of the current invention is generated in several manners. One manner that can be employed is through utilizing perforations or cut features in and along the body of the device. These features can be varied to provide the optimal criteria of axial tension force, torsional rigidity, and bending stiffness for a given application. There are several manners in which the force could be loaded into the axial tension members of the present invention. One of them is to have the threads of a screw-like body generate the axial tension that loads the member upon insertion of the body into the bone segments to provide the initial compression and stabilization. Alternatively, a delivery mechanism can be employed to load the axial force into the device. The force could also be preloaded with a retention mechanism, either external or internal or throughout the device, for example a resorbable material could be used. As stated there are many ways to generate, maintain and release the axial compressive force facilitating many procedural variations for the execution of delivering the therapeutic energy of the present invention.

In the present invention, apparatuses and methods are provided in which a device constructed with a Shape Memory Alloy, SMA, such as Nitinol provides tailored active axial, torsion, bending, radial, shear, and/or compression forces to bone segments. The present invention is directed to apparatuses, systems and methods for compressing and/or tensioning suitable materials, particularly for bone fragments, initially at time of implant and over a time period beyond implantation.

The present invention is further directed to joining members, such as active bone screws and methods of use thereof for securing portions of tissue and/or bones while providing a specific amount of desired flexion or elasticity that promotes stronger healing of a fracture or fusion, e.g. resulting in increased torsional strength of a healed fracture or fusion. The present invention is further directed to joining members, such as active rods and/or plates and methods of use thereof for securing portions of tissue and/or bones while providing a specific amount of desired flexion or elasticity that promotes stronger healing of a fracture or fusion, e.g. resulting in increased torsional strength of a healed fracture or fusion.

The described invention can be used with or without orthopedic trauma plates, and/or, intramedullary nails, and/or pins, rods, and/or external fixation devices. The described invention can be utilized with solid screws, cannulated screws, headed screws, and/or headless screws, rods, nails, plates, staples, suture anchors, and soft tissue anchors. Threads are typically depicted in this disclosure as the tissue anchoring mechanism. However, it is within the scope of the present invention to include all alternative anchoring mechanisms on one or more ends of the device that provide anchoring, including but not limited to, expanding mechanisms, cross engaging members, cements, adhesives, sutures, and others common in orthopedics.

The present invention is further directed to joining members, such as bone screws and methods of use thereof for use in securing bone rods and/or plates to portions of tissue and/or bones while providing a specific amount of desired flexion or elasticity that promotes stronger healing of a fracture or fusion, e.g. resulting in increased torsional strength of a healed fracture or fusion. In certain embodiments, such rods and/or plates are non-active rods and/or plates and the active joining members of the present invention provide an active force or flexion to the system. In certain embodiments, such rods and/or plates are active rods and/or plates and both the active rods and/or plates and the active joining members of the present invention both provide an active force or flexion to the system.

Certain embodiments of the present invention provide an apparatus for generating active compression comprising: a distal bone engagement portion; a proximal bone engagement portion having an external diameter greater than an external diameter of the distal bone engagement portion; and a central portion interposed between the proximal bone engagement portion and the distal bone engagement portion having a perforation formed there through that facilitates a change in a dimension of the apparatus. Wherein the apparatus has a unitary contiguous structure. Wherein the apparatus is cannulated. Wherein the proximal bone engagement portion comprises threads having a pitch that is distinct from a pitch of threads of the distal bone engagement portion. Wherein the distal bone engagement portion comprises threads. Wherein the perforation comprises a non-uniform shape. Wherein the perforation comprises a helical form. Wherein the change in the dimension of the apparatus comprises a change in length. Wherein the change in the dimension of the apparatus comprises a shortening of a length of the apparatus. Wherein the change in the dimension of the apparatus comprises a change in dimension of the apparatus over a period of greater than 12 hours.

Certain embodiments of the present invention provide an apparatus for generating active compression comprising: a cannulated body having a compression preload feature; a plurality of perforations formed through a sidewall of the cannulated body; and a dimension that changes upon deformation of the plurality of perforations through an activation of the compression preload feature. Wherein an exterior of the sidewall of the cannulated body comprises threads. Wherein the dimension comprises a length of the apparatus. Wherein the compression preload feature comprises a plurality of threads having different pitches formed on an exterior of the sidewall of the cannulated body. Wherein the activation comprises a rotation of the apparatus.

Certain embodiments of the present invention provide a method of actively compressing bone segments comprising: applying a longitudinal tensile stress to a cannulated body through deformation of perforations formed through a sidewall of the cannulated body; inserting the cannulated body into a first bone segment and a second bone segment; and releasing the tensile stress over a period of time; and compressing the first bone segment and the second bone segment through release of the tensile stress. Wherein applying a longitudinal tensile stress to a cannulated body through deformation of perforations formed through a sidewall of the cannulated body and inserting the cannulated body into a first bone segment and a second bone segment are simultaneous. Wherein applying a longitudinal tensile stress to a cannulated body through deformation of perforations formed through a sidewall of the cannulated body comprised rotating a plurality of threads having different pitches formed on an exterior of the sidewall of the cannulated body. Wherein applying a longitudinal tensile stress to a cannulated body through deformation of perforations formed through a sidewall of the cannulated body comprises lengthening the cannulated body.

Certain embodiments of the present invention provide an apparatus for generating active compression comprising: a proximal anchor portion; a distal anchor portion; a plurality of struts formed of a superelastic material interposed between the proximal anchor portion and the distal anchor portion; a first state having an axial elastic potential energy generated through deformation of at least one strut of the plurality of struts; and a second state wherein the axial elastic potential energy releases nonlinearly relative to a displacement of the proximal anchor portion relative to the distal anchor portion. Wherein the axial elastic potential energy comprises an axial tensile elastic potential energy. Wherein the axial elastic potential energy comprises an axial compressive elastic potential energy. Wherein a transition from the first state to the second state comprises a transition of the at least one strut of the plurality of struts from a high energy state to a low energy state. Wherein a transition from the first state to the second state comprises a transition of the at least one strut of the plurality of struts from a deformed state to an un-deformed state.

Certain embodiments of the present invention provide an apparatus for generating active compression of bone segments comprising: a distal bone engagement portion; a proximal bone engagement portion; a central portion that facilitates a change in a dimension of the apparatus interposed between the proximal bone engagement portion and the distal bone engagement portion having a perforation formed through a side wall of the central portion; and a limiting feature formed by opposing sides of the perforation that limits the change in the dimension of the apparatus facilitated by the perforation. Wherein the apparatus has a unitary contiguous structure; the apparatus is cannulated; the proximal bone engagement portion comprises threads having a pitch that are distinct from a pitch of threads of the distal bone engagement portion; the distal bone engagement portion comprises threads; the limiting feature limits a change in a length of the apparatus; the limiting feature limits a change in a circumference of the apparatus; the perforation comprises a helical form that defines a continuous helical strut; the limiting feature has a stepped shape; the perforation is form through the sidewall perpendicular to a longitudinal central axis of the apparatus and parallel to a radius of the longitudinal central axis; and/or the change in the dimension of the apparatus comprises a change in dimension of the apparatus over a period of greater than 12 hours.

Certain embodiments of the present invention provide an apparatus for generating active compression of bone segments comprising: a cannulated body having a compression preload feature; a perforation formed through a sidewall of the cannulated body; and a dimension that changes upon deformation of the perforation through an activation of the compression preload feature, the dimension that changes limited by corresponding change limiting features formed in opposing sides of the perforation. Wherein an exterior of the sidewall of the cannulated body comprises threads; the dimension that changes upon deformation of the perforation comprises a length of the apparatus; the compression preload feature comprises a plurality of threads having different pitches formed on an exterior of the sidewall of the cannulated body; and/or the activation of the compression preload feature comprises a rotation of the apparatus.

Certain embodiments of the present invention provide a method of actively compressing bone segments comprising: inserting a cannulated screw into a first bone segment and a second bone segment; applying a longitudinal tensile stress to a cannulated body through deformation of a perforation formed through a sidewall of the cannulated body; limiting the deformation of the perforation by engaging corresponding deformation limiting features formed in opposing sidewalls of the perforation; releasing the tensile stress over a period of time; and compressing the first bone segment and the second bone segment through said releasing the tensile stress. Wherein inserting the cannulated screw into the first bone segment and the second bone segment and applying the longitudinal tensile stress to the cannulated body through deformation of a perforation formed through the sidewall of the cannulated body are simultaneous; inserting the cannulated screw into the first bone segment and the second bone segment and applying the longitudinal tensile stress to the cannulated body through deformation of a perforation formed through the sidewall of the cannulated body are simultaneous; applying the longitudinal tensile stress to the cannulated body through deformation of a perforation formed through the sidewall of the cannulated body comprises rotating a plurality of threads having different pitches formed on an exterior of the sidewall of the cannulated body; and/or limiting the deformation of the perforation by engaging corresponding deformation limiting features formed in opposing sidewalls of the perforation comprises limiting an increase in a length or an increase in circumference of the cannulated body.

Certain embodiments of the present invention provide an apparatus for generating active compression between bone segments comprising: a proximal anchor portion; a distal anchor portion; a spring formed of a superelastic material interposed between the proximal anchor portion and the distal anchor portion; a first state having an axial elastic potential energy generated through a deformation of the spring; and a second state wherein the axial elastic potential energy releases nonlinearly relative to a displacement of the proximal anchor portion relative to the distal anchor portion. Wherein the spring comprises corresponding deformation limiting features formed on opposing sides of the spring; the axial elastic potential energy comprises an axial compressive elastic potential energy; a transition from the first state to the second state comprises a transition of the spring from a high energy state to a low energy state; a transition from the first state to the second state comprises a transition of the spring from a deformed state to a nondeformed state; the spring is positioned over a longitudinal shaft of the apparatus adjacent the proximal anchor portion; the spring is helical; and/or the spring is a beveled washer.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 7 is an illustration of exemplary bones in the human anatomy in which the disclosed invention could be utilized, in accordance with an aspect of the present invention;

FIG. 8 is an illustration of exemplary bones in the human hand anatomy in which the disclosed invention could be utilized, in accordance with an aspect of the present invention;

FIG. 9 is an illustration of exemplary bones in the human foot anatomy in which the disclosed invention could be utilized, in accordance with an aspect of the present invention;

FIG. 10 is an illustration of exemplary bones in the human foot anatomy in which the disclosed invention could be utilized, in accordance with an aspect of the present invention;

FIG. 11 is an illustration of exemplary bones in the human anatomy in which the disclosed invention could be utilized, in accordance with an aspect of the present invention;

FIG. 16 is a plan view of a bone fixation device, in accordance with an aspect of the present invention;

FIG. 17 is a side cross section view of a bone fixation device in a non-expanded state, in accordance with an aspect of the present invention;

FIG. 18 is a side view of a bone fixation device in a non-expanded state, in accordance with an aspect of the present invention;

FIG. 37 is a perspective view of a bone fixation device with a non-threaded expandable segment in a non-expanded state, in accordance with an aspect of the present invention;

FIG. 38 is a perspective view of a portion of a bone fixation device with a non-threaded expandable segment in an expanded state, in accordance with an aspect of the present invention;

FIG. 39 is a perspective view of a portion of a bone fixation device with a non-threaded expandable segment in a non-expanded state, in accordance with an aspect of the present invention;

FIG. 40 is a perspective view of a bone fixation assembly with a non-threaded expandable segment in a non-expanded state with a central member with distal and proximal retention features, in accordance with an aspect of the present invention;

FIG. 41 is a perspective view of a central member with distal and proximal retention features, in accordance with an aspect of the present invention;

FIG. 42 is a side view of a bone fixation device with a non-threaded expandable segment in a non-expanded state with distal and proximal retention features, in accordance with an aspect of the present invention;

FIG. 68 is a perspective view of a bone fixation device in a non-expanded state with variable minor and major diameters and triple lead pitch thread features, in accordance with an aspect of the present invention;

FIG. 69 is a perspective view of a bone fixation device in a non-threaded, non-expanded state with variable minor and major diameters and distal triple lead pitch thread and variable proximal thread features, in accordance with an aspect of the present invention;

FIG. 70 is a side cross section view of a bone fixation device in a non-expanded state with variable minor and major diameters and triple lead pitch thread features, in accordance with an aspect of the present invention;

FIG. 71 is a side cross section view of a bone fixation device in a non-threaded non-expanded state with variable minor and major diameters and distal triple lead pitch thread and variable proximal thread features, in accordance with an aspect of the present invention;

FIG. 83 is a side cross section view of a bone fixation assembly with a non-threaded expandable segment in a non-expanded state with a central member, in accordance with an aspect of the present invention;

FIG. 84 is a side view of a bone fixation assembly with a non-threaded expandable segment in a non-expanded state with a central member, in accordance with an aspect of the present invention;

FIG. 85 is a side cross section view of a bone fixation assembly with a non-threaded expandable segment in an expanded state with a central member and retention features, in accordance with an aspect of the present invention;

FIG. 86 is an end view of a bone fixation assembly with a non-threaded expandable segment in an expanded state with a central member and retention features, in accordance with an aspect of the present invention;

FIG. 87 is a side cross section view of a bone fixation assembly with a non-threaded expandable segment in an expanded state with a central member and retention features, in accordance with an aspect of the present invention;

FIG. 88 is a side view of a portion of a bone fixation device with a non-threaded expandable segment in a non-expanded state, in accordance with an aspect of the present invention;

FIG. 89 is a partial side view of a portion of a cut slot pattern of a bone fixation device with a non-threaded expandable segment in a non-expanded state, in accordance with an aspect of the present invention;

FIG. 90 is a partial side view of a portion of a cut slot pattern of a bone fixation device with a non-threaded expandable segment in a non-expanded state, in accordance with an aspect of the present invention;

FIG. 119 is a flow chart showing one embodiment of a method of manufacturing a bone fixation device according to the present invention;

FIG. 120 is a flow chart showing one embodiment of a method of manufacturing a bone fixation device according to the present invention;

FIG. 121 is a flow chart showing one embodiment of a method of manufacturing a bone fixation device according to the present invention;

FIG. 122 is a flow chart showing one embodiment of a method of manufacturing a bone fixation device according to the present invention;

FIG. 123 is a partial side view of a bone fixation device with a non-threaded expandable segment with multiple expansion properties in a non-expanded state, in accordance with an aspect of the present invention;

FIG. 124 is a partial side view of a bone fixation device with a non-threaded expandable segment with multiple expansion properties in a non-expanded state with deformation control features, in accordance with an aspect of the present invention;

FIG. 125 is a side view of a bone fixation device with a non-threaded expandable segment with multiple expansion properties in a non-expanded state, in accordance with an aspect of the present invention;

FIG. 126 is a side view of a bone fixation device with a non-threaded expandable segment with radial expansion properties in a non-expanded state, in accordance with an aspect of the present invention;

FIG. 127 is a side view of a bone fixation device with a non-threaded expandable segment with radial expansion properties in a partially-expanded state, in accordance with an aspect of the present invention;

FIG. 128 is a side view of a bone fixation device with a non-threaded expandable segment with radial expansion properties in a fully-expanded state, in accordance with an aspect of the present invention;

Figures 133, 134, 135:
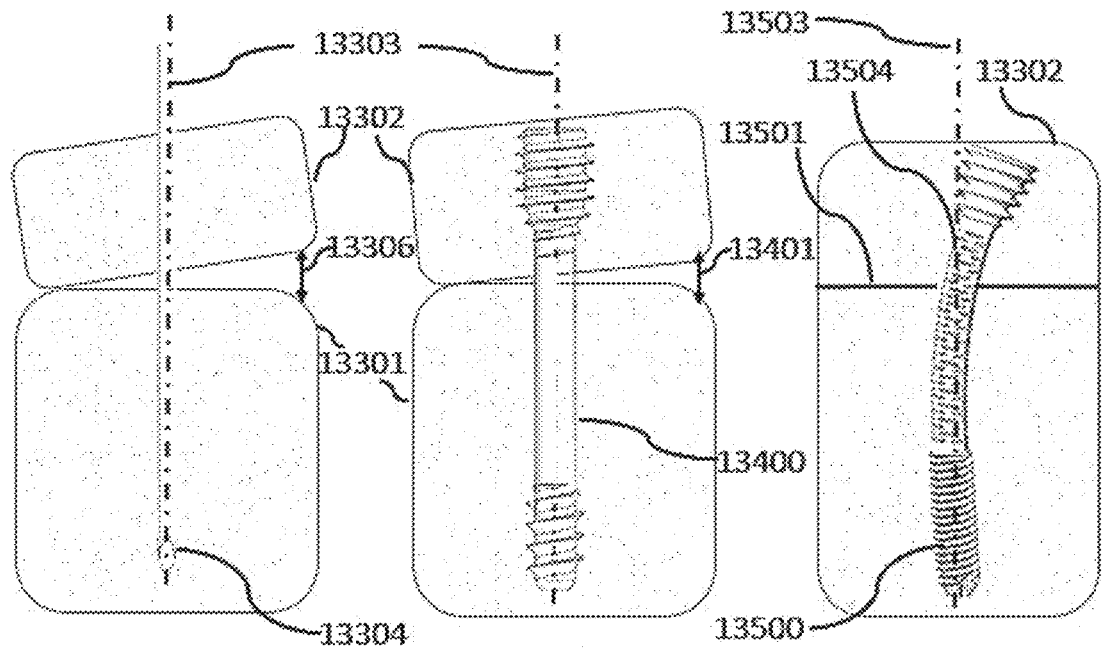
Figure 136:
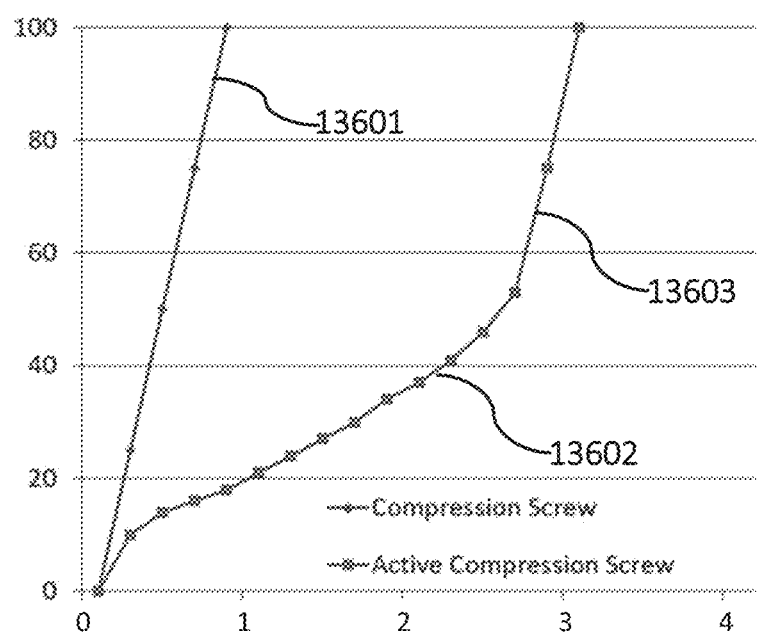

FIG. 129 is a side cross section view of a bone fixation device with a threaded distal segment and a non-threaded expandable segment in a non-expanded state, the expandable segment being of larger diameter than the minor diameter of the threaded section, the distal segment having a feature on an inner diameter that can engage and transfer a torque and axial load, in accordance with an aspect of the present invention;

FIG. 130 is a side cross section view of a bone fixation device assembly with a threaded distal segment and a non-threaded expandable segment in a non-expanded state, the expandable segment being of larger diameter than the minor diameter of the threaded distal segment, the distal segment having a feature on an inner diameter that can engage and transfer a torque and axial load, and a driving mechanism that can engage the distal feature and a proximal end of the device, in accordance with an aspect of the present invention;

FIG. 131 is a perspective view of a device assembly with a driving mechanism that engages a distal feature and a proximal end of a device, in accordance with an aspect of the present invention; and FIG. 132 is a perspective cross section view of a bone fixation device assembly with a threaded distal segment and a non-threaded expandable segment in a non-expanded state, the expandable segment being of larger diameter than the minor diameter of the threaded distal segment, the distal segment having a feature on an inner diameter that can engage and transfer a torque and axial load, and a driving mechanism that can engage the distal feature and a proximal end of the device, in accordance with an aspect of the present invention;

FIG. 133 is a side view of a bone fixation device being inserted into two non-reduced bone segments, in accordance with an aspect of the present invention;

FIG. 134 is a side view of a bone fixation device being inserted into two non-reduced bone segments in accordance with an aspect of the present invention;

FIG. 135 is a side view of a bone fixation device inserted into two reduced bone segments in a flexed state, in accordance with an aspect of the present invention;

FIG. 136 is a graph depicting the compressive force loaded over distance by a device according to the present invention relative to a standard screw.

Figure 137:
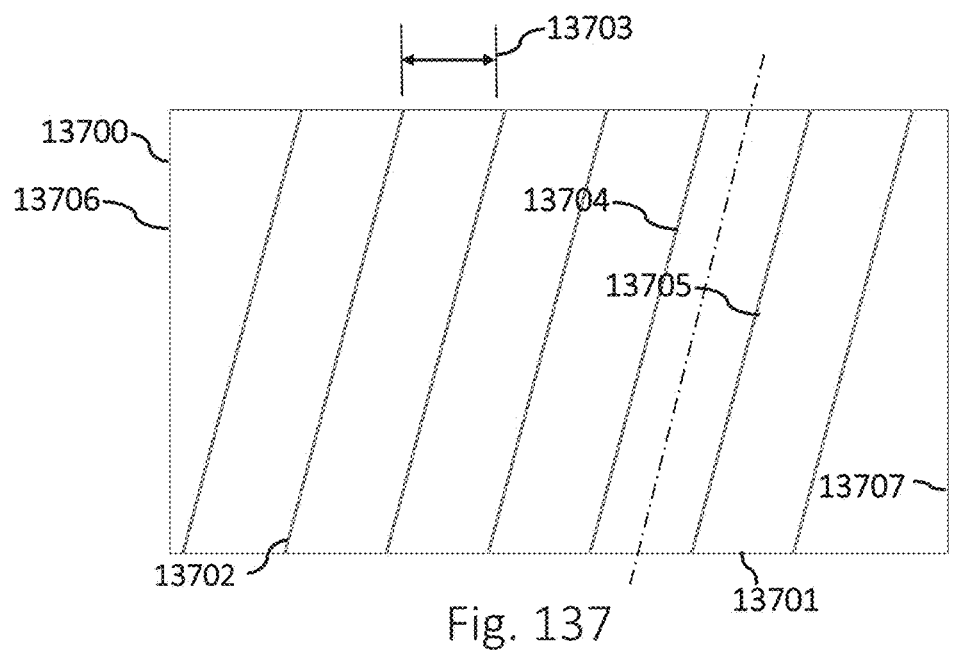

FIG. 137 is a partial side view of a portion of a cut slot pattern of a bone fixation device with a non-threaded helical expandable segment in a non-expanded state, in accordance with an aspect of the present invention.

Figure 138:
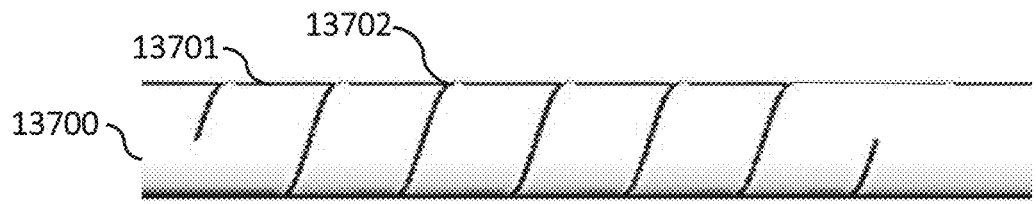

FIG. 138 is a partial side view of a bone fixation device with a non-threaded helical expandable segment in a non-expanded state, in accordance with an aspect of the present invention.

Figure 139:
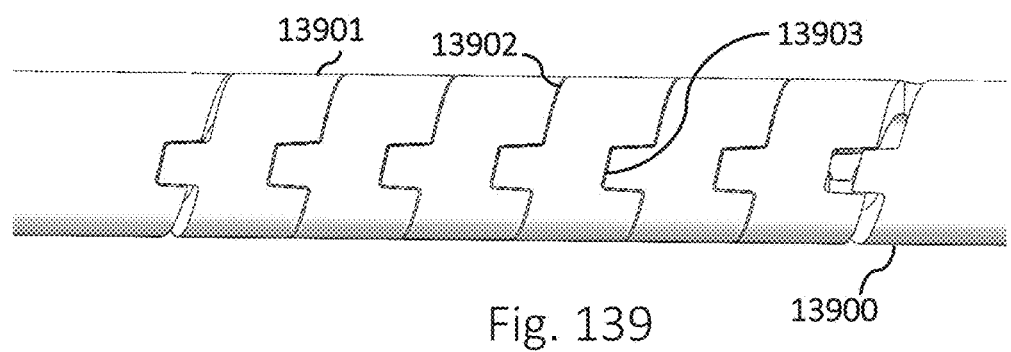

FIG. 139 is a partial side view of a bone fixation device with a non-threaded helical expandable segment with torsional engagement features in a non-expanded state, in accordance with an aspect of the present invention.

Figures 140, 141, 142:
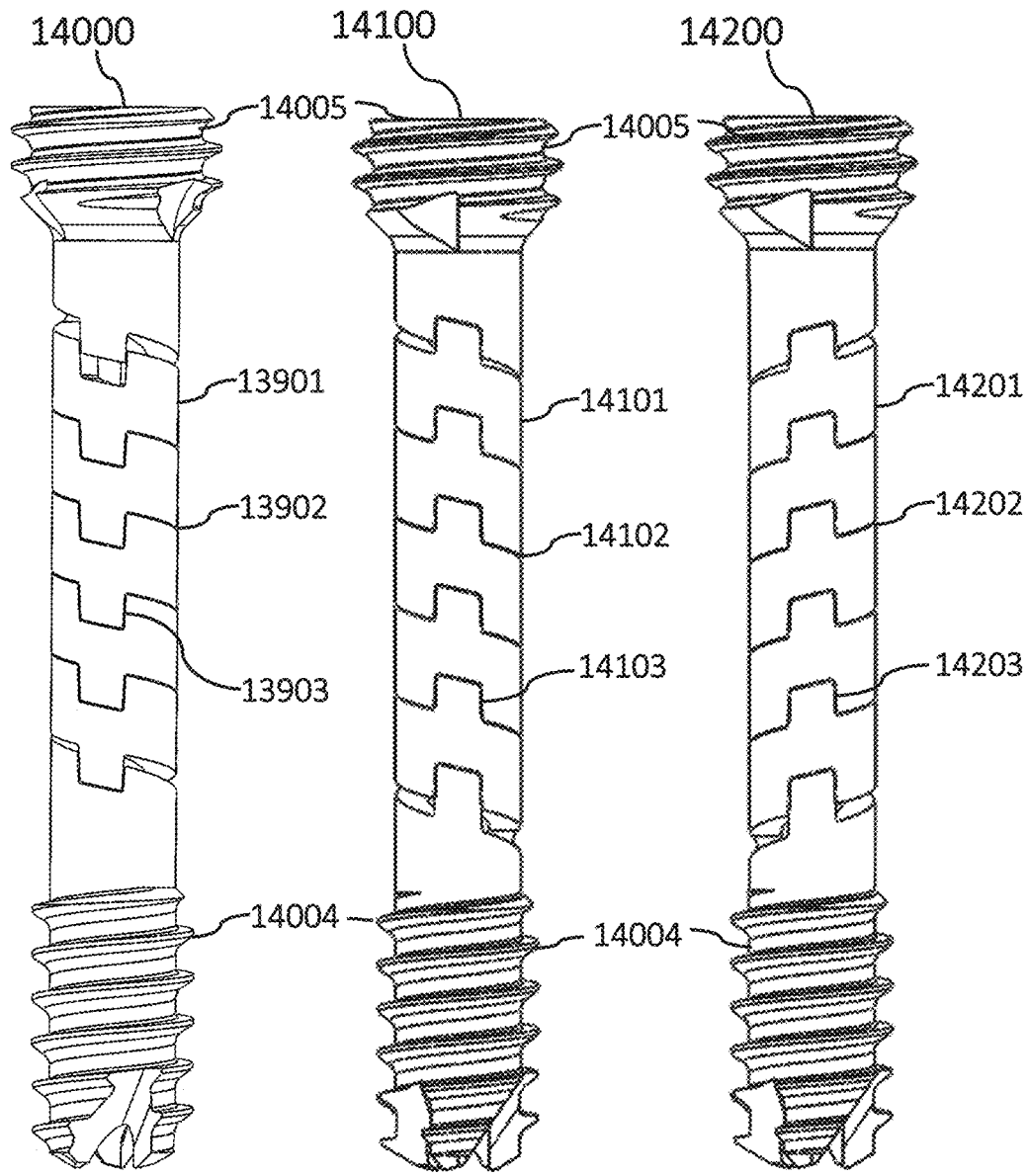

FIG. 140 is a side view of a bone fixation device with a non-threaded helical expandable segment with torsional engagement features in a non-expanded state, in accordance with an aspect of the present invention.

FIG. 141 is a side view of a bone fixation device with a non-threaded helical expandable segment with torsional engagement features in a non-expanded state, in accordance with an aspect of the present invention.

FIG. 142 is a side view of a bone fixation device with a non-threaded helical expandable segment with torsional engagement features in a non-expanded state, in accordance with an aspect of the present invention.

Figure 143:
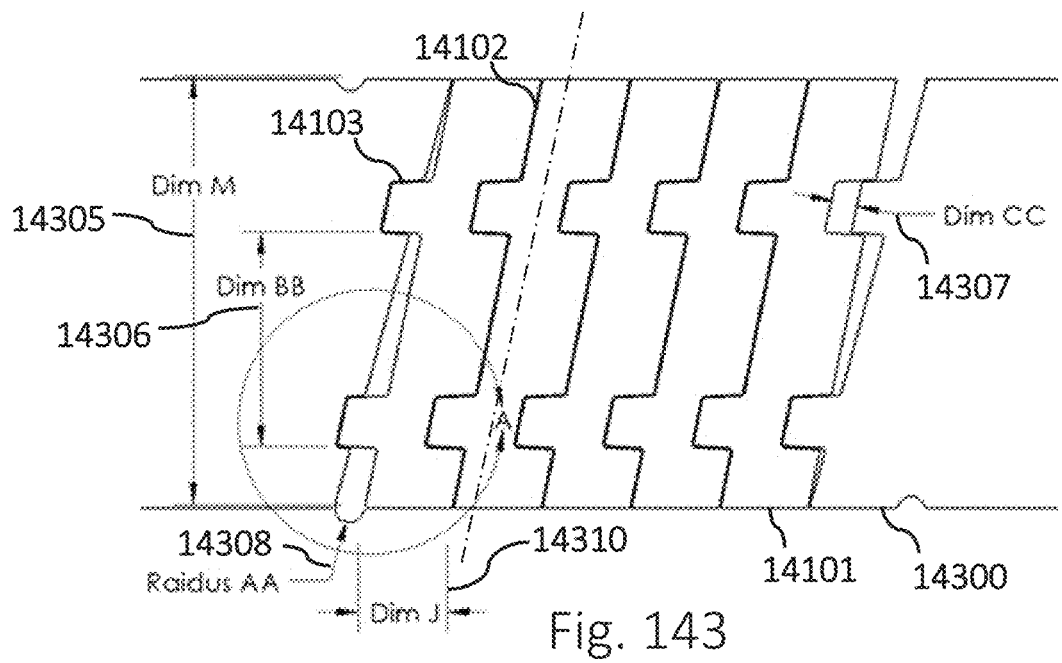

FIG. 143 is a partial side view of a portion of a cut slot pattern of a bone fixation device with a non-threaded helical expandable segment with torsional engagement features in a non-expanded state, in accordance with an aspect of the present invention.

Figure 144:
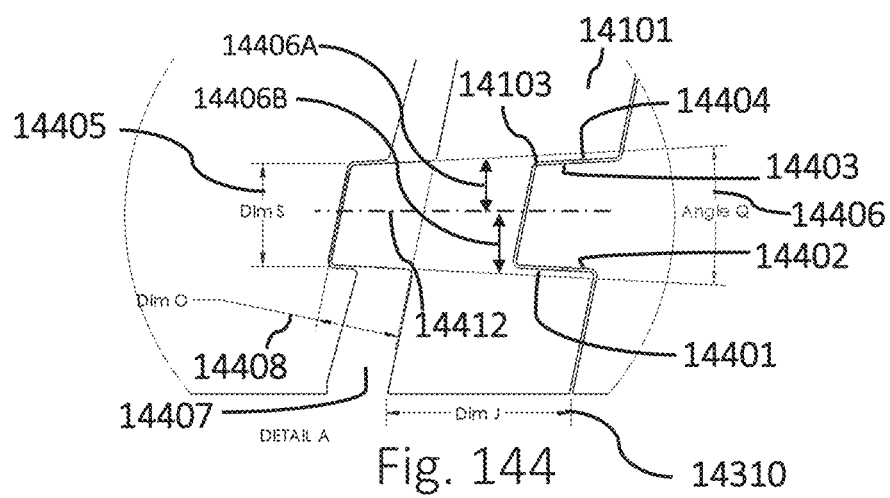

FIG. 144 is a partial side view scaled detail of a portion of a cut slot pattern of a bone fixation device with a non-threaded helical expandable segment with torsional engagement features in a non-expanded state, in accordance with an aspect of the present invention.

Figure 145:
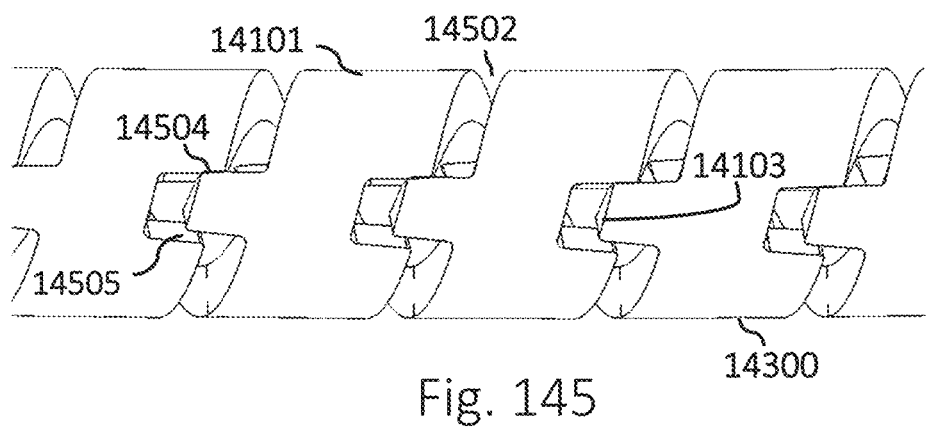

FIG. 145 is a partial side view of a bone fixation device with a non-threaded helical expandable segment with torsional engagement features in an expanded state, in accordance with an aspect of the present invention.

Figures 146, 147:
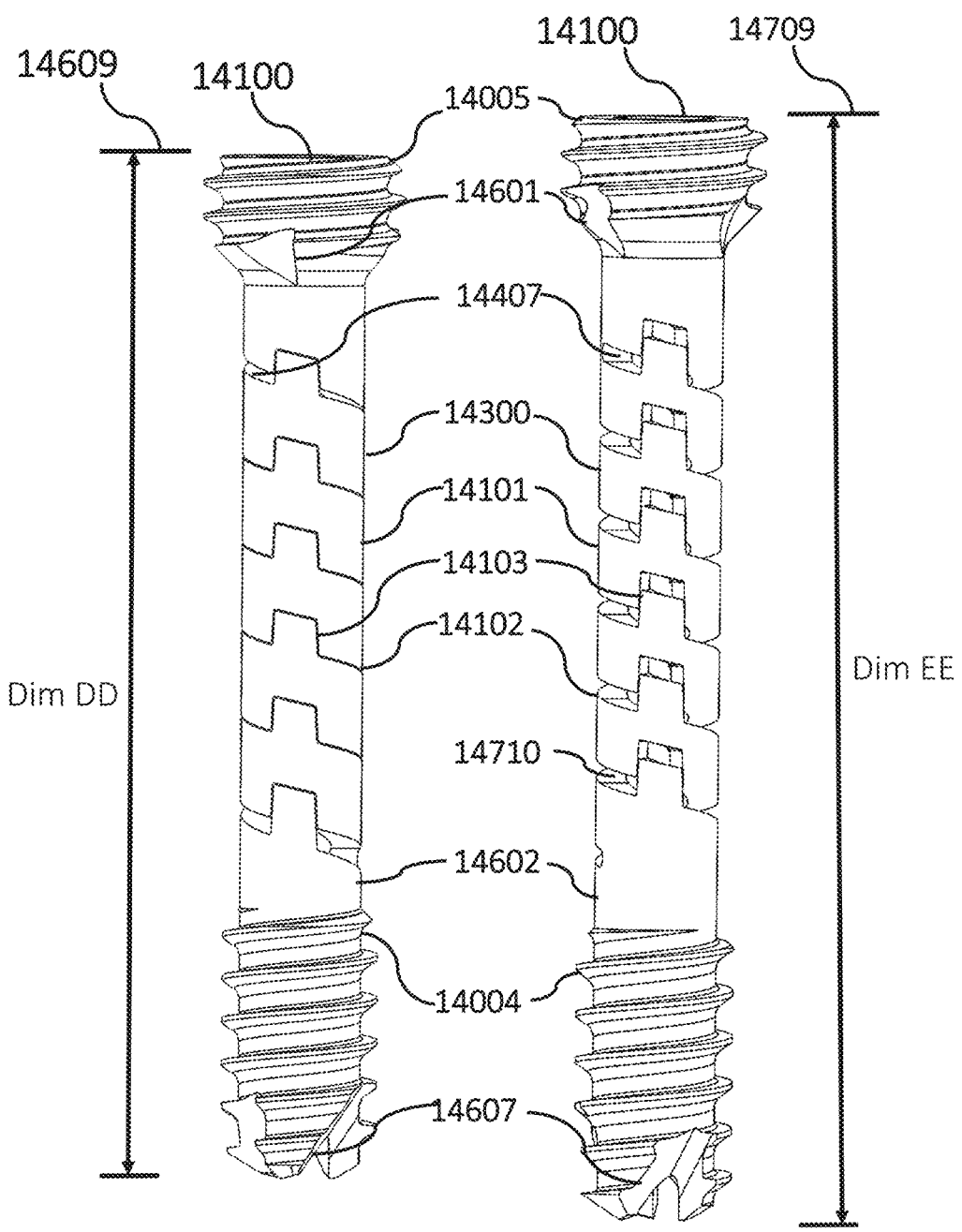

FIG. 146 is a side view of a bone fixation device with a non-threaded helical expandable segment with torsional engagement features in a non-expanded state, in accordance with an aspect of the present invention.

FIG. 147 is a side view of a bone fixation device with a non-threaded helical expandable segment with torsional engagement features in an expanded state, in accordance with an aspect of the present invention.

Figures 148, 149:
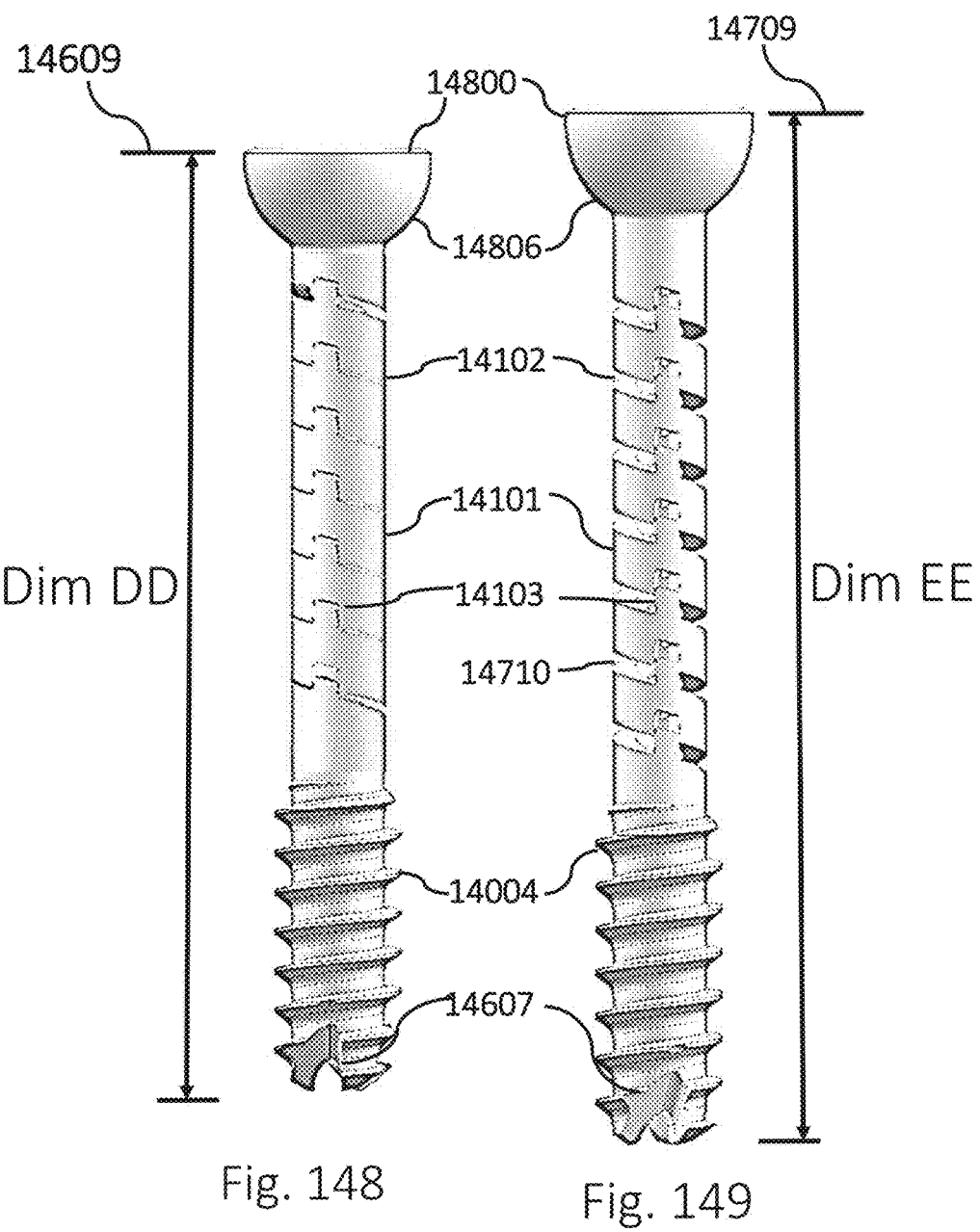

FIG. 148 is a side view of a bone fixation device with a non-threaded helical expandable segment with torsional engagement features in a non-expanded state, in accordance with an aspect of the present invention.

FIG. 149 is a side view of a bone fixation device with a non-threaded helical expandable segment with torsional engagement features in an expanded state, in accordance with an aspect of the present invention.

Figure 150:
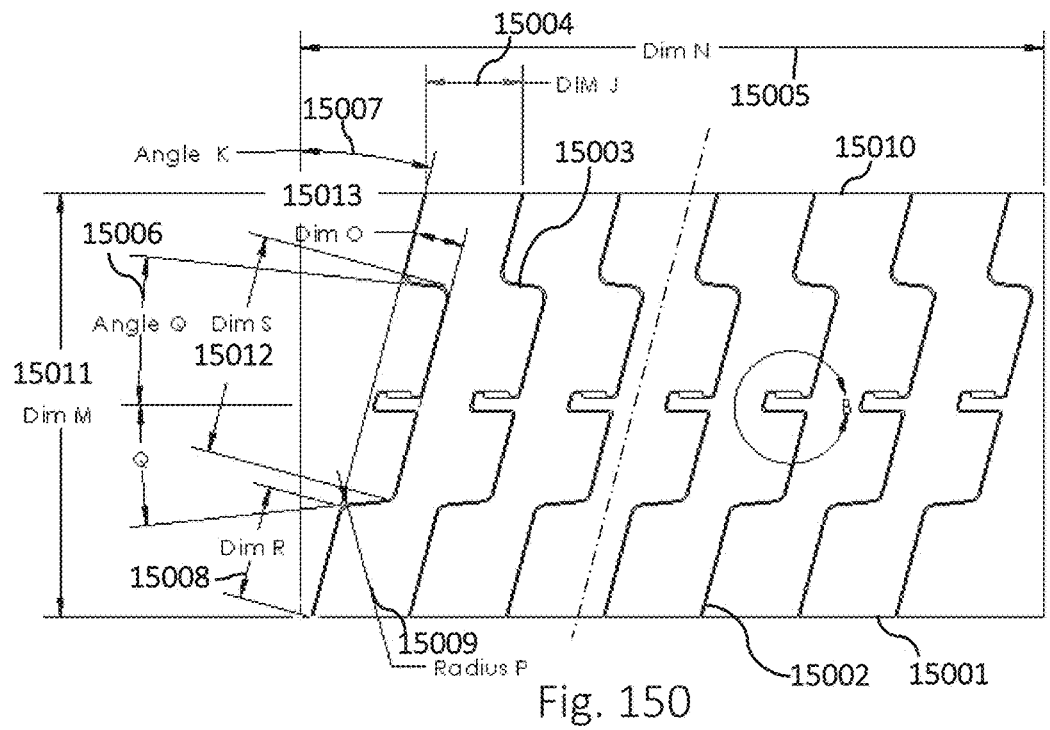

FIG. 150 is a partial side view of a portion of a cut slot pattern of a bone fixation device with a non-threaded helical expandable segment with torsional engagement features and axial length engagement features in a non-expanded state, in accordance with an aspect of the present invention.

Figure 151:
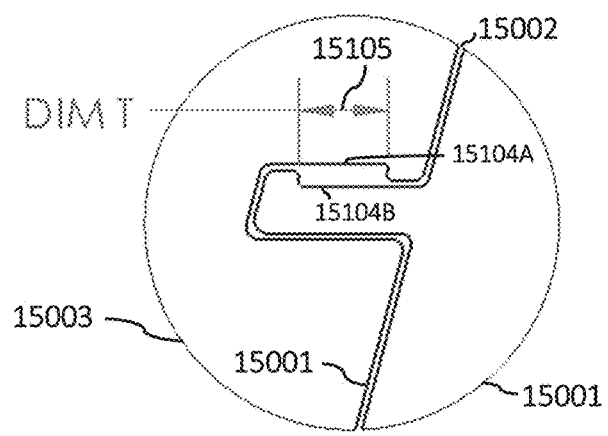

FIG. 151 is a partial side view scaled detail of a portion of a cut slot pattern of a bone fixation device with a non-threaded helical expandable segment with torsional engagement features and axial length engagement features in a non-expanded state, in accordance with an aspect of the present invention.

Figure 152:
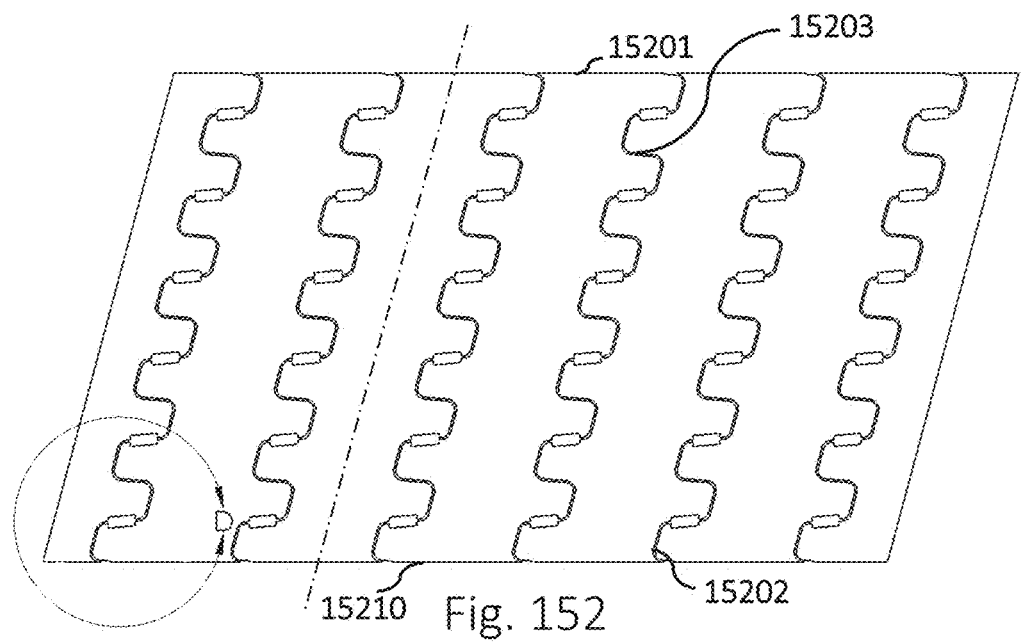

FIG. 152 is a partial side view of a portion of a cut slot pattern of a bone fixation device with a non-threaded helical expandable segment with torsional engagement features and axial length engagement features in a non-expanded state, in accordance with an aspect of the present invention.

Figure 153:
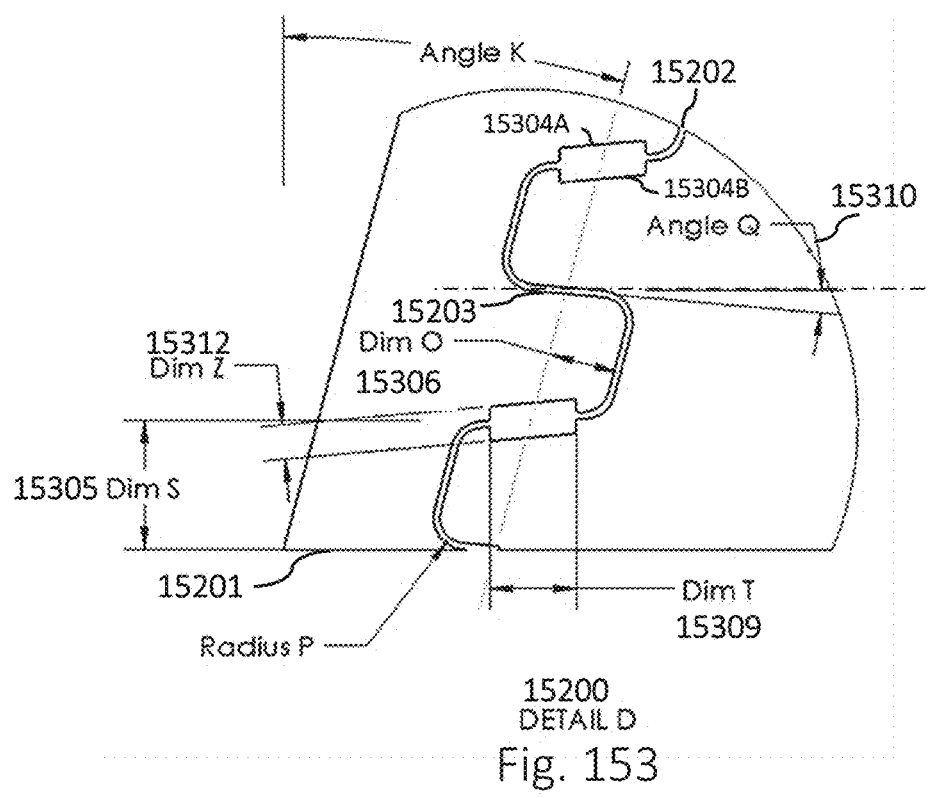

FIG. 153 is a partial side view scaled detail of a portion of a cut slot pattern of a bone fixation device with a non-threaded helical expandable segment with torsional engagement features and axial length engagement features in a non-expanded state, in accordance with an aspect of the present invention.

Figure 154:
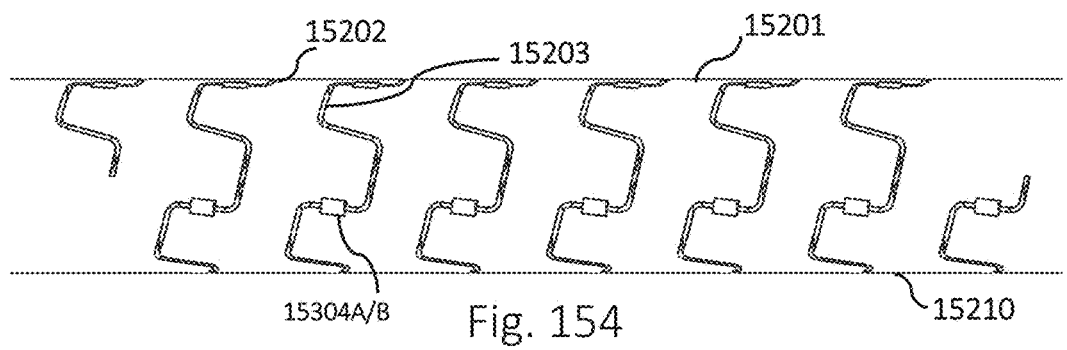

FIG. 154 is a partial side view of a portion of a cut slot pattern of a bone fixation device with a non-threaded helical expandable segment with torsional engagement features and axial length engagement features in a non-expanded state, in accordance with an aspect of the present invention.

Figure 155:
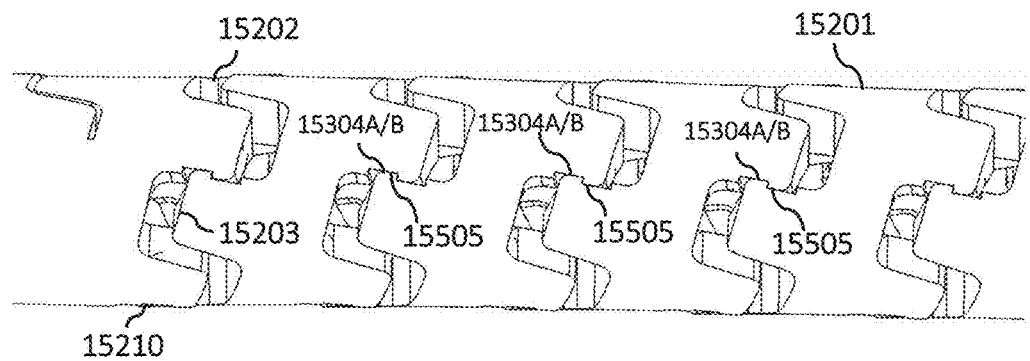

FIG. 155 is a partial side view scaled detail of a portion of a cut slot pattern of a bone fixation device with a non-threaded helical expandable segment with torsional engagement features and axial length engagement features in an expanded state, in accordance with an aspect of the present invention.

Figure 156:
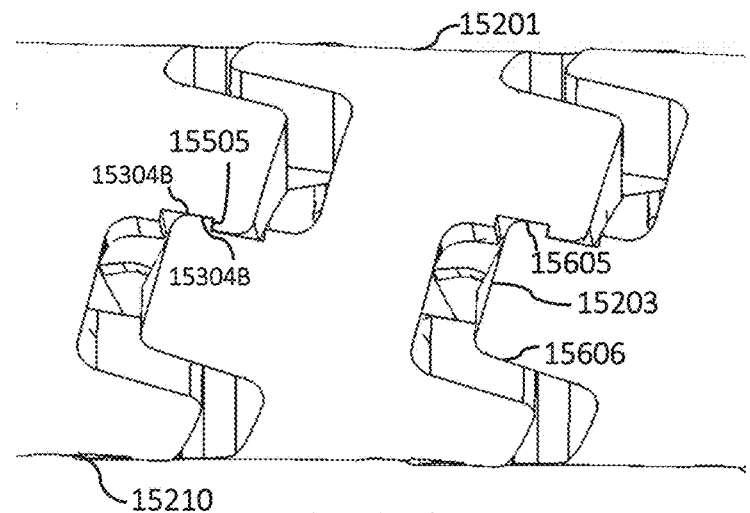

FIG. 156 is a partial side view scaled detail of a portion of a cut slot pattern of a bone fixation device with a non-threaded helical expandable segment with torsional engagement features and axial length engagement features in an expanded state, in accordance with an aspect of the present invention.

Figure 157:
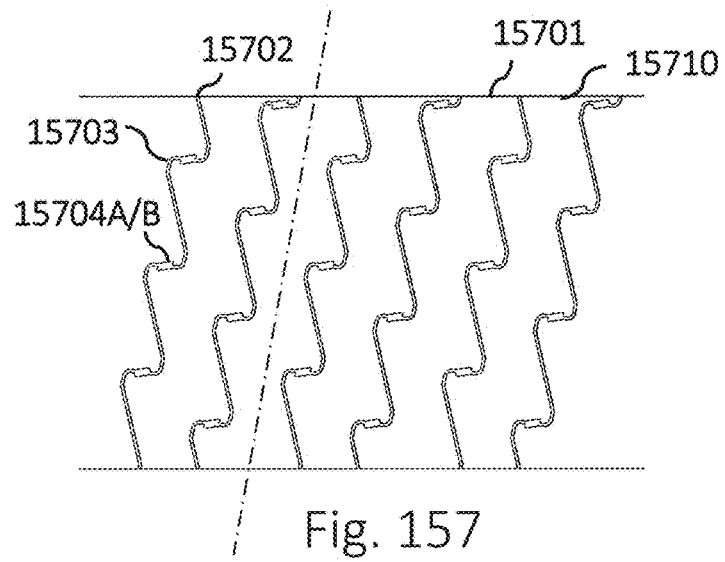

FIG. 157 is a partial side view of a portion of a cut slot pattern of a bone fixation device with a non-threaded helical expandable segment with torsional engagement features and axial length engagement features in a non-expanded state, in accordance with an aspect of the present invention.

Figure 158:
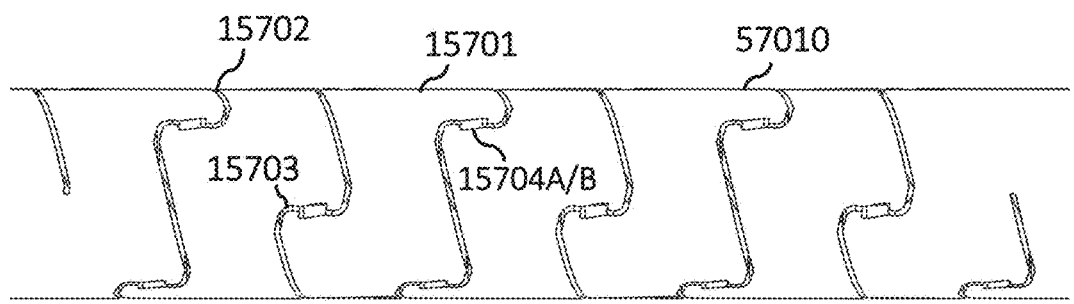

FIG. 158 is a partial side view of a portion of a cut slot pattern of a bone fixation device with a non-threaded helical expandable segment with torsional engagement features and axial length engagement features in a non-expanded state, in accordance with an aspect of the present invention.

Figure 159:
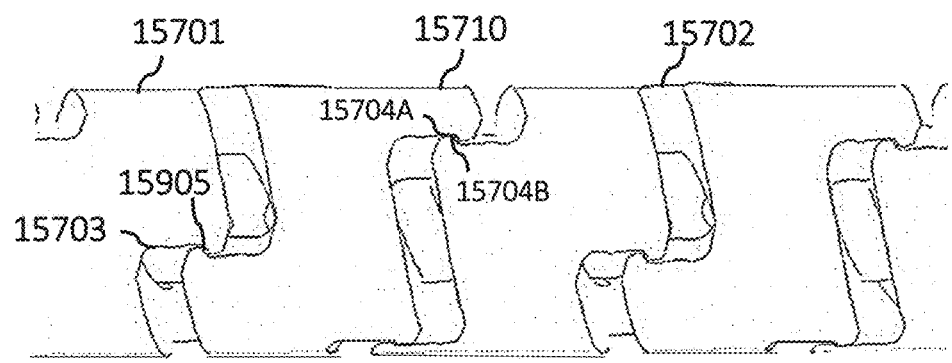

FIG. 159 is a partial side view scaled detail of a portion of a cut slot pattern of a bone fixation device with a non-threaded helical expandable segment with torsional engagement features and axial length engagement features in an expanded state, in accordance with an aspect of the present invention.

Figure 160:
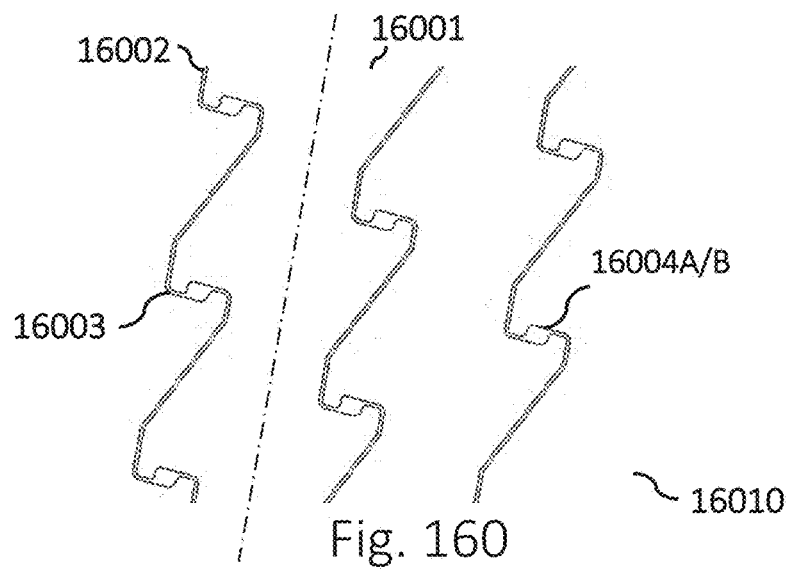

FIG. 160 is a partial side view of a portion of a cut slot pattern of a bone fixation device with a non-threaded helical expandable segment with torsional engagement features and axial length engagement features in a non-expanded state, in accordance with an aspect of the present invention.

Figure 161:
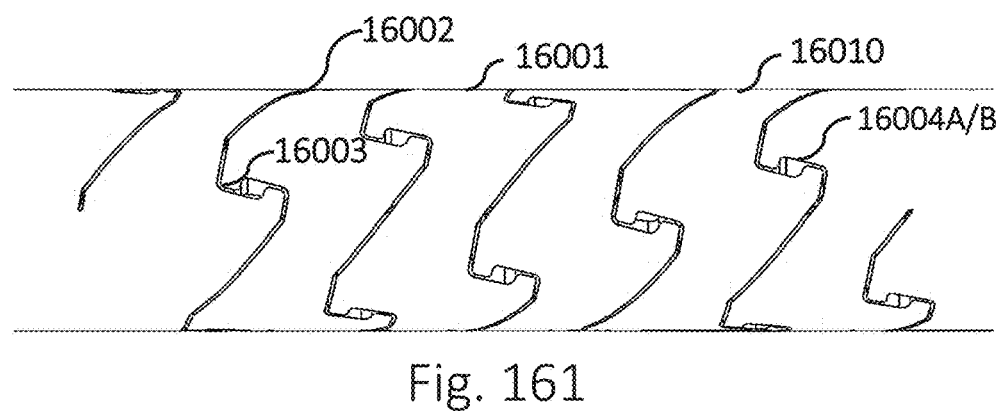

FIG. 161 is a partial side view of a portion of a cut slot pattern of a bone fixation device with a non-threaded helical expandable segment with torsional engagement features and axial length engagement features in a non-expanded state, in accordance with an aspect of the present invention.

Figure 162:
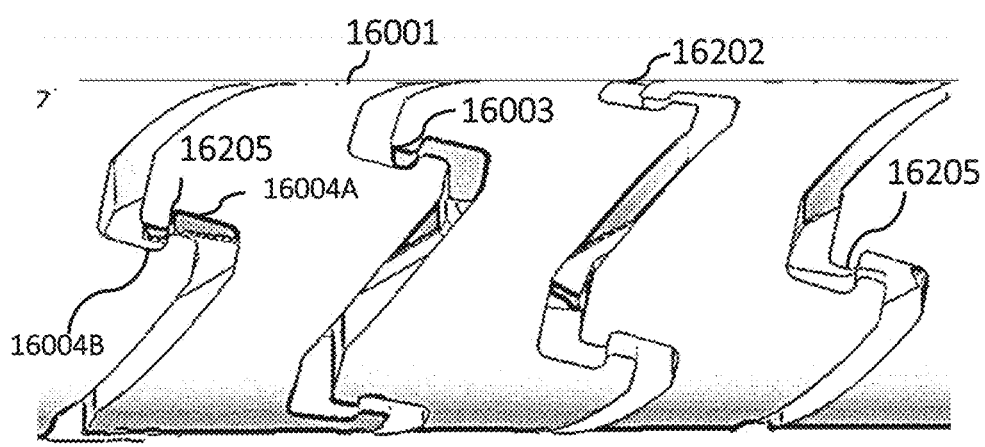

FIG. 162 is a partial side view scaled detail of a portion of a cut slot pattern of a bone fixation device with a non-threaded helical expandable segment with torsional engagement features and axial length engagement features in an expanded state, in accordance with an aspect of the present invention.

Figure 163:
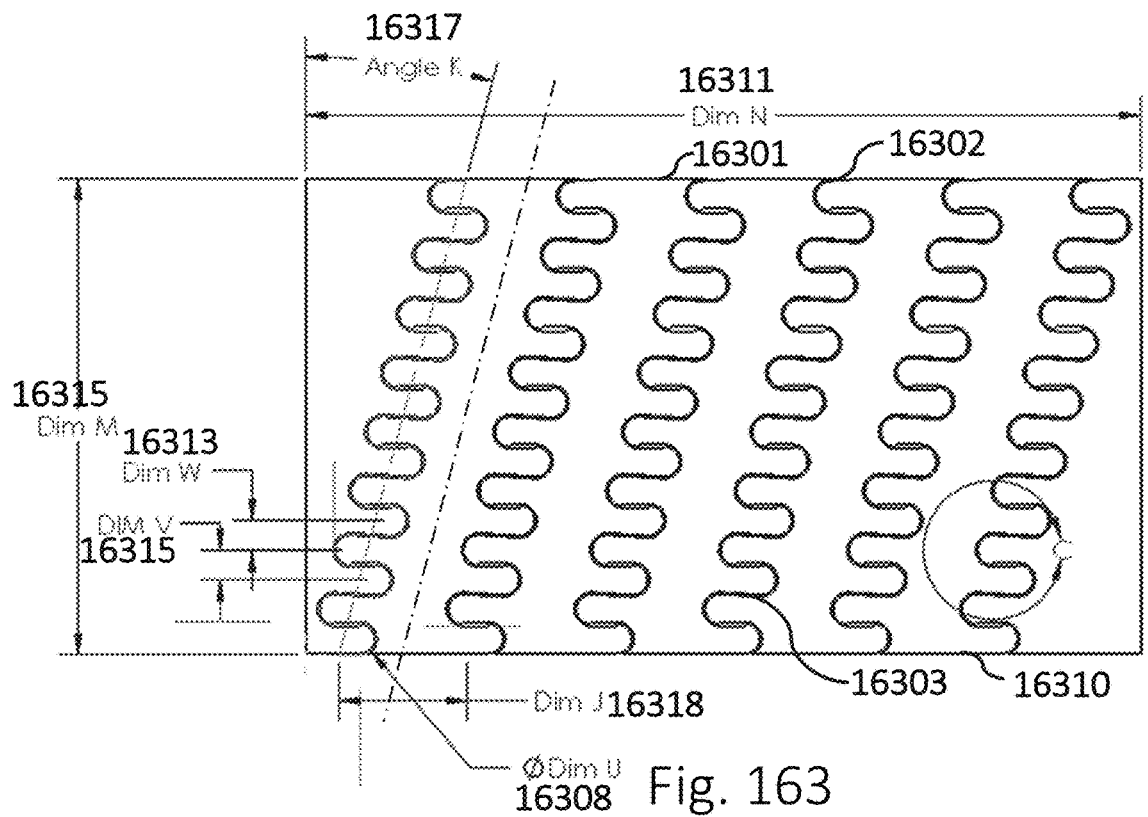

FIG. 163 is a partial side view of a portion of a cut slot pattern of a bone fixation device with a non-threaded sinusoidal expandable segment with torsional engagement features and axial length engagement features in a non-expanded state, in accordance with an aspect of the present invention.

Figure 164:
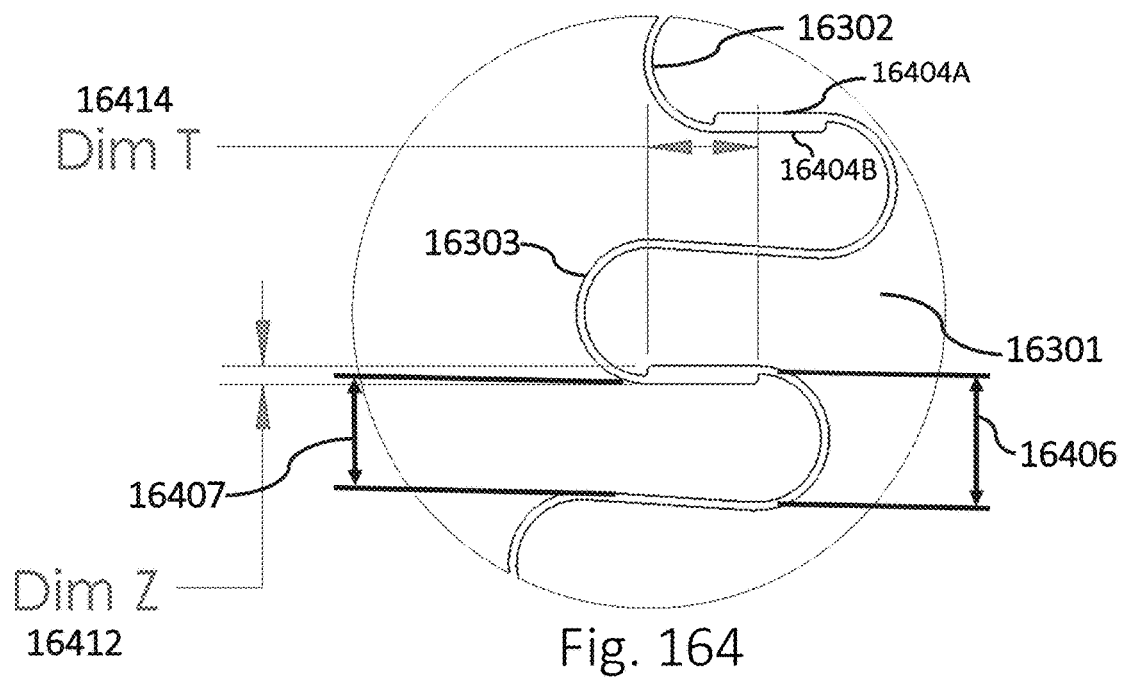

FIG. 164 is a partial detailed side view of a portion of a cut slot pattern of a bone fixation device with a non-threaded sinusoidal expandable segment with torsional engagement features and axial length engagement features in a non-expanded state, in accordance with an aspect of the present invention.

Figure 165:
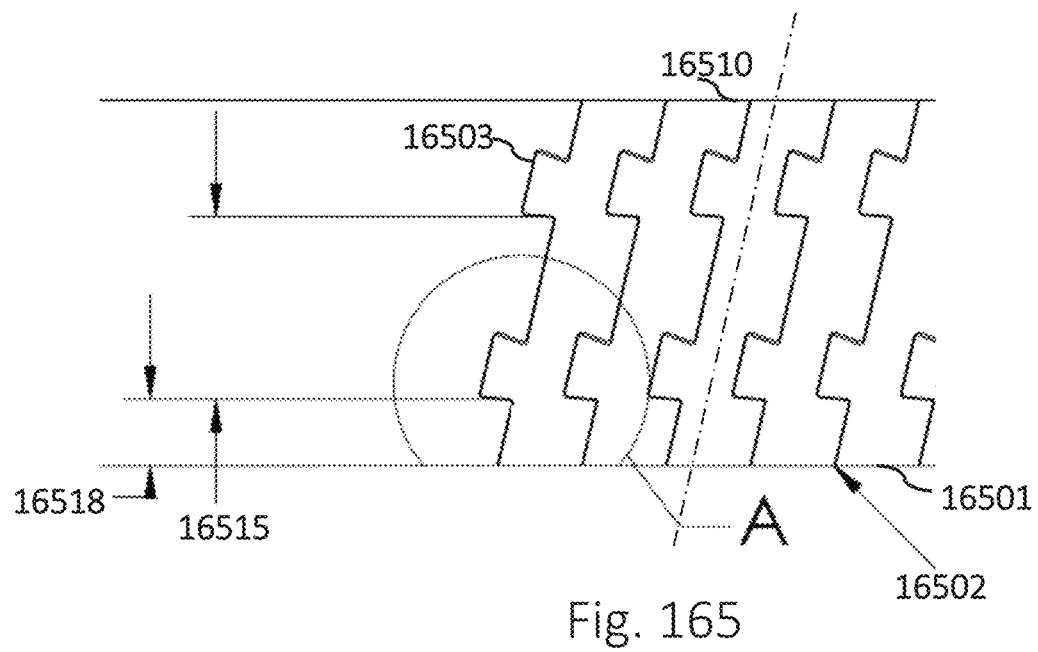

FIG. 165 is a partial side view of a portion of a cut slot pattern of a bone fixation device with a non-threaded expandable segment with trapezoidal torsional engagement features and axial length engagement features in a non-expanded state, in accordance with an aspect of the present invention.

Figure 166:
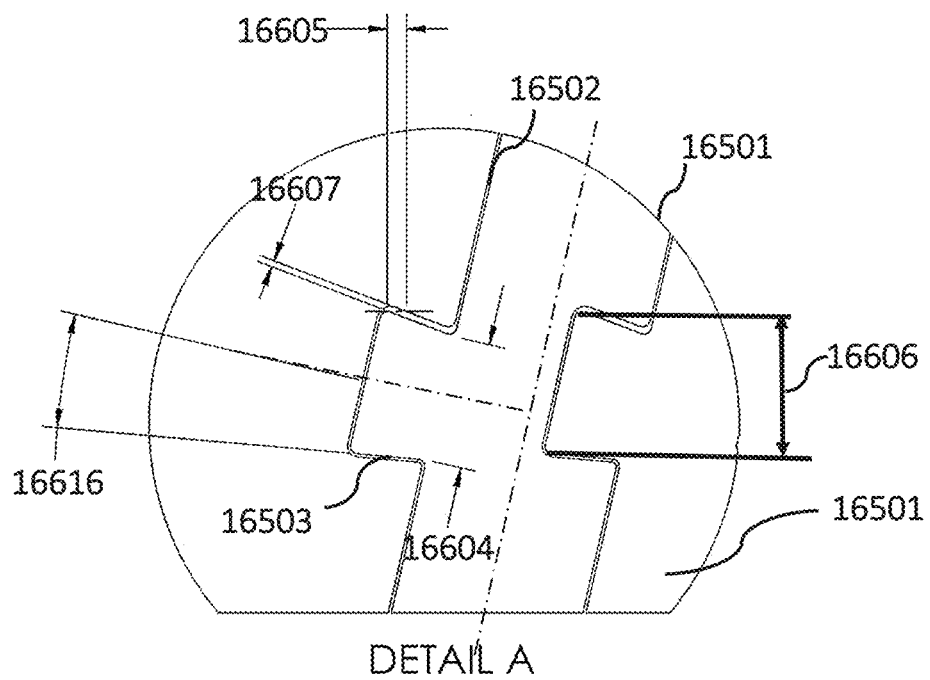

FIG. 166 is a partial detailed side view of a portion of a cut slot pattern of a bone fixation device with a non-threaded expandable segment with trapezoidal torsional engagement features and axial length engagement features in a non-expanded state, in accordance with an aspect of the present invention.

Figure 167:
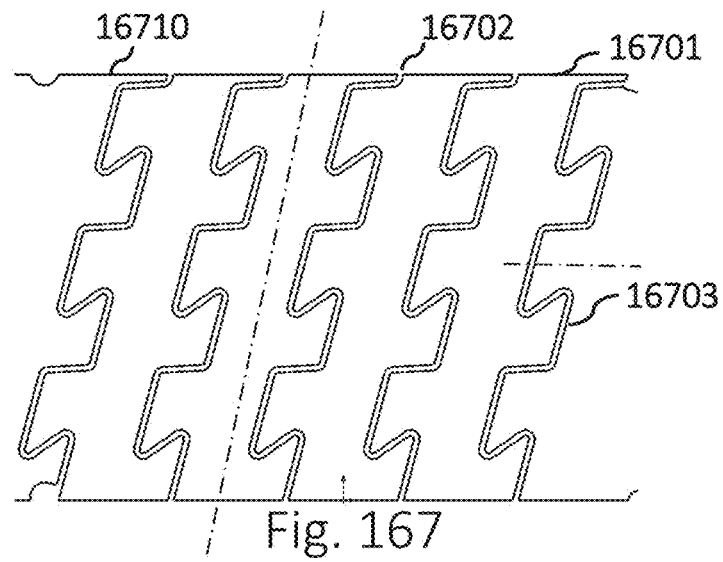
Figure 167:
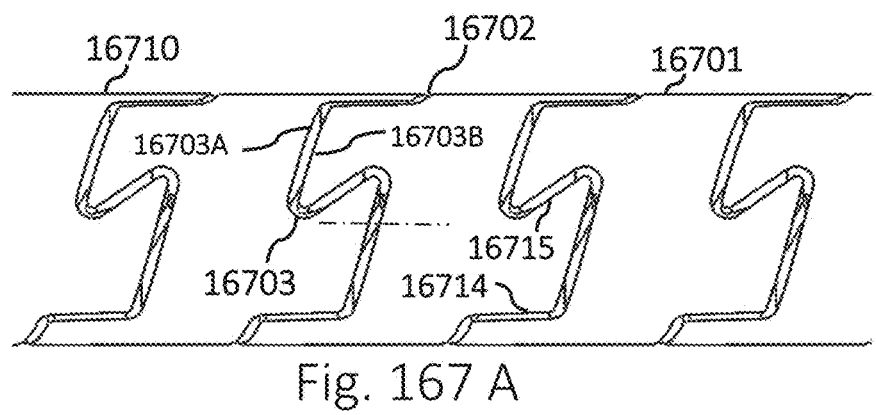

FIG. 167 is a partial side view of a portion of a cut slot pattern of a bone fixation device with a non-threaded helical expandable segment with torsional engagement features and axial length limiting features in a non-expanded state, in accordance with an aspect of the present invention.

FIG. 167A is a partial side view scaled detail of a portion of a cut slot pattern of a bone fixation device with a non-threaded helical expandable segment with torsional engagement features and axial length limiting features in a non-expanded state, in accordance with an aspect of the present invention.

Figure 167B:
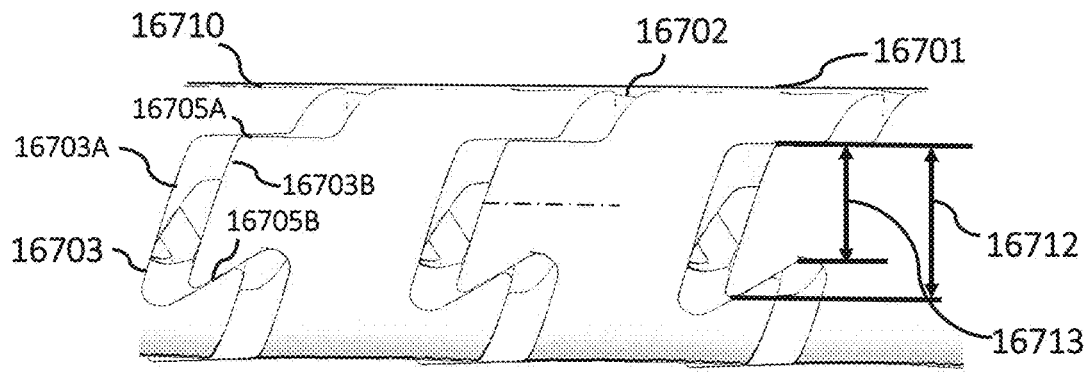

FIG. 167B is a partial side view scaled detail of a portion of a cut slot pattern of a bone fixation device with a non-threaded helical expandable segment with torsional engagement features and axial length limiting features in an expanded state, in accordance with an aspect of the present invention.

Figure 168:
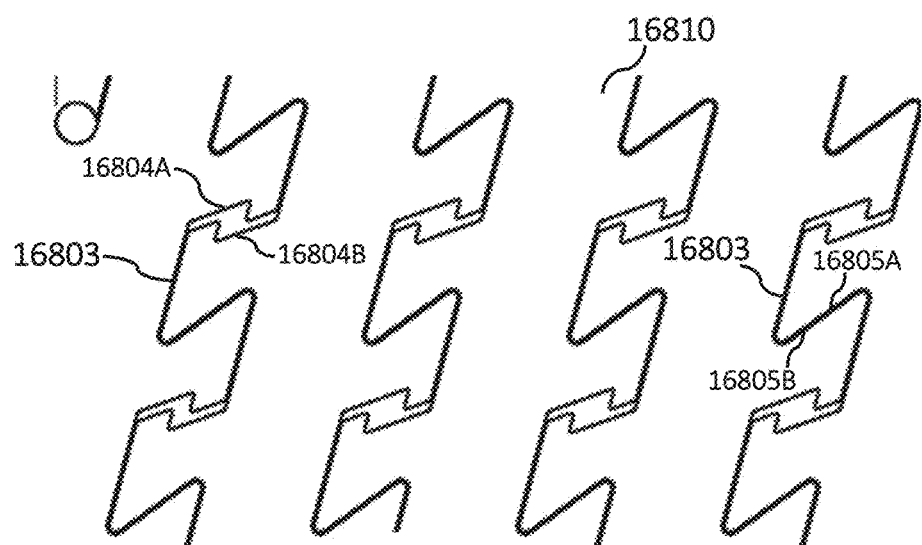

FIG. 168 is a partial side view of a portion of a cut slot pattern of a bone fixation device with a non-threaded helical expandable segment with torsional engagement features and axial length engagement features in a non-expanded state, in accordance with an aspect of the present invention.

Figure 168A:
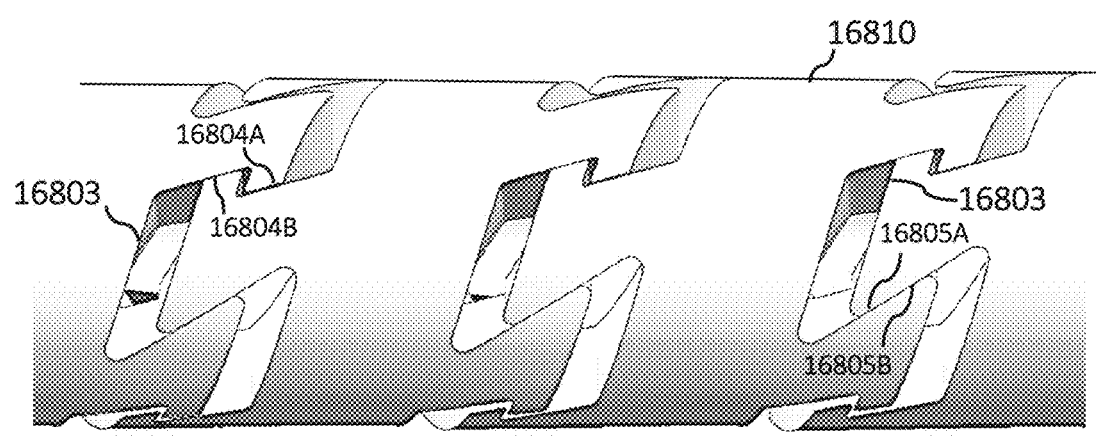

FIG. 168A is a partial side view scaled detail of a portion of a cut slot pattern of a bone fixation device with a non-threaded helical expandable segment with torsional engagement features and axial length engagement features in a deformed, expanded state, in accordance with an aspect of the present invention.

Figure 169:
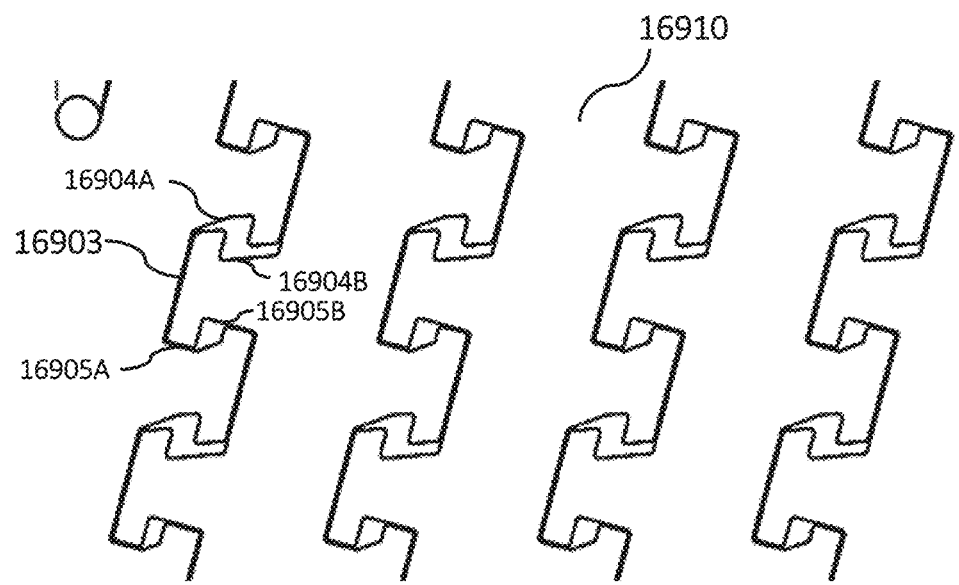

FIG. 169 is a partial side view scaled detail of a portion of a cut slot pattern of a bone fixation device with a non-threaded helical expandable segment with torsional engagement features and axial length engagement features in an expanded state, in accordance with an aspect of the present invention.

Figure 169A:
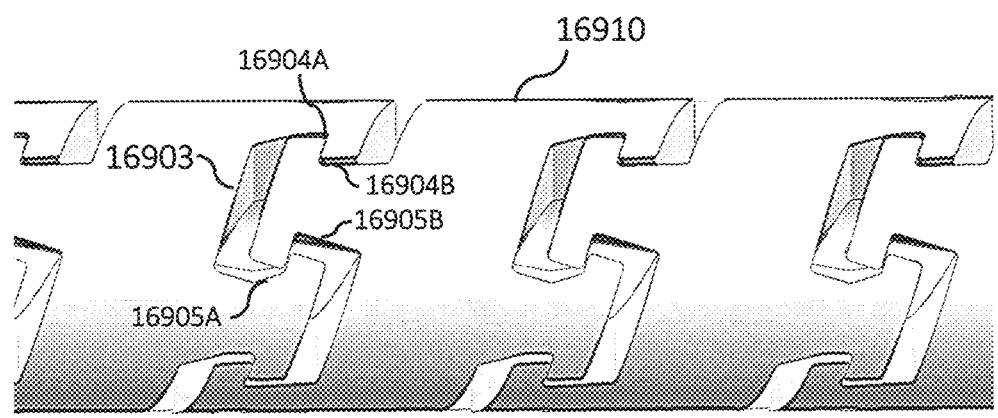

FIG. 169A is a partial side view scaled detail of a portion of a cut slot pattern of a bone fixation device with a non-threaded helical expandable segment with torsional engagement features and axial length engagement features in a deformed, expanded state, in accordance with an aspect of the present invention.

Figure 170:
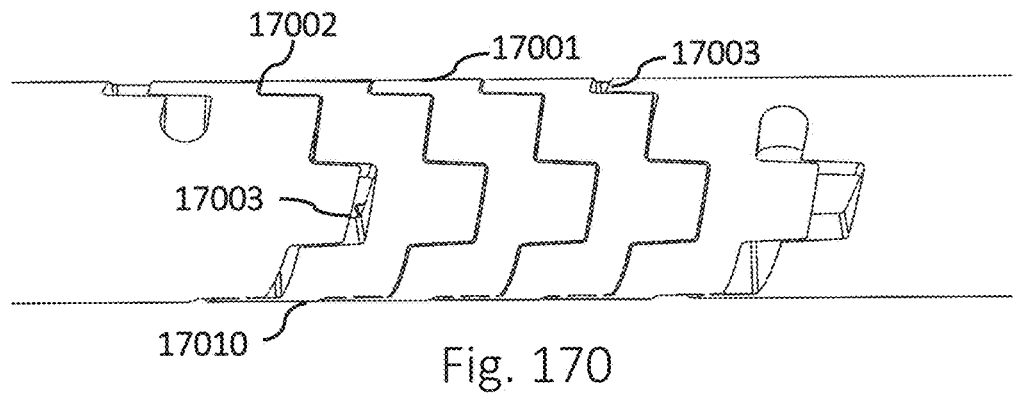

FIG. 170 is a partial side view of a bone fixation device with a non-threaded expandable segment in a non-expanded state, in accordance with an aspect of the present invention.

Figure 171:
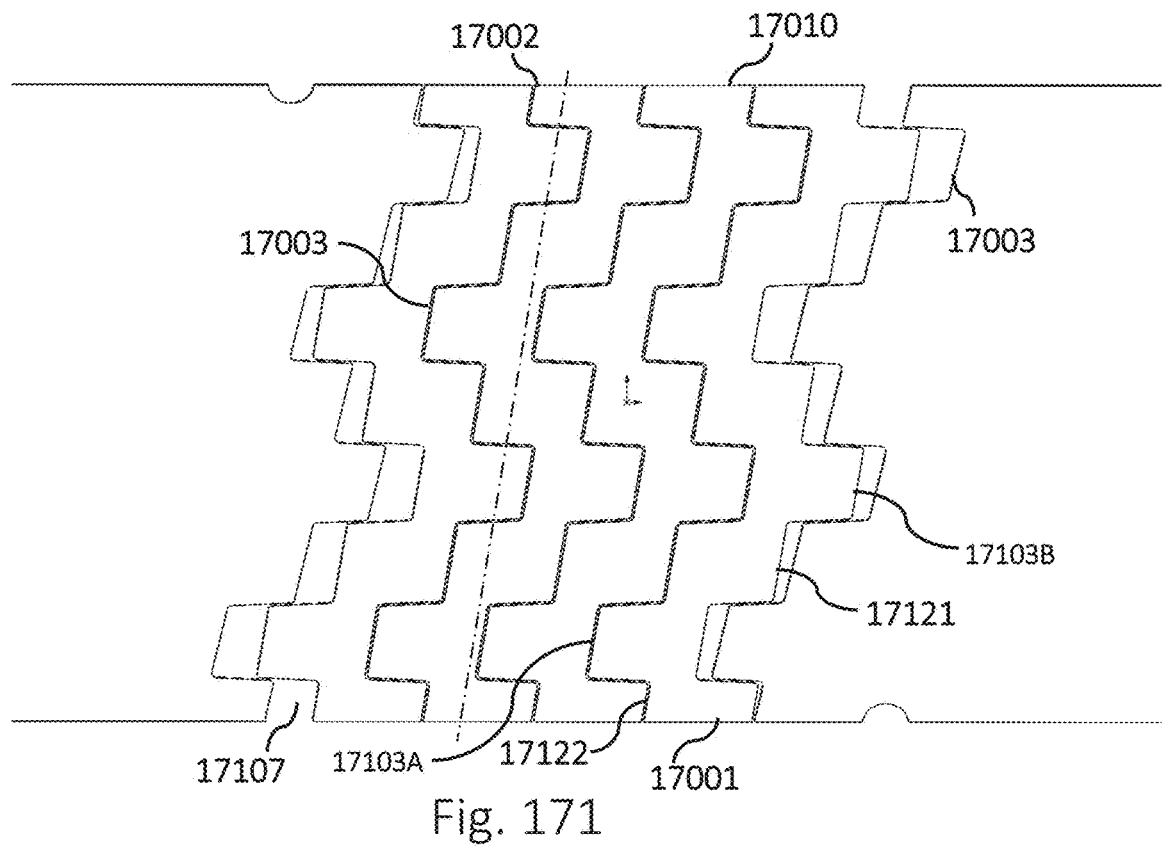

FIG. 171 is a partial side view of a portion of a cut slot pattern of a bone fixation device with a non-threaded expandable segment in a non-expanded state, in accordance with an aspect of the present invention.

Figure 172:
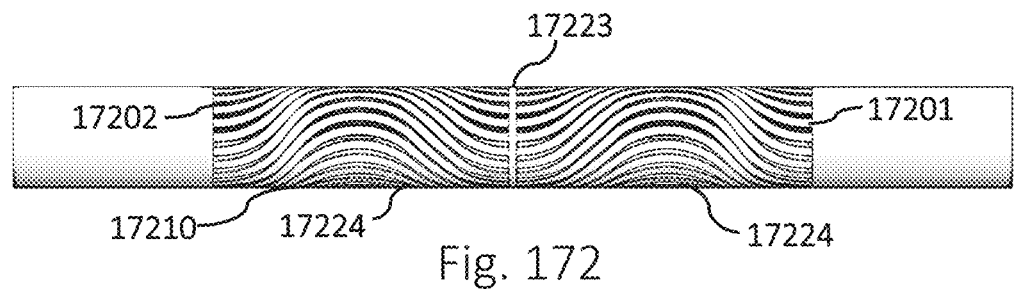

FIG. 172 is a partial side view of a bone fixation device with a non-threaded axial sinusoidal expandable segment in a non-expanded state, in accordance with an aspect of the present invention.

Figure 173:
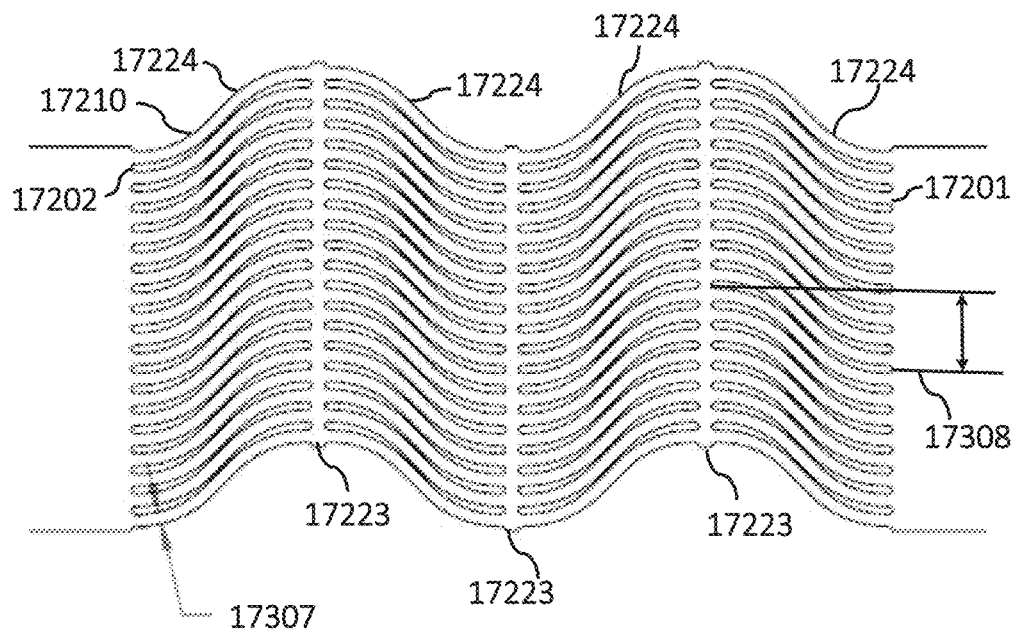

FIG. 173 is a partial side view of a bone fixation device with a non-threaded axial sinusoidal expandable segment in an expanded state, in accordance with an aspect of the present invention.

Figure 174:
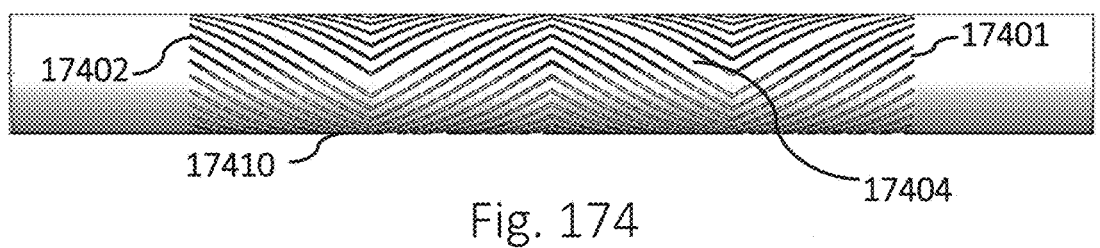

FIG. 174 is a partial side view of a bone fixation device with a non-threaded axial angled expandable segment in a non-expanded state, in accordance with an aspect of the present invention.

Figure 175:
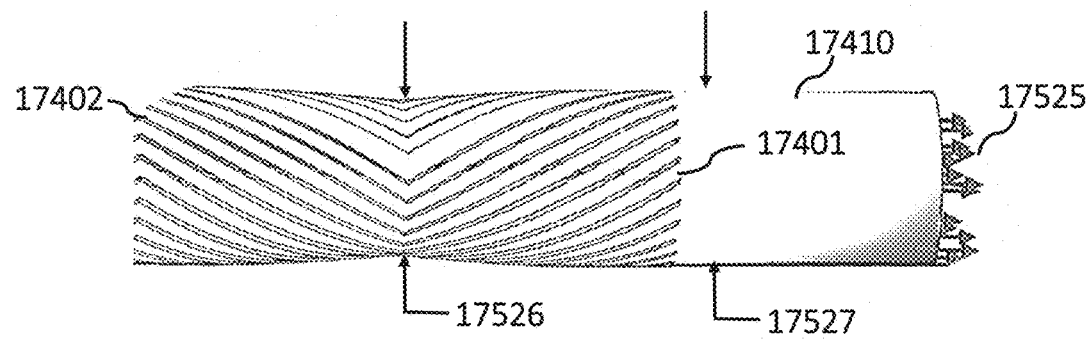

FIG. 175 is a partial side view of a bone fixation device with a non-threaded axial angled expandable segment in an expanded state, in accordance with an aspect of the present invention.

Figure 176:
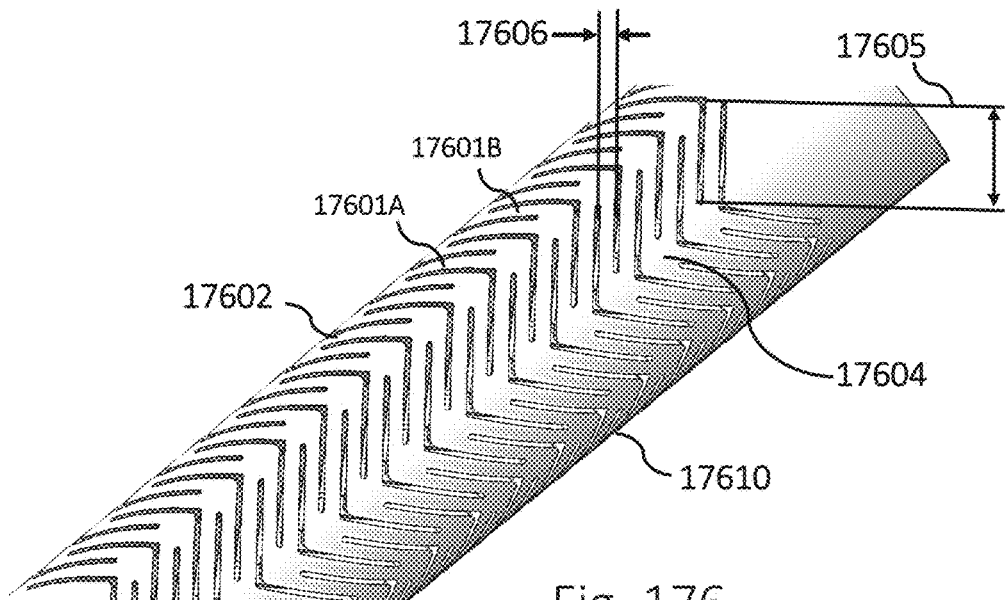

FIG. 176 is a partial side view of a bone fixation device with a non-threaded expandable segment in a non-expanded state, in accordance with an aspect of the present invention.

Figure 177:
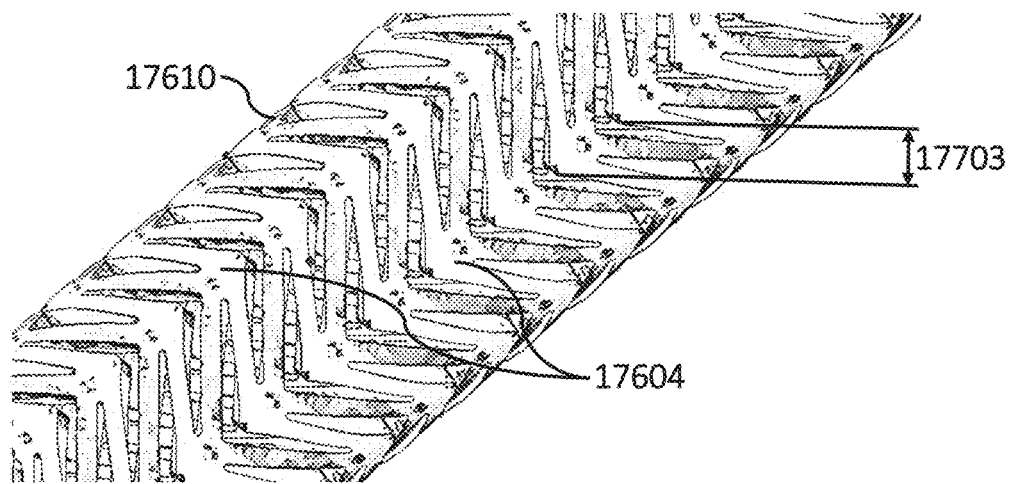

FIG. 177 is a partial enlarged detail side view of a bone fixation device with a non-threaded expandable segment in an expanded state, in accordance with an aspect of the present invention.

Figure 178:
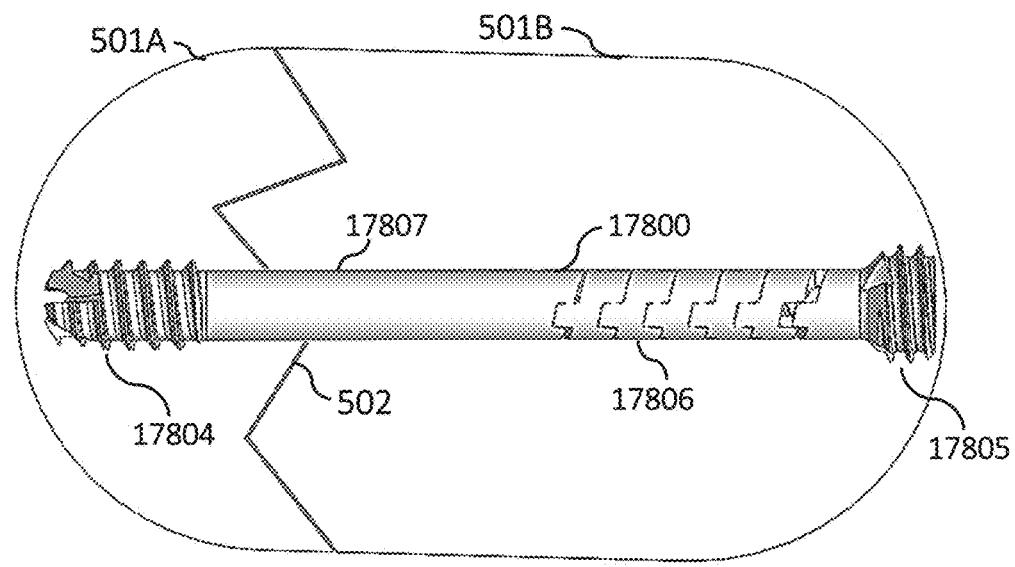

FIG. 178 is a side view of a bone fixation device inserted into two reduced bone segments in a non-expanded state, in accordance with an aspect of the present invention.

Figure 179:
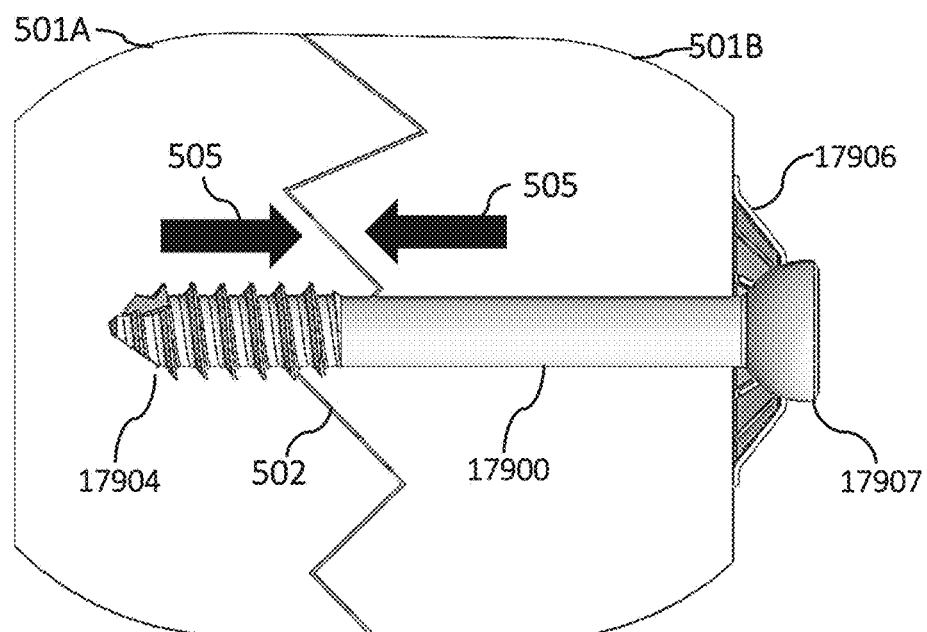

FIG. 179 is a side view of a bone fixation device inserted into two reduced bone segments, in accordance with an aspect of the present invention.

Figure 180:
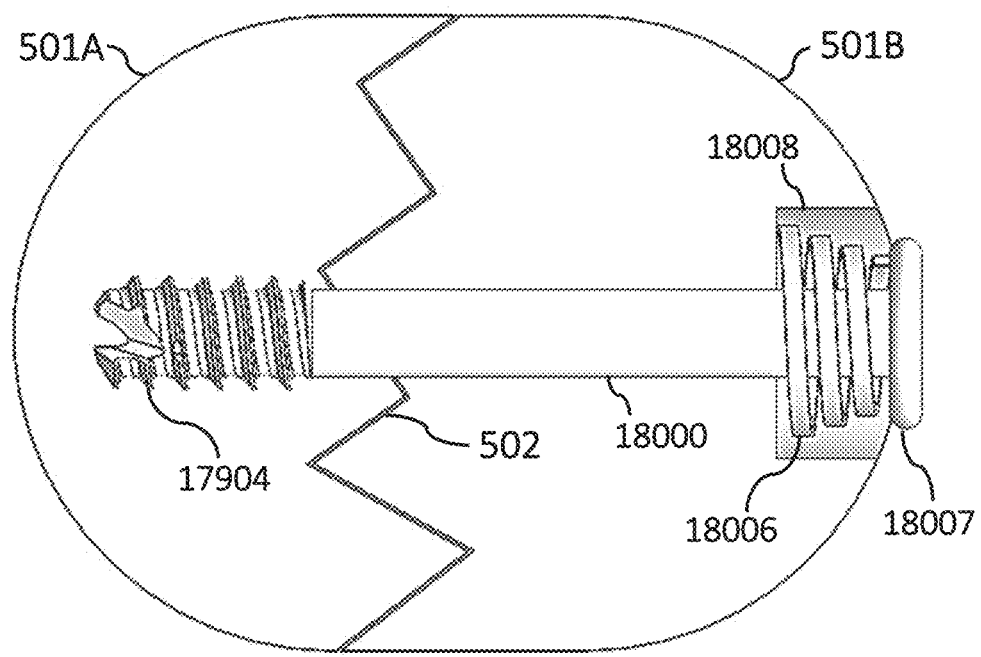

FIG. 180 is a side view of a bone fixation device inserted into two reduced bone segments in an expanded state, in accordance with an aspect of the present invention.

Figure 181:
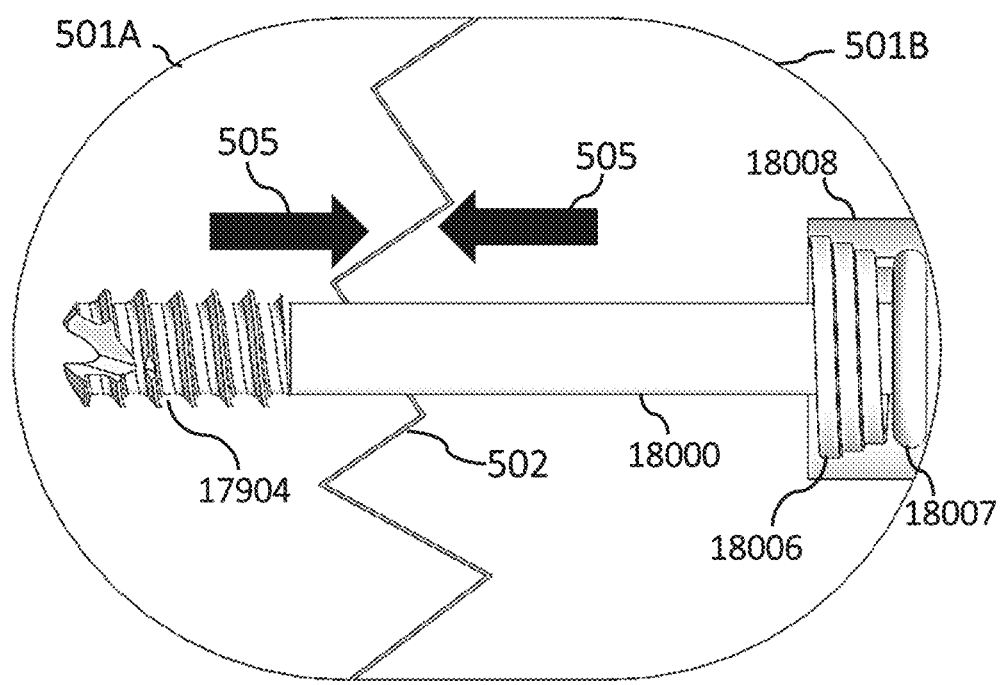

FIG. 181 is a side view of a bone fixation device inserted into two reduced bone segments in a non-expanded state, in accordance with an aspect of the present invention.

Figure 182:
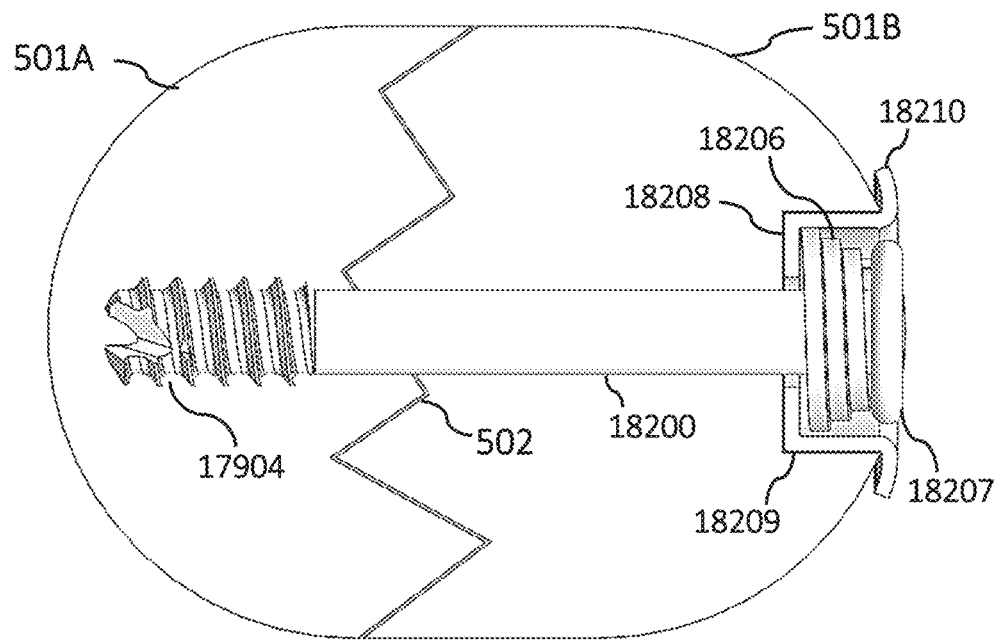

FIG. 182 is a side view of a bone fixation device inserted into two reduced bone segments in a non-expanded state, in accordance with an aspect of the present invention.

Figure 183:
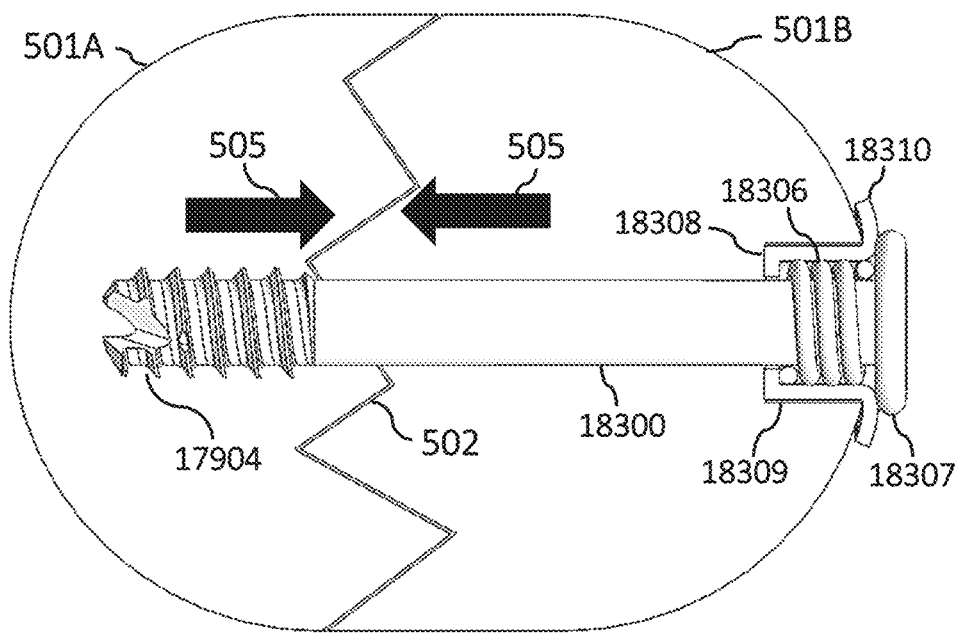

FIG. 183 is a side view of a bone fixation device inserted into two reduced bone segments in a non-expanded state, in accordance with an aspect of the present invention.

Figure 184:
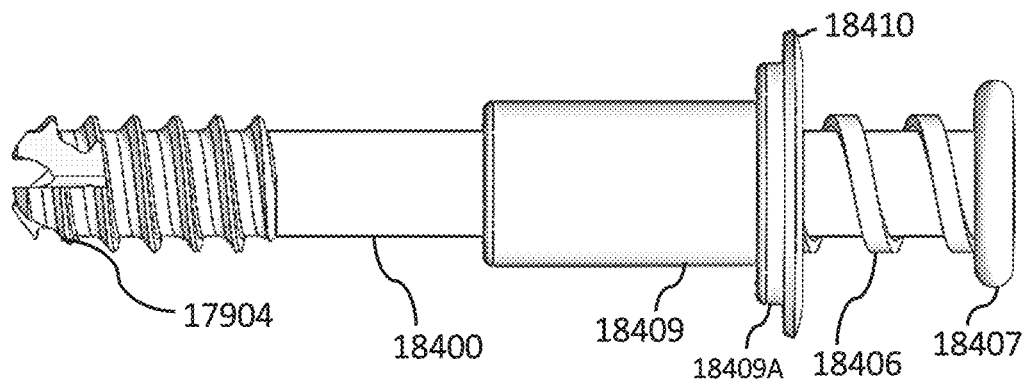

FIG. 184 is a side view of a bone fixation device in an expanded state, in accordance with an aspect of the present invention.

Figure 185:
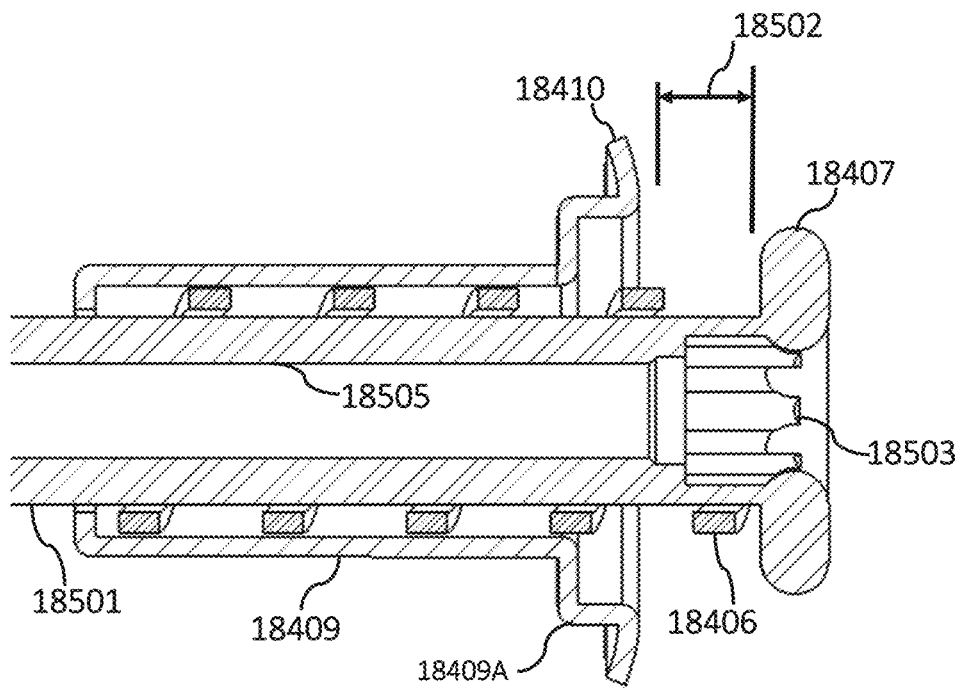

FIG. 185 is a partial cross section side view of a bone fixation device in an expanded state, in accordance with an aspect of the present invention.

Figure 186:
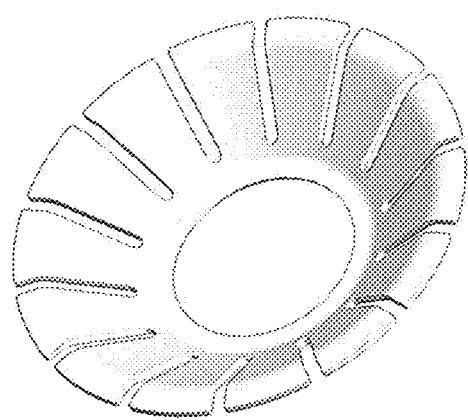

FIG. 186 is an isometric view of a bone fixation spring element device, in accordance with an aspect of the present invention.

Figure 187:
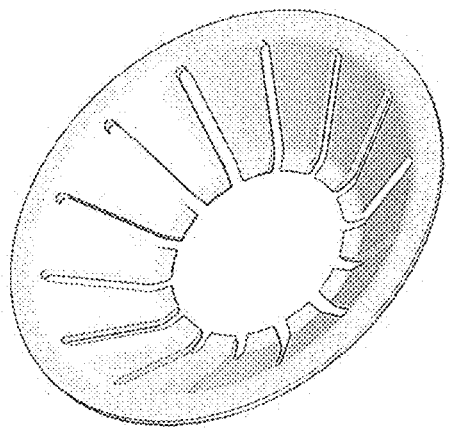

FIG. 187 is an isometric view of a bone fixation spring element device, in accordance with an aspect of the present invention.

Figure 188:
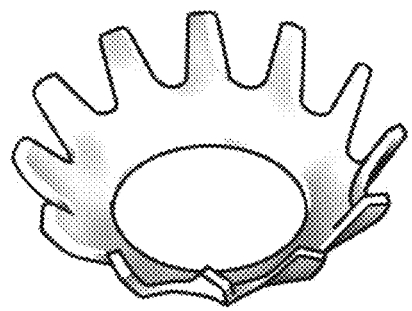

FIG. 188 is an isometric view of a bone fixation spring element device, in accordance with an aspect of the present invention.

Figure 189:
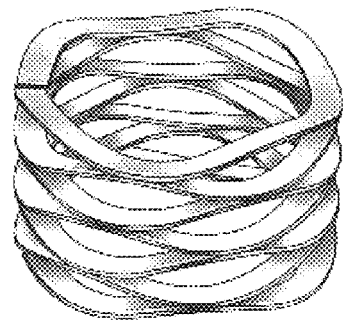

FIG. 189 is an isometric view of a bone fixation spring element device, in accordance with an aspect of the present invention.

Figure 190:
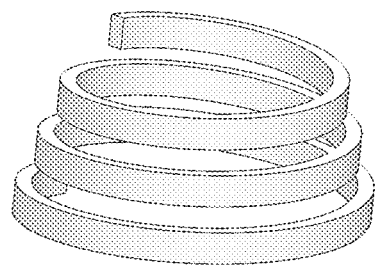

FIG. 190 is an isometric view of a bone fixation spring element device, in accordance with an aspect of the present invention.

Figure 191:
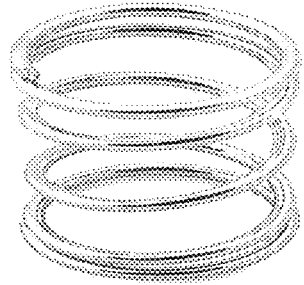

FIG. 191 is an isometric view of a bone fixation spring element device, in accordance with an aspect of the present invention.

Figure 192:
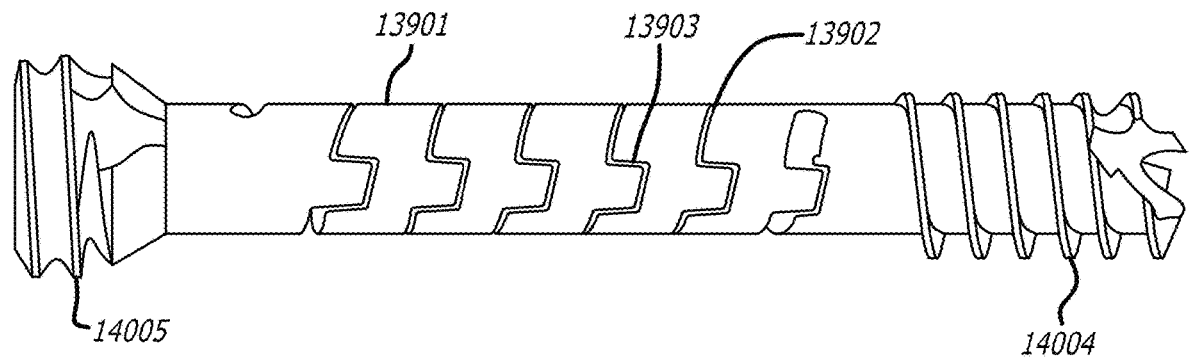

FIG. 192 is a side view of a bone fixation device reduced to practice with a non-threaded helical expandable segment with torsional engagement features in a non-expanded state, in accordance with an aspect of the present invention.

Figure 193:
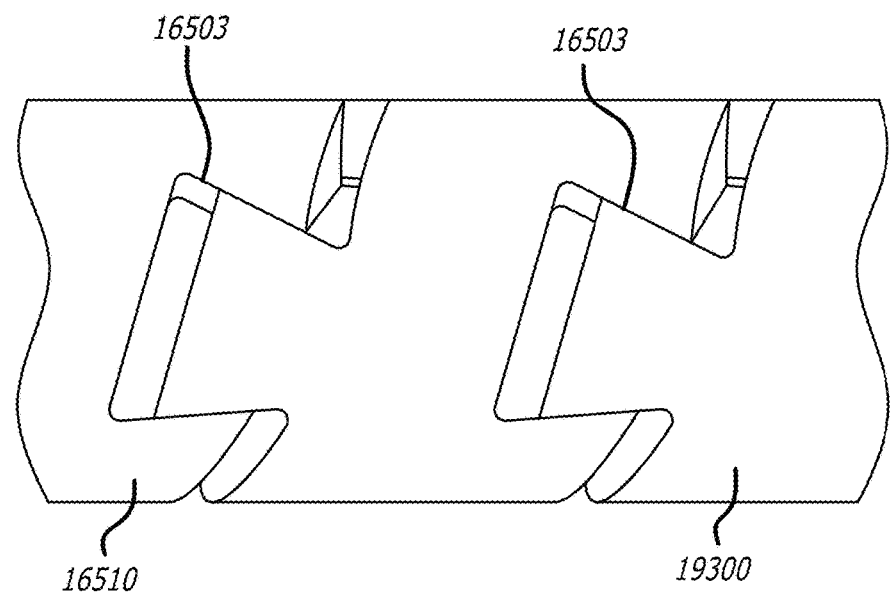

FIG. 193 is a partial side view of a bone fixation device reduced to practice with a non-threaded helical expandable segment with torsional engagement features in a non-expanded state, in accordance with an aspect of the present invention.

Figure 194:
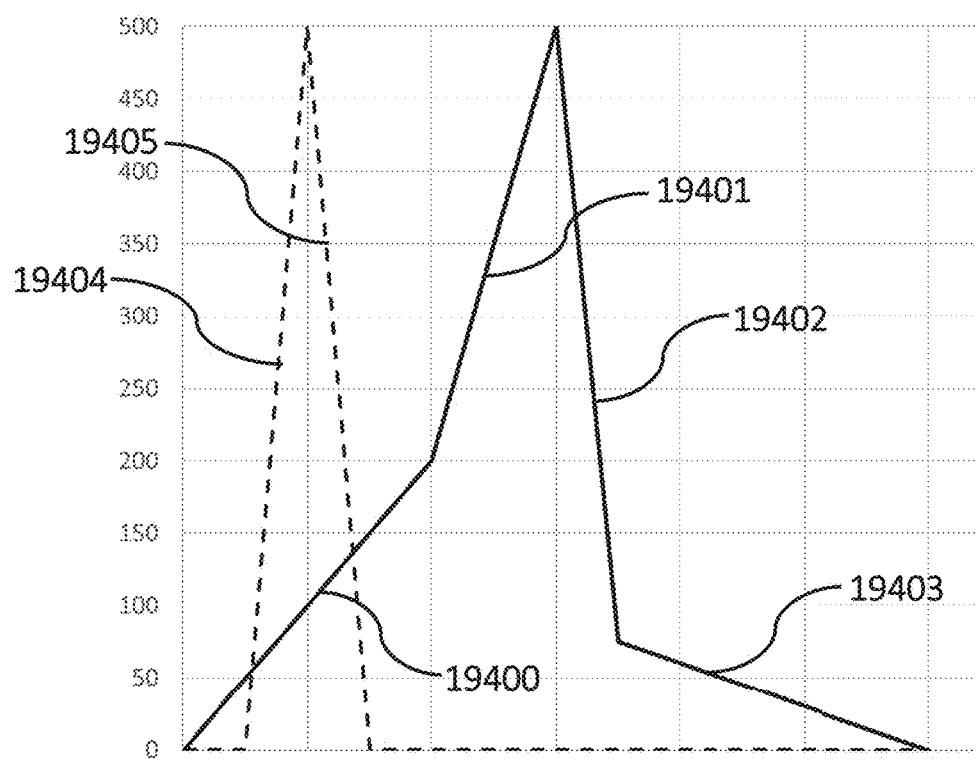

FIG. 194 is a graph with data from a device of the present invention that was reduced to practice of the compressive force unloaded over distance relative to a standard screw.

Figure 195:
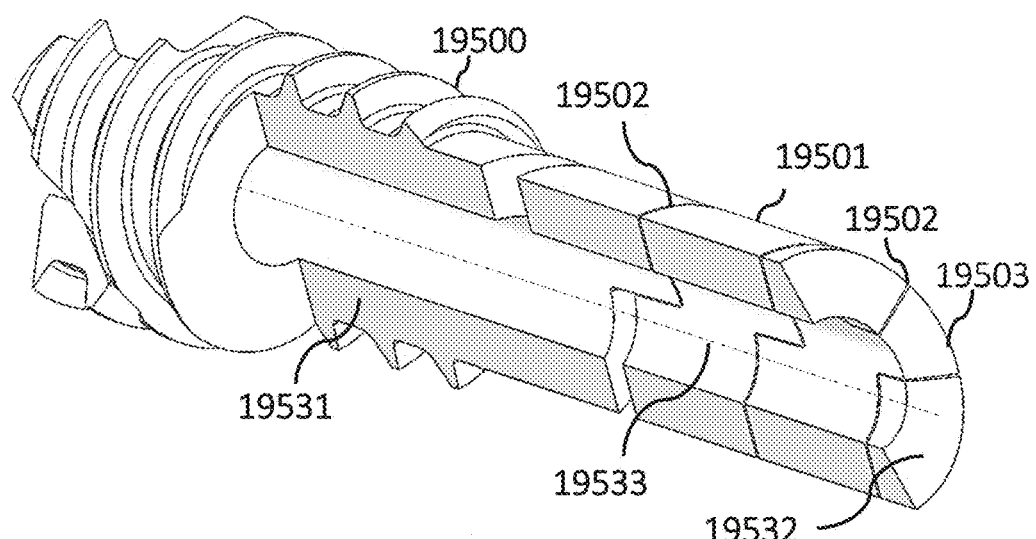

FIG. 195 is a partial perspective cross section view of a bone fixation device assembly with a threaded distal segment and a non-threaded expandable segment in a non-expanded state, in accordance with an aspect of the present invention.

Figure 196:
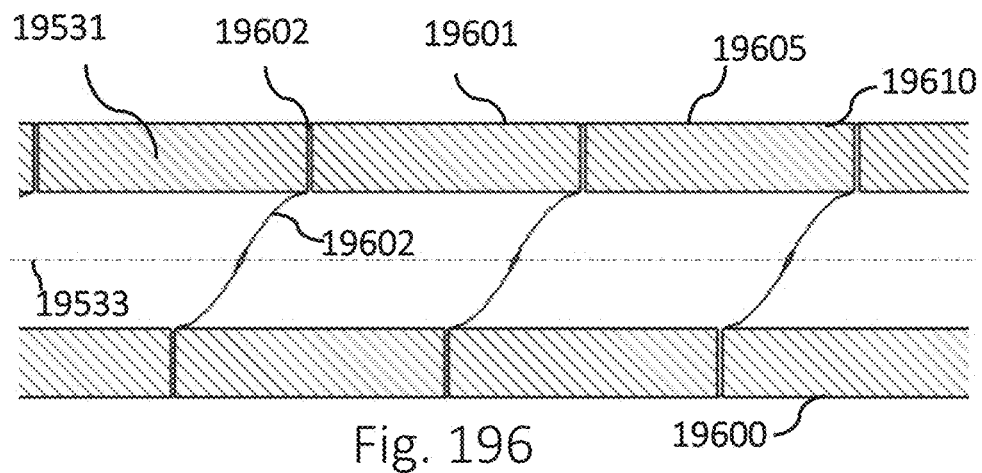

FIG. 196 is a partial side cross section view of a bone fixation device with a non-threaded helical expandable segment in a non-expanded state, in accordance with an aspect of the present invention.

Figure 197:
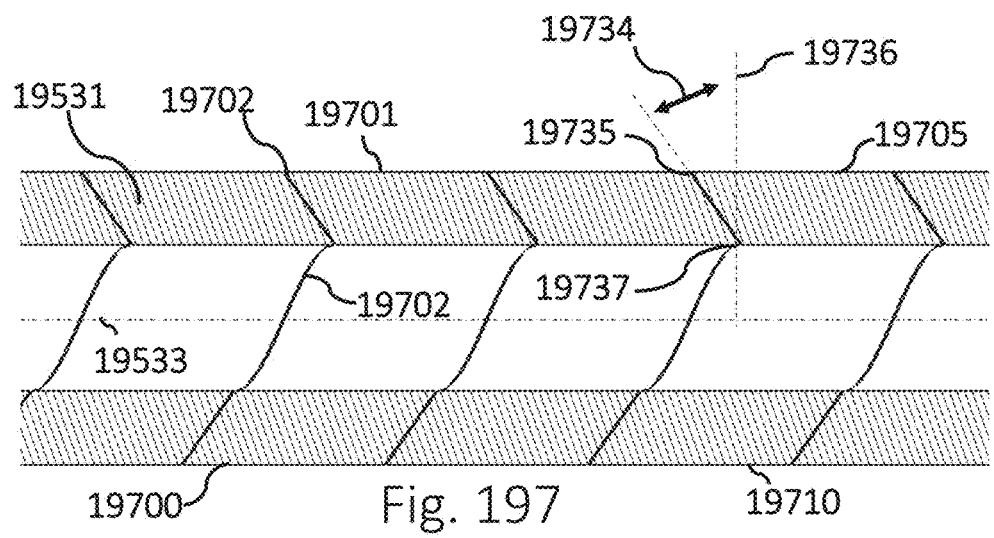

FIG. 197 is a partial side cross section view of a bone fixation device with a non-threaded helical expandable segment in a non-expanded state, in accordance with an aspect of the present invention.

Figure 198:
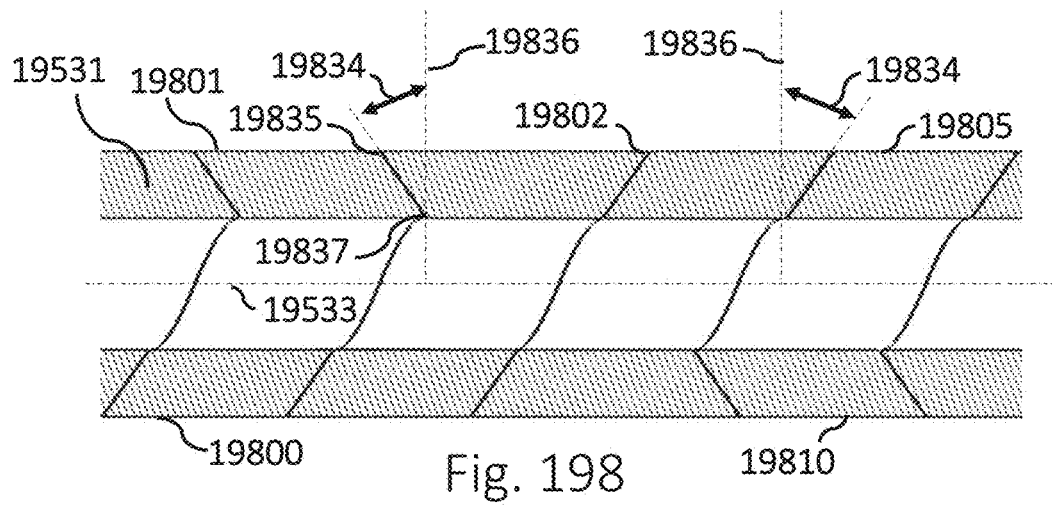

FIG. 198 is a partial side cross section view of a bone fixation device with a non-threaded helical expandable segment in a non-expanded state, in accordance with an aspect of the present invention.

Figure 199:
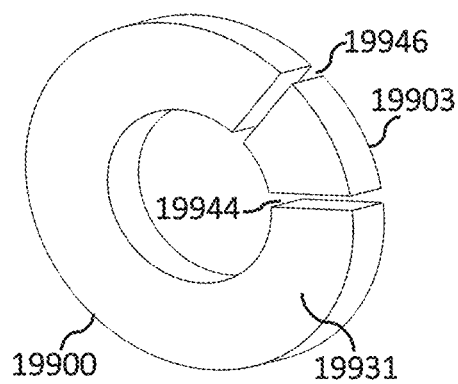

FIG. 199 is a partial cross section view of a bone fixation device with a non-threaded expandable segment in a non-expanded state, in accordance with an aspect of the present invention.

Figure 200:
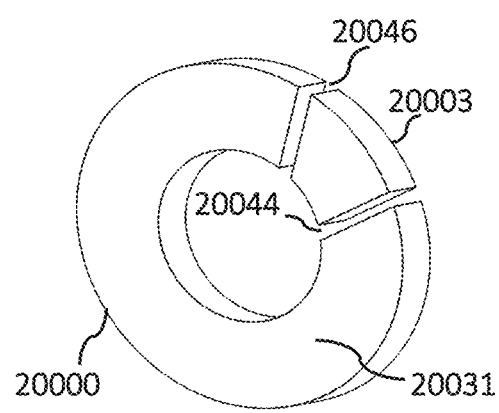

FIG. 200 is a partial cross section view of a bone fixation device with a non-threaded expandable segment in a non-expanded state, in accordance with an aspect of the present invention.

Figure 201:
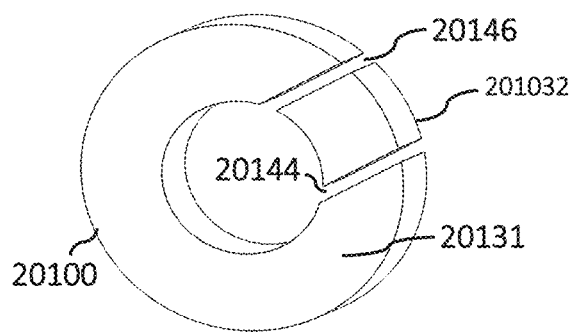

FIG. 201 is a partial cross section view of a bone fixation device with a non-threaded expandable segment in a non-expanded state, in accordance with an aspect of the present invention.

Figure 202:
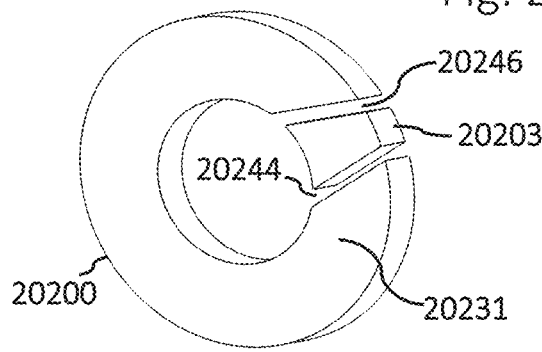

FIG. 202 is a partial cross section view of a bone fixation device with a non-threaded expandable segment in a non-expanded state, in accordance with an aspect of the present invention.

Figure 203:
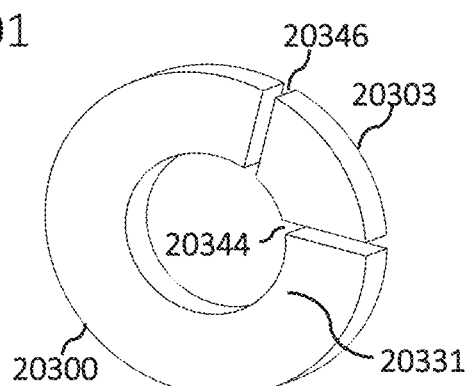

FIG. 203 is a partial cross section view of a bone fixation device with a non-threaded expandable segment in a non-expanded state, in accordance with an aspect of the present invention.

Figure 204:
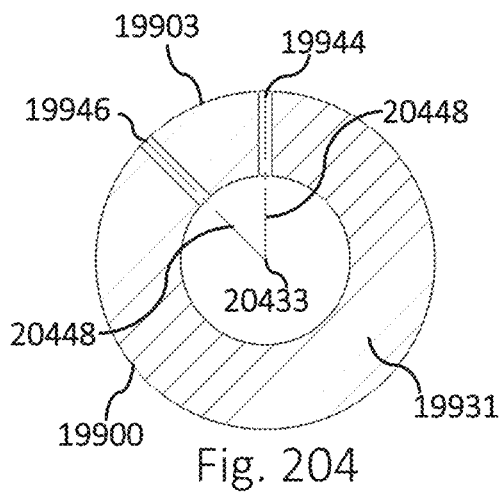

FIG. 204 is a cross section view of a bone fixation device with a non-threaded expandable segment in a non-expanded state, in accordance with an aspect of the present invention.

Figure 205:
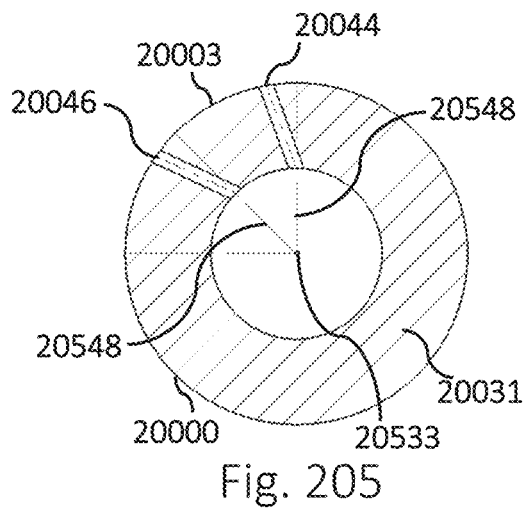

FIG. 205 is a cross section view of a bone fixation device with a non-threaded expandable segment in a non-expanded state, in accordance with an aspect of the present invention.

Figure 206:
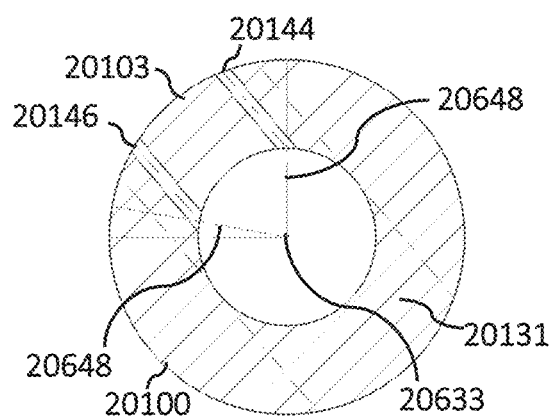

FIG. 206 is a cross section view of a bone fixation device with a non-threaded expandable segment in a non-expanded state, in accordance with an aspect of the present invention.

Figure 207:
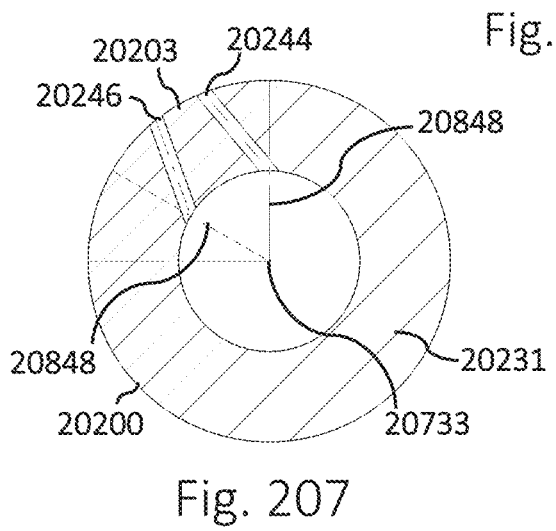

FIG. 207 is a cross section view of a bone fixation device with a non-threaded expandable segment in a non-expanded state, in accordance with an aspect of the present invention.

Figure 208:
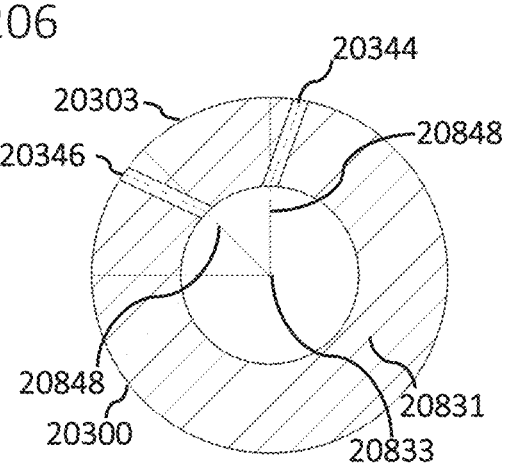

FIG. 208 is a cross section view of a bone fixation device with a non-threaded expandable segment in a non-expanded state, in accordance with an aspect of the present invention.

Figure 209:
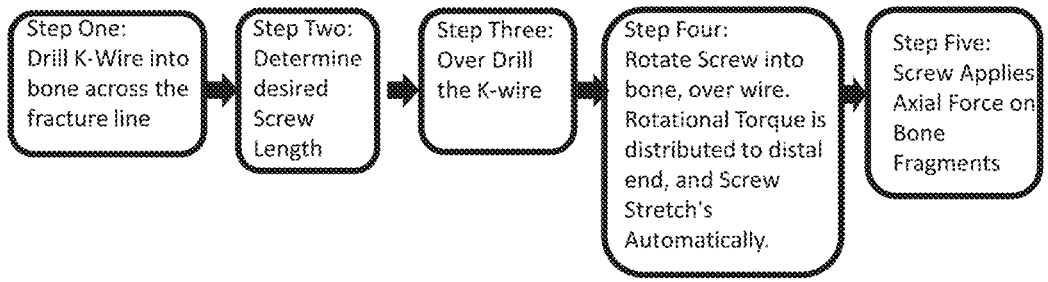

FIG. 209 is a flow chart showing one embodiment of a method of clinical application of a bone fixation device according to the present invention.

Figure 210:
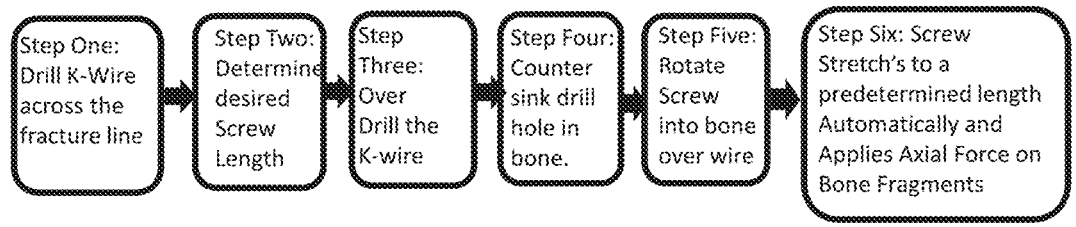

FIG. 210 is a flow chart showing one embodiment of a method of clinical application of a bone fixation device according to the present invention.

Figure 211:
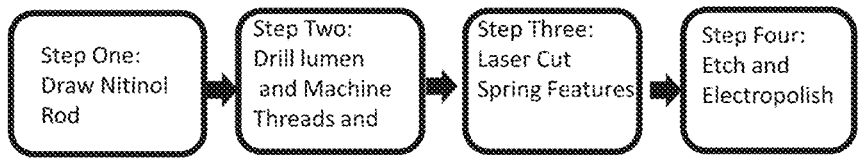

FIG. 211 is a flow chart showing one embodiment of a method of clinical application of a bone fixation device according to the present invention.

DESCRIPTION OF EMBODIMENTS

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

The present specification describes embodiments of apparatus and methods providing an actively compressing system that compress and secures bone segments. In one embodiment of the present invention, a structure of an orthopedic bone system is pre-loaded prior to insertion or effectively loaded during insertion into a desired orthopedic site to post-operatively provide active compression across a facture, or is post operatively loaded, after the device has been implanted. In certain embodiments, the actively compressing system includes an elastic, expandable portion. Further, a distal portion and a proximal portion are coupled to one another by the elastic, expandable segment that is configured to be tensioned and provide active compression between the distal and proximal portions.

In certain embodiments, a surgical procedure is provided that employs potentially fewer steps than current active compression screws, with a possible length change of at least 0-6 millimeters (mm) and an ability to provide 0-200 newton (N) of axial force, such axial force may, or may not, be adjustable compression over time.

Moreover, embodiment herein described provide a unitary body construction as well as other embodiments, potentially manufactured from common manufacturing techniques, possibly resulting in a lower cost of goods than current active compression platforms, and the potential ability to scale the design down to at least a 2.0 mm screw.

This application references U.S. Pat. No. 8,048,134 B2 filed Apr. 6, 2007, and International Application No. PCT/US2015/063472 Filled Dec. 2, 2015 which are incorporated herein by reference in their entirety.

As used herein, the terms set forth below have the following, associated definitions as known to those of skill in the art. "Pitch" is distance from one point on a screw thread to a corresponding point on the next thread, measured parallel to a longitudinal axis of the screw. "Pitch diameter"

on a straight screw thread, a diameter of an imaginary cylinder the surface of which passes through the thread at such a point as to make a width of the thread and a width of the space between threads equal. "Pitch diameter" on a tapered screw thread, a diameter, at a given distance from a reference plane perpendicular to an axis of an imaginary cone, the surface of which would pass through the threads at such point as to make equal the width of the threads and the width of the spaces cut by the surface of the cone.

"Lead" is a distance a screw thread advances on one rotational turn, measured parallel to the axis. On a single-thread screw the lead and the pitch are identical; on a double-thread screw the lead is twice the pitch; on a triple-thread screw the lead is three times the pitch. "Major diameter" is a largest diameter of an external or internal thread. "Minor diameter" is a smallest diameter of a thread. "Root" is a surface of the thread corresponding to the minor diameter of an external thread and the major diameter of an internal thread. Also defined as the bottom surface joining the flanks of two adjacent threads. The ends of the inventive joining features or screws can have any such features to help facilitate clinical therapy such as self-cutting, self-tapping threads, anti-rotation and/or anti back-out features, reverse cutting threads, profiles or features that aide in the locking of member into a plate, rod, nail, or other screw.

Generally stated, disclosed herein are bone fixation or joining devices that may include a first portion, a second portion, and at least one axial tension portion or feature. As used herein, the terms "bone fixation device," "bone fusion device," "medical device," "device," "joining member", and "implant" may be used interchangeable as they essentially describe the same device. As used herein, the terms "expanded," "loaded," "stressed," "stretched," and "lengthen" may be used interchangeable as they essentially describe the same feature or state. As used herein, the terms "relaxed," "unloaded," "reduced," "collapsed," and "shortened" may be used interchangeable as they essentially describe the same feature or state. Also, the terms "active", "actively", "dynamic", "dynamically", and "non-passive" can all be used interchangeably and are intended to have the same meaning of applying continuous force when loaded, and these terms may be used interchangeably.

Further, the corresponding insertion tool or tools may also be referred to as "tool" or "instrument" and these terms may be used interchangeably. In this detailed description and the following claims, the words proximal, distal, anterior, posterior, medial, lateral, superior and inferior are defined by their standard usage for indicating a particular part of a bone or implant according to the relative disposition of the natural bone or directional terms of reference. For example, "proximal" means the portion of an implant farthest from the insertion end, while "distal" indicates the portion of the implant nearest the insertion end. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure.

In the following description, certain specific details are set forth in order to provide a thorough understanding of various embodiments of the inventive active compression orthopedic screw system or device and method. However, one skilled in the relevant art will recognize that the present exemplary system and method may be practiced without one or more of these specific details, or with other methods, components, materials, etc. In other instances, well-known structures associated with orthopedic screw systems have not been shown or described in detail to avoid unnecessarily obscuring descriptions of the present exemplary embodiments.

As used in the present specification, and in the appended claims, the terms central member, deformable member, and expandable member shall be interpreted to include any number of members having a square, round, or oblong shaped cross-section, configured to store energy. Further, as used herein, the term "slideably coupled" shall be interpreted broadly as including any coupling configuration that allows for relative translation between two members, wherein the translation may be linear, non-linear, or rotational.

Unless the context requires otherwise, throughout the specification and claims which follow, the word "comprise" and variations thereof, such as, "comprises" and "comprising" are to be construed in an open, inclusive sense that is as "including, but not limited to." Reference in the specification to "one embodiment", "certain embodiments", or "an embodiment" means that a particular feature, structure, or characteristic described in connection with the embodiment is included in at least one embodiment. The appearance of the phrase "in one embodiment" in various places in the specification are not necessarily all referring to the same embodiment. Furthermore, the particular disclosed features, structures, or characteristics may be combined in any suitable manner in one or more embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The present active compression orthopedic joining member or screw system will be described herein, for ease of explanation only, in the context of a bone screw assembly configured to stabilize bones. The methods and structures disclosed herein are intended for application in any of a wide variety of bones and fractures and fusions, as will be apparent to those of skill in the art in view of the disclosure herein. For example, the bone fixation device of the present system and method is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art.

A wide variety of phalangeal and metatarsal osteotomies and fractures and fusions of the foot may also be stabilized using the bone fixation device of the present system and method. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may also be fixated and stabilized with the present exemplary system and method. Each of the foregoing may be treated in accordance with the present system and method, by advancing one of the active compression screw systems disclosed herein through a first bone component, across the fracture, and into the second bone component to fix the fracture.

One such embodiment of apparatus and methods for providing actively compressing systems that compress and secure bone segments has a unitary contiguous structure and generates the compressive force by driving a screw like body into the bone segments to be fused. According to one embodiment, an orthopedic bone fixation device for actively compressing a plurality of bone segments includes a first segment or portion positioned at a distal end of the device, a second segment or portion positioned at a proximal end of the device, and an elastic segment or portion having a first and a second end. The first end of the elastic segment is coupled to the first segment and said second end of the elastic segment is coupled to the second member, the elastic member or portion, in an expanded state, configured to exert a force drawing the first and second members or portions together. The elastic member and distal and proximal segments or portions being constructed as one unitary contiguous member or structure.

An implant for insertion in and stabilization of a bone material having a first and a second region is disclosed. The implant comprises a shaft including a longitudinal axis, a proximal portion, an expandable center section or portion and a distal portion. The proximal and distal portions may have proximal and distal threads formed thereon respectively. The proximal and distal threads each have minor and major diameters. The minor diameter of the proximal thread may or may not be substantially equal to the major diameter of the distal thread. The shaft of the implant may have an unthreaded expandable medial portion disposed between the proximal and distal portions that separates the proximal and distal portions and is changeable in length. When the screw implant is inserted by rotation into the bone material, the proximal and distal portions threadably engage the first and second regions, respectively, to provide compression therebetween, this force may or may not then elongate the expandable medial portion.

Advancement of the state of bone fusion and bone fixation devices and implants and the surgical management relating to the clinical presentation of damaged or fractured bones within the body is believed desirable. Active compression is useful to combat angular misalignment in addition to bone absorption. Certain embodiments of the present invention provide bone fixation devices or bone fusion devices used to treat patients suffering from either diseased or damaged bones include a member that has an expandable compression feature. The present invention provides in one aspect, a bone fixation device including a member and at least one axially and/or radially deformable feature or segment positioned between the distal end and the proximal end.

According to one embodiment, the implant of the present invention is a compression implant and is a bone screw. When the bone screw is threaded into two regions of the bone, a distal threaded portion and a proximal threaded portion individually threadably engage each of the two regions of the bone and stabilize the bone and potentially provide axial force to elongate the center section.

In certain embodiments, the bone screw apparatus is cannulated throughout its length to allow utilization with a suitable guide wire and cannulated tools for drilling and driving. In another embodiment, in order to compress two spaced-apart materials such as bone fragments, holes can be pre-drilled for both the primary screw and the secondary screw, and a driver can be used to screw into place the screw across the fracture line, with or without the center section elongated. Once the screw segment is in place, a separate driver can be used to turn or rotate the distal screw member further into place and to cause compression of the bone fragments and lengthen the central expandable segment.

The present inventive system and method provides an orthopedic screw system configured to provide a post-operative "active" compressive force on the joined bone segments for fusion. As used herein, the term "active" shall be interpreted as referring to a system configured to provide an active compressive force; rather than a "passive" fastener which would allow a compressive force but not itself provide a dynamic compressive force. The elongation of the inventive apparatus provides a continuous axial compression force onto the bone segments it is engaged into until such time that the elongation is reduced to its resting or non-expanded state. The bone tissue and apparatus will remain in a dynamic interaction of force applied by the apparatus until such time the bone yields or remodels to a zero or reduced stress relationship between the tissue and the apparatus.

In certain embodiments, under sufficient axial load, the device of the present invention stretches or is expandable in length. Therefore, the device can maintain an amount of compressive force at the fusion surface, even with subsidence or collapse of bone at the fusion surface over time. Dynamization or axial compression of transverse osteotomies has been shown to increase both the torsional stability and maximal torque of the fracture site when compared to locked rigid control.

The dynamic nature of the active compression design of the present invention allows for controlled axial compression at the fusion surface which potentially results in a decrease in stress shielding. The solid and the threaded screw and nail designs of know devices, by comparison, are statically locked and thus result in a greater degree of stress shielding. This decrease in stress shielding of the present invention is advantageous for improved bone healing and fusion.

The elongated compression segment embodiment of the present invention represents a fixation device that can provide active compression over a period of time to a fixation construct. The forces applied to the bone may have the ability to adapt to changes that may occur with bone gapping, movement, and/or, resorption. The elongated compression segment of the device of the present invention creates a dynamic or residual compressive force across the fusion interface. This dynamic force can adjust over time to accommodate for any potential gapping as a result of the surface vagaries, osteopenic bone, surgeon application, premature weight bearing or the presence of bone grafting material.

According to another embodiment, an active compression screw system according to the present invention may also be used to attach tissue or structure to the bone, such as in ligament reattachment and other soft tissue attachment procedures. The fixation device may also be used to attach sutures to the bone, such as in any of a variety of tissue suspension procedures. For example, according to one embodiment, soft tissue such as capsule, tendon, or ligament may be affixed to bone by employing the inventive device.

The inventive device and methods can also be used to attach a synthetic material such as mesh, to bone or allograft material, such as tensor fascia lata, to bone. In the process of doing so, retention of the material to bone may be accomplished with an enlarged head portion of the active compression orthopedic screw system shown in the figures to accept a suture or other material for facilitation of this attachment. The ability of the present active compression orthopedic screw may prevent loosening of the screw, thereby reducing the likelihood that the attached tissue or structure will be prematurely released from the bone. The ability of the screw to change in length may further shield the bone from the stress of the tension applied and therefore stress shield the attachment mechanism to the bone in this example the threads, yielding a better of stronger or more consistent, long term retention of the bone thread interface.

The combined features of the screw implant of the invention may result in improved compression performance in that the screw will generate bone or tissue compression more efficiently. Such screw implant can be used in several types of surgical procedures, such as, osteotomies where two separated pieces of the same bone are involved, arthrodesis connecting two or more bones together, and graft fixation where bone and other materials are anchored in place by the screws According to another embodiment in a stretched, expanded, loaded, or stressed state the length of the expandable or deformable member is increased by an axial force. The axial force results in the deflection of struts formed in the expandable or deformable member or portion to obtain an increased separation distance between the struts which then yields an overall increase in member length from the original, non-expanded or non-stretched state. The distance or amount of axial translation can vary from small displacements to large displacements, depending on multiple variables and desired performance characteristics.

These performance characteristic variables include, but are not limited to, expandable or deformable member or portion strut width, strut length, radius of end cut slots, width of cut slots, outer diameter of expandable or deformable member, inner diameter of expandable or deformable member, number of slots along the radius of the expandable or deformable member, shape of cut slots, angle of cut slots, number of slots along the axial length of the expandable or deformable member, number of expandable or deformable members, layers of expandable or deformable members, configuration of multiple members, the pattern of slots along the length of the expandable or deformable member or portion, the location of the beginning and ending slots along the length, overall length of the expandable or deformable member, the material, the surface treatment of the material forming the expandable or deformable portion or member, the surface finish, the machined profile of the expandable or deformable member, and the ratio and or relationship of these variables relative to each other. The terms perforation and cut slot and the plural forms thereof, are herein used interchangeably.

The desired characteristics to control within the inventive embodiment may include but are not limited to, amount of axial force applied to recover or achieve the length, the amount of axial force applied to increase the axial length or stretch or load the member, the amount of length change variable along the axial position of the member, the amount of force change as a ratio to change in length, the radial bending stiffness of the entire member along the axis, the torsional stiffness, the separation of individual strut members, the elastic limit of the material, the engagement in bone tissue, the insertion force of the member into bone, the removability of the member, the migration of the member in/through bone tissue, the resistance to migration of the member in bone tissue, the biocompatibility of the member, the procedural ease of use of the member, the ease of manufacturing of the member, the cost of the member, the number of elements employed to construct the member, and the manufacturing processes employed to construct the member.

There are many variables involved in the perforations or cut features that may affect the axial tension force, bending stiffness, and the torsional rigidity, of the construct. The perforations or cut features of the expandable or deformable portion of the device of the present invention can take on an infinite number of permutations of cell designs such as those already described and those including, but are not limited to; diamond shapes, wave forms, non-uniform shapes, sinusoidal shapes, slots, ovals, or round circles. Illustrative examples of some of these possible embodiments can be seen at least in FIGS. 88-112. These perforations or cut slot patterns can be repeating along the length or vary along the length, multiple shapes and sizes could be combined in the same construct, either along the length or around the circumference. The struts may vary in dimension along a length. The cross-section of the members can also take on an infinite number of permutations of cell designs such as those already demonstrated by prior art and known to those familiar to the art, these include but are not limited to; round, square, oval, etc., the features and dimensions can vary in wall thickness and cross-section along a length of the inventive device.

In certain embodiments, increasing the strut length increases the amount of deformation for a given loading condition. This is advantageous in that the increased change in length accommodate a larger change in bone tissue over time. The amount of force that is then exerted as compression could be reduced which may be a desired trait depending on the desired loading profile. The radius of end cut slots can affect the strain of the struts and increase or decrease the amount of recoverable deformation. The width of perforations or cut slots may facilitate more or less flexibility of the construct. The manufacturing process can also be affected by this width making different process possible with wider slots such as machine milling, or laser cutting with narrow slots.

The outer diameter of the expandable or deformable portion or member may affect the overall stiffness of the construct and axial tension force by increasing or decreasing the amount of structural material involved and changing the bending moment. The inner diameter of the expandable or deformable portion or member may affect the overall stiffness of the construct and axial tension force by increasing or decreasing the amount of structural material involved, it may also affect the manufacturing process used to create the construct. The inner diameter may also affect the assembly members or other features used to facilitate the method of application of the inventive embodiments.

The number of slots along the radius of the member also affect the axial tension force generated by the members, and/or the flexural stiffness of the construct. Employing more slots of shorter length or less slots of longer length or slots not evenly distributed about the radius may all facilitate the desired behavior of the construct. The shape of perforations or cut slots can affect the axial tension force, bending stiffness, and the torsional rigidity, of the construct by impacting the local deformation of the construct under load. The angle of cut slots relative to the axis of the member and also relative to the radius of the construct can facilitate different bending behaviors. The number of slots along the axial length of the member, the density of the slots, the pattern of slots, the location of the slots along the length, and the overall length of area covered by the slots can also impact the desired behavior of the inventive embodiments. The higher number of slots along the length, the greater change in length for a given design. The more slots around the circumference, the less length change for a given design and length. The number of slots formed around the circumference, in theory, defines the number of spring elements in parallel of the construct. The greater the number or cells around the circumference the higher the spring constant for each spring due to the short strut length available, assuming a constant strut width. The more cells along the length effectively reduce the spring constant allowing the structure increased stretched length.

Employing multiple the expandable or deformable portion or members facilitates achieving the desired design intent. For example, by employing nested or layered the expandable or deformable portion or members a flexible and a non-flexible layer may be employed concentrically together to yield an axial flexible and bending rigid configuration, or vise versa. The inventive embodiments employ of a unitary member or could be constructed from several different members and joined together in rigid form or in a manner that would leave degrees of freedom between the multiple bodies. The length of these individual members can impact the performance by either increasing or decreasing the desired behavior. The location of the member being axial, layered externally or layered internally can also be used to control the behavior of the inventive embodiments.

Material can also be used as a variable; elastic, stiff, absorbable, biocompatible, and any other material known to those in the art can be used individually or in combination with others to yield a desired feature set. The surface treatment of the material can also have an impact on the behavior of the structures. The ratio and or relationship of these variables relative to each other can be varied in spirit of the inventive disclosure by those familiar with the art and all combinations are considered herein encompassed in this disclosure.

The inventive embodiments further detailed herein and the variables described and shown in any one figure can be used with all the other examples either illustrated, captured in the text or known to those in the art.

Another embodiment is the ability for these axial tension members to increase and or decrease in radial diameter from the center axis. This feature could also yield additional clinical benefits by increasing tissue interface or procedural ease. The ability to adjust all of these variables to yield a desired axial or longitudinal tension over a given length that does not exceed the resistive force of the end retention features in the tissue for an extended period of time should help facilitate healing.

The present invention includes embodiments of apparatus and methods providing an actively compressing system that compresses and secures bone segments; with a unitary contiguous structure; by driving a screw like body into bone segments; that can deliver compressive force over 0.5 mm and in certain embodiments, more than 6 mm of bone absorption; that can deliver compressive axial force of 0-200N; that can deliver compressive axial force for more than 1 hours and potentially up to 48 hours or more after delivery into the bone; that can deliver a compressive axial force in different amounts over time; that can deliver a selected compressive axial force; that can deliver a compressive axial force in different amounts over time; and that can have a diameter of 2-20 mm.

The present invention includes embodiments of apparatuses and methods providing an actively compressing system that compresses and secures bone segments; with a unitary contiguous structure; by driving a screw like body into bone segments; that can deliver compressive force.

In certain embodiments, of the inventive method includes driving a screw like body into bone segments and then activating a compressive axial force.

In certain embodiments, of the inventive method includes driving a screw like body into bone segments and delivering a body into bone segments that has axial force generating members substantially the entire length of the body.

In certain embodiments, of the inventive method includes driving a screw like body into bone segments and delivering a body into bone segments that has axial force generating members in a defined region of the length of the body; with a unitary contiguous structure, delivered over a K-wire; or with a unitary contiguous structure that is solid; or with a structure that is cannulated; or by delivering a body into bone segments that has axial force generating members that utilizes perforations or cut features to achieve the axial tension force.

The apparatuses and methods of the present invention provide an actively compressing system that compresses and secures bone segments; with a unitary contiguous structure; by driving a screw-like body into bone segments. The screw-like body has axial force generating members that utilizes perforations or cut features to achieve the axial tension force and utilizes threaded regions of the body and the threaded regions' engagement with bone to preload the axial tension. Alternatively, the screw-like body has axial force generating members that utilizes perforations or cut features to achieve the axial tension force and utilizes a delivery mechanism to generate the axial preload. Alternatively, the screw-like body has axial force generating members that utilize perforations or cut features to achieve the axial tension force and uses an internal member to generate the axial preload.

The apparatuses and methods of the present invention provide an actively compressing system that compresses and secures bone segments with a unitary contiguous structure that has axial force generating members that utilizes perforations or cut features to achieve the axial tension force and uses resorbable material. Alternatively, axial force generating members utilize a structure that is made from shape memory alloy SMA or other material commonly used in the manufacture of implanted devices.

The apparatuses and methods of the present invention provide an actively compressing system that compresses and secures bone segments that has the ability to deform elastically along the central axis beyond that which a solid screw of any material could possibly elastically deform. This ability to deform allows for clinical applications that exceed current available options or solutions and for clinical application that could benefit from tissue fastening devices that provide axial mobile configurations.

The apparatuses and methods of the present invention provide screws designed to bend or transmit torque around a corner.

The apparatuses and methods of the present invention provide screws formed in a bent or curved or helical shape, and installed or delivered in a straight shape.

The apparatuses and methods of the present invention provide screws made out of PEEK or other materials.

The apparatuses and methods of the present invention provide screws processed in the elongated state, then formed back to the shortened state.

The apparatuses and methods of the present invention provide locking features on a screw head to work in conjunction with a plate, rod and/or staples.

The apparatuses and methods of the present invention provide screw design features, used with or without plates, rods and/or staples.

The apparatuses and methods of the present invention provide screws used in spine applications.

The apparatuses and methods of the present invention provide screws formed with an expanded center section, larger than distal and proximal threads.

The apparatuses and methods of the present invention provide solid screws, cannulated screws, headed screws.

The apparatuses and methods of the present invention provide passive thread features to prevent backing out, reverse cutting threads.

The apparatuses and methods of the present invention provide screws with a center portion larger than distal end, able to apply torque at the distal end; a driver inserted all the way past the proximal threads and center section into a socket at the distal end aiding in torsional rotation of the apparatus.

The apparatuses and methods of the present invention provide external or internal spring elements to increase and/or store and/or maintain a tensile force that, in turn, generates or provides a compressive force between two or more tissue segments.

The apparatuses and methods of the present invention provide hybrid screws; constructed of multiple materials such as but not limited to polymer plus metal, different alloys combined into the construction of the embodiments.

The apparatuses and methods of the present invention provide a fastener having no distinct enlarged proximal head and/or having a continuous thread diameter throughout the length of the screw in which the proximal and distal threads can be the same diameter.

Furthermore, the present invention provides methods of assembling the bone fixation device.

Additionally, the present invention provides methods of using the bone fixation device to compress segments of bone.

The apparatuses and methods of the present invention provide the ability to continuously apply a compressive force to bone segments over a distance or length in which the embodiment was initially stretched or lengthened. The mechanism providing this expansion and contraction or change in length comprises a continuous wrap member spanning the length of the expandable section. This wrap member comprises a single wrap encompassing the entire circumference. This wrap member comprises multiple wrap members spanning the length of the expandable section. The wrap member being similar in shape and function to a rectangular cross-section helical coil spring. The pitch of this wrap cut pattern having a direct relationship on the spring constant of the expanding section.

The apparatuses and methods of the present invention provide the ability to continuously apply a compressive force to bone segments over a distance or length in which the embodiment was initially stretched or lengthened. The mechanism providing this expansion and contraction or change in length comprises of a continuous wrap member or strut spanning the length of the expandable section. This wrap being integrated into any orthopedic screw design. These screws having standard heads, threaded heads, self-tapping and cutting thread profiles, cannulated screws, screws of any diameter, screws of any length, e.g. 2 mm diameter screws, 12 mm diameter screws, 20 mm length screws, 300 mm length screws.

The apparatuses and methods of the present invention provide the ability to continuously apply a compressive force to bone segments over a distance or length in which the embodiment was initially stretched or lengthened. The mechanism providing this expansion and contraction or change in length comprises of a continuous wrap member spanning the length of the expandable section. The wrap section being one continuous body with the distal threaded section and the proximal head of the body.

The apparatuses and methods of the present invention provide the ability to continuously apply a compressive force to bone segments over a distance or length in which the embodiment was initially stretched or lengthened. The mechanism providing this expansion and contraction or change in length comprises of a continuous wrap member spanning the length of the expandable section. The wrap section being one continuous body with the distal threaded section and the proximal head of the body. The wrap direction being in the same direction as the threads on the distal end. The wrap direction being in the opposite direction as the threads on the distal end.

The apparatuses and methods of the present invention provide the ability to continuously apply a compressive force to bone segments over a distance or length in which the embodiment was initially stretched or lengthened. This rotation of the body being limited by a limiting engagement feature. This rotation limiting feature existing on the wrap or strut member. This rotation limiting feature existing on the leading edge of the wrap member. This rotation limiting feature existing on the trailing edge of the wrap member. The embodiment having 1 to 100 rotation limiting features along the expanding section. The embodiment having 1 to 100 rotation limiting features along the circumference of the body. The embodiment having rotation limiting features along the circumference of the body spaced in a uniform pattern. The embodiment having rotation limiting features along the circumference of the body spaced in a varied pattern.

The apparatuses and methods of the present invention provide the ability to continuously apply a compressive force to bone segments over a distance or length in which the embodiment was initially stretched or lengthened. This distance being limited by a limiting feature. This length limiting feature existing on the wrap or strut member. This length limiting feature existing on the rotational engagement member. This length limiting feature existing on the leading edge of the wrap member. This length limiting feature existing on the trailing edge of the wrap member. This length limiting feature existing on the leading edge of the rotational engagement member. This length limiting feature existing on the trailing edge of the rotational engagement member. The length limiting feature integrated into the rotational engagement feature. The length limiting member having a mechanical engagement. The length limiting feature having a sliding engagement. The length limiting feature having a wedging engagement. The length limiting feature having a catching engagement. The invention having 1 to 100 length limiting features along the expanding section. The invention having 1 to 100 length limiting features along the circumference of the body. The invention having length limiting features along the circumference of the body spaced in a uniform pattern. The invention having length limiting features along the circumference of the body spaced in a varied pattern.

The apparatuses and methods of the present invention provide the ability to continuously apply a compressive force to bone segments over a distance or length in which the embodiment was initially stretched or lengthened. This change in length can be more than 20 percent of the entire constructs length. The distance in which the applied force can be applied can range from 0-20 percent of the bodies overall length, and can be set by the design.

The apparatuses and methods of the present invention provide the ability to continuously apply a compressive force to bone segments over a distance or length in which the embodiment was initially stretched or lengthened. This distance being limited by the design. This limiting feature allowing for application of a higher compressive force being applied to the bone segments than the spring force of the expanded mechanism. This is commonly called a preload. An example of this would be the spring mechanism can apply a constant or variable 50N of compression to the bone segments over a distance of 3 mm. Once the screw has stretched 3 mm, further engagement of the threads and bone tissue could yield a 200N compression between the bone segments. As the bone remodels or absorbs due to the compressive loading during healing the 200N force will resolve with in less than 1 mm of bone absorption, then the spring force of the expandable mechanism will load the bone at 50N until the 3 mm of stretch is reduced to 0 mm, which may or may not happen.

The apparatuses and methods of the present invention provide the ability to continuously apply a compressive force to bone segments over a distance or length in which the embodiment was initially stretched or lengthened having a stretch length that is limited by an interference mechanism.

The apparatuses and methods of the present invention provide the ability to continuously apply a compressive force to bone segments over a distance or length in which the embodiment was initially stretched or lengthened having a rotational engagement feature that limits the amount of rotation along the length of the expanding section. These rotational engagement features can enable the length change of the expanding mechanism. These rotational engagement features can resist the length change of the expanding mechanism. These rotational engagement features can limit the rotational positional change of the expanding mechanism during loading.

The apparatuses and methods of the present invention provide the ability to continuously apply a compressive force to bone segments over a distance or length in which the embodiment was initially stretched or lengthened having stress relieving cut patterns to allow for large deformations.

The apparatuses and methods of the present invention provide the ability to continuously apply a compressive force to bone segments over a distance or length in which the embodiment was initially compressed or shortened. This distance being limited by the design. This limiting feature allowing for application of a higher compressive force being applied to the bone segments than the spring force of the expanded mechanism. This is commonly called a preload.

The apparatuses and methods of the present invention provide the ability to continuously apply a compressive force to bone segments over a distance or length in which the embodiment was initially compressed or shortened. This distance being limited by the design. The force generating member being a compression spring. The force generating member being a compression washer. The force generating member being a compression wave spring. The spring mechanism residing on the exterior of the screw member or bone engagement member. The spring mechanism being on the surface of the bone.

The apparatuses and methods of the present invention provide the ability to continuously apply a compressive force to bone segments over a distance or length in which the embodiment was initially compressed or shortened. This distance being limited by the design. The force generating member being a compression spring. The force generating member being a compression washer. The force generating member being a compression wave spring.

The apparatuses and methods of the present invention provide the ability to continuously apply a compressive force to bone segments over a distance or length in which the embodiment was initially compressed or shortened. This distance being limited by the design. The force generating member being a compression spring. The spring mechanism residing beneath the surface of the bone.

The apparatuses and methods of the present invention provide the ability to continuously apply a compressive force to bone segments over a distance or length in which the embodiment was initially compressed or shortened. This distance being limited by the design. The force generating member being a compression spring. The spring mechanism residing beneath the surface of the bone. The spring mechanism residing inside of a retaining member. The retaining member engaging the bone and spring. The spring force being transmitted through the head of a screw to the distal bone segment.

The apparatuses and methods of the present invention provide the ability to continuously apply a compressive force to bone segments over a distance or length in which the embodiment was initially compressed or shortened. The spring force being transmitted through the head of a screw to the distal bone segment.

The apparatuses and methods of the present invention provide the ability to continuously apply a compressive force to bone segments over a distance or length in which the embodiment was initially stretched or lengthened. This distance being limited by the design. The spring force being transmitted through the head of a screw to the proximal bone segment. The spring force being transmitted through the distal threads of a screw to the distal bone segment.

The apparatuses and methods of the present invention provide the ability to continuously apply a compressive force to bone segments over a distance or length in which the embodiment was initially stretched or lengthened. This distance being limited by the design. The spring force being transmitted through the head of a screw to the proximal bone segment. The spring force being transmitted through the distal threads of a screw to the distal bone segment. The section of the joining apparatus being resistant to bending across the region of the bone segment interface. The section of the screw that extends across the fractured bone ends in a nonexpanding section.

The apparatuses and methods of the present invention provide the ability to continuously apply a compressive force to bone segments over a distance or length in which the embodiment was initially stretched or lengthened. The expanding section having a cut pattern. The cut pattern having beam members in angles relative to the axis. The cut pattern beams being shorter than the circumference of the body. The continuous body of the cut patterns having beams in bending and nodes of connection. The beams in bending creating the spring force for therapeutic effect. The cut pattern of beams alternating angles about the circumference of the body. The relative beam angles diverging from each other as the body is lengthened. The nodes at the ends of the beams increasing in axial separation distance relative to each other during axial tensile loading. The beam members acting as springs in series as a mechanism.

The apparatuses and methods of the present invention provide the ability to continuously apply a compressive force to bone segments over a distance or length in which the embodiment was initially stretched or lengthened. The expanding section having a cut slot pattern. The cut pattern having beam members in angles relative to the axis resembling a sinusoidal pattern. The beam members deflect to a lesser angle or deform to a straight configuration upon axial tensile loading. The beam members connected on each end to the body features that engage bone tissue. The beam members having circumferential support members at the apexes of a sinusoidal pattern. The beam members decreasing in diameter from their relative starting diameter. The beam members increasing in diameter from their relative starting diameter. The beam members acting as springs in parallel as a mechanism.

The methods and apparatus of the of present invention with features formed of cut paths that do not intersect with the central axis of the body. The methods and apparatus of the present invention with cut features that yield an overlap of one edge face relative to the adjacent edge face in a plane or axis orthogonal to the central axis. The methods and apparatus of the present invention which has a variable cut angle or plane throughout the cut path, relative to lines or planes orthogonal to the central axis.

Certain embodiments of the present invention provide apparatuses, such as bone fixation devices, having a strut or spring wrap member having features that substantially limit a rotation of the strut or spring wrap member about a longitudinal central axis of the device resulting from a torsional force input to the device along the longitudinal central axis of the device, thereby, resulting in longitudinal ends of the device rotating through or into patient tissue, e.g. bone matter, at substantially a same rate and frequency.

Certain embodiments of the present invention provide apparatuses, such as bone fixation devices, having a strut or spring wrap member having features that limit a torsional and/or rotational displacement or deformation of the strut or spring wrap member about a longitudinal central axis of the device when the feature is placed under rotational loading and/or axial loading.

Certain embodiments of the present invention provide apparatuses, such as bone fixation devices, having a strut or spring wrap member having features that limit the displacement of the device when an axial deformation is imparted onto the device.

Certain embodiments of the present invention provide apparatuses, such as bone fixation devices, having a strut or spring wrap member having axle length limiting features that have a two distinct loading curves that vary in slope.

Certain embodiments of the present invention provide apparatuses, such as bone fixation devices, having a strut or spring wrap member having axle length limiting features that can be designed to limit the amount of deformation under a given load.

Certain embodiments of the present invention provide apparatuses, such as bone fixation devices, having a strut or spring wrap member having axial length limiting features that also limit torsional displacement of an adjacent strut or spring wrap member.

Certain embodiments of the present invention provide apparatuses, such as bone fixation devices, having a strut or spring wrap member having features that enable axial translation or deformation up until a predetermined dimension of the device, e.g. an axial length or a circumference, at which time the features abruptly resist such deformation.

Certain embodiments of the present invention provide apparatuses, such as bone fixation devices, having a strut or spring wrap member having features that limit deformation or deflection of the strut or spring wrap member regardless of a direction of a rotational input applied to the device, i.e. having features that allow alternate axial displacement of the device within patient tissue without obstruction or binding of the device.

Certain embodiments of the present invention provide apparatuses, such as bone fixation devices, having a strut or spring wrap member having features that limit torsional rotation without imparting axial load or resistance in both axial directions of the device.

Certain embodiments of the present invention provide apparatuses, such as bone fixation devices, having a strut or spring wrap member having features that limit torsional deflection or deformation and that increase the overall torsional strength of the device.

Certain embodiments of the present invention provide apparatuses, such as bone fixation devices, having a strut or spring wrap member having features that limit axial deflection or deformation and increase the overall axial strength of the device.

Certain embodiments of the present invention provide apparatuses, such as bone fixation devices, having a strut or spring wrap member having features that limit torsional and axial deformation of the device and that increase the overall torsional and axial strength of the device.

Although embodiments of the present invention have been depicted and described in detail herein, it will be apparent to those skilled in the art that various modifications, additions and substitutions can be made without departing from the scope of the invention.

DETAILED DESCRIPTION OF THE FIGURES

Figures 1, 2, 3:
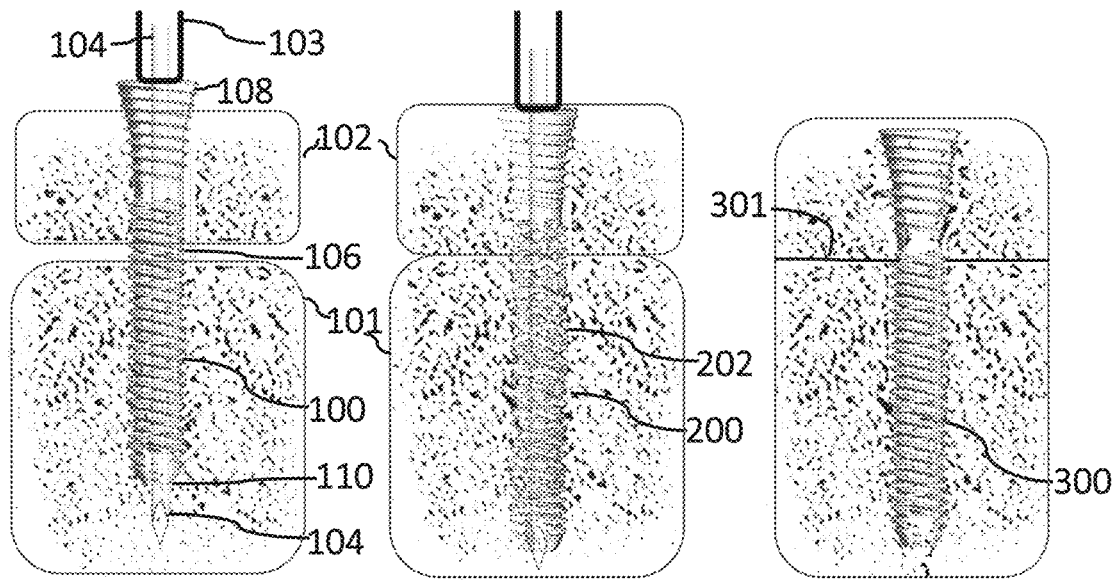
FIG. 1 is a side view of a bone fixation device being inserted into two non-reduced bone segments in a non-expanded state, in accordance with an aspect of the present invention.
FIG. 2 is a side view of a bone fixation device being inserted into two reduced bone segments in an expanded, tensioned state, in accordance with an aspect of the present invention.
FIG. 3 is a side view of a bone fixation device inserted into two reduced bone segments in a non-expanded state, in accordance with an aspect of the present invention.

FIGS. 1-3 depicts a representation of one embodiment of the present invention in which a member 100, shown in a contracted or shortened state, is inserted in to bone members 101 and 102 and then brings or draws bone members 101 and 102 towards one another, providing a compressive axial tension or force. The bone members 101 and 102 may represent one bone broken in two pieces or two bones that are to be fused together. The bone may, for example be a cortical or cancellous bone or both.

In operation, the joining member 100 is driven into the bone members 101 and 102 with a mechanical instrument, mechanism, or tool 103 that provides the forces needed to accomplish this action. This force could be that of rotating the member 100 and applying an axial force to facilitate a screwing of the member 100 into the bone members 101 and 102. The bone members may or may not be placed in close proximity to each other prior to insertion or placement of member 100. Bone members 101 and 102 may or may not have been pre-drilled with a pilot hole to facilitate placement of bone member 101 and 102.

Bone members 101 and 102 may, but need not necessarily, have member 104, depicted here as an axial member such as a K-wire, inserted prior to placement of member 100. The K-wire 104 may be placed to help facilitate the securing of bone members 101 and 102 relative to each other. The K-wire or member 104 may act as an axial alignment guide for a cannulated member 100. The member 104 may or may not be over drilled with a cannulated drill as a pre-drill step to a diameter that facilitates placement of member 100.

In certain embodiments, the member 100 changes in axial length, as indicated by a member 200, shown in FIG. 2. The change in length occurs over all or a portion of a deformable or expandable portion 202 of member 200. This change in length may be imparted onto the contracted or shortened member 100 prior to insertion into bone members 101 and 102. Alternatively, this change in length may be imparted onto the contracted or shortened member 100 during the insertion into bone members 101 and 102. Alternatively, this change in length may be imparted onto the contracted or shortened member 100 by the act or through the forces imparted onto the contracted or shortened member 100 by the delivery mechanism 103. Alternatively, this change in length may be imparted onto the contracted or shortened member 100 by the act or through the forces imparted onto the contracted or shortened member 100 by the delivery mechanism 103 in combination with a resistance to insertion imparted by the bone members 101 and 102.

The lengthened or axially elongated member 200, shown in FIG. 2, asserts a compressive force onto the bone members 101 and 102 that draws bone members 101 and 102 towards one another. The elongated member 200 shown in FIG. 2 applies force onto the bone members 101 and 102 through a mechanism, for example, in which threads 106 formed on an exterior of member 100, 200 engage the bone members 101 and 102 and a head 108 of the member 100, 200 and the pitch of the threads 106 function in combination to generate a compressive load or force across the two bone members 101 and 103 to help facilitate bone healing or fusion.

The elongated member 200 shown in FIG. 2 applies force onto the bone members 101 and 102 in such a way as to apply an active or continuous force over an extended period of time, for example over a period of time from 1 to 72 hours. The period of time can be that of the length of time for the force of the elongated member 200 to retract from extended state indicated as member 200 to retracted state indicated as member 100. This time to retract will be controlled, in part, by the reactive forces bone members 101 and 102 impart onto the engaging members or threads 106 of member 100, 200. This time to retract and related forces will be furthered controlled, in part, by the nature of the bone material that is engaged by the member 100, 200 by the thread 106 and, in part, by the features that enable the adjustable length of member 100, 200.

The mechanisms of control of the compressive force generated and related contraction period may, for example, include but are not limited to the amount of force imparted onto bone members 101 and 102; the amount of bone material engaged by the engagement features of the implant member 100, 200, e.g. by threads 106; and the surface area of the interface between the bone members 101 and 102 and the implant member 100, 200. The extend and adjustable period of time over which the continuous compressive force is applied to bone members 101 and 102 facilitates bone members 101 and 102 healing together and/or forming a fusing or union 301.

In addition to the acute compressive load generated by member 200, there is a stored energy or force of member 200 that can exhibit a continuous load over time and/or absorption of bone material. The stored compressive energy or preload provides a compressive force cross the bone elements to aide in the healing or fusion process. The preload can be imparted into the joining member 100, 200 in several manners. The preload could have been imparted to the member 100, 200 before it is inserted into the bone members 101 and 102. The preload could be imparted by the act of inserting the member 100, 200 into the bone member 101 and 102. Engagement features, e.g. threads 106, on the member 100, 200 can work in such a fashion that the tip or distal end 110 of the member 100, 200 is advanced at a rate that exceeds the advancement of the proximal end or head 103 of the member 100, thus resulting in an axial force and resulting lengthening of the member 100 indicated by member 200, details of which will be further described herein.

FIG. 3 shows a member 300 which represents a relaxed, contracted, state of member 200 in which the preload has dissipated over time to help facilitate the union or healing between bone members 102 and 101. This unloading can happen over an extended and adjustable period of time. This unloading and contraction can occur over or through several millimeters of bone absorption. The fusion 301 between bone members 101 and 102, shown in FIG. 3, is greatly aided by the compression force that remains and persists during the period of healing.

Figure 4:
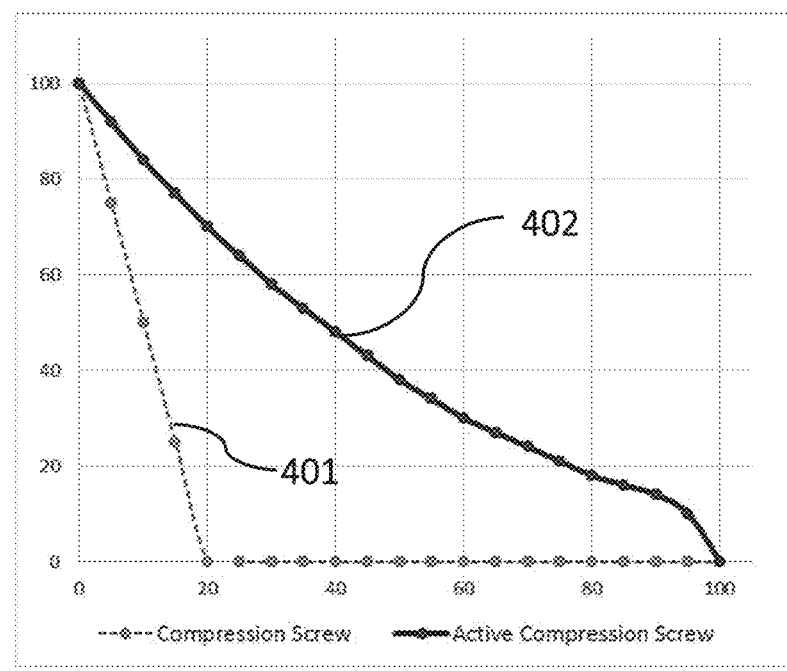
FIG. 4 is a graph depicting the compressive force applied over time by a device according to the present invention relative to a standard screw.

FIG. 4 is a graphical representation of certain differences between one embodiment of the inventive joining member and a standard screw. The vertical axis represents compressive force applied onto the bone segments as a percentage. The horizontal axis represents either time or amount of bone resorption or change in distance of the bone segments. The inventive apparatuses can demonstrate a compressive force over a greater change in length than either a standard screw or a currently available compression screw. This ability correlates directly to delivering a compressive force to bones over a longer period of time in a live tissue environment. As tissue remodels or resorbs to achieve a zero-stress state, the ever-changing length allows the pressure to be applied over a longer period of time. The graph depicts the difference between a standard screw 401 and an active compression screw 402.

This compressive load although being good for healing also yields an effect known as Wolff's law which holds that bone responds to load by increasing in density to account for the loading. If the load exceeds that of physiological norms and at acute points or focalized stress points the bone will remodel in a way to reduce that stress point to that of the surrounding bone. This happens with a standard screw rapidly. The load applied to bone through use of a standard compressive screw will resolve in a brief or acute period of compression because the length of the screw does not change and therefore the amount of remodeling needed to resolve that focal stress is minor and/or limited. The present invention is contrary to this effect in that the joining member of the present invention will continue to change in length as the bone remodels resulting in a compressive force that will continue over a longer period of time and or a greater distance of remodeling of bone tissue.

Generally speaking, when a spring is stretched from its resting position, it exerts an opposing force approximately proportional to its change in length. The rate or spring constant of a spring is approximately the change in the force it exerts, divided by the change in deflection of the spring. That is, it is the gradient or slope of a force versus deflection curve. An extension spring's rate is expressed in units of force divided by distance, for example pound per inch, lb./in, or Newton per meter, N/m. A linear spring is one with a linear relationship between force and displacement, meaning that the force and the displacement are directly proportional to each other. A graph showing force vs. displacement for a linear spring will always be a straight line having a constant slope. Typical compression screws yield this behavior. A typical compression screw does not change in length or only changes very little in length. the spring characteristics of typical compression screws and helical spring mechanisms are primarily dependent on the shear modulus of the material from which the typical compression screw or helical spring is formed.

In contrast, certain embodiments of the devices disclosed herein exhibit nonlinear behavior. A nonlinear spring has a nonlinear relationship between force and displacement. A graph showing force vs. displacement for a nonlinear spring will be more complicated and have a changing slope. The properties of the springs or deformable portions of the inventive devices disclosed herein, that are based on strut or beam bending and on material properties of superelastic materials, produce forces that vary nonlinearly relative to their displacement. The apparatuses and methods of the present invention provide members that impart a compressive force on at least two tissue members through axial tensile elastic potential energy released through a mechanism that uses beam bending and material properties of superelastic materials to produce forces that vary nonlinearly with displacement.

Figure 5:
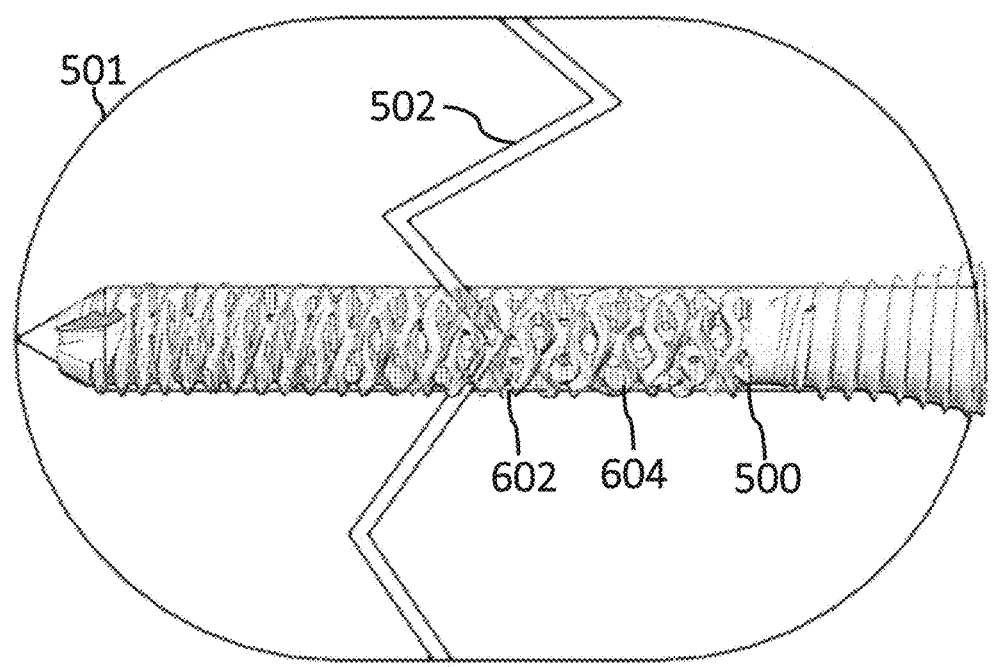
FIG. 5 is a side view of a bone fixation device inserted into two non-reduced bone segments in an expanded state, in accordance with an aspect of the present invention.
Figure 6:
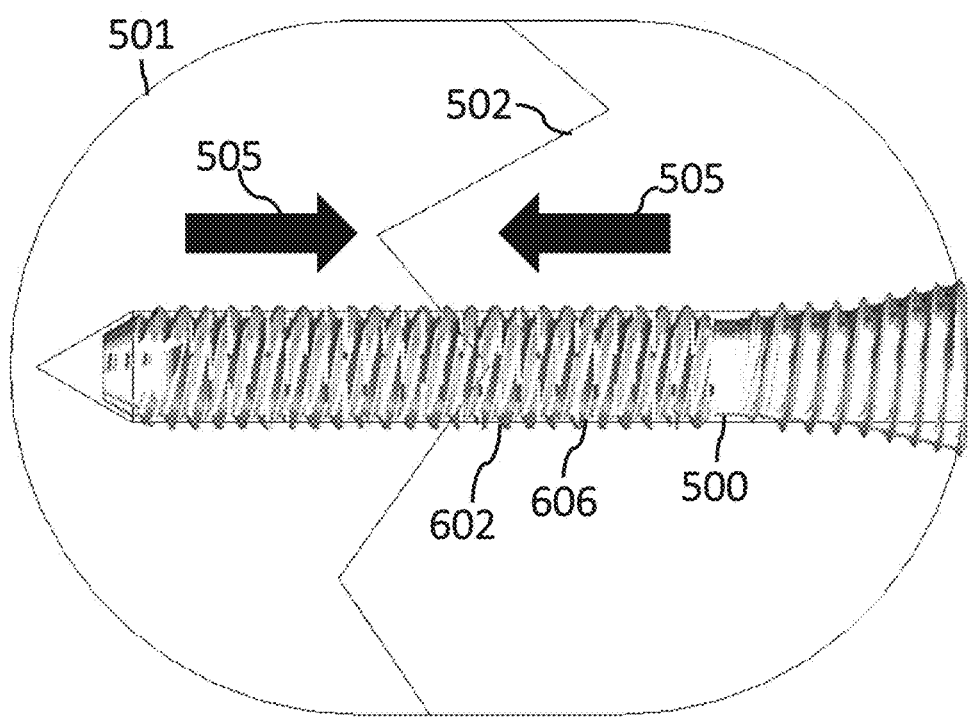
FIG. 6 is a side view of a bone fixation device inserted into two reduced bone segments in a non-expanded state, in accordance with an aspect of the present invention.

FIGS. 5 and 6 depict another representation of an embodiment of the present invention in which a bone element 501 with a compression zone 502 is brought together and compressed, both acutely and over time, with screw member 500. In FIG. 5, the screw member 500 is shown with a deformable portion 602 in an expanded/stretched/loaded/ state 604. FIG. 6 shows the deformable portion 602 of the member 500 in a compressed/unexpanded/unloaded state 606 in which a compressive force is applied in the directions indicated by arrows 505 to the compression zone 502 of bone 501 as the deformable portion 602 of the screw member 500 transitions from the expanded state 604 to the final, compressed state 606.

FIGS. 7-10 show the anatomy in which certain embodiments of the present invention can be utilized. The methods and structures disclosed herein are intended for application in any of a wide variety of bones and fractures. For example, the bone fixation device of the present exemplary system and method is applicable in a wide variety of fractures and osteotomies in the hand, such as interphalangeal and metacarpophalangeal arthrodesis, transverse phalangeal and metacarpal fracture fixation, spiral phalangeal and metacarpal fracture fixation, oblique phalangeal and metacarpal fracture fixation, intercondylar phalangeal and metacarpal fracture fixation, phalangeal and metacarpal osteotomy fixation as well as others known in the art. A wide variety of phalangeal and metatarsal osteotomies and fractures of the foot may also be stabilized using the bone fixation device of the present exemplary system and method. These include, among others, distal metaphyseal osteotomies such as those described by Austin and Reverdin-Laird, base wedge osteotomies, oblique diaphyseal, digital arthrodesis as well as a wide variety of others that will be known to those of skill in the art. Fractures of the fibular and tibial malleoli, pilon fractures and other fractures of the bones of the leg may also be fixated and stabilized with the present exemplary system and method. Each of the foregoing may be treated in accordance with the present system and method, by advancing one of the active compression screw systems disclosed herein through a first bone component, across the fracture, and into the second bone component to fix the fracture.

Figure 12:
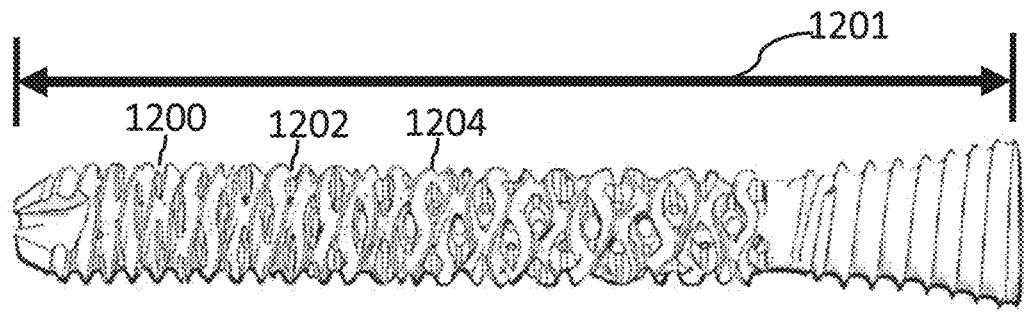
FIG. 12 is a side view of a bone fixation device in an expanded state, in accordance with an aspect of the present invention.
Figure 13:
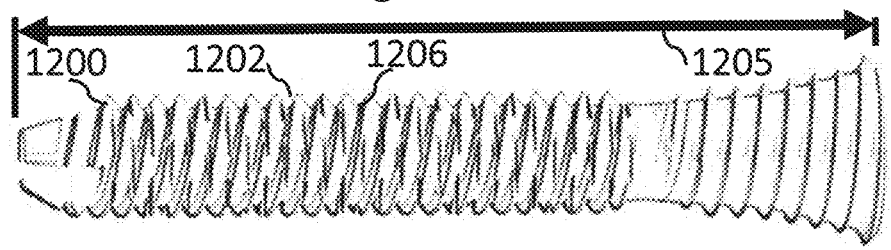
FIG. 13 is a side view of a bone fixation device in a non-expanded state, in accordance with an aspect of the present invention.
Figure 14:
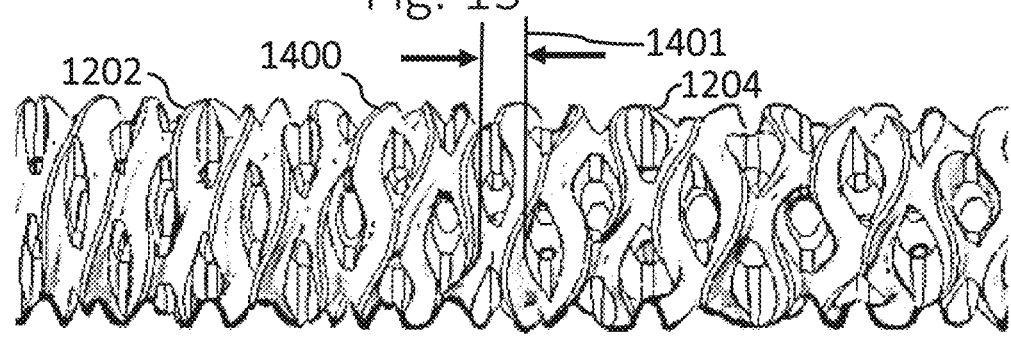
FIG. 14 is an enlarged side view of a portion of a deformable or expandable segment of a bone fixation device in an expanded state, in accordance with an aspect of the present invention.
Figure 15:
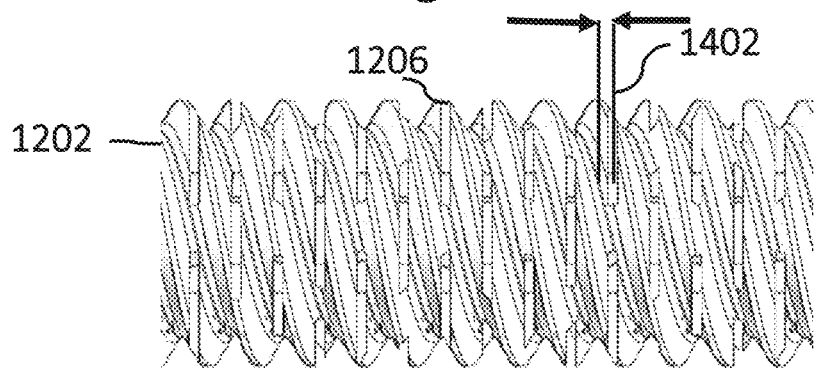
FIG. 15 is an enlarged side view of a portion of a deformable or expandable segment of a bone fixation device in an unexpanded state, in accordance with an aspect of the present invention.

FIGS. 12-15 show certain embodiments of the present invention. More particularly, FIGS. 12 and 14 depict an embodiment of a member 1200 having a deformable portion 1202 in a stretched, expanded, loaded, stressed, state 1204 in which a length 1201 of the member 1200 is increased by an axial force. In contrast, FIGS. 13 and 15 depict the member 1200 having a deformable portion 1202 in a contracted, unexpanded, unloaded, unstressed, state 1206 in which a length 1205 of the member 1200 is decreased relative to length 1201. The axial force resulting in the deflection of the struts 1400, shown in FIG. 13, to obtain an increased separation distance 1401 between the adjacent struts 1400, thereby yielding the increased length 1201 of member 1200, shown in FIG. 14 relative to length 1402 shown in FIG. 15. The distance or amount of axial translation can vary from small displacements to large displacements, depending on multiple variables and desired performance characteristics.

These performance characteristic variables include but are not limited to the strut width, the strut length, a radius of end cut slots forming the struts, width of cut slots, outer diameter of member, inner diameter of member, number of slots along the radius of the member, shape of cut slots, angle of cut slots, number of slots along the axial length of the member, number of members, layers of members, configuration of multiple members, the pattern of slots along the length, the location of the beginning and ending slots along the length, overall length of the member, the material, the surface treatment of the material, the machined profile member, the ratio and or relationship of these variables relative to each other.

The desired characteristics to control within the inventive embodiment may include but are not limited to, amount of axial force applied to recover the length, amount of axial force to increase the axial length or stretch or load the member, amount of length change variable along the axial position of the member the amount of force change as a ratio to change in length, the bending stiffness of the entire member along the axis, the separation of individual strut members, the elastic limit of the material, the engagement in bone tissue, the insertion force of the member into bone, the removability of the member, the migration of the member in/through bone tissue, the resistance to migration of the member in bone tissue, the biocompatibility of the member, the procedural ease of use of the member, the ease of manufacturing of the member, the cost of the member, the number of elements that construct the member, manufacturing processes to construct embodiment.

A diameter of the inventive joining member 1200 can be from 1 mm-20 mm, the length of the member 1200 can range, for example, from 4 mm to over 400 mm. A difference in the distance 1201 of the stretched configuration 1204 and the distance 1206 of the upstretched member 1200 is in the range of 0.2%-20% or more of the overall length of the member 1200. A change or difference in the lengths 1401 and 1402 between the struts 1400, shown in FIGS. 14 and 15, facilitates, in part, the difference in the distance 1201 of the stretched configuration 1204 and the distance 1206 of the upstretched member 1200. change or difference in the lengths 1401 and 1402 between the struts 1400 can be from 0.1% to over 200% of the relaxed length 1401. The dimensions are also applicable to the other embodiments of the inventive joining member disclosed herein.

FIGS. 16-18 depict another embodiment of the present invention. FIG. 17 is a cross sectional view of a cannulated member 1500 along lines A-A shown in FIG. 18. Line A-A may also indicate a longitudinal axis through member 1500. The member 1500 is a threaded screw with slots 1702 machined along a length of a deformable portion 1701. A distal tip of the screw 1500 has cutting features 1803, triple lead threads 1802, transition zone 1801, single lead tapered head section 1800, driver engagement feature 1700. The drive engagement feature 1700 may employ any common fastener interface, for example, flathead, Philips, hex head, star head, hexalobe, or other. A difference in the thread pitches of the single lead tapered head section 1800 and the triple lead threads 1802 can, in certain embodiments, provide the axial force required to stretch the members 1500 while driving the member 1500 into the bone. The cross-section view of FIG. 17 further illustrates that the entire device is one unitary member. This unitary member can be made on one manufacturing machine greatly reducing the cost of goods of this embodiment compared to other active compression screws.

Figure 20:
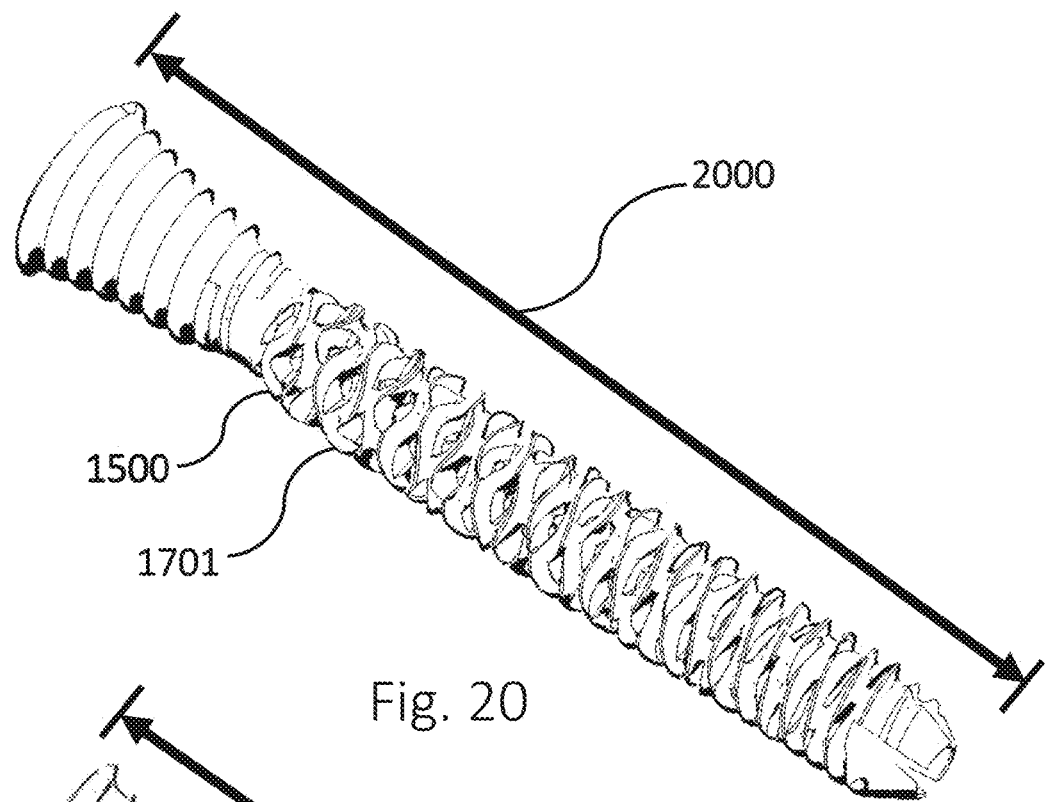
FIG. 20 is a perspective view of a bone fixation device in an expanded state, in accordance with an aspect of the present invention.
Figure 19:
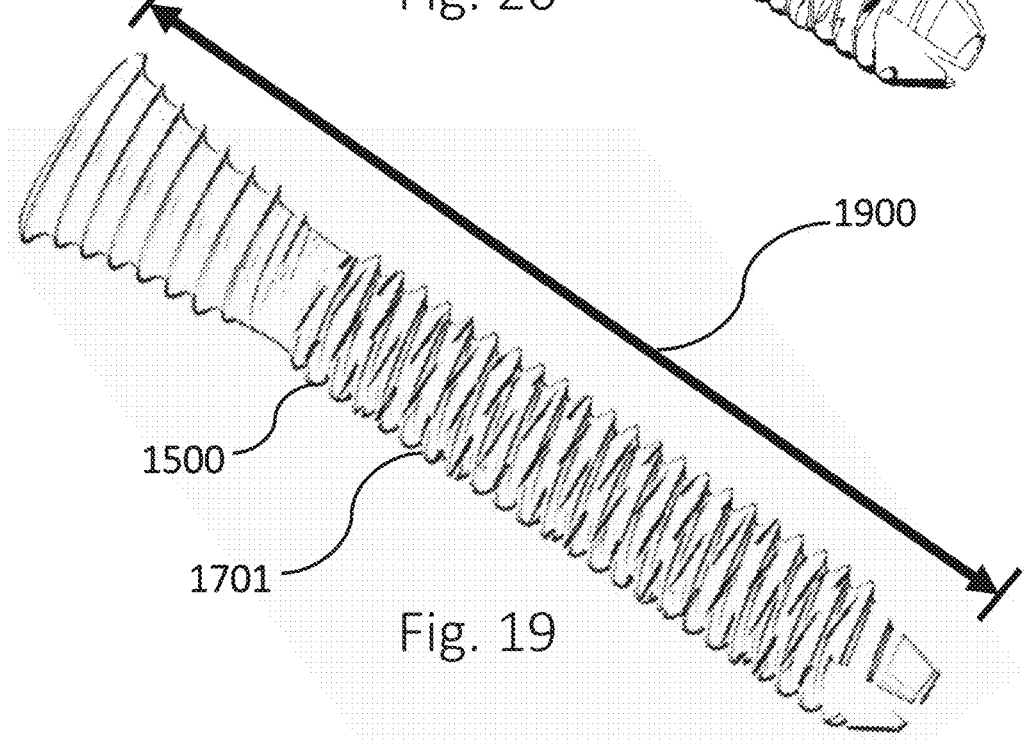
FIG. 19 is a perspective view of a bone fixation device in a non-expanded state, in accordance with an aspect of the present invention.

FIGS. 19 and 20 show another representation of the member 1500 shown in FIGS. 16-18. FIG. 20 depicts a stretched configuration 2000 wherein the amount of change in length is variable along a length of the deformable portion 1701 of the member 1500. FIG. 19 depicts a contracted configuration 1900 of the deformable portion 1701 of the member 1500. In certain embodiments, the deformable portion of the inventive member is deformed in a uniform amount along the length of the deformable portion. In certain embodiments, the deformation is variable along the length of the member. The amount or degree of change in length from state 1900 to state 2000 can be influenced by the variables previously described herein. The expanded state 2000 can also facilitate the integration of the surrounding bone tissue into the device which may be desirable to help stabilize the bone fusion.

The expanded state 2000 can also facilitate the deployment of a material from the inner diameter into the surrounding bone tissue. Biologics, antibiotics, bone graft, BMP, bone cement, pharmaceuticals, and any other material used to help facilitate bone healing could be deployed through the expansion features of the member 1500 or through the expansion features of any of the embodiments herein disclosed.

FIGS. 21, 22, 23, and 24 show additional embodiments of the present invention in which a member employs, for example, a distal threaded portion with a triple lead thread pitch and a proximal head portion with a tapering single point thread. When implanted, the difference in thread pitch of the distal threaded portion and the head yields a force along the axis that could stretch the middle section shown here without threads and with cut features that allow for a change in length of the screw body under an axial force. In certain embodiments, it is desirable to have the center, deformable section 2002 without threads to enable a section of the screw to pass through the bone without applying friction against that section which could facilitate a compression load being applied between the distal threaded portion and the head of the member.

Figure 21:
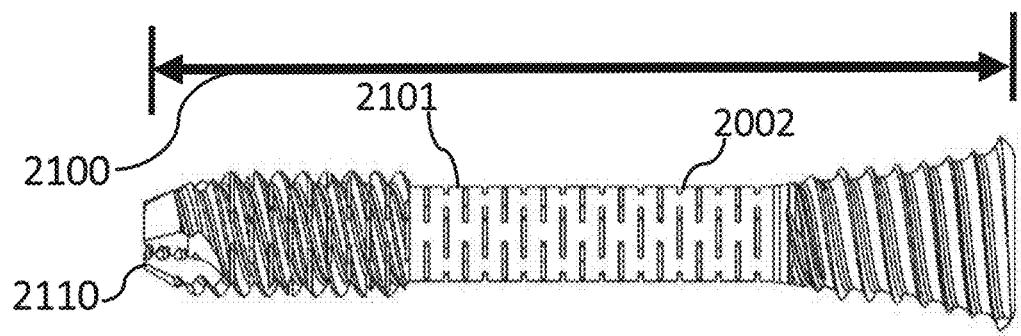
FIG. 21 is a side view of a bone fixation device with a non-threaded expandable segment in a non-expanded state, in accordance with an aspect of the present invention.
Figure 22:
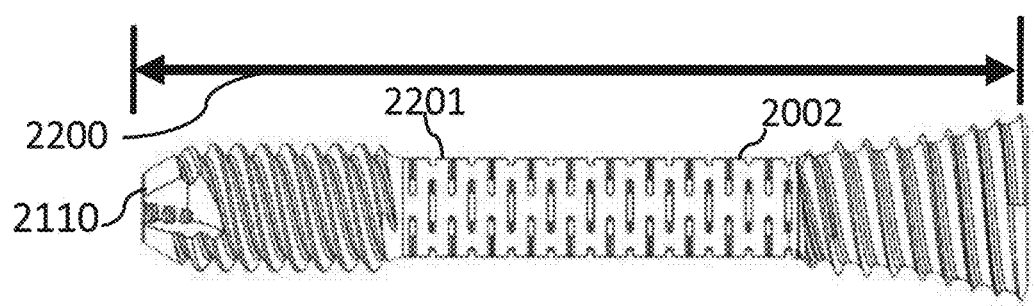
FIG. 22 is a side view of a bone fixation device with a non-threaded expandable segment in an expanded state, in accordance with an aspect of the present invention.
Figure 23:
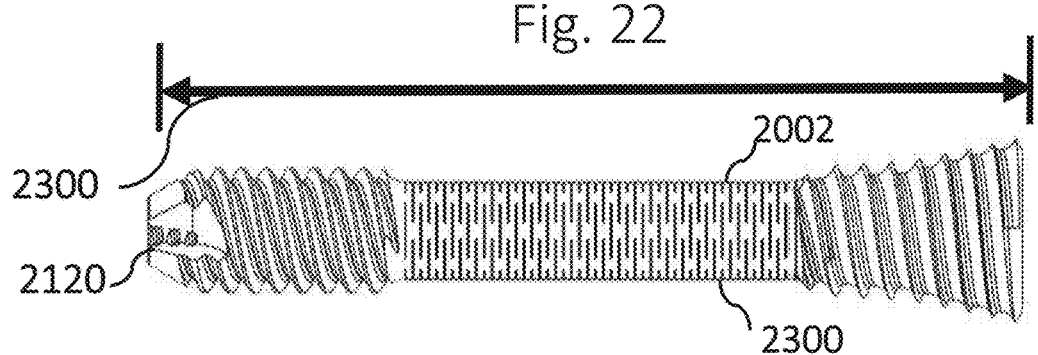
FIG. 23 is a side view of a bone fixation device with a non-threaded expandable segment in a non-expanded state, in accordance with an aspect of the present invention.
Figure 24:
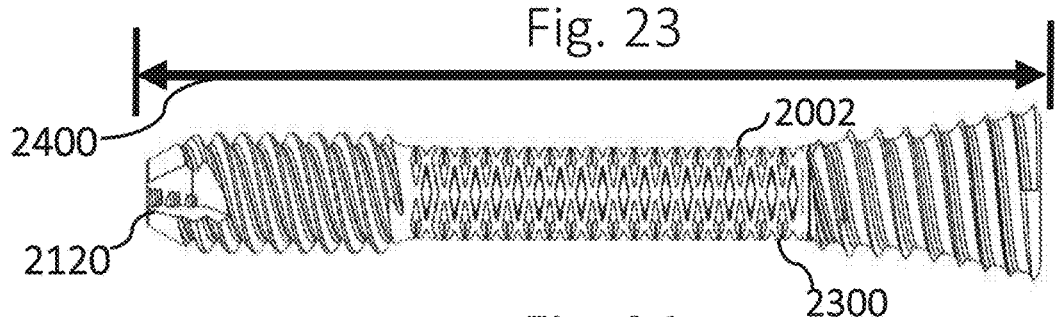
FIG. 24 is a side view of a bone fixation device with a non-threaded expandable segment in an expanded state, in accordance with an aspect of the present invention.

FIGS. 21 and 22 show the same device 2110 in a stretched and relaxed state. FIGS. 23 and 24 show the same device 2120 in a stretched and relaxed state. The device 2110 employs struts having a width 2101 that are thicker than the struts of device 2120 having a width 2300. This difference can yield a different deformation of deformable section 2002 for a given force. For example, the device 2110 shown in FIG. 21 may lengthen a distance of 2200 relative to length 2100, but for the same load the device 2120, shown in FIG. 23, may lengthen a distance of 2400 relative to length 2300. The change in length from length 2300 to 2400 being greater than the change in length from length 2100 to 2200. There are many variables involved in the cut features that may affect the axial tension force, bending stiffness, and the torsional rigidity, of the construct. The cut features can take on that of an infinite number of permutations of cell designs such as diamond shapes, wave forms, non-uniform, sinusoidal, slots, ovals, or round circles. Illustrative examples of some of these embodiments can be seen in FIGS. 83, 84, 87, 88, 90, 91, and 92 and other figures as well.

These patterns can be repeating along the length or vary along the length, multiple shapes and sizes could be combined in the same construct or deformable portion or sections of the inventive device, either along the length or around the circumference. The struts may vary in dimension along a length of the particular strut and a length of the respective deformable portion. The cross-section of the members can also take on an infinite number of permutations of cell designs such as those already demonstrated, including but not limited to round, square, oval, symmetrical and asymmetrical. The features and dimensions can vary in wall or material thickness and in cross-section.

Increasing the strut length can increase the amount of deformation for a given loading condition. This could be advantageous in that the overall change in the entire structure could be increased and therefore the change in length could accommodate a larger change in bone tissue over time. The amount of force that is then exerted as compression could be reduced which could be a desired trait, depending on the desired loading profile.

The radius of end cut slots can affect the strain of the struts and increase or decrease the amount of recoverable deformation. The width of cut slots may facilitate more or less flexibility of the construct. The manufacturing process can also be affected by this width making different processes possible with wider slots such as machine milling, or laser cutting with narrow slots.

The outer diameter of member may affect the overall stiffness of the construct and axial tension force by increasing or decreasing the amount of structural material involved and changing the bending moment. The inner diameter of the member may affect the overall stiffness of the construct and axial tension force by increasing or decreasing the amount of structural material involved, it may also affect the manufacturing process used to create the construct. The inner diameter may also affect the assembly members or other features used to facilitate the method of application of the embodiment.

The number of slots along the radius of the member could affect the axial tension force generated by the members, and/or the flexural stiffness of the construct. More slots of shorter length or less slots of longer length or slots not evenly distributed about the radius may all facilitate the desired behavior of the construct. The shape of cut slots can affect the axial tension force, bending stiffness, the torsional rigidity, of the construct by impacting the local deformation of the construct under load. The angle of cut slots relative to the axis of the member and also relative to the radius of the construct can facilitate different bending behaviors.

The number of slots along the axial length of the member, the density of the slots, the pattern of slots, the location of the slots along the length, and the overall length of the area covered by the slots can also impact the desired behavior of the embodiments. Multiple members could be used to facilitate the desired design intent by having nested or layered members in which a flexible and a non-flexible layer together to yield an axial flexible and bending rigid configuration. The embodiment can be formed of a unitary member or can be constructed from several different members and joined together in rigid form or in a manner that would leave degrees of freedom between the multiple bodies. The length of these individual members can impact the performance of the member by either increasing or decreasing the desired behavior. The location of the member being axial, layered externally or layered internally can also be used to control the behavior of the embodiments.

Material can also be used as a variable; elastic, stiff, absorbable, biocompatible, and any other material can be used individually or in combination with others to yield a desired feature set. The surface treatment of the material can also have an impact on the behavior of the structures. The ratio and or relationship of these variables relative to each other can be varied in spirit of the inventive disclosure by those familiar with the art and all combinations are considered herein encompassed in this disclosure in the spirit of brevity. The illustrative examples further detailed herein are that brief illustrative examples, and the variables in any one figure could be used with all the other examples either illustrated, captured in the text or known to those in the art.

Figure 28:
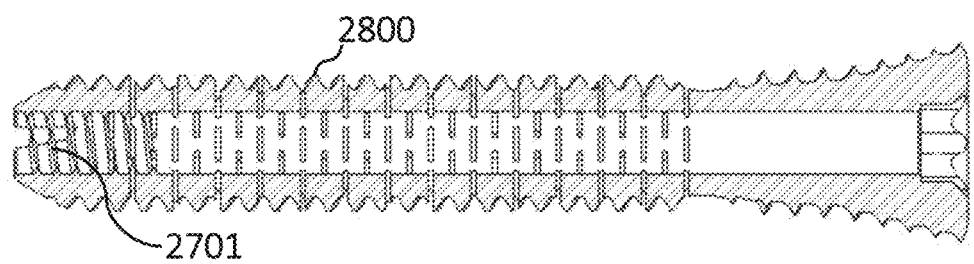
FIG. 28 is a side cross section view of a bone fixation device with a threaded distal segment in a non-expanded state, in accordance with an aspect of the present invention.
Figure 27:
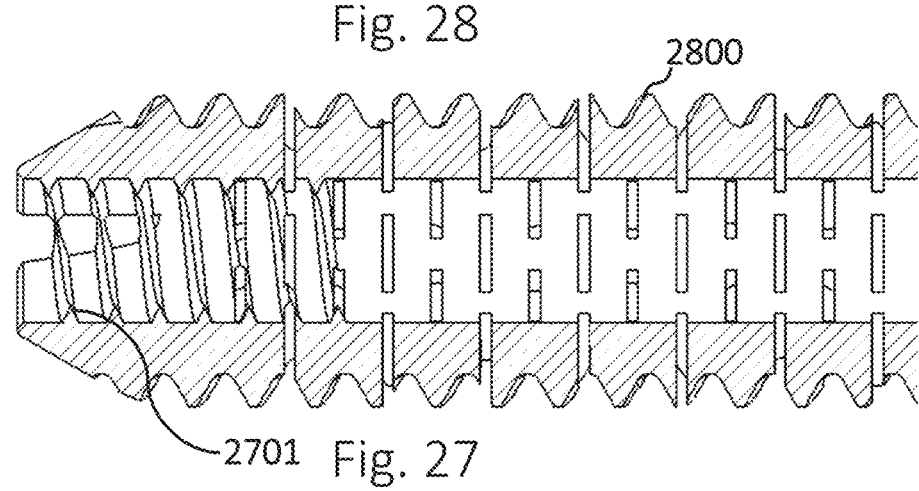
FIG. 27 is an enlarged side cross section view of a bone fixation device with a threaded distal segment in a non-expanded state, in accordance with an aspect of the present invention.
Figure 26:
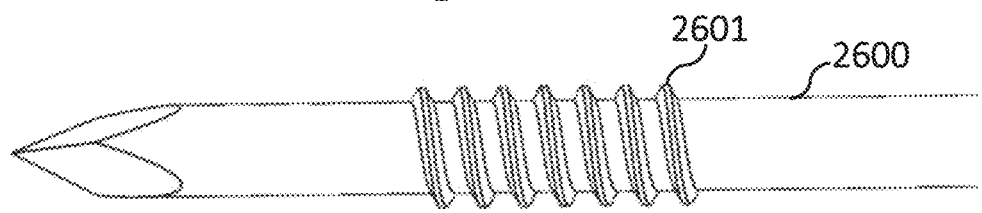
FIG. 26 is a side view of a threaded central member, in accordance with an aspect of the present invention.
Figure 25:
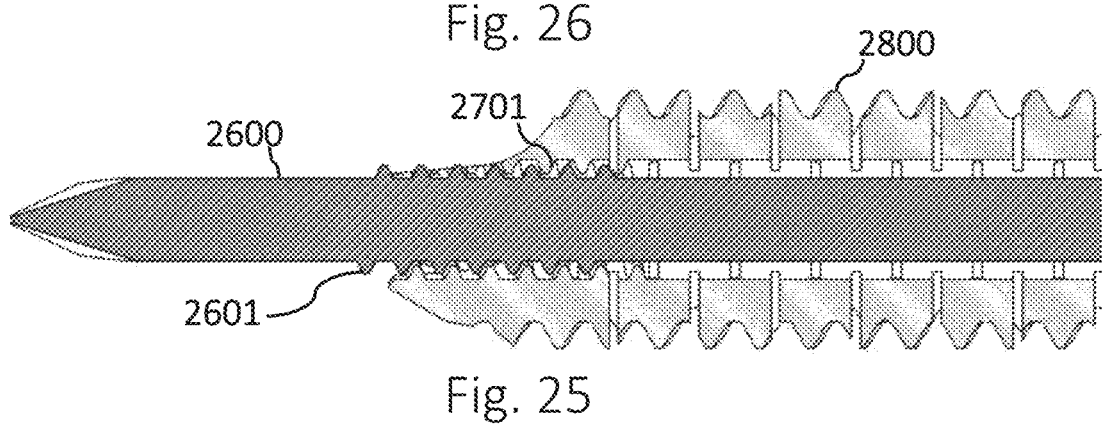
FIG. 25 is a side cross section view of a bone fixation assembly with a threaded expandable segment in a non-expanded state and a distal inner thread with a threaded central member, in accordance with an aspect of the present invention.

FIGS. 25-28 show another embodiment of the present invention in which a distal portion and a proximal portion of a device 2800 employs features that facilitate the application of a longitudinal force or tensile stress to the device 2800. FIG. 26 depicts a central axial member 2600 with an engagement feature depicted as threads 2601. The threads 2601 engage with complementary features, for example, threads 2701 formed within an interior of the device 2800, as shown in FIGS. 25, 27, and 28. Through the engagement of the threads 2601 of the central axial member 2600 and the threads 2701 within the device 2800, axial force can be applied to the member 2800.

This mechanism allows for application of an axial force in either compression or tension and this may be done after the screw is inserted into the bone, or after just the distal tip is inserted, or before the screw is inserted. It may be desired to preload a compression or tension stress to the screw implant before insertion into the bone tissue. This preload stretch will then need to be maintained throughout the implantation procedure. There are many ways to obtain and maintain the loaded or stretched condition this being but one possible embodiment.

Figure 29:
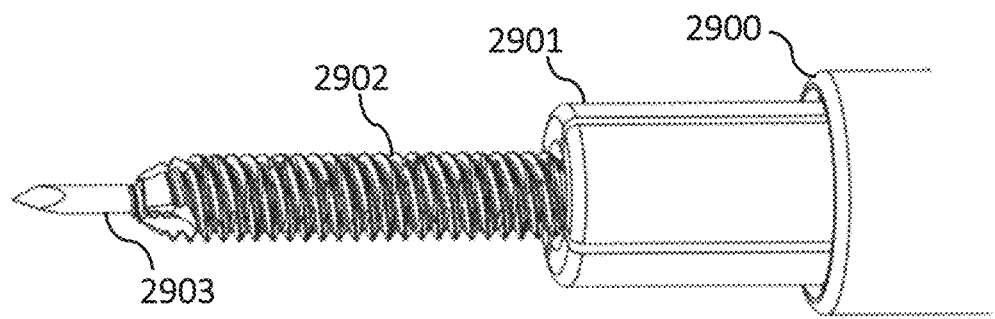
FIG. 29 is a perspective view of a bone fixation assembly with a threaded expandable segment in a non-expanded state and a distal inner thread with a threaded central member and a proximal head retention collet mechanism, in accordance with an aspect of the present invention.
Figure 30:
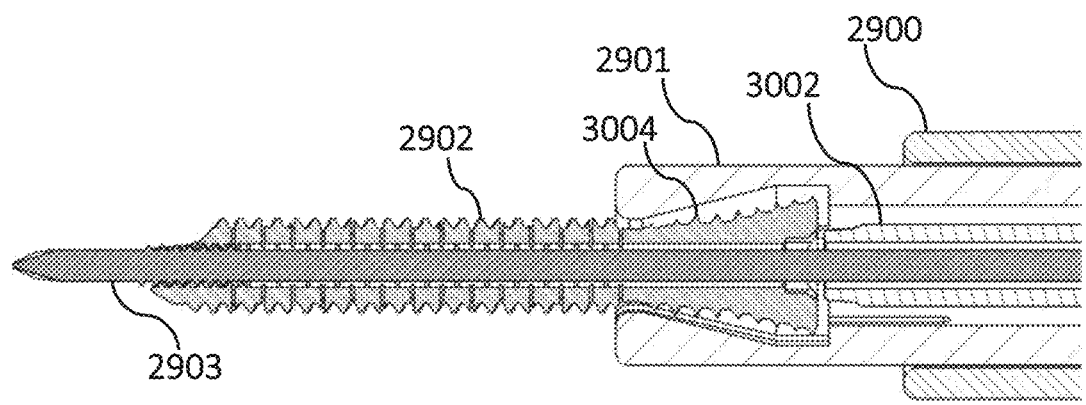
FIG. 30 is a side cross section view of a bone fixation assembly with a threaded expandable segment in a non-expanded state and a distal inner thread with a threaded central member and a proximal head retention collet mechanism, in accordance with an aspect of the present invention.
Figure 31:
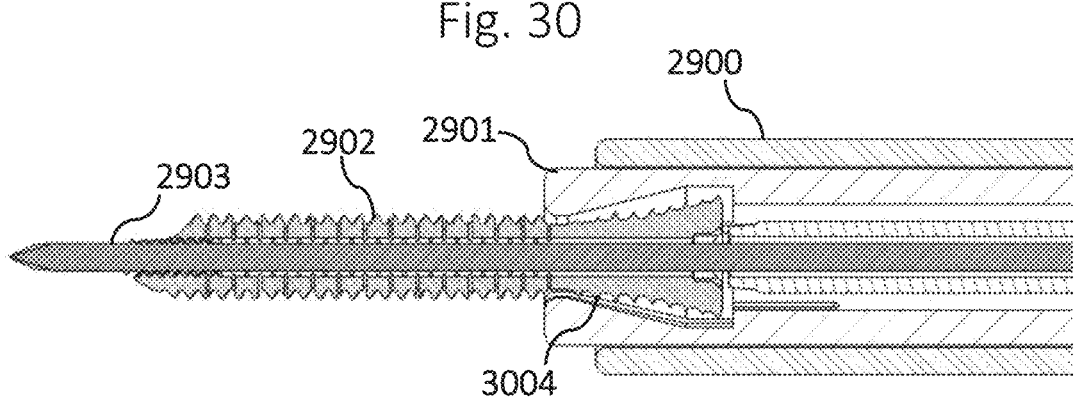
FIG. 31 is a side cross section view of a bone fixation assembly with a threaded expandable segment in a non-expanded state and a distal inner thread with a threaded central member and a proximal head retention collet mechanism, in accordance with an aspect of the present invention.

FIGS. 29, 30, and 31 show another embodiment of the present invention in which a distal, internal portion of the member 2902 is threaded such as that described above with regard to the embodiment shown in FIGS. 25-28. In the present embodiment, a head 3004 of the screw member 2902 is captured or retained in order to apply an axial force. This illustrative method of retaining the head 3004 of the screw 2902 is but one possible solution. A collet 2901 fits over the head 3004, an internal surface of fingers of the collet 2901 being formed so as to fit the exterior contour of the head 3004. A compression sleeve 2900 advances axially over the collet 2901 in order to capture the head 3004 within the fingers of collet 2901, as shown in FIG. 30. The screw 2902 is rotated about the axis by a driving mechanism 3002 that passes through the collet 2901 and engages an engagement portion of the head 3004, such as the drive engagement feature 1700 described with respect to embodiments shown in FIG. 16.

An axial force is applied to the screw member 2902 by applying opposing forces onto the threaded central member 2903 against the collet member 3001 and/or the driving member 3002. Depending on when the axial loading condition is to be applied during the procedure of inserting the device into bone, these three members can act in concert to apply either a tensile elongating force or compressive shortening force along the length of the screw 2902. The collet 2901 and/or driving mechanism 3002 may control the rotation of the screw head about the axis. The threaded central member 2903 may also be able to control the rotation of the screw 2903 about the axis of the screw 2902. The collet 2901 alternatively may allow rotation of the screw within the collet 2901 while applying an axial force. The driving member 3002 is an optional member shown here as illustrative.

The threaded central member 2903 can be introduced into the screw before, during, or after the screw 2902 is inserted into the bone. The length of the respective compression sleeve 2900, threaded central member 2903, collet 2901, and driving mechanism 3002 are such that control of the members 2902 is as desired for the given procedure potentially coupled with a mechanism that allowed for and facilitated the application of the desired force in the proper sequence. Member 2902 is similar to that of those shown earlier, however any of the given embodiments or combinations of disclosed herein could be used with this mechanism to achieve the desired outcome.

Figure 32:
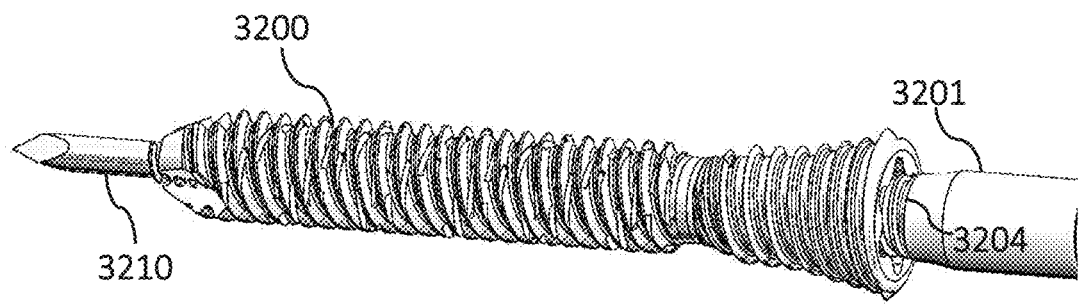
FIG. 32 is a perspective view of a bone fixation assembly with a threaded expandable segment in a non-expanded state and a distal inner thread with a threaded central member and a proximal head retention driver mechanism, in accordance with an aspect of the present invention.
Figure 33:
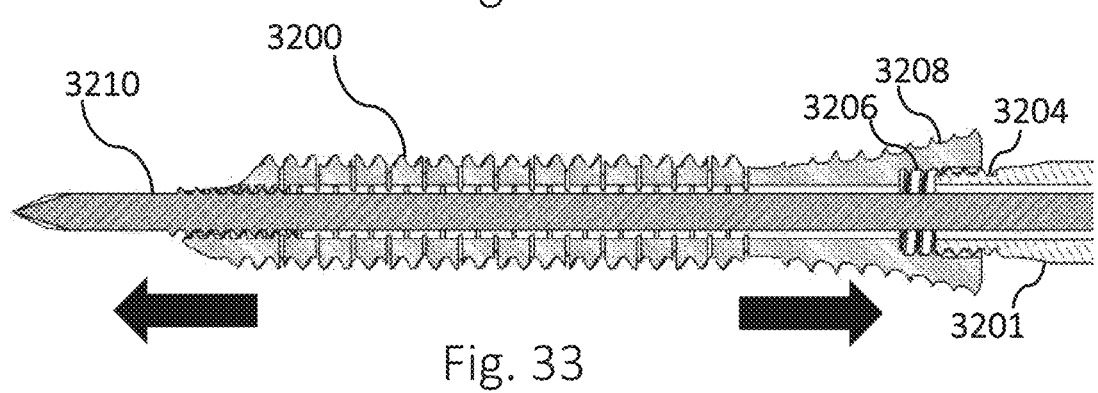
FIG. 33 is a side cross section view of a bone fixation assembly with a threaded expandable segment in a non-expanded state and a distal inner thread with a threaded central member and a proximal head retention driver mechanism, in accordance with an aspect of the present invention.
Figure 34:
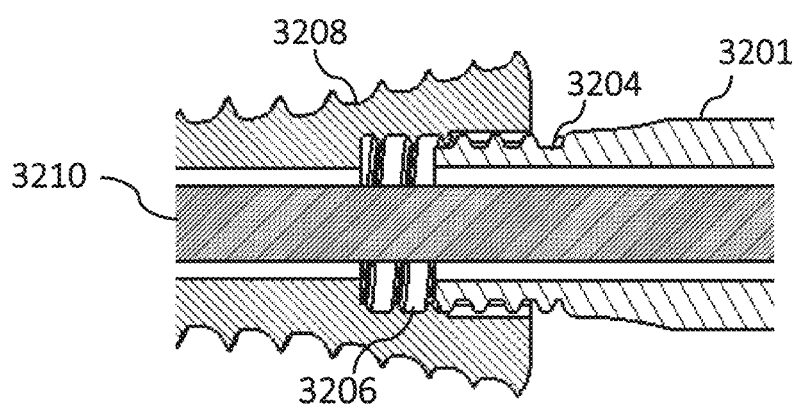
FIG. 34 is a side cross section, enlarged view of a portion of a bone fixation assembly with a threaded expandable segment in a non-expanded state and a distal inner thread with a threaded central member and a proximal head retention driver mechanism, in accordance with an aspect of the present invention.

FIGS. 32, 33, and 34 show another embodiment of the present invention in which a distal, internal portion of a joining member 3200 is threaded such as that described above with regard to the embodiment shown in FIGS. 25-28. This embodiment is illustrative of yet another manner in which axial and rotational load is applied to the joining member or screw body along and about its axis. A driver member 3201 employs threads 3204 in addition to or in place of any other engagement features. The threads 3204 engage threads 3206 on a head 3208 of the screw 3200. The driver member 3201 and a central threaded member 3210 can then apply an axial force along the length of the member 3200 in compression or tension.

Alternatively, an internal surface of the distal end of the member 3200 may be stepped down or reduced in diameter and an external surface of the central threaded member 3210 may have a corresponding step up or increased diameter. The stepped features interfering such that the central threaded member 3210 does not pass axially beyond the step feature in the screw 3200. This combination would allow for an axial tensile force to be applied along the length of the screw between the driver and tip of the screw through the central member. The same effect could be accomplished by not engaging the threads rotationally on the screw and central member, thus allowing for one-way axial loading to be applied.

Figure 35:
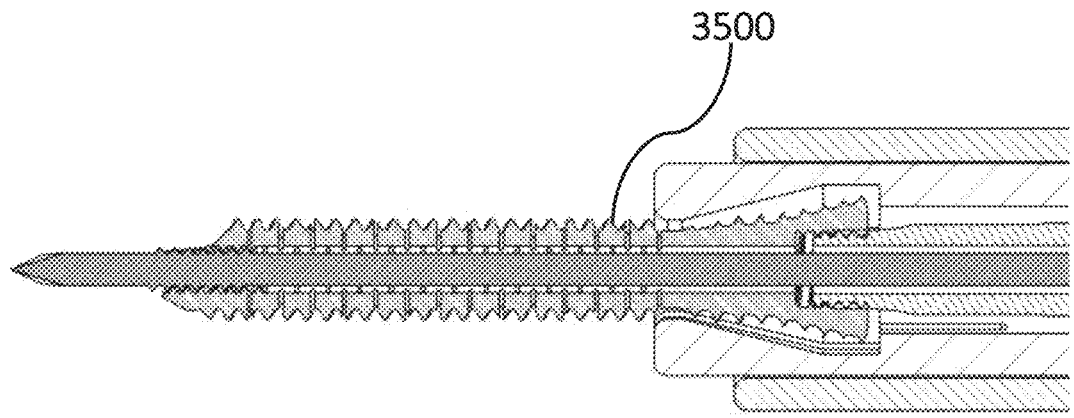
FIG. 35 is a side cross section view of a bone fixation assembly with a threaded expandable segment in a non-expanded state and a distal inner thread with a threaded central member and a proximal head retention driver mechanism and a proximal head retention collet mechanism, in accordance with an aspect of the present invention.
Figure 36:
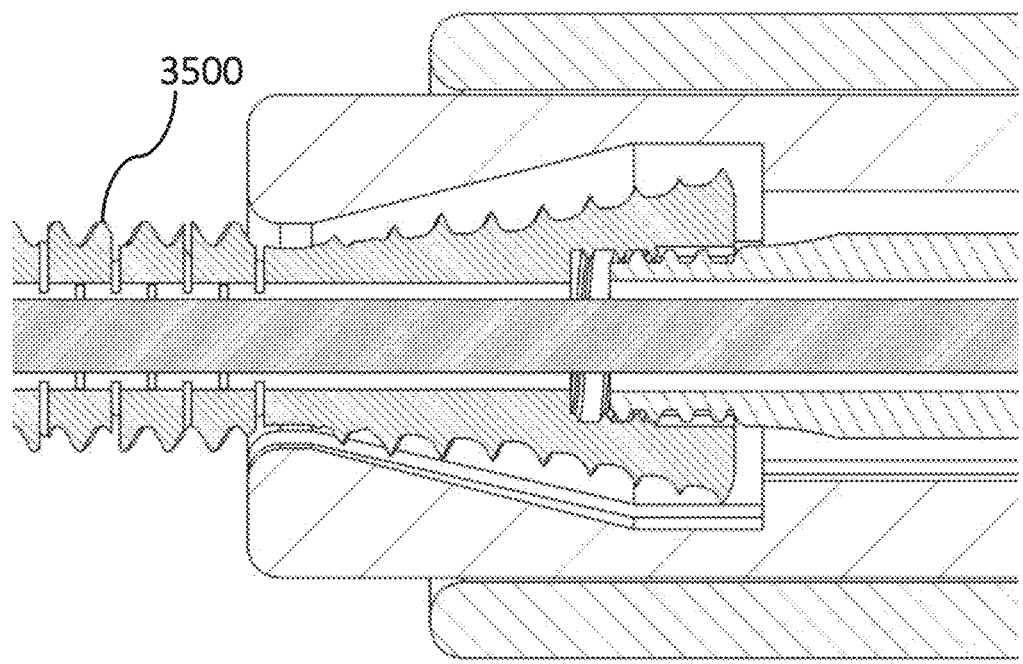
FIG. 36 is a side cross section close up view of a bone fixation assembly with a threaded expandable segment in a non-expanded state and a distal inner thread with a threaded central member and a proximal head retention driver mechanism and a proximal head retention collet mechanism, in accordance with an aspect of the present invention.

FIGS. 35 and 36 show another embodiment of the present invention in which a distal, internal portion of a joining member 3500 is threaded such as that described above with regard to the embodiment shown in FIGS. 25-28 and a collet mechanism as described with respect to the embodiment shown in FIGS. 29-31, further coupled with the threaded driver features described with respect to the embodiment shown in FIGS. 32-34; as an illustrative example of combining any and all of the features disclosed herein.

FIGS. 37-39 show another embodiment of the present invention in which device 3700 employs a deformable section similar to the deformable section 2002 without threads as described with respect to the embodiments shown in FIGS. 21-24. A deformable portion 3702 employs cut slot features 3704. FIG. 38 shows such cut slot features 3704 of the deformable portion 3702 of device 3700 in a stretched or strained state, and FIG. 39 shows such cut slot features 3704 of the deformable portion 3702 of device 3700 in a FIG. 38 and relaxed of unstrained state. Conversely and alternatively, the strained and relaxed states of the member 3700 can be opposite if the initial state of the member 3700 was that of an expanded condition and the closed, reduced state required an axial force to obtain the compressed state shown in FIG. 39. The above-described, alternative configuration can and does apply to all the embodiments disclosed herein.

The amount of length change of the member 3700 is a result or function of a change in a dimension, for example a width, of cut slot features 3704. It is also a function of the number of cut slot features 3704 employed along the length or longitudinal axis of the member 3700. A small change in individual slot gap width could be obtained by many materials common to the construction of orthopedic bone screws including but not limited to, titanium's, stainless steels, cobalt chromes, SMA's (shape memory alloys), nitinol, magnesium's, plastics, PEEK, PLLA, PLGA, PGA and other alloys. The amount of change desired could range from 0 mm to over 10 mm depending on the application of mechanism and procedural application.

FIGS. 40, 41, and 42 show another embodiment of the present invention in which a device 4000 employs a deformable section similar to the deformable section 2002 described with respect to the embodiments shown in FIGS. 21-24. In certain applications, it may be desirable to apply an axial force to the device or screw 4000 and maintain that load until a point in time in which it is desired to release the load. The present embodiment is but one example of a mechanism that would facilitate such an application. The member or screw body 4000 employs receiving features 4002 trans-axially positioned in a distal portion and a proximal portion of member 4000, depicted in FIGS. 40 and 42 as holes or apertures. The receiving features 4002 are designed to receive complementary features or pins 4106 positioned through holes 4104 of a central member 4100.

The features 4106 are inserted into the holes 4104 of the central member 4100 and receiving features 4002 of the screw 4000 during manufacturing while the screw is in a loaded or stretched state. In certain embodiments, the features 4106 are made of a material that is biocompatible but having the material properties required to retain the loaded or strained condition of the screw. Materials include but are not limited to all the materials the screw and central member can be constructed from, and, in certain embodiments, are formed of any of the bioabsorbable materials or any of the other material concepts listed herein. In operation, a driver 4008 applies an axial rotation force to deploy the screw 4000 into the bone with the central member 4100 assembled within the screw 4000. The central member can then be removed from the screw 4000 through application of additional force, either axial or rotational. The force will shear off the members 4106 in the receiving features 4002 of the screw member 4000. The central member then can be removed if desired.

Alternatively, in embodiments in which the pins 4106 are formed of a bioabsorbable material, the screw member 4000 can be implanted in a stretched state and, over a prescribed amount of time after implantation, the pins are absorbed by the body and the axial compression force is exerted between bones or bone fragments to facilitate healing and/or fusion.

Figure 43:
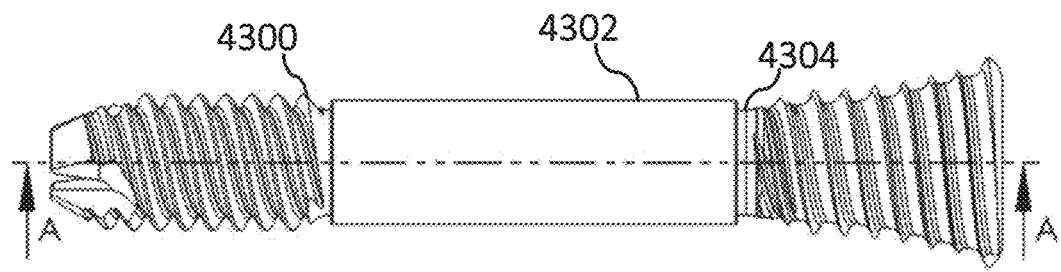
FIG. 43 is a side view of a bone fixation device with a non-threaded expandable segment in a non-expanded state with a central exterior stiffening member, in accordance with an aspect of the present invention.
Figure 44:
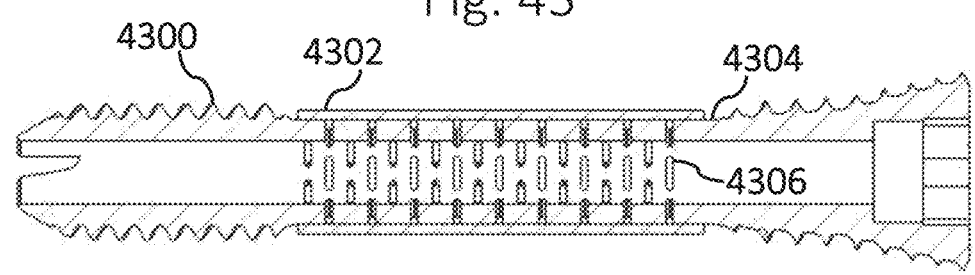
FIG. 44 is a side cross section view of a bone fixation device with a non-threaded expandable segment in a non-expanded state with a central exterior stiffening member, in accordance with an aspect of the present invention.

FIGS. 43 and 44 show another embodiment of the present invention in which a screw member 4300 employs a member 4302 to provide resistance to radial flexion or bending of the screw member 4300 relative to axis A-A. The member 4302 can, for example, be a sleeve or tube that is applied over an outside diameter of a deformable portion 4304 employing cut slots 4308. The sleeve 4302 can be free floating or attached to the screw 4300 so as to allow the screw member to still change in length relative to the sleeve member 4300. For example, the sleeve 4302 can be attached a one point or at one end to the screw 4300. The sleeve member 4302 can be applied and then welded or joined to itself so as to form a continuous circumferential member around a portion of screw member 4300. The sleeve member 4302 can, alternatively, be threaded onto the screw and then reside in the area with no threads. The sleeve member 4302 could be made from the same material as the screw or any of the other materials described herein. The sleeve member 4302 may further employ features to help maintain a preload of the screw member 4300.

Figure 45:
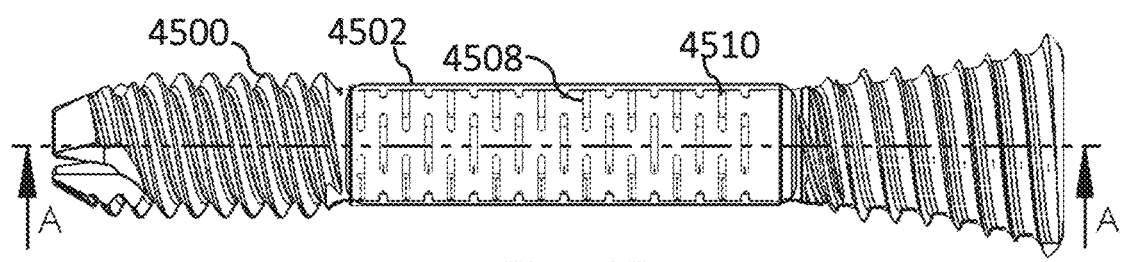
FIG. 45 is a side view of a bone fixation device with a non-threaded expandable segment in an expanded state with a central dissolvable member, in accordance with an aspect of the present invention.
Figure 46:
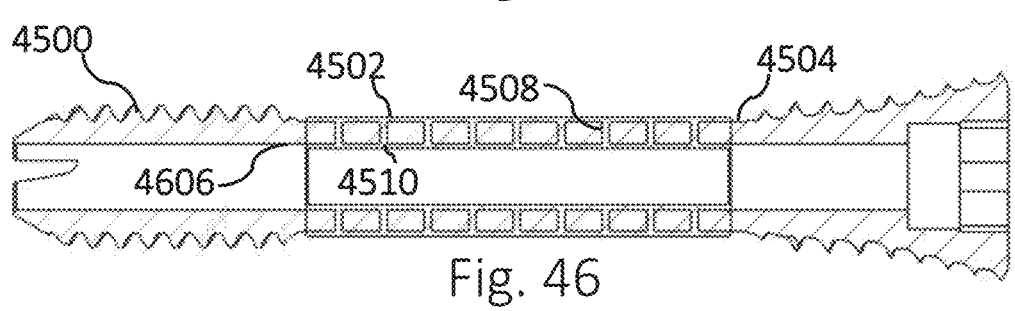
FIG. 46 is a side cross section view of a bone fixation device with a non-threaded expandable segment in an expanded state with a central dissolvable member, in accordance with an aspect of the present invention.

FIGS. 45, and 46 show another embodiment of the present invention in which a screw member 4500 which employs filler member 4502 that functions, in part, to occupy the space or voids 4510 formed by cut slots 4508, thereby limiting the ability of the screw member 4500 to change or decrease in length. The member 4502 may cover an outer surface 4504 of the screw member 4500 and/or fill all or a portion of an interior 4606 of the screw member 4500, in addition to occupying the space or voids formed by the cut slots 4508.

The filler member 4502 is formed of a material that changes in physical and/or chemical properties upon insertion into and exposure to bodily tissue. In certain embodiments, the filler member 4502 is formed of a material that is dissolvable, bio-absorbable, resorbable, amorphic, degradable, soluble, flexible, meltable and/or disintegrable. In certain embodiments, the filler member 4502 is formed of a material that changes in properties such that it becomes or transforms to a state that is not strong enough to resist a compressive force imparted on opposing struts defining the spaces or voids 4510 formed by cut slots 4508. Alternatively, the filler member 4502 is formed of a material that change in material properties such that it is no longer present in the spaces or voids 4510 formed by cut slots 4508.

The rate at which the material from which the filler member 4502 is formed allows the struts to move and apply compressive force can be controlled by material selection and or adjusting material formulation. Depending upon the application, it may be desired to apply the compressive force immediately after implantation or soon thereafter. Materials that may facilitate this could be similar to sugars, salts, or other biocompatible soluble materials. The desired rate of force application may be over several weeks or months, in which absorbable materials could facilitate this behavior, such as poly(lactic-co-glycolic acid) (PLGA); poly(glycolic acid) (PGA); polylactic acid (PLA); polycaprolactone (PCL) and the various copolymers that can be made by combining the same. The materials such as collagen, hydroxyapatite, calcium phosphates, polyvinyl chlorides, polyamides, silicones, polyurethanes, and hydrogels could be used as they can also be formulated to change in material properties over time. There are many approaches for material absorption and disintegration known to those familiar with the art and are herein incorporated in concept.

In certain embodiments, the material from which the filler member 4502 is formed is a flexible material that can only be compressed to a known dimension, but that can stretch or elongate. This embodiment could be used to aide in imparting a radial bending stiffness but not limit the extension properties of the expandable member.

Generally speaking, the present embodiment employs a material, in addition to the material or materials from which the joining member or screw is formed, that in one state is rigid enough to maintain the struts of cut slots of the deformable portion of the device in one position during insertion into tissue, then after that insertion the additional material has a second state in which the material changes properties such that the struts or slots have the force to overcome that of the additional material, and the rate at which this can be adjusted ranges from times of less than one minute to several months.

Figure 47:
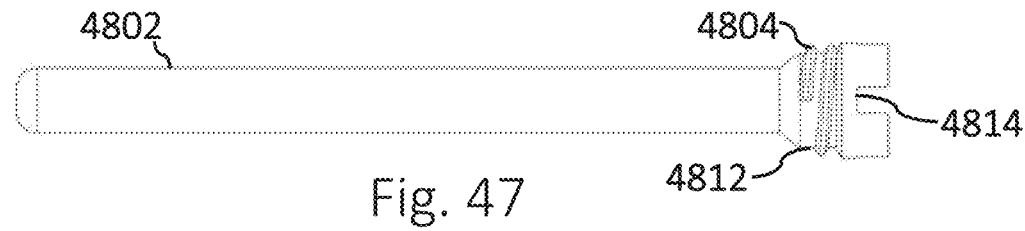
FIG. 47 is a side view of a threaded central member with a proximal head retention mechanism, in accordance with an aspect of the present invention.
Figure 48:
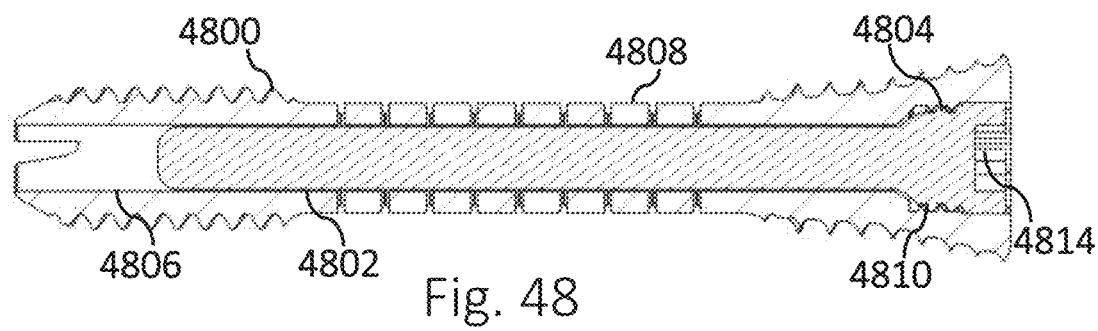
FIG. 48 is a side cross section view of a bone fixation assembly with a non-threaded expandable segment in a non-expanded state and a proximal inner thread with a threaded central member with a proximal head retention mechanism, in accordance with an aspect of the present invention.
Figure 49:
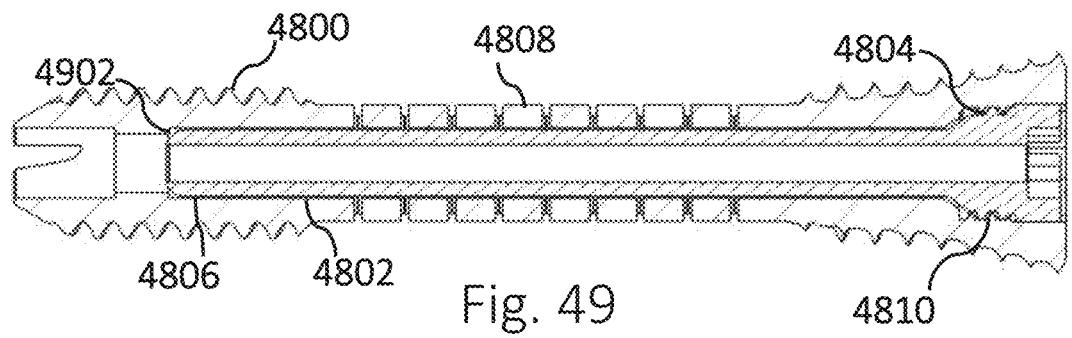
FIG. 49 is a side cross section close up view of a bone fixation assembly with a non-threaded expandable segment in an expanded state and a proximal inner thread with a threaded central cannulated member with a proximal head retention mechanism, in accordance with an aspect of the present invention.

FIGS. 47-49 show additional embodiments of the present invention in which a joining member or screw 4800 employs an inner member 4802 insertable within a lumen 4806 of screw 4800 for the purpose of adding radial stiffness to the member or screw 4800. The inner member 4802 may reside within an entire length of the implant member 4800 or a portion less than the entire length of the member 4800. The inner member 4802 is added or inserted into the screw member 4800 pre-implantation, during, or post implantation into the body. The inner member 4802 can be solid or cannulated. FIG. 47 depicts a solid member 4802 with a threaded head 4804 having a tool engagement feature 4814. As shown in FIG. 48, during assembly, member 4802 is inserted into lumen 4806 of member 4800 and extends a length exceeding that of a deformable portion 4808 of screw 4800. The threaded head 4804 of inner member 4802 is rotated to engage a receiving feature 4810 formed within head 4812 of screw 4800 in order to join together or couple the inner member 4802 and the screw 4800 with a mechanical interlock feature shown by way of example only as threads.

The embodiment shown in FIG. 49 is similar to the embodiments described above and shown in FIGS. 47 and 48, and further employs an interference feature 4902 within a lumen 4806 that interferes or resists the inner member 4802 upon insertion and engagement of the threaded head 4804 of the inner member 4802 with the receiving feature 4810 formed within head 4812 of screw 4800 such that the deformable portion 4808 is stretched or preloaded. The interference feature 4902 can take the form of a reduced or stepped diameter that resists further insertion of the inner member 4802 absent expansion of the deformable portion 4808 of screw 4800. The screw 4800 can then be deployed into bone with the inner member 4802 pre-inserted and therefore the screw 4800 pre-loaded.

Upon delivery of the screw 4800, inner member 4802 can be removed which will release the preload and allow the expandable portion 4808 to apply active compression load to the tissue through the distal and proximal exterior threaded members. The inner member 4802 does not have to be removed completely to accomplish this activation. The inner member 4802 length and head thread 4804 depth can be designed such that the inner member 4802 can be unscrewed the distance of the desired shortening of the expandable section without being removed from the head of the screw 4800. This scenario allows for the inner member 4802 to be retained in order to provide, for example, radial stiffness. The inner member 4802 can be cannulated or solid to better facilitate procedural implantation over a wire. The assembly can be delivered over a K-wire with a one-piece cannulated driver or a nested two-piece cannulated driver, as described above The inner member 4802 can be made of a material that is dissolvable over time as previously described.

The interference feature 4902 can also be shaped as to engage a driver feature to help facilitate delivery by helping distribute or carry torque load to the distal end of the screw and/or axial load or stretching of the screw. The cross section of the driver feature can be any that helps facilitate the load transfer such as but not limited to; hex, star, Philips, slotted, or other.

Figure 50:
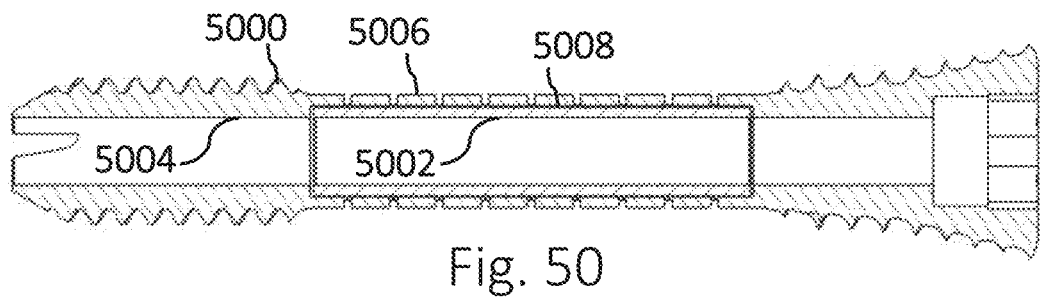
FIG. 50 is a side cross section view of a bone fixation device with a non-threaded expandable segment in a non-expanded state with a central interior stiffening member, in accordance with an aspect of the present invention.
Figure 51:
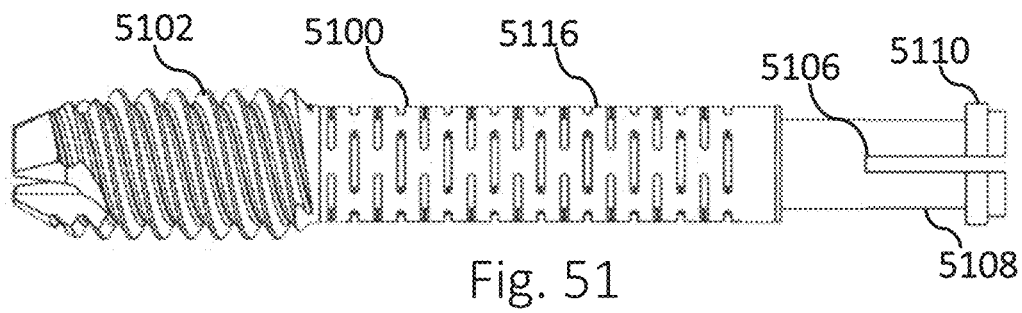
FIG. 51 is a side view of a bone fixation multi component device with a non-threaded expandable segment in a non-expanded state with a central interior stiffening member without a captured but potentially freely rotating proximal head member, in accordance with an aspect of the present invention.
Figure 52:
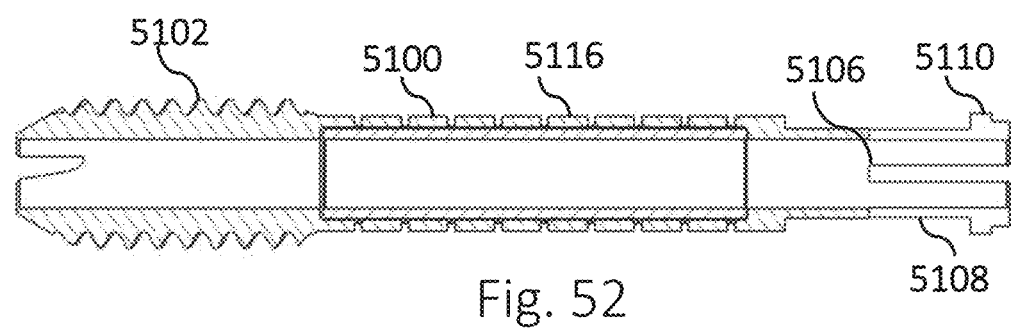
FIG. 52 is a side cross section view of a bone fixation multi component device with a non-threaded expandable segment in a non-expanded state with a central interior stiffening member without a captured but potentially freely rotating proximal head member, in accordance with an aspect of the present invention.

The embodiment of the joining member or screw 5000 shown in FIG. 50 employs a cannulated member 5002 positioned within a lumen 5004 of member 5000. The cannulated member 5002 extends a length distally exceeding that of the deformable portion 5006. The cannulated member 5002 resides in a surface recess or mating feature 5008 having a diameter greater than a diameter of the lumen 5004 of the screw 5000. The difference in diameters may be equal to substantially equal to a thickness of a side wall of the cannulated member 5002 such that the presence of the cannulated member 5002 does not effectively reduce the diameter of the lumen 5004. In certain embodiments, the mating feature 5008 is machined in the lumen 5004. The cannulated member 5002 is slightly shorter in length than the mating feature 5008 to allow for axial length change in the screw body. The mating feature 5008 can be inserted in many different ways into the lumen 5004, including, but not limited to: employing a cut tube configuration that collapses and then expands within the lumen 5004; employing a threaded tube configuration that is passed into a thread the mating feature 5008; employing a multi-part screw 5000 that is joined around the member; and all other methods of construction described herein.

FIGS. 51-54 show additional embodiments of the present invention in which a member 5100 employs a feature set that allows a distal threaded portion 5102 to rotate separate or independent from a rotation of a proximal head portion 5304. The screw member 5100 employs a tool engagement feature 5106 for insertion of the distal threaded portion 5102 into bone, one of more deflecting members 5108, and a head retention feature 5110. The proximal head portion 5304 employs a tool engagement feature 5412 and a receiving feature 5414. The receiving feature 5414 of the proximal head portion 5304 is configured to accept the head retention feature 5110 of the screw member 5100 so as to longitudinally and radially couple the distal threaded portion 5102 to the proximal head portion 5304 while allowing rotational freedom between the distal threaded portion 5102 and the proximal head portion 5304, e.g. through a lip and groove configuration.

Loading of the device 5100 may be achieved by rotating the distal threaded portion 5102 and the proximal head portion 5304 sequentially at a different or a same rate; rotating both the distal threaded portion 5102 and the proximal head portion 5304 simultaneously at a different or a same rate; after implantation, by further rotating the distal threaded portion 5102 or the proximal head portion 5304 while the other portion is maintained stationary; or by rotating the distal threaded portion 5102 and the proximal head portion 5304 in opposite directions. A nested driver set or independent drivers can be used to independently engage the tool engagement feature 5106 of the screw member 5100 and the tool engagement feature 5412 of the proximal head portion 5304.

Figure 53:
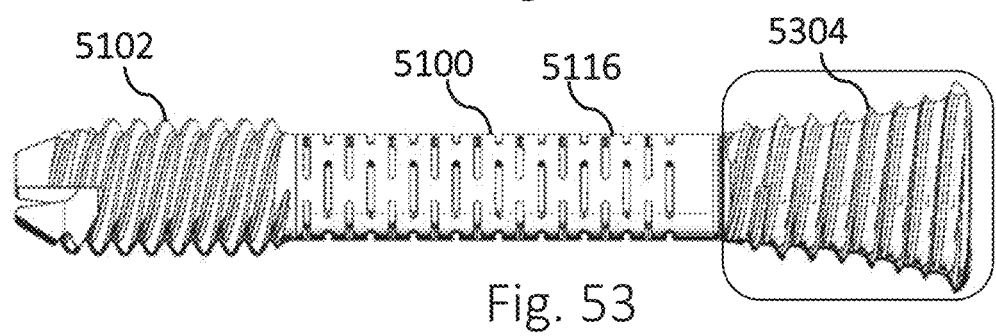
FIG. 53 is a side view of a bone fixation multi component device with a non-threaded expandable segment in a non-expanded state with a central interior stiffening member and a captured but potentially freely rotating proximal head member, in accordance with an aspect of the present invention.
Figure 54:
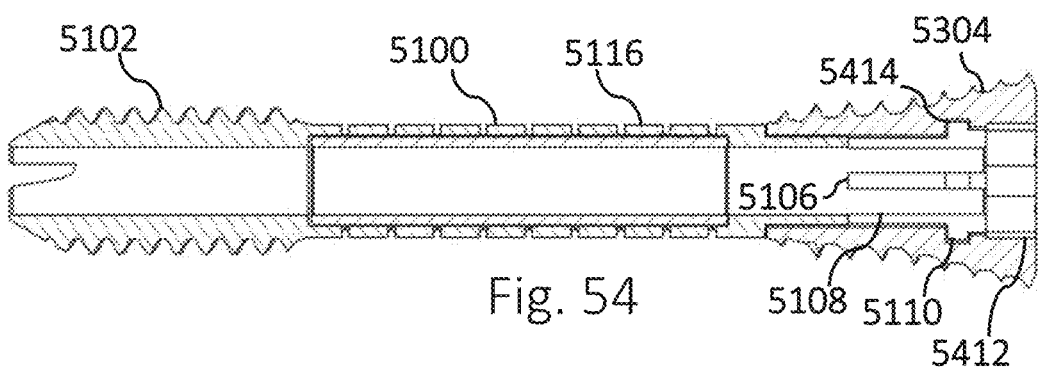
FIG. 54 is a side cross section view of a bone fixation multi component device with a non-threaded expandable segment in a non-expanded state with a central interior stiffening member and a captured but potentially freely rotating proximal head member, in accordance with an aspect of the present invention.

The proximal head portion 5304 is shown in FIGS. 53 and 54 with threads but need not include such. Assembly or attachment of the distal threaded portion 5102 to the proximal head portion 5304 may be facilitated through radial, inward deflection of the one or more deflecting members 5108 so as to allow for engagement of the receiving feature 5414 of the proximal head portion 5304 and the head retention feature 5110 of the distal threaded portion 5102.

For the sake of clarity, the screw 5100 shown in FIGS. 51-54 is shown as employing a cannulated member such as that described with respect to the cannulated member 5002 shown in FIG. 50. However, the screw 5100 may, but need not, employ such a cannulated member and is shown as employing such merely as an example of the various combinations of inventive features contemplated.

An example of procedural implementation: Drive distal end 5102 which may elongate center section 5100, bodies rotates relative to proximal end 5304 but is connected. A first driver engages distal member 5100 potentially using feature 5106 and elongates center as distal threads 5102 engage bone while proximal end 5300 swivels and remains stationary. A second driver that may be cannulated engages the proximal end 5304 and the first driver, effectively driving both distal and proximal ends the same distance into the bone, while maintaining pre-load and active compression.

Alternatively, the entire screw body could be driven into the bone at one time and then the distal end 5102 could be further driven independently effectively lengthening the expandable section and creating the axial load.

Figure 55:
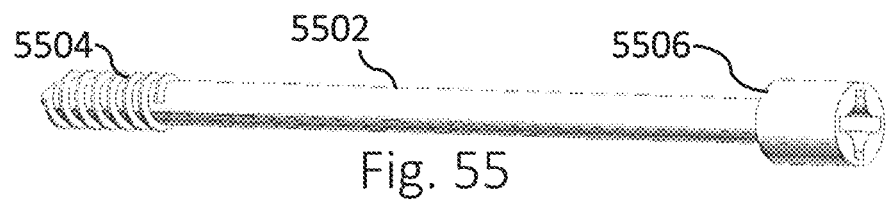
FIG. 55 is a perspective view of a central interior stiffening member with threaded distal engagement features and a proximal head member, in accordance with an aspect of the present invention.
Figure 56:
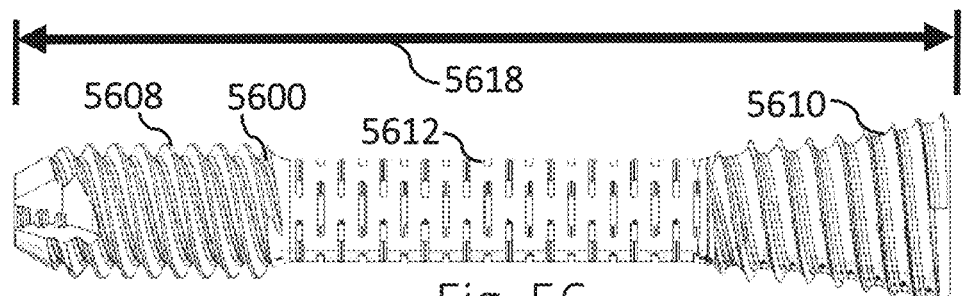
FIG. 56 is a side view of a bone fixation multi component device with a non-threaded expandable segment in an expanded state with threaded distal engagement features, in accordance with an aspect of the present invention.
Figure 57:
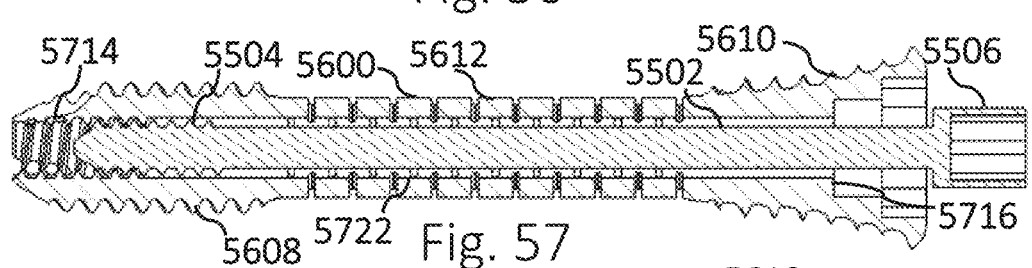
FIG. 57 is a side cross section view of a bone fixation multi component device with a non-threaded expandable segment in an expanded state with a central interior stiffening member with threaded distal engagement features and a proximal head member, in accordance with an aspect of the present invention.
Figure 58:
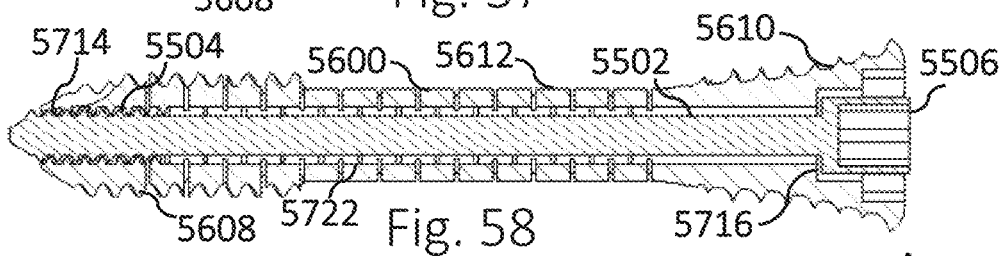
FIG. 58 is a side cross section view of a bone fixation multi component device with a non-threaded expandable segment in a non-expanded state with a central interior stiffening member with threaded distal engagement features and a proximal head member, in accordance with an aspect of the present invention.
Figure 59:
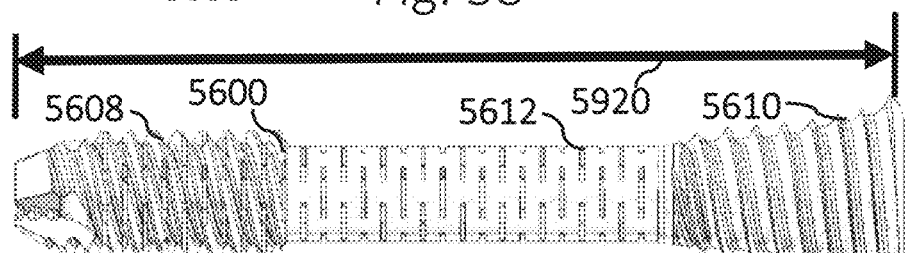
FIG. 59 is a side view of a bone fixation multi component device with a non-threaded expandable segment in a non-expanded state with a central interior stiffening member with threaded distal engagement features and a proximal head member, in accordance with an aspect of the present invention.
Figure 60:
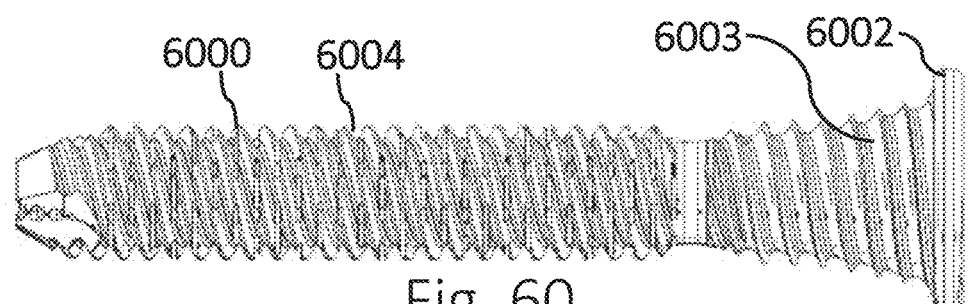
FIG. 60 is a side view of a bone fixation device in a non-expanded state with a proximal head engagement feature, in accordance with an aspect of the present invention.
Figure 61:
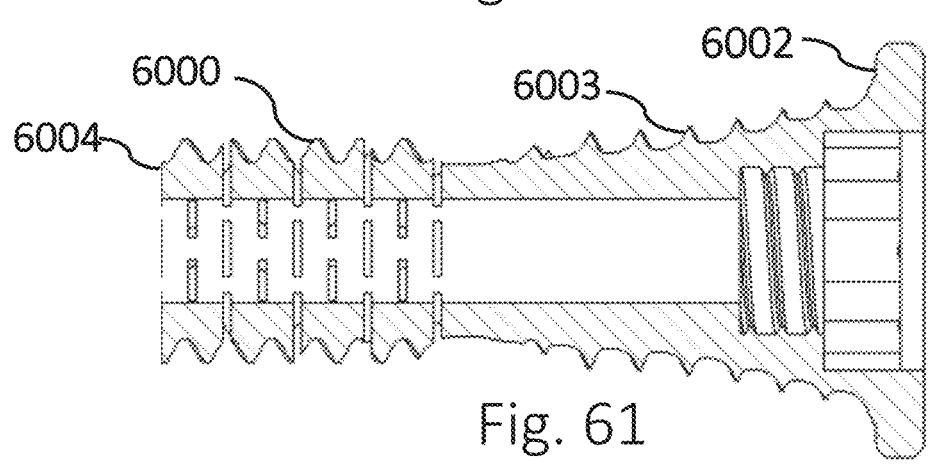
FIG. 61 is a side cross section close up view of a bone fixation device in a non-expanded state with a proximal head engagement feature, in accordance with an aspect of the present invention.
Figure 62:
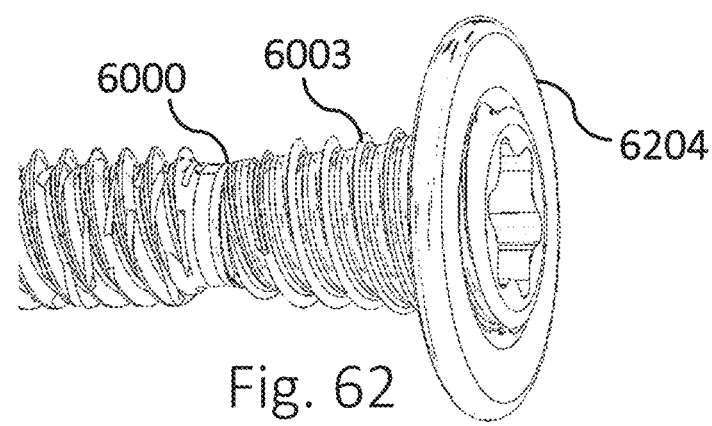
FIG. 62 is a perspective view of a bone fixation device in a non-expanded state with a freely rotating proximal head engagement feature, in accordance with an aspect of the present invention.
Figure 63:
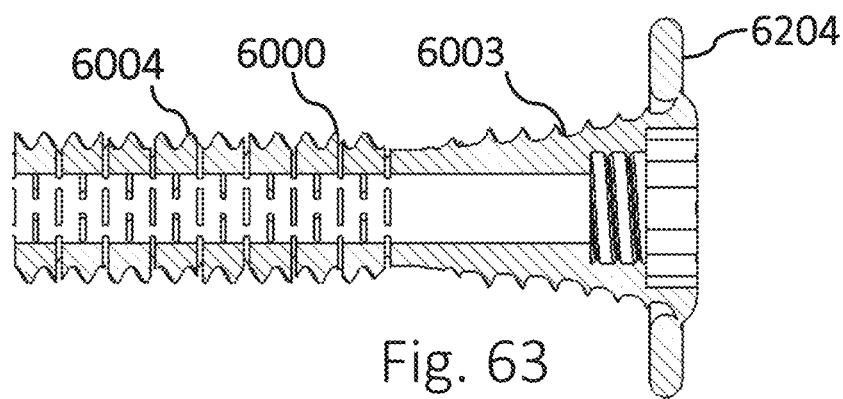
FIG. 63 is a side cross section close up view of a bone fixation device in a non-expanded state with a freely rotating proximal head engagement feature, in accordance with an aspect of the present invention.

FIGS. 55-59 show an additional embodiment of the present invention in which an axial force of joining member 5600 may originate from or be assisted by employing a central member 5502. As shown in FIGS. 55, 57, and 58, the central member 5502 has a distal engagement feature 5504, such as threads, and a proximal head 5506. As shown in FIGS. 57-59, the joining member or screw 5600 has a distal portion 5608, a proximal head portion 5610, a deformable portion 5612 interposed there between, and a lumen 5722. While the proximal head portion 5610 of the screw 5600 is shown as being threaded, the proximal head portion 5610 need not be threaded.

The distal portion 5608 has an inner engagement feature 5714 that is complementary to the distal engagement feature 5504 of the central member 5502, and the proximal head portion 5610 has an inner engagement feature 5716 that is complementary to an exterior of the proximal head 5506 of the central member 5502. The joining member or screw 5600 has a first state with a length 5618, shown in FIGS. 56 and 57 in which the deformable portion 5612 is in a lengthened or expanded state. The joining member or screw 5600 has a second state with a length 5920, shown in FIGS. 58 and 59 in which the deformable portion 5612 is in a shortened or compressed state.

In one embodiment, the central member 5502 is inserted into the lumen 5722 and (1) the distal engagement feature 5504 of the central member 5502 is engaged with the inner engagement feature 5714 of the distal portion 5608 of the screw 5600, for example by rotation, and (2) the proximal head 5506 of the central member 5502 is engaged with the inner engagement feature 5716 of the proximal head portion 5610 of the screw 5600. These engagements may occur prior to or after implantation of the screw 5600 into bone matter. These engagements limit the distal advancement of the central member 5502 through lumen 5722 of screw 5600. Continued rotation or engagement of the central member 5502 relative to the screw 5600 applies an axial load of tension on the central member 5502 and simultaneously a compressive axial force on the screw 5600. Depending upon the relative elastic modulus of the materials from which the central member 5502 and the screw 5600 are formed, several different outcomes may be achieved.

For example, if the central member 5502 is less elastic than the screw 5600, the act of engagement will result in a shortening or compression of the screw 5600 from the lengthened state 5618 to the shortened state 5920, shown in FIGS. 56 and 59, respectively. If the central member 5502 is more elastic than the screw 5600, the act of engagement will result in a lengthening or stretching of stretched central member 5502 and, hence, applying an axial compressive force to the screw 5600. Depending on the design the screw 5600 and/or the deformable portion 5612 of the screw 5600, the force exerted onto the components by the stretched central member 5502, this could then result in a compressive force applied to the bone transmitted through the distal portion 5608 and the proximal head portion 5610 of the screw 5600. The rate of this change in length of the screw 5600 will be dependent on the amount of force the central member exhibits onto the assembly. The central member can, for example, be constructed from a material with high elastic modulus such as nitinol, and the screw member can, for example, be made of any suitable material for orthopedic implants.

In certain alternative embodiments, the proximal head 5506 of the central member 5502 has threads that are complementary to threads of the inner engagement feature 5716 of the proximal head portion 5610 of the screw 5600, similar to the embodiment described above and shown in FIGS. 47-49. A difference of the thread pitch of the threaded distal engagement feature 5504 and threaded proximal head 5506 of the central member 5502 could be such that the proximal head 5506 advances faster than the threaded distal engagement feature 5504 through the lumen 5722 of the screw 5600. Thereby, resulting in an axial tension stress along the screw member 5600. The loaded condition of the screw 5600 would have a length similar to or greater than length 5618 shown in FIG. 56. In this embodiment, screw member 5600 would function like the other embodiments described herein with an elastically expandable portion 5612. Application of the central member 5502 into this described construct would elongate the deformable portion 5612. The construct could be inserted into the bone and then the central member 5502 could be removed releasing the axial compression of the expandable section.

FIGS. 60-63 show additional embodiments of the present invention in which a joining member 6000 is similar to other embodiments presented herein and further employs additional feature 6002 and/or 6204 that function to increase the amount of force required to penetrate or set a head portion 6003 of the screw member 6000 into the desired tissue or bone by increasing an effective diameter of a head 6003 of the member 6000. These embodiments enable a greater axial force to be applied to the screw member 6000, thereby more easily loading the deformable portion 6004 of the screw member 6000. Member 6002 can be a non-unitary or unitary enlarged lip, edge, or flange associated with the head portion 6003 of screw 6000. Feature 6204 is an independent component that is non-unitary with the screw 6000 having a form such as a spring washer that adds to the compressive force upon the system by applying additional axial tension. Feature 6204 allows for independent rotation of the screw member 6000 relative to the feature 6204. The features 6002 and 6204 may be employed independent of one another or in combination with one another on any of the joining members herein disclosed.

Figure 64:
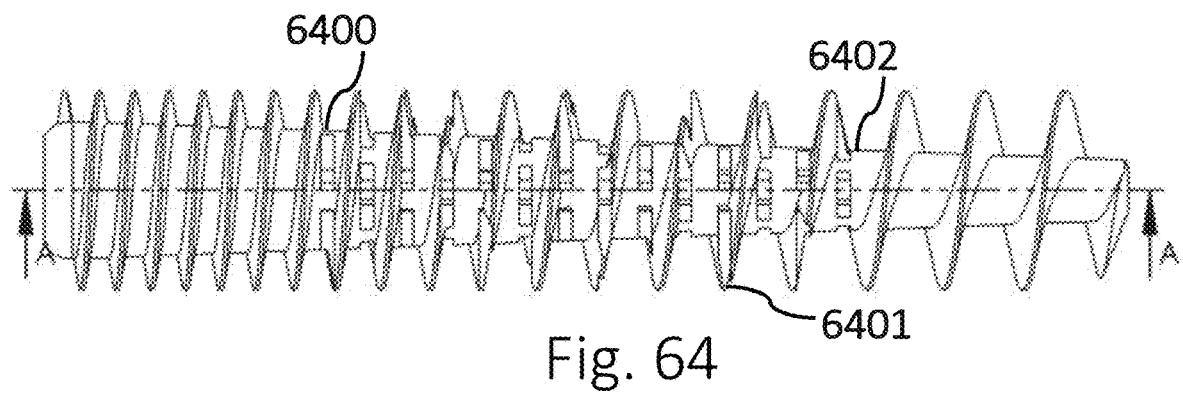
FIG. 64 is a side view of a bone fixation device in a non-expanded state with a tapered minor diameter and variable pitch thread features, in accordance with an aspect of the present invention.
Figure 65:
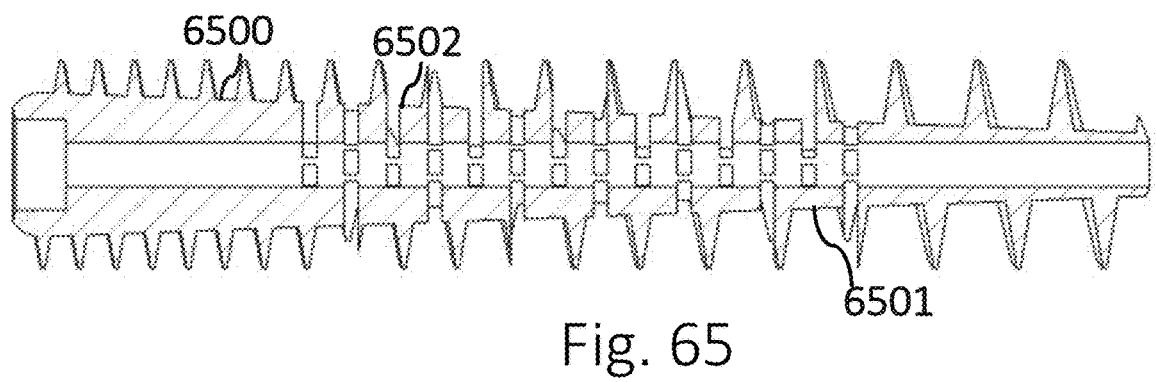
FIG. 65 is a side cross section view of a bone fixation device in a non-expanded state with a tapered minor diameter and variable pitch thread features, in accordance with an aspect of the present invention.

FIGS. 64-71 show additional embodiments of the present invention. These features are depicted as representational and can be employed or otherwise combined with any of the embodiments herein disclosed. The variables of thread pitch and minor and major diameter can all be adjusted to maximize the compression force the screw can create. This in combination with an expandable length and active axial tension force feature could yield an improved clinical efficacy for bone fusion. FIG. 64 shows a side view of a bone fixation device 6400 having an expandable or deformable section in a non-expanded state, a tapered minor diameter 6402, and a variable pitch thread 6401. FIG. 65 shows a side cross section view of a bone fixation device 6500 having an expandable section 6502 in a non-expanded state, a tapered minor diameter 6501, a variable pitch thread, and a cannulation.

Figure 66:
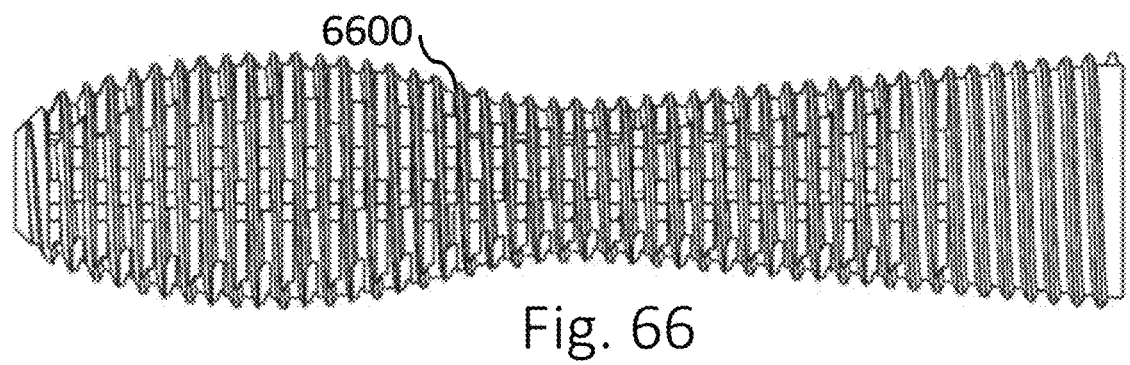
FIG. 66 is a side view of a bone fixation device in a non-expanded state with variable minor and major diameters and triple lead pitch thread features, in accordance with an aspect of the present invention.
Figure 67:
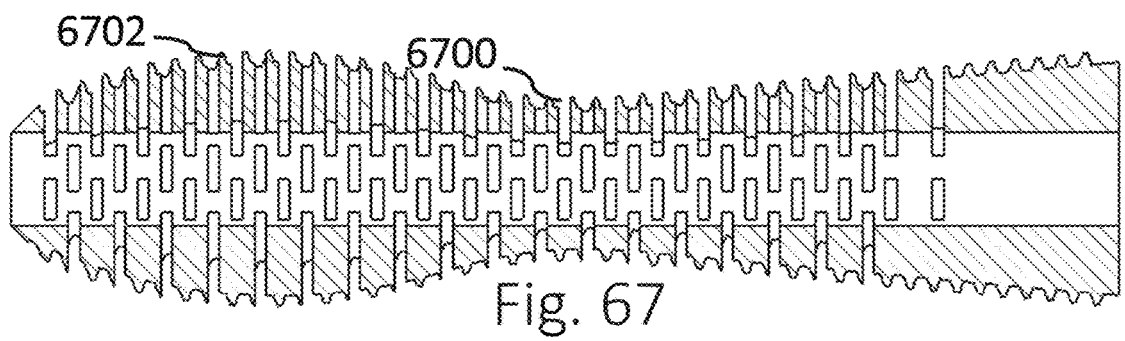
FIG. 67 is a side cross section view of a bone fixation device in a non-expanded state with variable minor and major diameters and triple lead pitch thread features, in accordance with an aspect of the present invention.

FIG. 66 is a side view of a bone fixation device 6600 with an expandable section in a non-expanded state, variable minor and major diameters, and a triple lead pitch thread. FIG. 67 shows a side cross section view of a bone fixation device 6700 having an expandable section 6702 in a non-expanded state with variable minor and major diameters and triple lead pitch thread features. FIG. 68 shows a perspective view of a bone fixation device 6800 having an expandable section 6802 in a non-expanded state, variable minor and major diameters 6801, and a triple lead pitch thread. FIG. 69 is a perspective view of a bone fixation device having a non-threaded expandable section 6901 in a non-expanded state, variable minor and major diameters, a distal triple lead pitch thread 6900, and a variable proximal thread features 6902.

FIG. 70 shows a side cross section view of a bone fixation device having an expandable section 7001 in a non-expanded state, a variable minor and major diameter 7002, a triple lead pitch thread 7000. FIG. 71 shows a side cross section view of a bone fixation device with a non-threaded, expandable section 7101 in non-expanded state, variable minor and major diameters, a distal triple lead pitch thread 7100, and variable proximal threads 7102.

Figure 72:
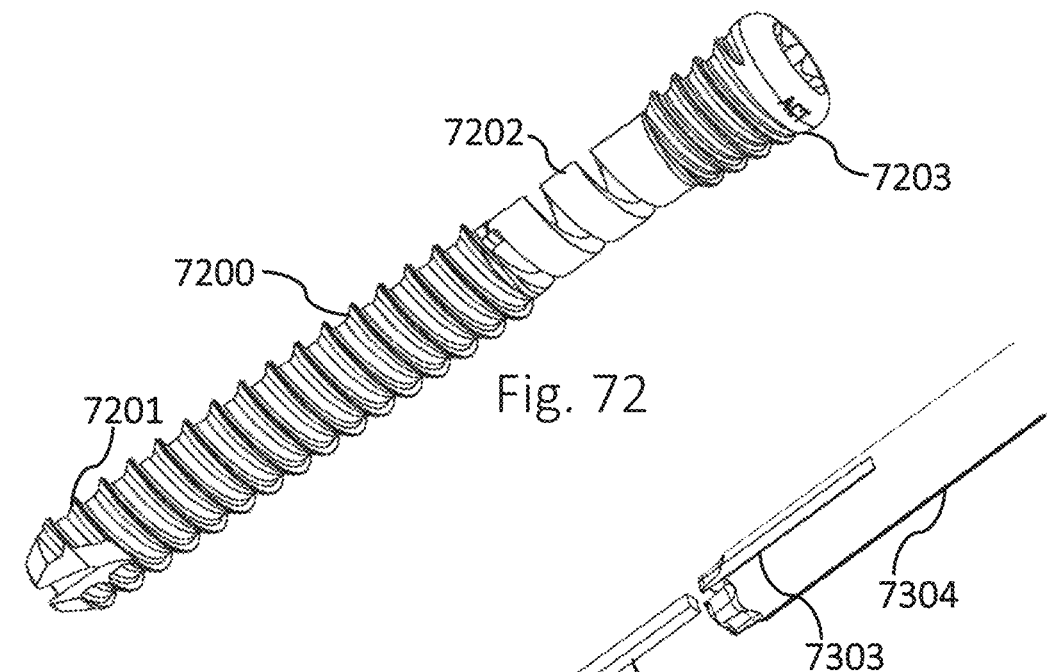
FIG. 72 is a perspective view of a bone fixation device with a non-threaded helical expandable segment in a non-expanded state, in accordance with an aspect of the present invention.
Figure 73:
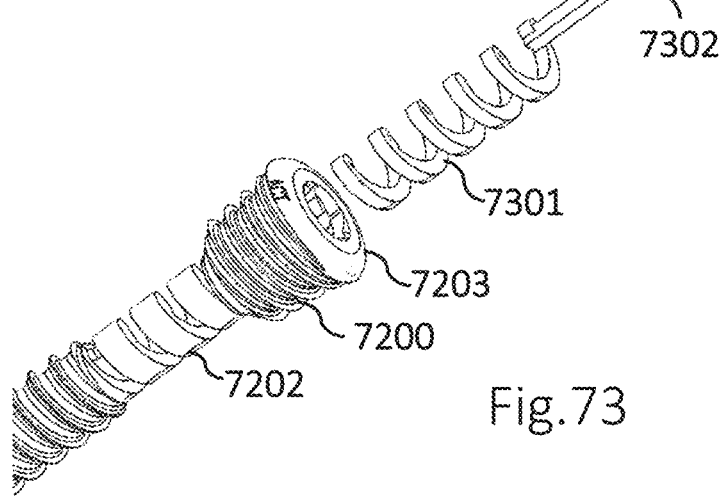
FIG. 73 is a perspective view of a bone fixation assembly with a non-threaded helical expandable segment in a non-expanded state with a helical expansion member and driver, in accordance with an aspect of the present invention.
Figure 79:
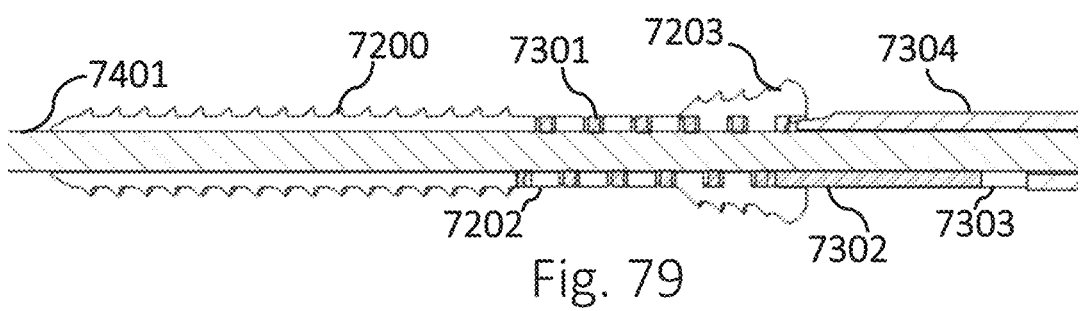
FIG. 79 is a side cross section view of a bone fixation assembly with a non-threaded helical expandable segment in an expanded state with a helical expansion member and driver and central member, in accordance with an aspect of the present invention.

FIGS. 72-79 show yet another embodiment of the present invention in which a joining member or screw 7200 employs a helical deformable portion or section 7202, a preload member 7301, and a delivery and activation mechanism. FIG. 72 depicts the screw 7200 employing the expandable section 7202, a distal portion 7201, and a threaded head 7203. Implementation of the screw 7200 is achieved through employment of the three primary components depicted in FIG. 73: the screw 7200, the helical preload member 7301 having an engagement stem 7302, and a driver 7304 having a receptive feature 7303. FIG. 79 shows the components in an assembled state in cross-section.

Figure 74:
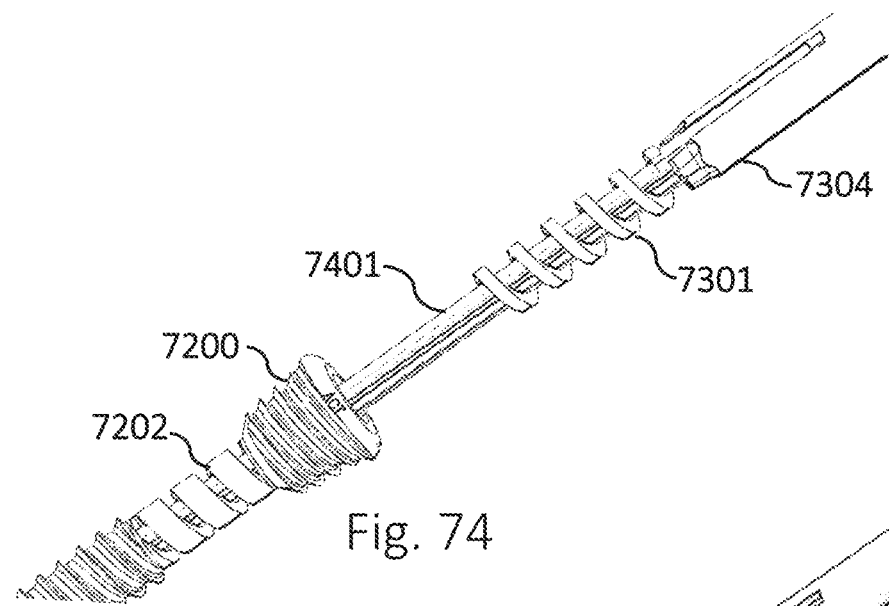
FIG. 74 is a perspective view of a bone fixation assembly with a non-threaded helical expandable segment in a non-expanded state with a helical expansion member and driver and central member, in accordance with an aspect of the present invention.
Figure 75:
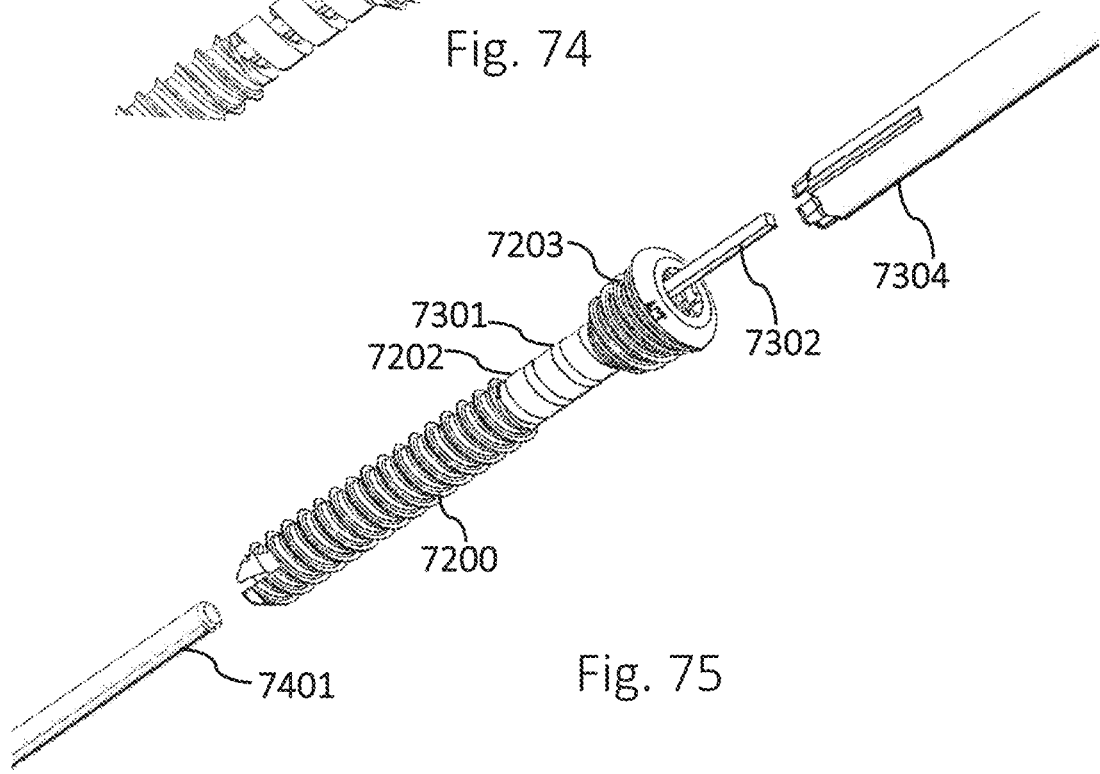
FIG. 75 is a perspective view of a bone fixation assembly with a non-threaded helical expandable segment in an expanded state with a helical expansion member and driver and central member, in accordance with an aspect of the present invention.
Figure 76:
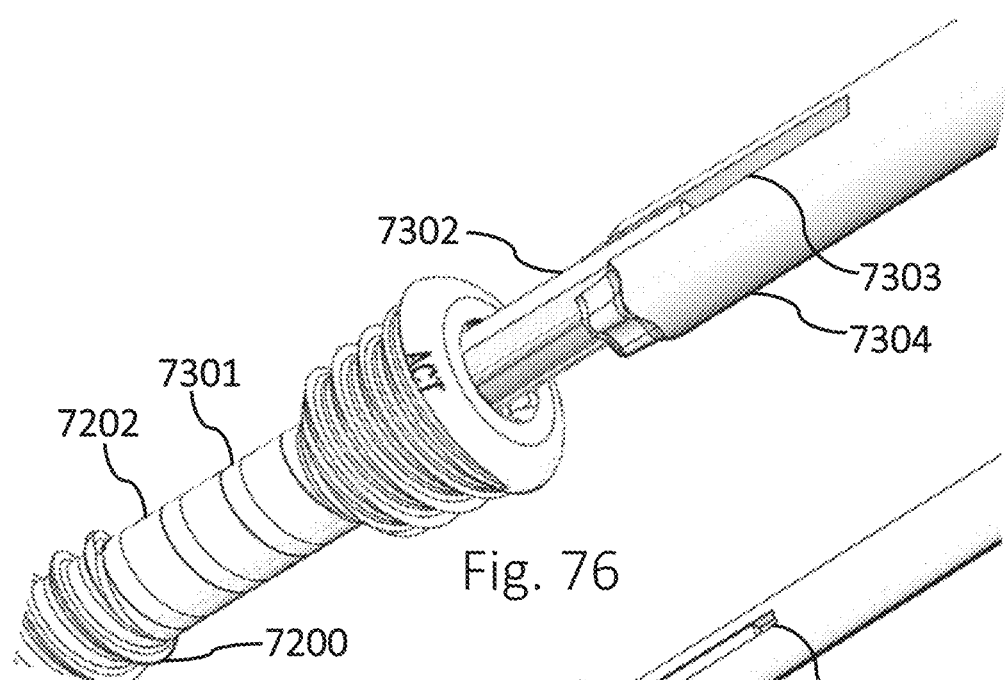
FIG. 76 is a perspective view of a bone fixation assembly with a non-threaded helical expandable segment in an expanded state with a helical expansion member and driver and central member, in accordance with an aspect of the present invention.
Figure 77:
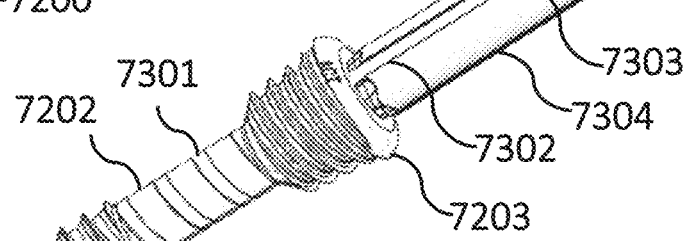
FIG. 77 is a perspective view of a bone fixation assembly with a non-threaded helical expandable segment in an expanded state with a helical expansion member and driver, in accordance with an aspect of the present invention.
Figure 78:
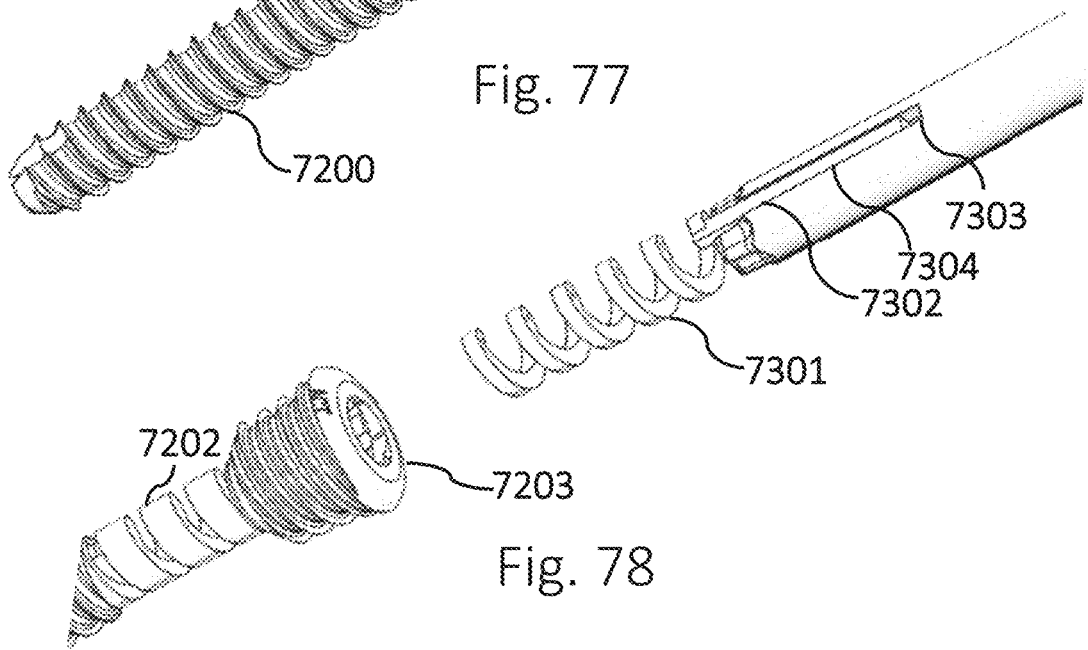
FIG. 78 is a perspective view of a bone fixation assembly with a non-threaded helical expandable segment in a non-expanded state with a helical expansion member and driver, in accordance with an aspect of the present invention.

FIG. 74 depicts the driver 7304 engaged with the helical preload member 7301 over a central wire member 7401. The preload member 7301 has a strut width that is wider than the helical gap width of helical deformable portion 7202. The preload member 7301 is then rotated into the screw 7200 and a proximal portion is seated within the head 7203 of the screw 7200. The driver 7304 and the central wire member 7401 can then be removed from the assembly as shown in FIG. 75. The screw can then be inserted into the bone tissue preloaded. The central member and driver could be attached to the screw and driven into the bone tissue. Then the helical member could be rotated in the opposite direction and removed, allowing the helical section to compressively load the bone tissue.

In an alternative embodiment, external threads of the screw thread 7200 and the helical expansion member 7202 could be threaded in opposite directions such that when the distal portion 7201 of the screw is inserted into the bone tissue the helical loading member would be expanded to create a loading condition as the head of the screw is inserted into the tissue.

FIGS. 80-87 show yet additional embodiments of the present invention. The active compression concept and the related manners of implementation can also be applied to other constructs other than screws. For example, rods are commonly used in orthopedics to repair broken bones and fuse joints. The present embodiments illustrate rods with receiving features that engage trans-axial screws or pins. Alternatively, one or both end of this configuration could be threaded to engage bone tissue or any of the previously described embodiments can be made to receive trans-axial members. In the present embodiment, jigs are used to facilitate the procedure of implanting these rod members into tissue.

Figure 80:
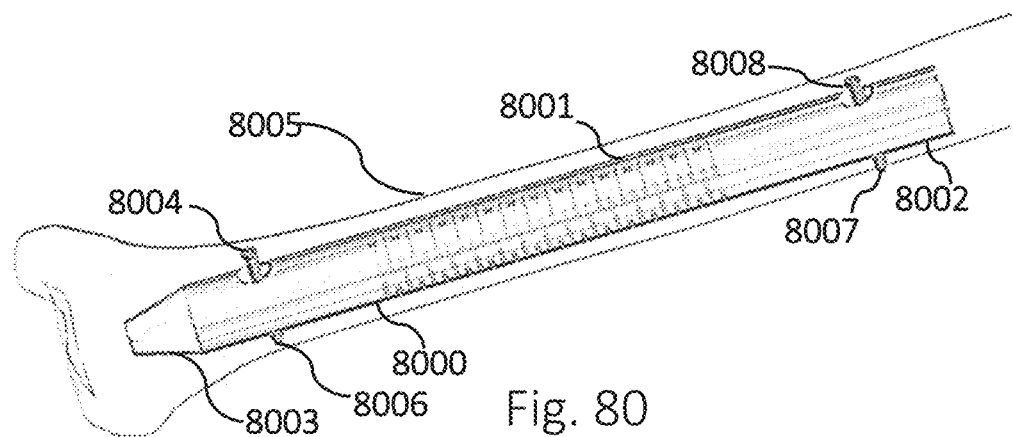
FIG. 80 is a perspective view of a bone fixation assembly with a non-threaded expandable segment in a non-expanded state with trans axial engagement members in a bone, in accordance with an aspect of the present invention.

FIG. 80 depicts a device 8000 implanted in a bone 8005. Device 8000 employs an expandable section 8001, distal engaging members 8004 and 8006, a distal portion 8003, a proximal portion 8002, and proximal engaging members 8007 and 8008. FIGS. 80, 81, 83, and 84 show the device 8000 a contracted state 8101, and FIGS. 82, 85, and 87 show the device 8000 in an expanded state 8201. The distal engaging members 8004 and 8006 and the proximal engaging members 8008 and 8007 can be employed in any combination such as 3 and 4 or 6 and 8 and can be positioned in multiple planes or uniplanar. They could be threaded or unthreaded and, they can employ features that allowed for micro-motion. They can be slots or have a mesh-like structure. They can be anything know to those familiar to the art.

Figure 81:
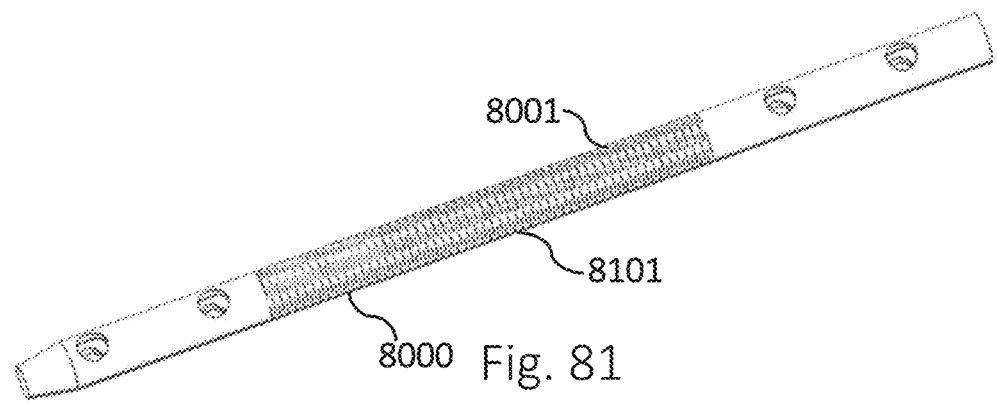
FIG. 81 is a perspective view of a bone fixation assembly with a non-threaded expandable segment in a non-expanded state, in accordance with an aspect of the present invention.
Figure 82:
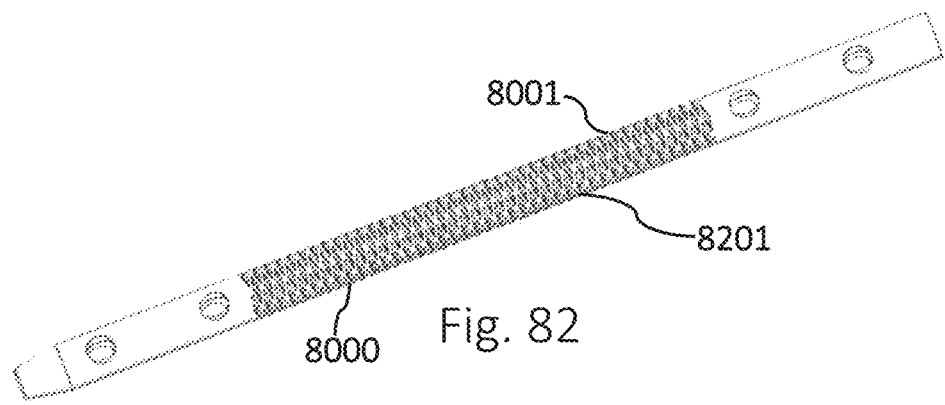
FIG. 82 is a perspective view of a bone fixation assembly with a non-threaded expandable segment in an expanded state, in accordance with an aspect of the present invention.

Conversely the embodiments shown in FIGS. 81 and 82 can be independent embodiments with different activation mechanisms, as previously described herein.

FIGS. 85-87 show the expanded and contracted states of the device 8000 and one possible method for transforming the device 8000 from the contracted state to the expanded state through employing member 8701 and stops 8703 and 8702. For example, stop 8703 is inserted into member 8200 and then member 8701 is inserted into a lumen of device 8200. The stop 8703 restricts the axial forward advancement of member 8701 and, with additional axial force of advancement the center expanding member 8701, deformable portion 8001 becomes stressed or longitudinally expanded. Stop 8702 is then inserted to lock member 8701 within the device 8200 and, at least temporarily fix the device 8200 in that expanded state 8201. The device 8200 can then be used to treat a broken bone or fusion. Once implanted into the desired anatomy with engaging members 8004, 8006, 8007 and/or 8008, or any suitable engagement strategy, the stops 8703 and/or 8702 are either removed, dissolved, weakened, sheared, or some other suitable action that will allow member 8701 to transverse axially toward the distal end such that the deformable portion 8001 is allowed to retract or collapse and the device 8200 reduces in length, either immediately or over a prescribed time period.

FIGS. 88-93 show embodiments and configurations of a cut slot patterns employed in the expandable or deformable portions or sections of any embodiments of the present invention herein disclosed. This pattern can be employed to cut a tube of material to manufacture all or a portion of a member 8800. FIG. 88 depicts a flat or unidimensional representation of the member 8800 having the cut slot pattern 8801. FIGS. 89 and 90 are progressive enlargements of a portion of the cut slot pattern 8801 shown in FIG. 88. Spaces or voids 9002 between struts 9004 are areas where material is not present. It will be understood that FIGS. 88-90 may similarly show the pattern 8801 wrapped around a tubular member.

Figure 91:
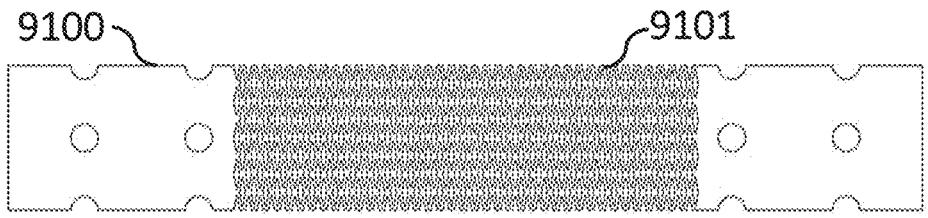
FIG. 91 is a side view of a portion of a bone fixation device with a non-threaded expandable segment in an expanded state, in accordance with an aspect of the present invention.
Figure 92:
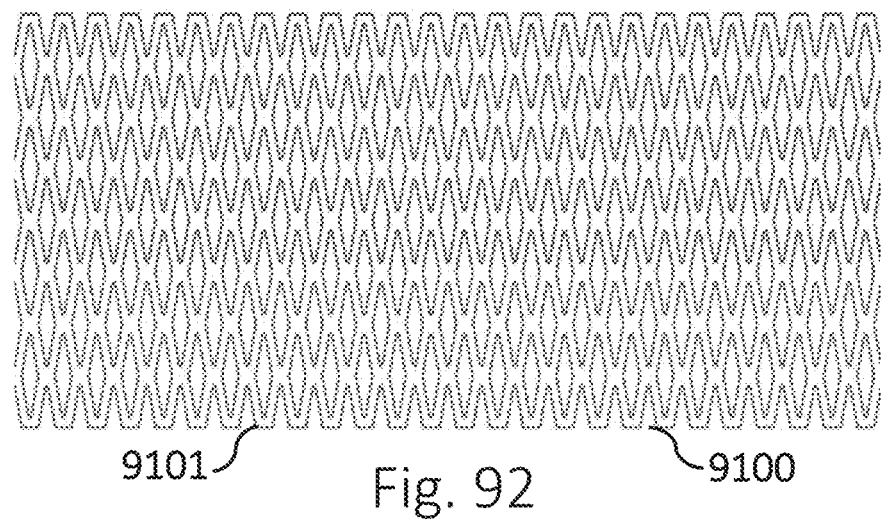
FIG. 92 is a partial side view of a portion of a cut slot pattern of a bone fixation device with a non-threaded expandable segment in an expanded state, in accordance with an aspect of the present invention.
Figure 93:
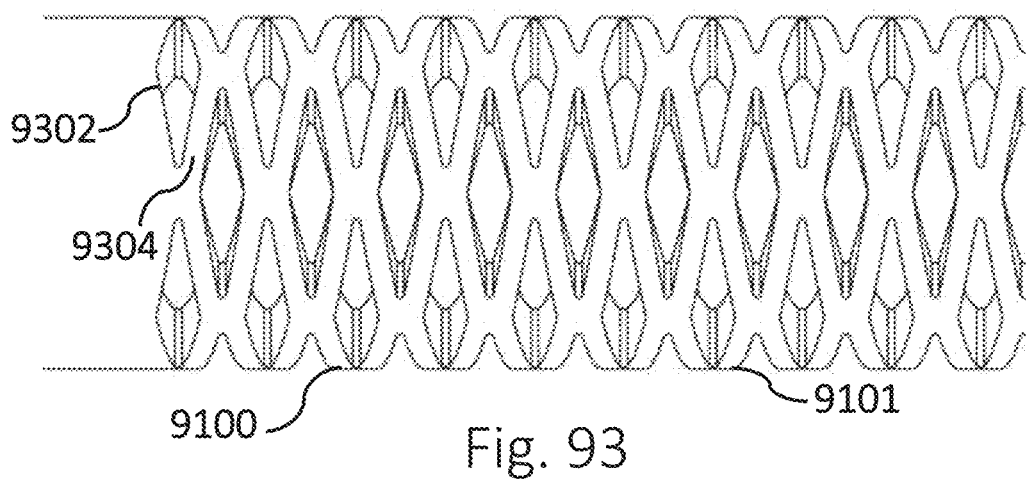
FIG. 93 is a partial side view of a portion of a cut slot pattern of a bone fixation device with a non-threaded expandable segment in an expanded state, in accordance with an aspect of the present invention.

FIG. 91 depicts a flat or unidimensional representation of a member 9100 having a cut slot patter 9101. FIGS. 92 and 93 are progressive enlargements of a portion of the cut slot patter 9101 shown in FIG. 91. Spaces or voids 9302 between struts 9304 are areas where material is not present. It will be understood that FIGS. 91-93 may similarly show the pattern 8801 wrapped around a tubular member.

In certain embodiments, the member 8800 shown in FIGS. 88-90 and the member 9100 shown in FIGS. 91-93 are the same member employing the same cut pattern in an unexpanded state, FIGS. 88-90, and an expanded state, FIGS. 91-93. Alternatively stated, expansion or lengthening of the cut pattern 8801 can result in the cut pattern 9101 having spaces or voids 9302 that define a greater internal void area than the spaces or voids 9302 of the cut pattern 8801 shown in FIGS. 88-90.

Figure 94:
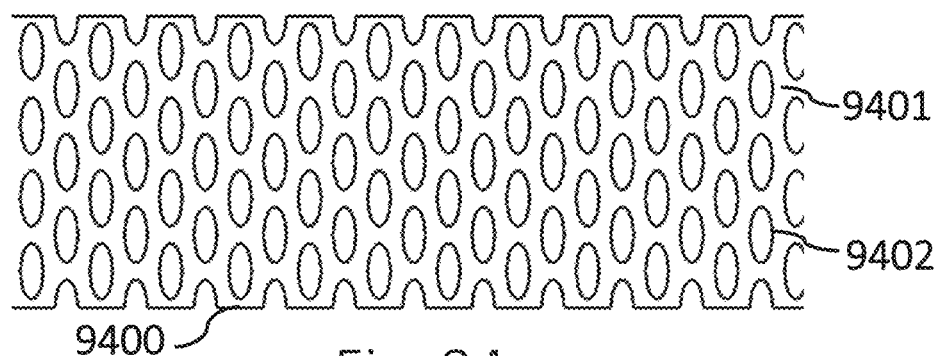
FIG. 94 is a partial side view of a portion of a cut slot pattern of a bone fixation device with a non-threaded expandable segment in an expanded state, in accordance with an aspect of the present invention.
Figure 95:
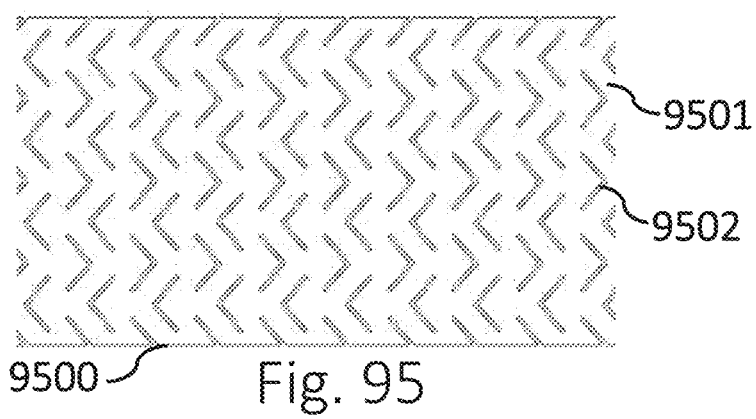
FIG. 95 is a partial side view of a portion of a cut slot pattern of a bone fixation device with a non-threaded expandable segment in a non-expanded state, in accordance with an aspect of the present invention.

FIGS. 94-101 show additional embodiments and configurations of cut slot patterns employed in the expandable or deformable portions or sections of any embodiments of the present invention herein disclosed. It will be understood that the cut slot patterns shown in FIGS. 94-101 can represent a flat or unidimensional representation of a cut pattern employed to form a tubular structure or member or, alternatively, may represent the pattern already formed as a tubular structure or member. FIG. 94 shows a cut slot pattern 9400 having oval cut slots 9402. The oval cut slots 9402 can yield higher strut 9401 strain relief during deformation, as well as, facilitate the integration of material or tissue ingrowth between the slots. FIG. 95 shows a cut slot pattern 9500 employing greater than and less than symbols or side-ways chevron shaped cut slots 9502. The cut slots 9502 can yield alternate strut 9501 strain profiles during deformation and can facilitate different axial and torsional stiffness profiles.

Figure 96:
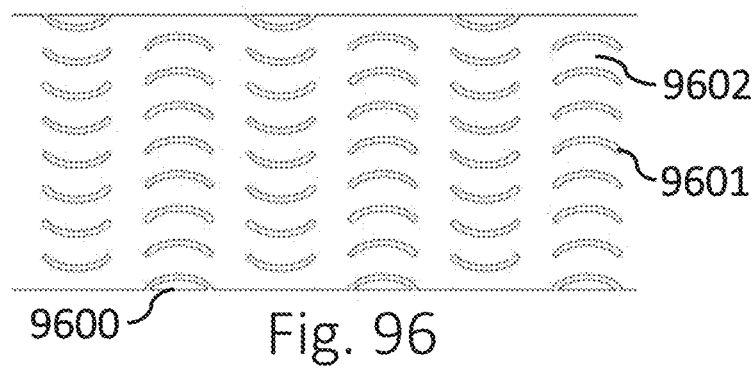
FIG. 96 is a partial side view of a portion of a cut slot pattern of a bone fixation device with a non-threaded expandable segment in a non-expanded state, in accordance with an aspect of the present invention.
Figure 97:
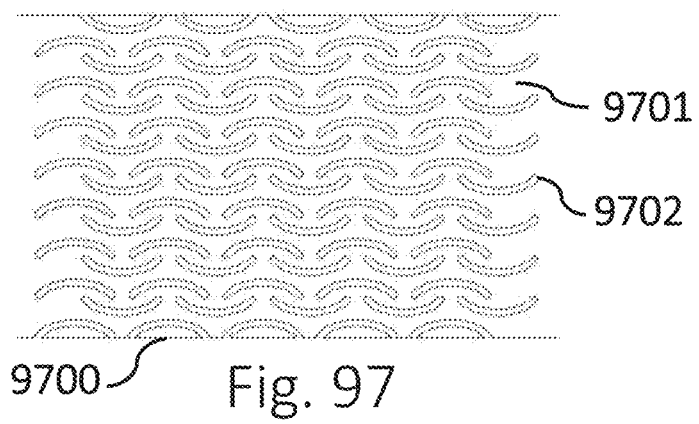
FIG. 97 is a partial side view of a portion of a cut slot pattern of a bone fixation device with a non-threaded expandable segment in a non-expanded state, in accordance with an aspect of the present invention.
Figure 98:
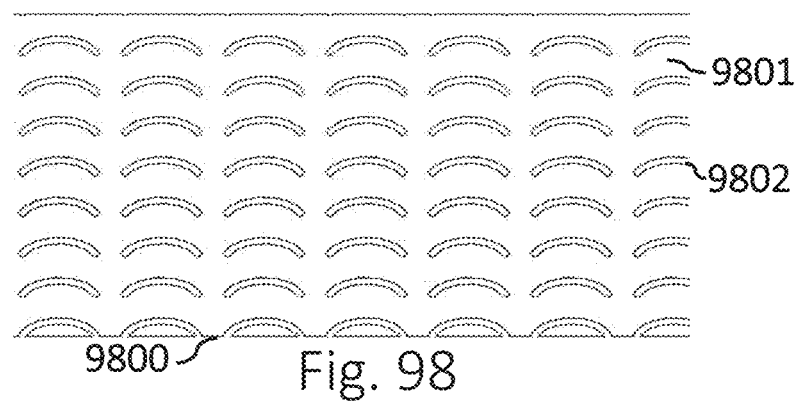
FIG. 98 is a partial side view of a portion of a cut slot pattern of a bone fixation device with a non-threaded expandable segment in a non-expanded state, in accordance with an aspect of the present invention.
Figure 99:
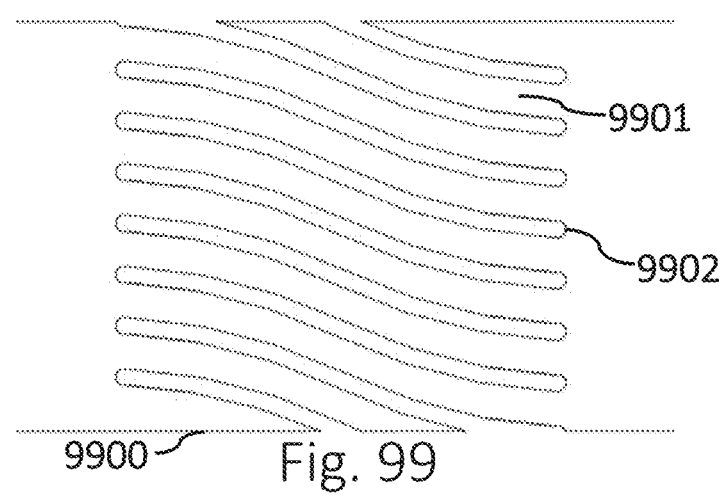
FIG. 99 is a partial side view of a portion of a cut slot pattern of a bone fixation device with a non-threaded expandable segment in a non-expanded state, in accordance with an aspect of the present invention.

FIG. 96 shows a cut slot pattern 9600 employing alternating curved cut slots 9602. The curved cut slots 9601 yield alternate strut 9602 strain profiles during deformation and facilitate the different axial and torsional stiffness profiles. FIG. 97 shows a cut slot pattern 9700 employing overlapping alternating curved cut slots 9702. The overlapping alternating curved cut slots 9702 yield alternate strut 9701 strain profiles during deformation and facilitate different axial and torsional stiffness profiles. FIG. 98 shows a cut slot pattern 9800 employing repeating interrupted curved cut slots 9802. The repeating interrupted curved cut slots 9802 yield alternate strut 9801 strain profiles during deformation and facilitate different axial and torsional stiffness profiles. FIG. 99 shows a cut slot pattern 9900 employing longitudinal "S" or curved cut slots 9902. The longitudinal curved cut slots 9902 yield alternate strut 9901 strain profiles during deformation and facilitate different axial and torsional stiffness profiles.

Figure 100:
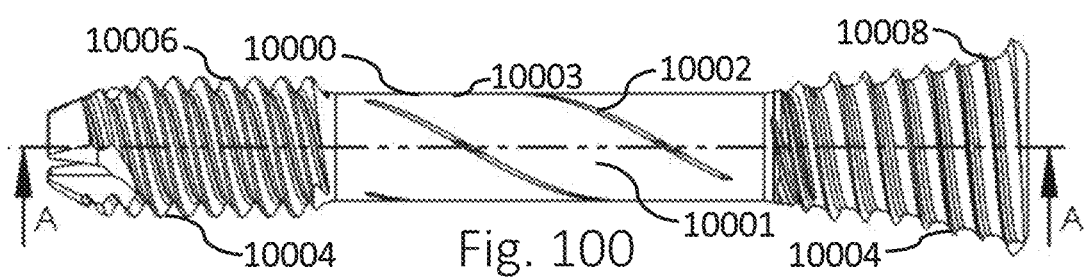
FIG. 100 is a side view of a bone fixation device with a non-threaded helical expandable segment in a non-expanded state, in accordance with an aspect of the present invention.
Figure 101:
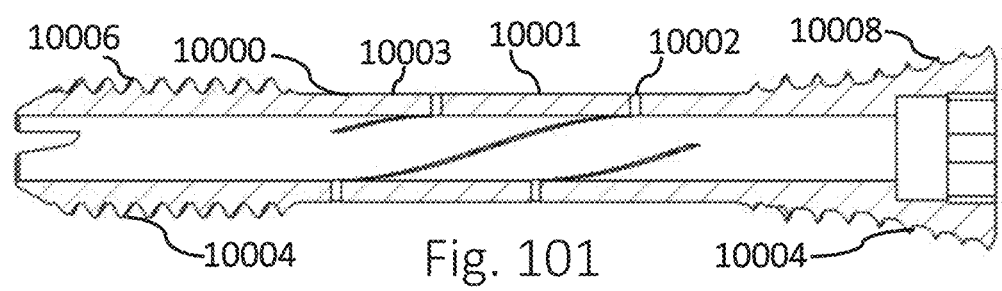
FIG. 101 is a side cross section view of a bone fixation device with a non-threaded helical expandable segment in a non-expanded state, in accordance with an aspect of the present invention.
Figure 102:
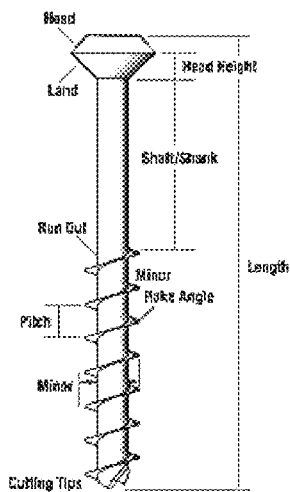
FIG. 102 is a side view of a bone fixation device with a non-threaded segment, in accordance with an aspect of the present invention.

FIGS. 100 and 101 show a cut slot pattern 10000 employing lengthwise or longitudinal "S" or curved symmetric repeating cut slots 10002. The cut slots 10002 yield alternate strut 10001 strain profiles during deformation and facilitate different axial and torsional stiffness profiles. The cut slot pattern 10000 can, for example, be employed to form a helical expansion or deformable portion 10003 of a screw member 10006. The cut slots 10002 of the cut slot pattern 10000 of the deformable portion 10003 can be oriented in an opposite direction than threads 10004 of the member 10006. After a distal end of the screw 10006 is inserted into the bone tissue, the helical deformable portion 10003 creates a loading condition upon or prior to insertion of a head portion 10008 of screw 10006 into the tissue.

FIGS. 99, 100 and 101 can also be configured such that the diameter of the expandable 10003 section can either increase or decrease upon loading and unloading of the member. This might be advantageous to either increase bone tissue interface as the diameter expands or to help facilitate mechanical interlock upon a delivery mechanism as the diameter decreased.

Figure 103:
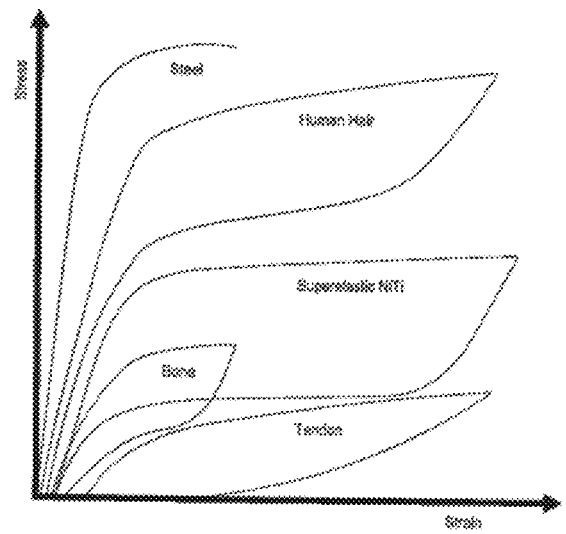
FIG. 103 is a graph showing material strain curves, in accordance with an aspect of the present invention.

FIG. 103 is a depiction of various stress strain curves of various materials potentially relevant to the embodiments of the present invention. Superelastic nitinol exhibits a constant stress feature, the loading and unloading curve is substantially flat over large strains. The superelastic nitinol modulus is much more similar to that of bone than other common materials used to make screws like titanium alloys or stainless-steel alloys. Constructing the embodiments of the present invention yields an implant that would potentially not stress shield the bone. This allows the design of devices that apply a constant stress over a wide range of shapes. A super-elastic material used to form the embodiments may be a shape memory alloy (SMA), super-elasticity is a unique property of SMA. An initial increase in deformation strain creates great stresses in the material, followed by a stress plateau with the continued introduction of strain. As the strain is reduced, the stress again plateaus, providing a substantially constant level of stress. This property of the super-elastic material allows the embodiments of the present invention to be preloaded with compressive forces prior to or once inserted in desired bone segments.

According to one embodiment of the present invention, super-elastic materials used to form the embodiments include, but are in no way limited to, a shape memory alloy of nickel and titanium commonly referred to as nitinol. The embodiments may be formed of nitinol, according to one exemplary embodiment, because nitinol can provide a low constant force at human body temperature. The Nitinol could be optimized to be in the super elastic Austenite phase at human body temperature. This is accomplished by heat setting the austenite finish temp Af below 98.6 degrees Fahrenheit. This would ideally be done after the machining of the screw so as to also anneal any residual strain. Additionally, nitinol exhibits a reduction in elongation at a rate of approximately 10%, which is approximately equal to the subsidence rate of an orthopedic body. However, it will be under stood that many materials can be used for the construction of the embodiments herein disclosed.

FIGS. 102 and 104-107 show screw or joining member features that are commonly varied to maximize the effectiveness of the fastener with various applications including but not limited to; thread pitch, thread angle, tip design, cutting features, self-tapping, self-drilling, minor diameter, major diameter, rake angle, run out, shank length, head size, head angle, cannulation, tapered threads, single point, multiple point starts, triple threads, variable pitch, variable taper, variable minor and major diameters. In certain embodiments of the present invention any and/or all of these variables are employed to maximize the performance of the fastener. Features of screws previously in existence can be utilized in combination with the inventive embodiments disclosed herein to achieve the active compression feature.

Figure 104:
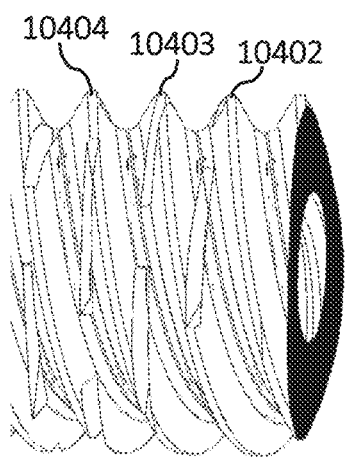
FIG. 104 is a perspective enlarged view of a bone fixation device with a triple lead threaded expandable segment in a non-expanded state, in accordance with an aspect of the present invention.
Figure 105:
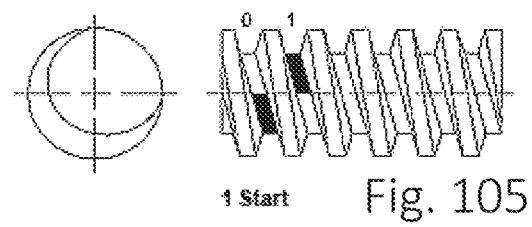
FIG. 105 is a side and an enlarged end view of a bone fixation device with a single lead threaded segment, in accordance with an aspect of the present invention.
Figure 106:
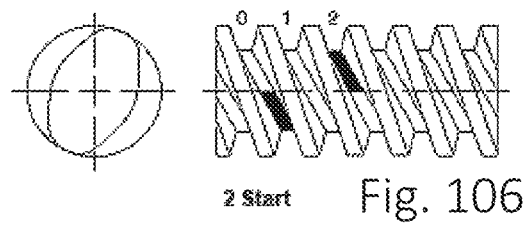
FIG. 106 is a side and an enlarged end view of a bone fixation device with a double lead threaded segment, in accordance with an aspect of the present invention.
Figure 107:
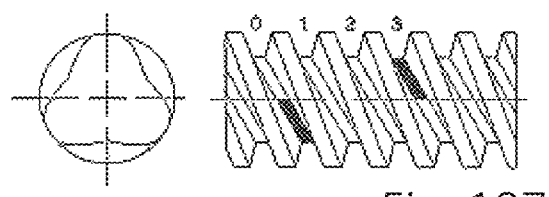
FIG. 107 is a side and an enlarged end view of a bone fixation device with a triple lead threaded segment, in accordance with an aspect of the present invention.

FIG. 104 depicts a screw with a triple start thread design. This means that there are three independent "ridges" 10402, 10403, and 10404 wrapped around the cylinder of the screw's body. Each time that the screw's body rotates one turn of 360 degrees, it will advance a distance axially equal to the total width of all three ridges 10402, 10403, and 10404. By way of comparison, FIG. 105 depicts a single start thread design; FIG. 106 shows a double start thread design; and FIG. 107 shows a triple start thread design. The advantage of using multiple starts is that the amount of travel can be increased for a given rotational motion, this coupled with having different starts, and/or pitches on longitudinally opposite ends or portions of the same screw can create an axial force along the length of the screw between the different threaded sections.

Figure 108:
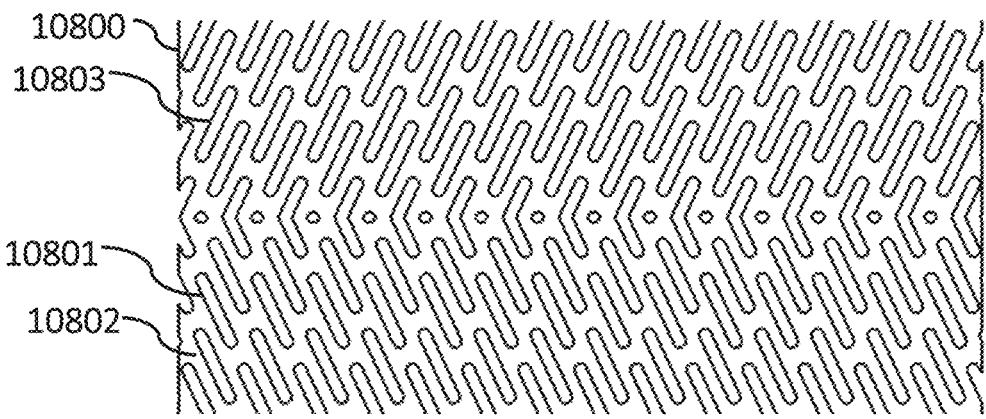
FIG. 108 is a plan enlarged view of a portion of a cut slot pattern of a bone fixation device with a non-threaded expandable segment in a non-expanded state, the segment would yield two different patterns as wrapped about the circumference of the body, in accordance with an aspect of the present invention.

FIG. 108 shows a cut slot pattern 10800 employing repeating interrupted cut slots 10801. The cut slots 10801, 10803 and, hence, struts 10802 are nonparallel to and are non-orthogonal to a longitudinal axis of the joining member or screw in which the cut slot pattern 10800 is employed. Alternatively stated, the cut slots 10801, 10803 and, hence, struts 10802 of the cut slot pattern 10800 are oblique to the longitudinal axis of the joining member or screw in which the cut slot pattern 10800 is employed. Through the oblique orientation, the cut slot pattern 10800 yields alternate strut 10802 strain profiles during deformation and facilitates different axial and torsional stiffness profiles.

The cut slots 10803 are oriented differently within the cut slot pattern 10800 than the cut slots 10801. This creates a non-uniform pattern around the circumference of the deformable portion within which cut slop pattern 10800 is employed. This non-uniform pattern around the circumference of the deformable portion yields non-uniform behavior or stress and strain profiles of the deformable portion about an axis in which the cut slot pattern is employed. This non-uniform behavior has clinical benefits by allowing more deformation in one plane or direction relative to another plane or direction. Any combination of patterns could be combined to achieve the desired behavior. Varying the cut slot pattern, cut slot density, cut slot length, cut slot shape, and the other variables described herein can be combined throughout the length and around the circumference of the deformable portion to yield the desired mechanical behavior.

Figure 109:
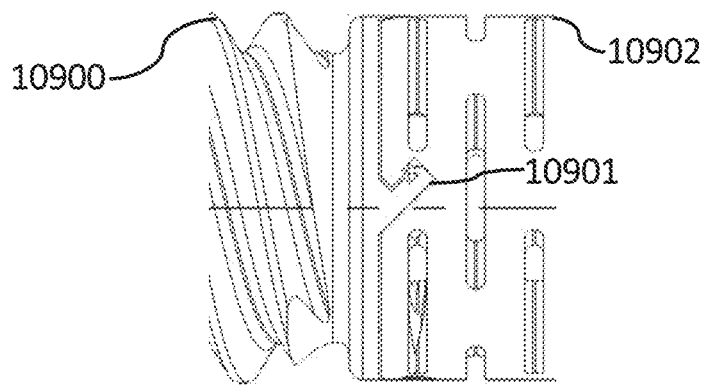
FIG. 109 is an enlarged elevation view of a joining feature of a bone fixation device with a non-threaded expandable segment and a threaded segment in joined state, in accordance with an aspect of the present invention.

FIG. 109 shows an embodiment of a joining member according to the present invention formed of a non-unitary construction. It will be understood that all of the embodiments herein disclosed can be made from several independent pieces or components and then joined together. By way of example, the various independent components that may be employed to form a joining member may include, but are not limited to, a distal threaded portion, a central deformable portion, a proximal head portion, and an internal or external radially stiffening member. The advantages of a non-unitary construct include, but are not limited to, ease of manufacturing, cost of fabrication, material property optimization, and customization.

The materials that may be employed for formation of the any of the independent components include, but are not limited to, titanium alloys, stainless steels, cobalt chromes, polymers like PEEK, biodegradable materials like magnesium, PLLA, PLG, and others. The embodiments included herein could be all constructed from multiple segments and then joined together in manufacturing or in the clinical setting. The method of joining, coupling, or forming a union of the independent components includes, for example, snap fit, welding, bonding, sintering, or other methods know in the art. The independent components can be made from different types of materials or from the same type of material. The multiple segments design can facilitate manufacturing processes that are simpler and/or more cost effective. The multiple segments design can provide a customization feature in the clinical setting allowing the user to combine the desired independent components together to construct a desired joining member. FIG. 109 shows one example of a union or coupling 10901 of a distal threaded portion 10900 and a deformable or expandable portion 10902.

Figure 110:
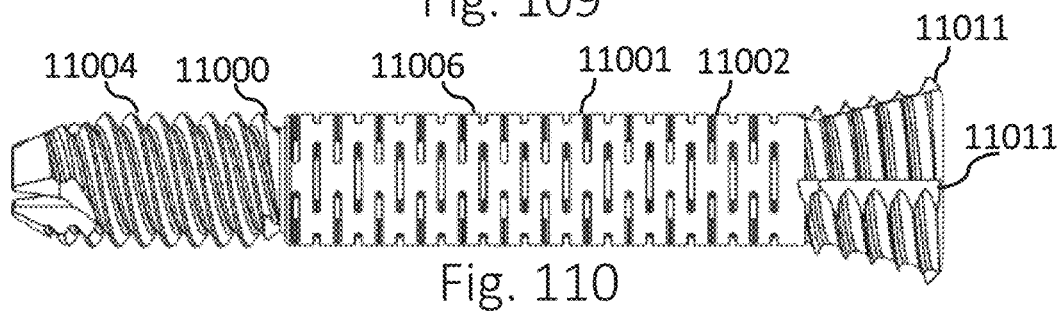
FIG. 110 is a side view of a bone fixation device with a non-threaded expandable segment in a non-expanded state the segment being of larger diameter than the minor diameter of the threaded section, in accordance with an aspect of the present invention.
Figure 111:
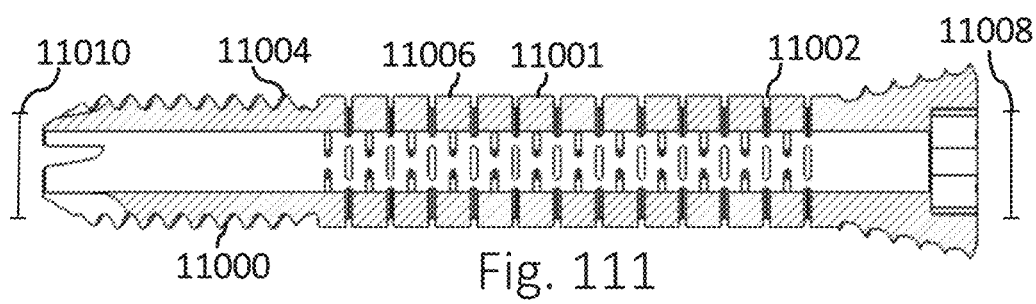
FIG. 111 is a side cross section view of a bone fixation device with a non-threaded expandable segment in a non-expanded state the segment being of larger diameter than the minor diameter of the threaded section, in accordance with an aspect of the present invention.

FIGS. 110 and 111 show a cut slot pattern 11001 employing radially repeating cut slots 11002. The radially repeating cut slots 11002 yield alternate strut 11001 strain profiles during deformation and facilitate different axial and torsional stiffness profiles. The cut slot pattern 11001 can be employed in a joining member or screw 11000 having distal threaded portion 11004 and a deformable portion 11006. The deformable portion 11006 has an exterior diameter 11008 that is greater than a minor diameter 110010 of the distal threaded portion 11004. This larger diameter of the deformable portion 11006 can allow employing a thicker cross-sectional wall, the thickness of which can be manipulated in order to adjust an axial tension or an axial and/or a torsional stiffness of the screw 11000. The screw 11000 may be implanted by preparing a tissue cavity formed with a stepped diameter drill so as to facilitate an interference between the tissue and the screw that is optimized. This embodiment demonstrates a feature that could be utilized on any of the embodiments disclosed herein. An anti-rotation or anti back-up feature 11011 may further be employed so as to promote the securing of the screw into the tissue. The feature 11011 is shown here as a cut into the threads which creates an edge that the tissue engages upon rotation in the direction that would loosen or remove the screw. The feature 11011 can take many forms that include but are not limited to expanding tangs, cut patterns, assembled members, or other. This anti-rotation or anti back-up feature can also be employed on any embodiment herein disclosed.

Figure 112:
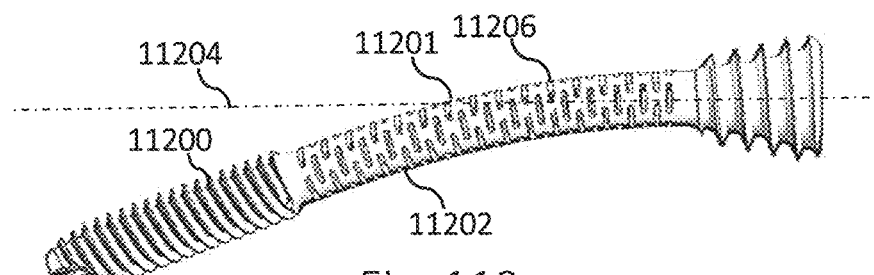
FIG. 112 is a side view of a bone fixation device with a non-threaded expandable segment in a non-expanded state the segment being bent off axis from that of the threaded section, in accordance with an aspect of the present invention.

FIG. 112 shows a cut slot pattern 11201 employing radially repeating cut slots 11202. The radially repeating cut slots 11201 allow for a deformable portion 11206 of a joining member or screw 11200 to radially bend or deform relative to a longitudinal axis 11204. The property radially bending or deforming may be imparted in any of the embodiments herein disclosed. This radial deformation may or may not be fully elastic in nature, i.e. a joining member employing this property of radial deformation may or may not return to its original shape symmetry about axis 11204. The property allows the joining member or screw 11200 to screw or join tissue along a nonlinear path. This feature may be useful in an environment where there is a desire to bend in a repetitive nature, because the strain levels could be designed to have a long fatigue life compared to that of a solid screw undergoing the same amount of deformation. The bending force of the member can be designed by varying all the previously described features to obtain a desirable clinical therapy.

In another embodiment, the joining member or screw is inserted in a straight or axial fashion and the resting state of the screw could be off axis or bent. The bending force of the screw can then be used as a desired therapy to move the bone fragments once implanted. Screws or joining members can be formed in a bent or curved or helical shape, and installed or delivered in a straight shape to obtain a desired clinical therapy.

Figure 113:
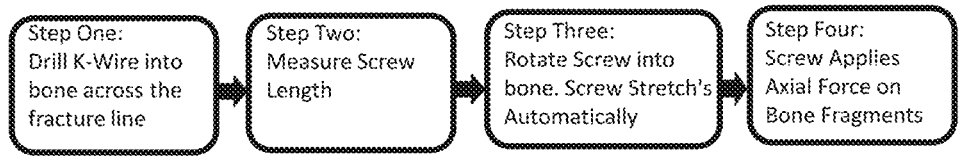
FIG. 113 is a flow chart showing one embodiment of a method of clinical application of a bone fixation device according to the present invention.

FIG. 113 is a flow chart depicting one possible method and procedural progression for insertion of a joining member of the present invention into bone tissue to facilitate a desired therapy. The progression starts with the inserting of a K-wire or guide pin into the desired location of placement, for example, transecting a fracture plane of the bone. Once the wire is placed, a measurement of the desired joining member length can be made utilizing the relative length of the wire and surface of the bone. The inventive joining member can then be inserted, for example by rotation, into the bone over the K-wire. The end of the joining member can have self-cutting and self-tapping features that allow it to displace the bone tissue as it advances forward through the bone. As a head of the joining member engages the bone, the additional friction due to the increased size of the head, and a differential pitch and/or starts of the head relative to the distal portion of the joining member will apply a compressive force to the bone segments across the fracture plane.

This force will also apply an axial tension feature of the joining member effectively elongating it and storing potential energy into the axial tension. After insertion is complete, the stored axial tension energy will continue to apply force onto the bone across the fracture plane yielding a desired therapeutic beneficial pressure to aide healing.

Figure 114:
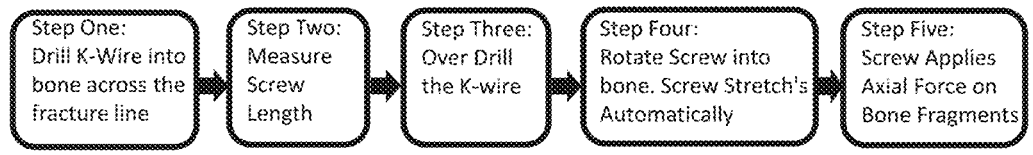
FIG. 114 is a flow chart showing one embodiment of a method of clinical application of a bone fixation device according to the present invention.

FIG. 114 is a flow chart depicting one possible method and procedural progression for insertion of a joining member of the present invention into bone tissue to facilitate a desired therapy. The progression starts with the inserting of a K-wire or guide pin into the desired location of placement, for example, transecting a fracture plane of the bone. Once the wire is placed, a measurement of the desired joining member length can be made utilizing the relative length of the wire and surface of the bone. Following this, a cannulated drill is inserted over the K-wire to increase the diameter of the hole and potentially facilitate a better mechanical fit between the bone and the joining member. The joining member can then be rotated into the bone over the K-wire. The end of the joining member can have self-cutting and self-tapping features that allow it to displace the bone tissue as it advances forward through the bone. As a head of the joining member engages the bone, an additional friction due to the increased size of the head and a differential pitch and/or starts of the head relative to a distal portion of the joining member will apply a compressive force to the bone segments across the fracture plane. This force will also be applied to an axial tension feature of the screw effectively elongating the joining member and storing potential energy into the axial tension. After insertion is complete, the stored axial tension energy will continue to apply force onto the bone across the fracture plane yielding a desired therapeutic beneficial pressure to aide healing.

Figure 115:
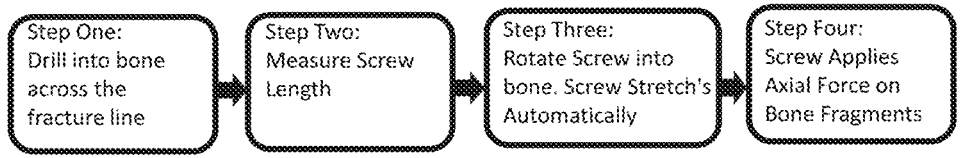
FIG. 115 is a flow chart showing one embodiment of a method of clinical application of a bone fixation device according to the present invention.

FIG. 115 is a flow chart depicting one possible method and procedural progression for insertion of a joining member of the present invention into bone tissue to facilitate a desired therapy. The progression starts with the inserting of a drill into the desired location of placement, for example transecting a fracture plane of the bone. Once drilled, a measurement of the desired joining member length is made utilizing a measurement depth gauge and surface of the bone. A joining member can then be rotated into the bone. The end of the joining member can have self-cutting and self-tapping features that allow it to displace the bone tissue as it advances forward through the bone. As a head of the joining member engages the bone, the additional friction due to an increased size of the head and a differential pitch and/or starts of the head relative to a distal threaded portion of the joining member will apply a compressive force to the bone segments across the fracture plane. This force will also be applied to an axial tension feature of the joining member effectively elongating it and storing potential energy into the axial tension. After insertion is complete, the stored axial tension energy will continue to apply force onto the bone across the fracture plane yielding a desired therapeutic beneficial pressure to aide healing.

Figure 116:
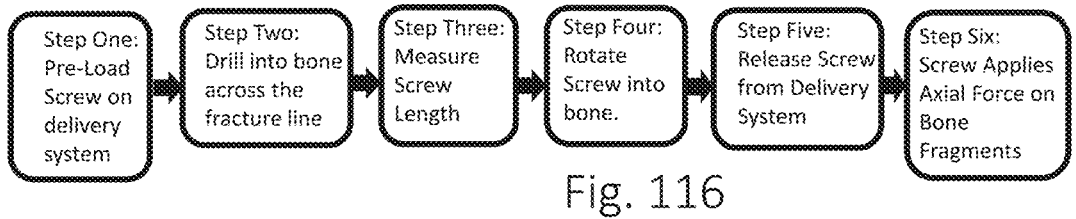
FIG. 116 is a flow chart showing one embodiment of a method of clinical application of a bone fixation device according to the present invention.

FIG. 116 is a flow chart depicting one possible method and procedural progression for insertion of a joining member of the present invention into bone tissue to facilitate a desired therapy. The progression starts with the pre-loading of a joining member onto a delivery mechanism. This preload is an axially stretching an axial tension feature of the inventive joining member and holds the pre-load during the insertion of the joining member into bone. This preload could be done in the manufacturing factory or in the clinical setting by the end user. The next step is insertion of a drill into the desired location of placement, for example transecting a fracture plane of the bone. Once drilled, a measurement of the desired joining member length can be made utilizing a measurement depth gauge and surface of the bone. The joining member can then be rotated into the bone. The end of the joining member can have self-cutting and self-tapping features that allow it to displace the bone tissue as it advances forward through the bone. Once the screw member is implanted into the bone, a mechanism to release the preloaded axial tension force is activated. The joining member will apply a compressive force to the bone segments across the fracture plane. After release of the stored energy the stored axial tension energy will continue to apply force onto the bone across the fracture plane yielding a desired therapeutic beneficial pressure to aide healing.

Figure 117:
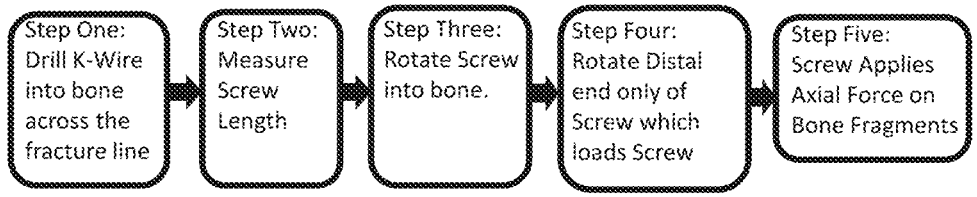
FIG. 117 is a flow chart showing one embodiment of a method of clinical application of a bone fixation device according to the present invention.

FIG. 117 is a flow chart depicting one possible method and procedural progression for insertion of a joining member of the present invention into bone tissue to facilitate a desired therapy. The progression starts with the inserting of a K-wire or guide pin into the desired location of placement, for example transecting a fracture plane of the bone. Once the wire is placed a measurement of the desired joining member length can be made utilizing the relative length of the wire and surface of the bone. The joining member can then be inserted, for example by rotation, into the bone over the K-wire. The end of the joining member can have self-cutting and self-tapping features that allow it to displace the bone tissue as it advances forward through the bone. As the head of the joining member engages the bone, the additional friction due to the increased size of the head and a differential pitch and/or starts of the head relative to a distal portion of the joining member will apply a compressive force to the bone segments across the fracture plane. At this point the distal portion of the joining member can be further driven forward while the proximal head remains stationary which would create further force across the fracture plane. This force will also be applied to the axial tension feature of the joining member effectively elongating it and storing potential energy into the axial tension. After insertion is complete, the stored axial tension energy will continue to apply force onto the bone across the fracture plane yielding a desired therapeutic beneficial pressure to aide healing.

Figure 118:
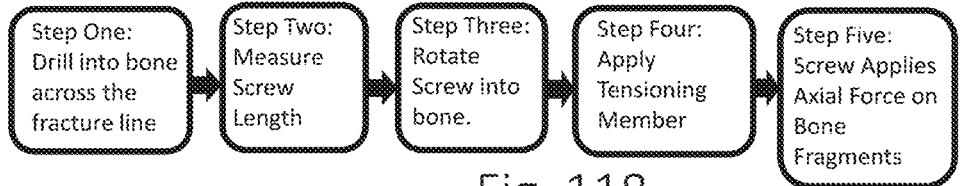
FIG. 118 is a flow chart showing one embodiment of a method of clinical application of a bone fixation device according to the present invention.

FIG. 118 is a flow chart depicting one possible method and procedural progression for insertion of a joining member of the present invention into bone tissue to facilitate a desired therapy. The progression starts with the inserting of a drill into the desired location of placement, for example transecting a fracture plane of the bone. A measurement of a desired joining member length is made utilizing a depth measurement instrument and surface of the bone. The joining member can then be inserted into the bone, for example, by rotation. The end of the joining member can have self-cutting and self-tapping features that allow it to displace the bone tissue as it advances forward through the bone. As a head of the joining member engages the bone, an additional friction due to the increased size of the head and a differential pitch and/or starts of the head relative to a distal portion of the joining member will apply a compressive force to the bone segments across the fracture plane. At this point, a tensioning member can be applied to the joining member which would create further force across the fracture plane. The tensioning member may be separate member that is assembled into the joining member to provide additional axial tension to the assembly. This force will also be applied to the axial tension feature of the joining member effectively elongating it and storing potential energy into the axial tension. After insertion is complete, the stored axial tension energy will continue to apply force onto the bone across the fracture plane yielding a desired therapeutic beneficial pressure to aide healing. This additional axial tension member could also provide an additional resistance to bending to the assembly.

Figure 119:
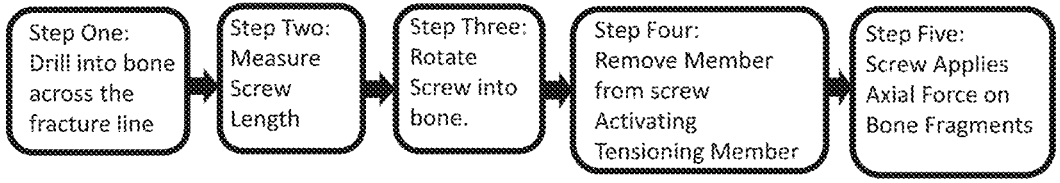

FIG. 119 is a flow chart depicting one possible method and procedural progression for insertion of a joining member of the present invention into bone tissue to facilitate a desired therapy. The progression starts with the pre-loading of a joining member. This preload is an axially stretching of the axial tension feature of the inventive joining member and holds the pre-load during the insertion of the joining member into bone. This preload could be achieved in the manufacturing factory or in the clinical setting by the end user. The progression continues with the inserting of a drill into the desired location of placement, for example transecting a fracture plane of the bone. A measurement of the desired joining member length can be made utilizing a depth measurement instrument and surface of the bone. The joining member can then be, for example, rotated into the bone. The end of the joining member can have self-cutting and self-tapping features that allow it to displace the bone tissue as it advances forward through the bone. As a head of the joining member engages the bone, an additional friction due to the increased size of the head and a differential pitch and/or starts of the head relative to a distal portion of the joining member will apply a compressive force to the bone segments across the fracture plane. At this point the preload member could be removed from the joining member which would create further force across the fracture plane. The pre-loading member may be a separate member that is assembled into the joining member. After insertion is complete, the stored axial tension energy will continue to apply force onto the bone across the fracture plane yielding a desired therapeutic beneficial pressure to aide healing.

Figure 120:

FIG. 120 is a flow chart depicting one possible method and manufacturing progression for the construction of a joining member according to the present invention. From an ingot of metal such as Nitinol with an appropriate chemical structure of, for example, nickel 55.8%, titanium 44.185%, oxygen 0.01%, and carbon 0.005%, and ingot transition temperature of less than 5 degrees Celsius, tubing is drawn to an appropriate inner and outer diameter, wall thickness, and desired physical properties such as a tensile strength around 145,000 PSI, and percent elongation of over 10 percent. It will be understood that the above values are reference values and the actual values can vary depending on the desired characteristics of the final construct. The next step is to machine the desired outer profile of threads and features into the tubing material. This machining can be standard machining techniques, cryogenic machining, EDM (electrical discharge machining), grinding, or other techniques know to those in the art.

After the desired profile is obtained, the axial tension features are added to the construct. These features are obtained by removing the desired material by using methods understood by those in the industry such as laser cutting, EDM, chemically etched, and water jet machined. Once all the features are formed in the construct, the piece can then undergo a thermal heat setting or annealing. The purpose of the heat set could be to relieve any residual stresses in the part from any of the previous machining steps. Additional physical or dimensional changes could be imparted onto the structure through the heat treatment steps. The heat set could be a dial-in or adjustment of the austenite transition temperature.

A final step is the finishing of the surface finish of the part. This could be done through a series of either chemically etching or mechanically etching of the heavy oxide surface from the part. Once the surface is relatively uniform, an electro-polishing process to both smooth the surface and establish roughly a 200 angstrom layer of titanium oxide is employed. These two process steps also serve to further remove any heat affected areas on the parts resulting from any of the machining or cutting processes. These steps also improve the biocompatibility, the corrosion resistance, and fatigue life of the construct. The parts at this point could enter a final cleaning process and then packaging. Sterilization of the screws could be done by the manufacturer or at the clinical site.

Figure 121:

FIG. 121 is a flow chart depicting one possible method and manufacturing progression for the construction of a joining member according to the present invention. The present method is similar to the process described with respect to FIG. 120, with the exception that the early step of drawing into a tube would be replaced with drawing into a solid rod. Starting with a solid rod will then require that the construct is cannulated. Such cannulation being created through machining, gun drilling, EDM, or other method know to those in the art.

Figure 122:

FIG. 122 is a flow chart depicting one possible method and manufacturing progression for the construction of a joining member according to the present invention. The present method is similar to the process described with respect to FIG. 120, with the exception that the creation of the cut slots ultimately forming the deformable portion of the member for creation of an axial tension feature is formed before the machining of the exterior or screw features, such as the distal and proximal threads.

Joining members and/or screws according to the present invention can also be processed in an elongated state and then formed back to a shortened state during the heat setting step. This technique facilitates easier manufacturing of the cut slot features and electro-polishing steps. In addition to the methods described herein, multipart constructs could have all these included variations and more. The methods described in FIGS. 120-122 are centered around Nitinol material. However, the methods for other materials such as other titanium alloys and/or stainless-steel alloys would be similar. The final steps when using other materials may include that of adding a surface coating like anodizing or plating and or passivation. Additionally, alternative manufacturing methods also include deposition, molding, casting, sintering, and others know to those in the art are included herein as potential manufacturing techniques of the disclosed invention.

The methods described and shown with regard to FIGS. 113-122 are described as being performed in a progression or sequence of distinct steps only for the sake of clarity. It is understood and within the scope of the present invention that such steps be performed in alternate progressions or sequences and embodiments may omit steps shown and/or described in connection with the illustrative methods. Embodiments may include steps that are neither shown nor described in connection with the illustrative methods. Illustrative method steps may be combined. For example, one illustrative method may include steps shown in connection with another illustrative method.

Figure 123:
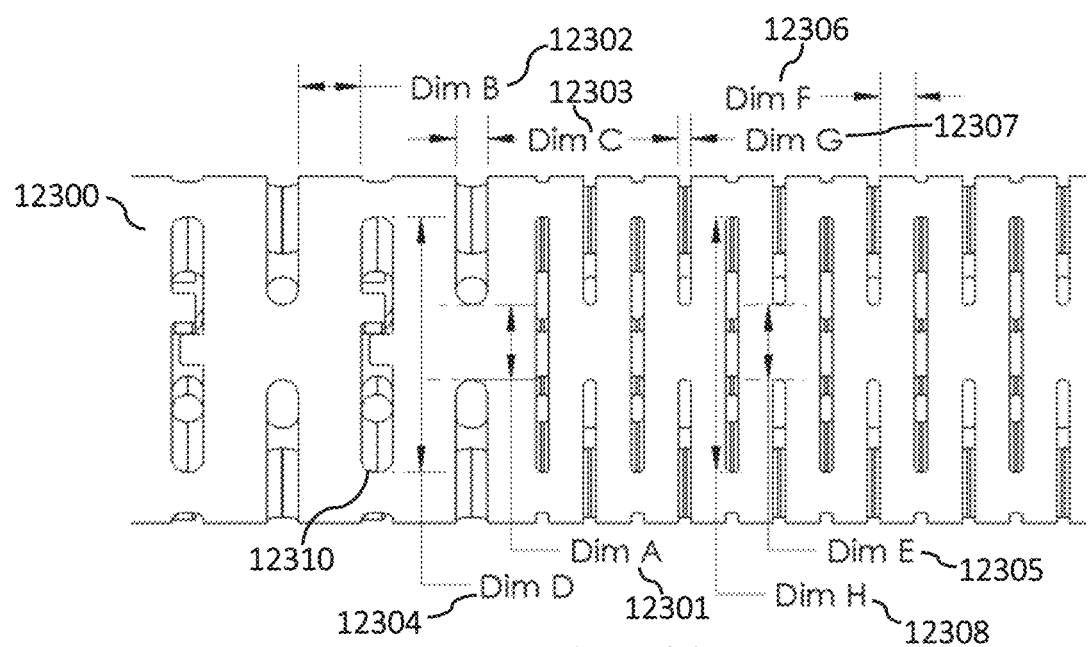
Figure 124:
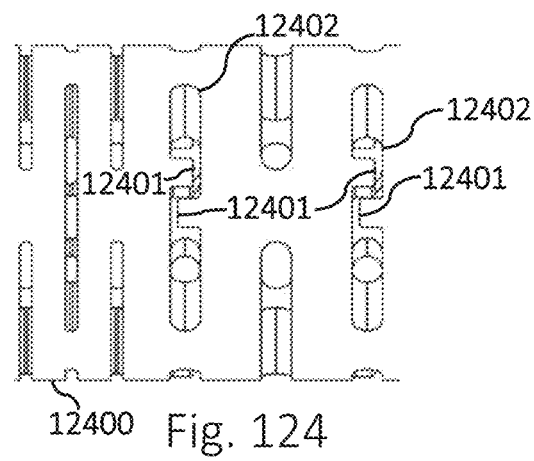
Figure 125:
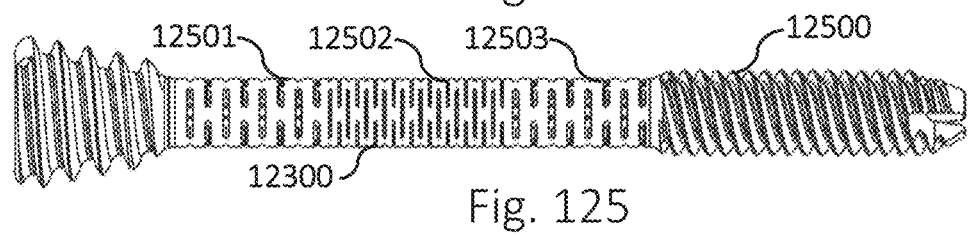

FIGS. 123-125 depict additional embodiments of a joining member that can be employed in conjunction with those embodiments and joining members previously disclosed. FIG. 125 illustrates a deformable or expandable portion 12300 of a joining member 12500 that employs a plurality of different sections 12501, 12502, and 12503. The sections 12501, 12502, and 12503 have different axial and bending spring properties due to the differences in geometry of the cut slot features along the longitudinal axis of the deformable portion 12300. The ability to have one, two, three, or more different sections yielding different behavior facilitates clinical advantages to the deformable portion 12300, such as evenly or unevenly distributing a radial bending or flexion load over a given length, facilitating radial bending around a defined length of the member, and facilitating a resistance to a torsional load upon insertion. In certain embodiments of the present invention, the cut slot pattern can be asymmetric around a circumference of the central deformable section. For example, the cut slot pattern can employ different dimensions around a circumference of the central deformable section in order to create asymmetric mechanical properties.

The sections 12501, 12502, and 12503 may employ different axial stiffness while maintaining the same radial bending stiffness, allow preferential bending in one or more defined planes, allow a same radial bending stiffness and different axial stiffness, or allow any and all the design parameters disclosed herein to be adjusted in order to yield the desired results. As shown in FIG. 123, the parameters that can be varied include, but are not limited to, a Dim A apex or node dimension or width 12301; a Dim B strut width 12302; a Dim C window or cut width 12303, an end of the cut slot width by the apex or node radius 12310; a Dim D length of the strut 12304, and a thickness of the strut or wall thickness of the material of the member. These variables work in concert together to yield the desired characteristics which can be varied depending on the clinical indication.

One embodiment may employ the following exemplary algorithm of ratios and relationships; a Dim A 12301 of no less than 1.5 times a Dim B 12302; a Dim B 12302 of within 50% of the strut width; a radius 12310 of sufficient size to stay under 15% strain during deformation which then dictates a value of the Dim C 12303; a number of struts circumferentially around the longitudinal axis and overall diameter of the member will dictate a Dim D length of strut 12304 which will have a profound impact on the amount of deflection of the embodiment. Therefore, with a joining member that is 3.5 mm in diameter at its distal threaded portion, the dimensions could be in the ranges of wall thickness WT of 1 mm; 3 struts circumferentially; Dim B 12302 0.75 (WT); Dim A 12301 1.125 mm; Dim D 12302 2.5 mm; Dim C 12303 0.006-0.020 in. Depending on the torsional and axial stiffness requirement. these numbers could be adjusted to dial in the spring effect desired. As illustrated within the same embodiment one can have another set of features that are the same with different dimensions along the length such as a Dim E 12305, a Dim F 12306, a Dim G 12307, and a Dim H 12308 which is illustrated here as about half the thickness of Dim B which could yield a different axial spring force.

FIG. 124 illustrates another embodiment slot cut pattern 12400 employing a cut slot 12402 having opposing features 12401. The opposing features 12401 facilitate limiting the motion or deformation, both axially and torsionally, of the cut slot pattern 12400 by interrupting such displacement. If the struts attached to the opposing features 12401 are displaced toward one another, the opposing members 12401 come in contact, or interfere, with one another, thereby limiting the deformation of the cut slot 12402. It will be understood that the opposing features 12401 can be of any shape that would fit into the limited space available and not otherwise obstruct the functionality of the strut members.

Figure 126:
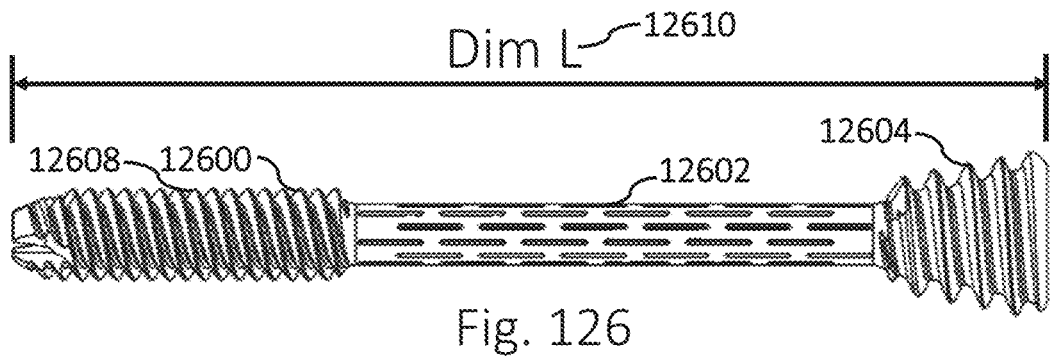
Figure 127:
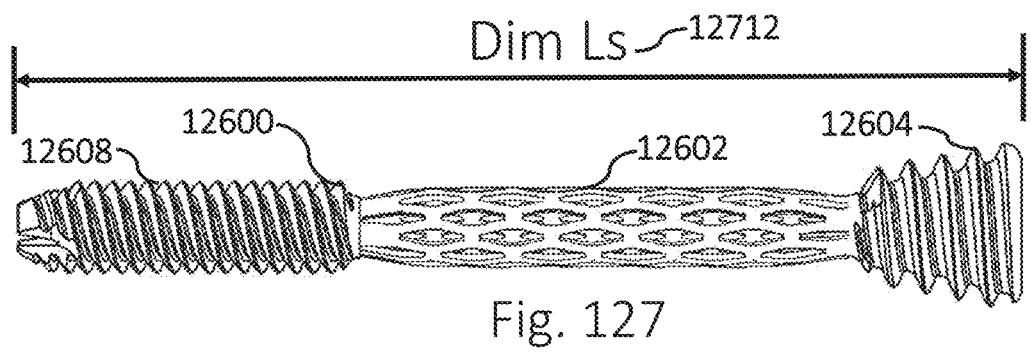
Figure 128:
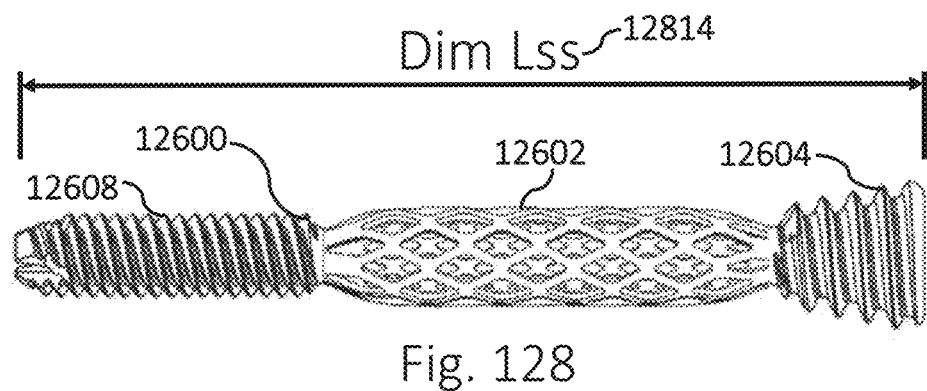

FIGS. 126-128 show yet another embodiment of the present invention in which a joining member 12600 employs a deformable portion 12602 that deforms or expands in a radial and a longitudinal direction. In certain embodiments, the deformable portion 12602 has an initial, relaxed state having an external diameter that is larger than an external diameter of a distal portion and/or a proximal portion, such as that shown in FIG. 127 or FIG. 128. Such an expansion may facilitate the ability to apply torque at the distal portion of a joining member 12600. For example, a driver could be inserted through a lumen of the joining member 12600 all the way past a proximal head portion 12604 and a deformable portion 12602 and into a socket or receiving feature of a distal portion 12608. The distal portion 12608 could then be driven further into the tissue thereby transforming the joining member 12600 from a length Dim Ls 12712 (FIG. 127) or Dim Lss 12814 (FIG. 128) to a length Dim L 12610 (FIG. 126) while reducing the diameter of the deformable portion 12602 and creating the axial tension force within member 12600. This expanded diameter deformable portion can also improve its retention of the joining member within the bone tissue thereby increasing the joining member's effectiveness.

In another embodiment, the deformable portion 12602 can be formed to have an initial, reduced diameter providing the desired retention force. These expanded or decreased diameters can be facilitated by a geometry of the cut slots of the deformable portion 12602, as well as, by the heat setting of the member 12600.

As shown in FIG. 126, member 12600 can have the length Dim L 12610 which is the maximum length of the member 12600 when the proximal head portion 12604 and the distal portion 12608 are at the farthest distance from each other. As shown in FIG. 126, the struts of the deformable portion 12602 are primarily parallel with a longitudinal axis of the member 12600. When the deformable portion 12602 is allowed to or activated to shorten in configuration, thereby shortening the member 12600 to a length Dim Ls 12712, as shown in FIG. 127, the cut slots of the deformable portion 12602 change in shape and the struts are no longer parallel with the longitudinal axis of the member 12600 and the overall diameter of the deformable portion 12602 increases. The amount of this diameter increase will depend on the amount of displacement of angle of the struts 12703 and the length of the struts of the deformable portion 12602. As depicted in FIG. 128, at a length Dim Lss 12814, the cut slots of the deformable portion 12602 further change in shape and the struts are even less parallel with the longitudinal axis of the member 12600 and the overall diameter of the deformable portion 12602 further increases.

The member 12600 can be manufactured to initially assume any of the states shown in FIGS. 126-128 through specified heat treatment. The initial or resting configuration can be set as to yield a specific amount of force applied over length change. The member 126 can be held in a delivery system in a strained state until such time a shortening of the device was desired. Any of the aforementioned mechanism or additional members could accomplish said therapy.

FIGS. 129-132 show yet another embodiment of the present invention in which a joining member employs a deformable portion 12900 that deforms or expands in a longitudinal direction. In certain embodiments, the apparatuses and methods of the present invention provide screws with a center deformable portion having an outer diameter that is larger than a diameter of a distal portion and that is able to apply torque at the distal portion; a driver inserted through and way past a proximal portion and a center deformable portion and into a socket formed in an interior of a distal portion aiding in torsional rotation of the apparatus.

In certain embodiments, the deformable portion 12900 has an initial, relaxed state having an external diameter that is larger than a minor diameter of the distal threaded portion. The body also having a feature on the distal portion inner diameter that can engage and transfer a torque and axial load.

An interference or engagement feature 12901 that is shaped to engage a driver feature can also be employed in order to help facilitate delivery by helping distribute or carry torque load to the distal portion of the screw and/or axial load or stretching of the screw. The cross section of the driver feature can be any that facilitates the load transfer such as but not limited to; hex, star, Philips, slotted, or others.

Certain embodiments can also employ a proximal engagement feature 12905 shown here as a hexalobe, and an inner lumen 12902 that is stepped or that changes in diameter along the length of the axis one or more times. An increased proximal inner diameter of lumen 12902 can facilitate a larger diameter engagement driver 13001 allowing for a larger torque application. The expandable or deformable portion 12900 is depicted here with an outer diameter that is the same as the major diameter of the distal threads 12904. The distal lumen portion 12903 is depicted here having a diameter that is smaller than a diameter of the proximal lumen portion 12907. This configuration is illustrative and the proximal and distal lumen portions can have the same diameter, also the outer diameter of the expandable or deformable portion 12900 can be larger or smaller than that of the maximum diameter of the distal threads 12904.

The inner diameter of the engagement feature 12901 is large enough to allow a K-wire to pass through to aide in the clinical delivery of the screw. A drive member 13001 has a distal drive member 13002 with an engagement feature illustrated here as a hex driver. The distal driver member 13002 can be articulated axially and rotationally either in concert with or independent of a proximal drive mechanism 13000 and an engagement feature 13003. The mechanism is capable of delivering an axial load and a torsional load at both the distal and proximal ends of the screw embodiment. The distal drive member 13001 can also be cannulated to allow for passage over a Kwire.

FIGS. 133, 134 and 135 depict a representation of one embodiment of the present invention in which a K-wire member 13304 is inserted into bone members 13301 and 13302 along an axis 13303. The bone members 13301 and 13302 are not completely reduced and a gap 13306 remains on a portion of the surfaces of the bone segments 13301 and 13302. A known or standard screw member 13400 can be employed to brings or draw bone members 13301 and 13302 towards one another, providing a compressive axial tension or force. The bone members 13301 and 13302 may represent one bone broken in two pieces or two bones that are to be fused together. The bone may, for example be a cortical or cancellous bone or both. The standard screw 13400 draws the segments together but, disadvantageously, the axial path 13303 is maintained relative to the bone segments and the gap 13401 may not be fully reduced.

In contrast, a joining member 13500 according to the present invention, is operable to change in axial length and an axial alignment. The change in dimension occurs over all or a portion of a deformable or expandable portion 13504 of member 13500. The lengthened or axially displaced member 13500, shown in FIG. 135, asserts a compressive force onto the bone members 13301 and 13302 that draws the bone members 13301 and 13302 towards one another. This compressive force in combination with the axial flexibility of the inventive device allows the gap 13306 to be more completely reduced to a reduced state 13501. This ability to deviate from an original axis of entry 13303, 13503 and the axial and the radial flexibility of the member 13500 promotes more complete bone segment apposition and therefore facilitates bone members 13301 and 13302 healing together and/or forming a fusing or union 13501.

In addition to the acute compressive load generated by member 13500, there is a stored energy or force of deformable portion 13504 that can exhibit a continuous load over time and/or absorption of bone material. The stored compressive energy or preload advantageously provides a compressive force across the bone elements to aide in the healing or fusion process.

FIG. 136 is a graphical representation of certain differences between one embodiment of the inventive joining member and a standard screw in a loading profile. The vertical axis represents compressive force applied onto the bone segments as a percentage. The horizontal axis represents a change in distance of the bone segments or penetration of the screw member into the bone tissue. The inventive apparatuses can demonstrate a compressive force to bone segments or tensile force on the apparatus over a greater change in length than either a standard screw or a currently available compression screw. The graph depicts the difference between a standard screw, such as that shown in FIG. 102, and an active compression screw such as any embodiment disclosed herein.

FIGS. 137 and 138 depict another embodiment of the invention. FIGS. 137 and 138 show a partial side view of a portion of a cut slot pattern of a bone fixation device with a non-threaded helical deformable segment in a non-expanded state, in accordance with an aspect of the present invention. FIGS. 137 and 138 show a cut slot pattern 13700 employing a longitudinal helix that wraps around a central longitudinal axis to form a portion of a body of the bone fixation device. A cut slot 13702 yields alternate strut 13701 dimensions and strain profiles during deformation and facilitates different axial and torsional stiffness profiles.

The cut slot pattern 13700 can, for example, be employed to form the deformable portion 10003 of a screw member 10006 (FIGS. 100 and 101). The cut slots 13702 of the deformable portion can be oriented in the same or an opposite direction than threads 10004 and 10008 of the member 10006. After a distal end of the screw 10006 is inserted into the bone tissue, the helical deformable portion 10003 employing cut slot pattern 13700 creates a loading condition upon or prior to insertion of a head portion 10008 of screw 10006 into the tissue. The helical cut slot pattern 13700 acts as a spring member to provide an elastic deflection that can store energy to be imparted to the screw engagement features of distal threads and proximal head features. The cut slots 13702 of the cut slot pattern 13700 can have a constant pitch as depicted in FIGS. 137 and 138 or can have a variable pitch. This embodiment acts as an extension spring in tension. For description purposes the strut 13701 of the cut slot pattern 13700 have a leading edge 13704 which corresponds to the distal direction 13706 and a trailing edge 13705 which corresponds to a proximal direction 13707. The figures can also be interpreted in opposite direction.

The cut slot pattern 13700 shown in FIGS. 137 and 138 can also be configured such that a diameter of the deformable portion formed by the cut slot pattern 13700 can either increase or decrease upon loading and unloading of the member. This can be advantageous to increase bone tissue interface as the diameter expands and to facilitate mechanical interlock upon a delivery mechanism as the diameter decreases. The loading of the center section can either increase or decrease the distance between the struts 13701. Spring behavior is well known and all the variables that effect spring force can be used here to achieve a desired clinical outcome. A pitch 13703 can be altered to match a desired spring force and bending stiffness, the width of the struts 13701 corresponding to the pitch 13703.

FIG. 137 is a partial view of a flat representation of a pattern that is machined onto a tube or curved surface. This flat pattern could be used to program a laser cutter that is programmed in two-dimensional machine code. Similarly, FIGS. 137, 143, 150, 152, 157, 160, 163, 165, 167, 171, and 173 can each represent such partial flat pattern views. FIGS. 138, 139, 154, 158, 161, 168, 170, 172, 174, and 176 illustrate partial views of a tube and/or deformable portion which the corresponding flat pattern is wrapped onto. These partial views can illustrate a machined tube with the corresponding flat pattern.

FIG. 138 is a partial side view of a bone fixation device with a non-threaded helical expandable segment in a non-expanded state, in accordance with an aspect of the present invention. The ends not shown here can, for example, employ a distal screw tip and a proximal screw head.

FIGS. 139-149 depict another embodiment of the disclosed invention, in which a deformable portion is loaded in multiple directions. First, the deformable portion is subjected to a torsional load from the act of driving the screw into tissue or removing from the tissue. The load is transmitted from the proximal head of the screw member to the distal threads of the screw member through or across the deformable portion. This loading can either have the effect of lengthening or shortening the deformable portion depending on the direction of the cuts of the cut pattern and the direction of the torsion applied. For example, the length of a wound spring form or shape loaded in the direction of the winding grows during its loading. Likewise, the diameter also changes during the loading. In certain applications, it may be desirable to minimize the amount of angular deflection from the proximal end to the distal end of the screw member.

Additionally, the deformable portion is loaded in either compression or tension by the forces imparted by the distal and proximal ends of the screw and their interactions with the tissue during the action of inserting and or removing from tissue. This axial loading can impart a torsional loading aspect to the distal end relative to the proximal end. In certain applications, it may be desirable to minimize the amount of angular deflection from the proximal end to the distal end of the screw.

FIGS. 139-149 illustrate torsional engagement features along an entirety or through portions of the length of the deformable portion. The torsional engagement features serve several functions. As the struts of the deformable portion wind or unwind, the engagement features of one strut engage the corresponding engagement features of a next or adjacent strut, thereby limiting the displacement of the individual struts in a torsional aspect. The torsional load can be transferred throughout the entire length of the construct limiting overall rotational displacement relative to each end. Depending on the design, the torsional engagement features can aide in the lengthening of the deformable portion, or can inhibit such lengthening.

Furthermore, the torsional engagement features can aid in the shortening of the deformable portion during unwinding if desired. The torsional engagement features can be designed to be neutral to the force vector to yield no advantage for either lengthening or shortening. The angle of the edges of the torsional engagement features relative to the vector or direction of the applied force can be manipulated to yield many different desired behaviors in the deformable portion of the fixation member. For example, the shape could be such that it encourages the lengthening initially and then resists it after a specific length has been obtained. The position and shape of the engagement features can be such that an axial bending load is imparted on the structure to yield a shape change that might be an asset to therapy.

FIG. 139 is a partial side view of a deformable portion of a bone fixation device employing torsional engagement features, in a non-expanded state, in accordance with an aspect of the present invention. The torsional engagement feature 13903 is a feature that extends into or interlocks or interdigitates with an adjacent receiving engagement feature 13903. The shape, size, number, location of the cut slots 13902 that form the engagement feature 13903 can vary extensively. The cut pattern 13900 takes a path to yield torsional engagement features 13903 which attached or are incorporated into or are part of the struts 13901. In the example shown in FIG. 139, there are effectively six turns of the helical strut 13901, hence, each turn must absorb about one sixth of the total stretch or compression. If such deformation is, for example, approximately 3 mm, each torsional engagement feature should move or displace, for example, about 0.5 mm or 0.020 inches. As the number of turns increases the individual travel is reduced and vice versa. The deformable section could be made to deform at a constant rate or amount along the length. The deformable section could be made to deform at a variable rate or amount along the length having one section deform more than another. The illustrative figures disclosed here are representative of the concept herein described.

FIGS. 140-142 illustrate some of the variables of the torsional engagement features of the present invention. The helical wrapped strut 13901 of members 14000 and struts 14101 of member 14100, shown in FIGS. 140 and 141, respectively, are oriented in an opposite direction relative to the strut 14201 of a member 14200, shown in FIG. 142. Helical wrapped struts 13901 and 14101 are oriented in an opposite direction relative to distal threads 14004 and proximal threads 14004. On the other hand, helical wrap struts 14201 are in a same direction relative to the distal threads 14004 and proximal threads 14005. The engagement features 13903 employed in the member 14000 are oriented in a distal direction on struts 13901 and, in members 14100 and 14200, the engagement feature 14103 and 14203 are oriented in a proximal direction on the struts 14101 and 14201, respectively.

FIG. 192 is a picture of a side view of the bone fixation device or member 14000 reduced to practice.

These described embodiments respond differently to rotational loads applied in either a clockwise or counterclockwise manner, additionally or in conjunction with an axial compressive or tensile load. These different behaviors of the mechanisms yield desired therapeutic effects in conjunction with the procedure used. The directions of the wrap of struts 13901 and 14101 relative to 14201 may be in the same direction as or opposite to the distal threads 14004 and or proximal threads 14005 and serve to vary the application of these features to yield different desired spring, lengthening, compressive and/or tensile reaction. The corresponding engagement features are positioned on opposing or adjacent distal or proximal sides of adjacent strut or struts of member. To achieve a desired expansion, tensile force, rotational stability, diameter expansion or contraction, these features and their dimension, shapes, location, and frequency are constructed in various combinations to yield a desired mechanistic behavior.

Embodiments of members 14000, 14100, and 14200 are depicted as side views of cannulated headless screws for bone fixation with a non-threaded helical deformable center segment with torsional engagement features, in a non-expanded state. These screws or members have proximal threads 14005 that allow for threading into the tissue at the site of therapy. The distal threads 14004 can have the same, less, or more pitch than the proximal threads to yield an axial load of tension, neutral or compression.

FIG. 143 is a partial side view of a portion of a cut slot pattern 14300 of a bone fixation device, for example device 14100 shown in FIG. 141, with a non-threaded helical deformable portion with torsional engagement features, in a non-expanded state. The embodiment shown in FIG. 143 shows additional variables of the torsional engagement features. The number of engagement features 14103 employed around a circumference shown here as two and number of struts 14101 shown here as five for a total of twelve engagement features 14103, can be varied to achieve a desired mechanical behavior. The number of engagement features per helical wrap of the strut can vary from one to 100, or more, depending on the diameter of the screw or tube member and the size of the engagement feature. Different numbers of features can yield different torsional responses, elongation properties, stress and strain profiles, and bending stiffness.

FIG. 144 is a scaled partial side view detail of a portion of a cut slot pattern 14300 of a bone fixation device with a non-threaded helical expandable segment with torsional engagement features, in a non-expanded state, near the beginning or end of the cut pattern. A radius 14308 (Radius AA) and a dimension 14407, FIG. 144, illustrate features that serves several functions. The machined gap or dimension 14407 is minimized throughout most of a cut pattern. The ends of the cut pattern can benefit from an increase in the radius 14308 (Radius AA) and the dimension 14407 becoming larger, or with more distance between the helical members. The end of this cut slot could also benefit from having a geometry that will have a lower strain when the member is loaded, such as radius 14308. The size of a gap or dimension 14307 (Dim CC) can vary from the lowest machining width possible, e.g. around 0.0005 inches, depending on the material wall thickness, to as great as the pitch dimension 14310 (Dim J). An increased dimension 14407 can also facilitate processing steps such as electropolishing, chemical etching and/or grit blasting. The radius 14308 facilitates a clearance area to allow desired media to gain access to the side walls of the strut. The rest of the deformable portion can be deformed or stretched during processing to obtain a desired gap distance or strut separation such as that shown in FIG. 145 as gap 14502.

A dimension 14305 (Dim M) represents a circumferential dimension of the embodiment in this flat pattern illustration. A dimension 14306 (Dim BB) is a measurement of the distance between engagement features 14103. The dimension 14306 can be equal to a width dimension 14405 (Dim S), described below, or as high as the circumference dimension 14305 (Dim M) multiplied by the number of helical wrapped struts 14101.

An angle 14406 (Angle Q) is a measurement of the angle of the engagement feature axially orientated edges relative to a longitudinal central axis of the screw member. The angle 14406 can vary from zero degrees, which would be parallel to an axis 14412 of the member, to parallel with a pitch angle 15007 (Angle K), FIG. 150.

The shape and angles of sides 14402 and 14403 of the engagement feature 14103 can be symmetric or can have different shapes and/or angles. A leading edge 14409 of the engagement feature 14103, having the width or dimension 14405 (Dim S), can be parallel to the pitch angle 15007, as shown in FIG. 150, or can be at a non-zero degree angle relative to the pitch angle 15007, depending on the desired functionality. Width 14405 (Dim S) can be in a range from a few thousandths to the value of the circumference dimension 14305 (Dim M) multiplied by the number of struts 14101. A height 14408 (Dim O) of the engagement feature 14103 can vary up to a practical maximum of the pitch 14310 (Dim J).

Receiving edges 14401 and 14404 and complementary edges 14402 and 14403 of engagement feature 14103 have different contact and relative interaction characteristics depending on the loading of the entire construct. For example, the complementary edge 14403 is the effective engagement edge in this design as shown by an interface 14504, FIG. 145. As the deformable portion of a member is loaded, the complementary edge 14403 slides relative to and potential against or in contact with the receiving edge 14404, while a gap or space 14505 remains between the receiving edge 14401 and the complementary edge 14402.

Accordingly, the angle 14406 (Angle Q) can impact the interactional behavior of the two edges sliding against each other by impacting the two forces on them, kinetic and static friction. The angles 14406A and 14406B of the two opposing complementary edges 14402 and 14403 relative to the longitudinal central axis can be the same or different. Similar to an incline plane, the narrower the angle 14406A, the lower the force required to initiate and maintain sliding motion. The surface finish and material type of the edge features also impacts this relationship by effecting the frictional coefficient. The angle 14406A can result in a higher force needed to slide the engagement feature relative to the strut with angular values that are parallel to or less than the axis angle. Conversely it may act as a ramp to facilitate the sliding of the two edges relative to each other as depicted in FIG. 144 with an angle greater than the axis of, for example, approximately six degrees.

The complementary edge 14402 is not in contact with the receiving edge 14401 depending on the loading and angle of the edge shown here as approximately five degrees. However, if the angle is decreased, as shown in FIG. 169, engagement with or locking of the respective receiving edges and complementary edges is achieved, thereby effectively limiting the expansion of the deformable portion.

FIG. 145 is a partial side view of a bone fixation device, e.g. device 14100 shown in FIG. 141, with a non-threaded helical deformable segment having a cut pattern 14300 with torsional engagement features, in an expanded or loaded state. The elongated state of cut pattern 14300 demonstrates a potential behavior of the engagement feature 14103 having edges coming in contact at interface 14504 and a clearance or gap 14505 between the opposite engagement feature edges. This behavior is the result of loading in a torsional aspect and or a stretching/tension loading aspect or both combined. The amount of overall twist about the axis of the tube along the length of the member is limited by the engagement features 14103.

FIG. 146 is a side view of the bone fixation device 14100 with a non-threaded helical deformable portion with torsional engagement features, in a non-expanded state. FIG.

147 is a side view of the bone fixation device 14100 with a non-threaded helical expandable segment with torsional engagement features, in an expanded state. A length 14609 (Dim DD) is less than a length 14709 (Dim EE). A loading of the member 14100 with an external tensile and/or torsional force yields an increase in length of the construct depicted in the comparison of the member 14100 shown in FIG. 146 and FIG. 147.

Self-cutting thread features such as 14601 and 14607 can be used on the screw. Segments 14602 that do not have cut slots, i.e. that are not within the cut pattern 14300 having cut slots 14102 and struts 14101, may or may not be present and may have lengths spanning a majority of the length of the member 14100. The gaps 14407 can be constructed such that they are equivalent to the expanded gap 14710 for a given loading condition. The members illustrated in FIGS. 146 and 147 are merely illustrative of the concept of the herein disclosed invention. The expandable, torque transferring, length limiting features described here can be implemented on any screw, rod, or other implement to fixate bone tissue, such as the embodiments depicted in FIGS. 148 and 149.

FIGS. 148 and 149 show a similar embodiment of the present invention as shown in FIGS. 147 and 148, with the exception that the embodiment shown in FIGS. 148 and 149 show the above described features and deformable portion on a headed screw or member 14800 employing non-threaded head 14806. This embodiment can provide a simpler insertion technique, by allowing the delivery rotations to number as many as the clinician determines is appropriate. The more turns yielding a longer screw construct, as the distal threaded end would continue to drive into the tissue. FIG. 148 is a side view of a bone fixation device or member 14800 with a non-threaded helical expandable segment with torsional engagement features, in a non-expanded state. FIG. 149 is a side view of a bone fixation device or member 14800 with a non-threaded helical expandable segment with torsional engagement features, in an expanded state.

FIGS. 150-169 show examples of yet another embodiment of the present invention. These examples cover features that share the ability to limit the extension or stretch of a portion or an entirety of a construct, joining member, or deformable portion. The ability to control the lengthening of the overall member has several benefits. One such benefit is to allow for a maximum length to be obtained and then an additional application of axial load to be applied to the bone segments. This additional load could be applied through further rotations of the screw which would engage the tissue distally and add a compression force that was above the force required to stretch the screw to the designed amount. Clinically this is called preload. The tissue remodels over time and this load is quickly absorbed in the case of a standard orthopedic screw, because very little tissue needs to be remodeled to reduce the load to a net zero force with a static length screw, less than a fraction of a millimeter. With the embodiments described herein, the load would first be absorbed by the tissue up to the point the elongation mechanism was activated and then the load would be imparted by the elongation mechanism until the distance was completely relaxed, this distance could be several millimeters. The ability to control the expanded state could also prohibit the over expansion of the elongation section which may be desirable to minimize the yielding of the construct.

FIG. 150 is a side view of a portion of a cut slot pattern of a bone fixation device with a non-threaded helical expandable segment with torsional engagement features and axial length engagement features, in a non-expanded state. This embodiment has only one engagement feature 15003 per helical wrap of strut 15001. When tension force is applied to the screw member, it may be desirable to limit the overall expansion or deformation of a deformable portion 15010. Hence, length limiting features, shown in FIG. 151, can be made through various physical features formed in cut slot 15002 of engagement feature 15003. The concept of having a member that both expands in length but that is also limited in such expansion, illustrated in FIGS. 150 thru 169, allows application of a greater tensile force absent a resulting change in length or diameter beyond a predetermined or designed value.

With reference to FIGS. 150 and 151, a dimension 15008 (Dim R) is shown here to be the same on each of the struts 15001, however a dimension 15008, a dimension 15012 (Dim S), and a dimension 15103 (Dim O) can vary on each of struts 15001 which would change the cross section of the helical wrap member 15010 and the forces the engagement features 15003 exert during torsional loading of the member. A radius 15009 (Radius P) can also be varied along with an angle 15006 (Angle Q) to maximize the width of the helical member and or facilitate different frictional characteristics. An overall length 15005 (Dim N) of the deformable portion 15010 is limited by the length of screw, the threaded portions, and the head. An angle 15007 (Angle K) is the pitch of the struts 15001 and is related on a dimension 15004 (Dim J). A dimension 15011 (Dim M) represents the circumferential dimension of the construct. Alternatively, the dimension 15004 can be variable through the deformable portion 15010.

FIG. 151 is a partial side view scaled detail of a portion B, shown in FIG. 150, of a cut slot pattern 15010 of a bone fixation device with a non-threaded helical expandable segment having torsional engagement features 15003 and integrated corresponding axial length engagement features 15104A and 15104B in a non-expanded state. A dimension 15105 (DIM T) is a dimension between the elongation limiting engagement feature 15104A and 15104B on torsional engagement feature 15003. The dimension 15105 corresponds to the length the adjacent struts 15001 will move apart from each other before the elongation limiting engagement features 15104A and 15104B engage fully or contact one another and prevent further elongation. This dimension 15105 can be altered to adjust the overall deformation or elongation of the entire structure.

FIGS. 152-156 illustrate another embodiment of the invention employing a semi-symmetric geometry and a slot cut pattern 15210 having locking features or length engagement features on the engagement side or leading edge of the torsional engagement features. As torsional engagement features 15203 are loaded in torsion and tension, the limiting features 15304A and 15304B come into contact at point 15505 and limit the rotation and length changes of the construct.

FIG. 152 is a partial side view of a portion of a cut slot pattern 15210 having cut slots 15202 of a bone fixation device with a non-threaded helical expandable segment or deformable portion with torsional engagement features 15203 on both the leading and trailing edge of the helical struts 15201 and axial length engagement features 15304A and 15304B on the engagement or sliding edge, in a non-expanded state.

FIG. 153 is a partial side view scaled detail of a portion D shown in FIG. 152 of a cut slot pattern 15210 of a bone fixation device with a non-threaded helical expandable segment with torsional engagement features 15203 and axial length engagement features 15304A and 15304B in a non-expanded state. A dimension 15309 (Dim T) can be altered to affect the overall lengthen limiting feature of the construct, which is limited by a dimension 15306 (Dim O) a length of the engagement feature. Dimension 15312 (Dim Z) is a dimension of the interference feature or offset of axial length engagement features 15304A and 15304B. A dimension 15312 can be set to give a robust engagement or shallow to give a weak or less engaging mechanism depending on the desired effect. An effective range of dimension 15312 (Dim Z) is a couple of thousandths of an inch to the value of a dimension 15305 (Dim S) the engagement feature width. A dimension 15306 is half of Dim O 14408 the height of the engagement feature. A relationship of an angle 15310 (Angle Q, the angle of a side of the engagement features 15203 relative to a longitudinal central axis of construct) and the relative orientation of the axial length engagement features 15304A and 15304B will yield different engagement. One could arrange it to have a sliding engagement, no contact until the point of engagement, an ever-increasing load to final engagement, etc.

In the present embodiment, the length limiting feature is shown only on one side of the torsional engagement feature but could be placed on the other edge also or instead of. The angle of approach, height and length of the engagement features can be altered as to optimize the desired engagement. The depth 15312 (Dim Z) can be steep to give a robust engagement or shallow to give a weak or less engaging mechanism, depending on the desired effect. The relationship of the angle 15310 (Angle Q) and the relative orientation of the axial length limiting features 15304A and 15304B will yield different engagement. One can arrange it to have a sliding engagement, no contact until the point of engagement, an ever-increasing load to final engagement, etc.

FIGS. 154-156 illustrate the cut pattern 15210 shown in FIG. 152 formed onto a tube and machined into a construct. The cut pattern 15210 has length limiting features 15304A and 15304B. FIG. 154 is a partial side view of a portion of the cut slot pattern 15210 of a bone fixation device with a non-threaded helical expandable or deformable segment with torsional engagement features 15203 and axial length engagement features 15304A and 15304B in a non-expanded state into a tube.

FIGS. 155 and 156 are partial side view scaled details of a portion of a cut slot pattern 15210 of a bone fixation device with a non-threaded helical expandable or deformable segment with torsional engagement features 15203 and axial length engagement features 15304A and 15304B, in an expanded state under a tensile load with the length engagement features engaged at points 15505. FIGS. 155 and 156 show the cut pattern 15210 in a stretched configuration with the length limiting features 15304A and 15304B engaged at points 15505 such that length limiting features 15304A and 15304B transmit force from one to the other. This act of engagement allows length limiting features 15304A and 15304B to distribute the axial and torsional force to the adjacent strut 15201 at the point of contact 15505. The net effect of this interference is a limiting of the elongation and torsional rotation of the entire cut pattern 15210. The engagement features 15203 have a leading-edge side 15605 and a trailing edge side 15606. The definitions of the leading and trailing edge sides are generally dependent on the specific cut pattern direction and the loading of force application onto the construct.

FIGS. 157-159 illustrate another embodiment of the invention having a cut pattern with cut slots having a different geometry or shape of torsional engagement features and length engagement features. The geometry is similar to that of a triangle. The shape of the of torsional engagement features and length engagement features of the previous embodiments have been similar to trapezoids, rectangles, parallelograms, rhombus, or the like. The differences in feature geometry of the cut pattern 15710 formed by cut slots 15702 may yield less or more material in the cross-sectional area of helical struts 15701 and effect the spring force of the construct. The geometric shape may also yield a torsional engagement feature 15703 that demonstrate a higher yielding point and thus are able to withstand higher loading conditions. The amount of engagement or length of the length engagement features 15704A and 15704B will also have an impact on the amount of load or force the cut pattern 15710 can withstand before yielding. The number of torsional engagement features 15703 along the length of the strut 15701 will also impact the load distribution along the strut 15701. The number of torsional engagement features 15703 is not symmetric per wrap member. The number and/or position is offset so as to maximize the cross-sectional areas at any one point along the helical strut 15701, this gives a stepped appearance to the cut pattern.

FIG. 157 is a partial side view of a portion of the cut slot pattern 15710 of a bone fixation device with a non-threaded helical expandable segment with torsional engagement features 15703 and axial length engagement features 15704A/B, in a non-expanded state. FIG. 158 is a partial side view of a portion of a cut slot pattern 15710 of a bone fixation device with a non-threaded helical expandable segment with torsional engagement features 15703 and axial length engagement features 15704A/B, in a non-expanded state. FIG. 159 is a partial side view scaled detail of a portion of a cut slot pattern 15703 of a bone fixation device with a non-threaded helical expandable segment with torsional engagement features 15703 and axial length engagement features 15704A and 15704B in contact or engaged at point 15905, in an expanded state. The faces move apart from one another upon clockwise rotation minimizing friction until the engagement features 16004A and 16004B catch or interfere at some point along the deformation then they transfer the loading. During counterclockwise rotation they would engage with less loading.

FIGS. 160-162 illustrate another embodiment of the invention having a cut pattern with cut slots having a different geometry or shape of torsional engagement features and length engagement features. The geometry is similar to that of a triangle. The number of engagement features is not symmetric per wrap member and is offset such as to maximize the cross-sectional areas at any one point along the helical strut, this gives a stepped appearance to the pattern. A cut pattern 16010 having struts 16001 formed of cut slots 16002 employs length engagement features 16004A/B on a trailing edge of a torsional engagement feature 16003. The leading edge of the torsional engagement feature 16003 is minimized so there is little to no contact until the length limiting features 16004A/B come into contact at point 16005. This set of features yields a different rotational lengthening behavior than the other designs. This embodiment has little frictional resistance to lengthening until the length limiting features 16004A and 16604B engage at point 16205.

FIG. 160 is a partial side view of a portion of a cut slot pattern 16010 of a bone fixation device with a non-threaded helical expandable segment with torsional engagement features 16003 and axial length engagement features 16004A/B, in a non-expanded state. FIG. 161 is a partial side view of a portion of a cut slot pattern 16010 of a bone fixation device with a non-threaded helical expandable segment with torsional engagement features 16003 and axial length engagement features 16004A/B, in a non-expanded state. FIG. 162 is a partial side view scaled detail of a portion of a cut slot pattern 16010 of a bone fixation device with a non-threaded helical expandable segment with torsional engagement features 16003 and axial length engagement features 16004A/B, in an expanded state. A gap 16205 indicates an expansion of the cut pattern 16010 at cut slots 16002.

FIGS. 163 and 164 depict another embodiment of the invention employing two length limiting features. A cut pattern 16310 formed with cut slots 16302 employs torsional engagement features 16303 having length limiting dimensions or dimensional features and independent length limiting features 16404A/B, similar to those previously described.

The torsional engagement features 16303 have length limiting dimensions or dimensional features in the form of a first width or dimension 16406 that is larger than a second width or dimension 16407. The orientation of this dimension difference of the torsional engagement features 16303 defines an interference of adjacent sides of the torsional engagement features 16303 upon lengthening or expansion of cut pattern 16310 and expansion of a distance 16311 (Dim N). Alternatively stated, the differences in the dimensions 16406 and 16407 limit the amount of axial travel and force engagement of the edges of the receiving and protruding portions of the torsional engagement features 16303. A dimension 16313 (Dim W), a dimension 16315 (Dim V), and a radius 16308 (Dim U) define the size and frequency of the torsional engagement features 16303 employing axial length limiting dimensions.

The length limiting features 16404A/B employ a dimension 16412 (Dim Z) and a dimension 16414 (Dim T) that is similar to the other embodiments described herein. It will be understood that the length limiting features 16404A/B are redundant with the axial length limiting dimensions of the torsional engagement features 16303 and that both the length limiting features 16404A/B axial length limiting dimensions of the torsional engagement features 16303 independently are sufficient to limit the axial lengthening of the cut patters 16310. In other words, both the length limiting features 16404A/B and the axial length limiting dimensions of the torsional engagement features 16303 do not need to be present to create interference of the side edges of torsional engagement features 16303 and thereby limit the axial lengthening of the cut patterns 16310. The interference fit between the side edges can be sufficient to limit the travel or lengthening of the cut pattern 16310.

FIG. 163 is a partial side view of a portion of a cut slot pattern 16310 with an overall length 16311 (Dim N) and a pitch 16318 (Dim J) with a resulting pitch angle 16317 (Angle K) of a bone fixation device having a circumference 16315 (Dim M) with a non-threaded sinusoidal expandable segment with torsional engagement features 16303 having axial length limiting dimensions and axial length engagement features 116404A/B, in a non-expanded state. FIG. 164 is a partial detailed side view of a portion C shown in FIG. 163 of the cut slot pattern 16310 of a bone fixation device with a non-threaded sinusoidal expandable segment with torsional engagement features 16303 having axial length limiting dimensions and axial length limiting features 16404A/B, in a non-expanded state. For example, a radius 16308 (Dim U) can be 0.025 inches which corresponds to a dimension 16406. Dimension 16407 could have a value of 0.020 which would result in an interference fit on each of the engagement features.

FIGS. 165 and 166 show embodiments of the present invention similar to the embodiments shown in FIGS. 163 and 164 in that the torsional engagement features employ length limiting dimensions or dimensional features through a differential sizing or width of different portions of the torsional engagement features in order to create an interference fit or lengthening stop upon axial expansion, e.g. the differential widths of the torsional engagement feature prevents the protruding and receiving portions of the torsional engagement features from fully separating from one another. For the sake of clarity and by way of example only, in the embodiment shown in FIGS. 165 and 166, independent length limiting features, such as those previously described, are not employed within the cut slots of the cut pattern.

A cut pattern 16510 has struts 16501 employing torsional engagement features 16503 having length limiting dimensions or dimensional features formed of cut slot 16502. An angle 16616 and the length of the engagement feature 16503 help define the angle of force and the surface area upon which such force is applied when such length limiting dimensions of the torsional engagement features 16503 are engaged. These dimensions can either increase or decrease the amount of resistance generated during axial lengthening of the cut slot pattern 16510. Dimension 16515 and 16518 define, in part, the frequency and size of the engagement features.

FIG. 165 is a partial side view of a portion of a cut slot pattern 16510 of a bone fixation device with a non-threaded expandable segment with trapezoidal torsional shaped engagement features 16503 having length limiting dimensions or dimensional features, in a non-expanded state. FIG. 166 is a partial detailed side view of a portion A shown in FIG. 165 of a cut slot pattern 16510 of a bone fixation device with a non-threaded expandable segment with trapezoidal shaped torsional engagement features 16503 having length limiting dimensions or dimensional features, in a non-expanded state. FIG. 166 depicts dimension 16605 and 16607 which define an increased gap area in the cut pattern. This increase in gap directly correlates to the expansion distance before the length limiting dimensions of the torsional engagement features 16503 restricts the axial deformation of the construct. The relative difference in dimension 16606 and 16604 will yield the interference between the members and produce the wedging or limiting of axial deformation.

FIG. 193 is a picture of a side view of a portion of a bone fixation device 19300 employing the cut slot pattern 16510 shown in FIG. 165 with a non-threaded expandable segment with trapezoidal torsional shaped engagement features 16503 having length limiting dimensions or dimensional features, in a non-expanded state, reduced to practice.

FIGS. 167, 167A, and 167B depict another embodiment of the invention that incorporates features described previously herein. In this embodiment, the shape of the torsional engagement features having length limiting dimensions or dimensional features is asymmetric. The engagement feature 16703 leading edge side 16714 is angled to slidably engage with a slight ramp in the angle promoting length change, and an edge 16715 which is angled sharply against the axis of deformation provides a positive stop. The angle of edge 16715 also acts as a ramp to apply force to the surfaces together once they come into contact. This asymmetry provides further means for controlling the torsional force required for axial lengthening of the cut slot pattern and the robustness of the axial length limiting characteristics of the cut slot pattern.

FIGS. 167 and 167A are partial side views of portions of a cut slot pattern 16710 of a bone fixation device with a non-threaded helical expandable segment with torsional engagement features having axial length limiting dimensions or dimensional features, in a non-expanded state. FIG. 167B is a partial side view of a portion of the cut slot pattern 16710 of a bone fixation device with a non-threaded helical expandable segment with torsional engagement features having axial length limiting dimensions or dimensional features, in an expanded state.

FIGS. 167, 167A, and 167B show the cut pattern 16710 having struts 16701 employing torsional engagement features 16703 having length limiting dimensions or dimensional features formed of cut slots 16702. The torsional engagement features 16703 employ length limiting dimensions or dimensional features that generate an interference engagement between the sides or edges of receiving torsional engagement features 16703A and the sides or edges of protruding torsional engagement features 16703B resulting in contact points 16705A and 16705B. The length limiting dimensions or dimensional features of torsional engagement features 16703 are defined, in part, by a dimension 16712 being greater that a dimension 16713.

Furthermore, the leading and trailing sides or edges of the rotational engagement features 16703 employ angles that facilitate the axial lengthening of the cut pattern 16710 by having a sliding contact engagement. The entire or portions of the cut slot 16702 can be machined at a larger width and/or with a potential overall shorter path thus simplifying manufacturing and shortening manufacturing time. The angle of the torsional engagement features 16703 can also facilitate the removal of the screw body by adding additional contact pressure along the features.

FIGS. 168 and 168A are partial side views of a portion of another embodiment of the present invention employing a cut slot pattern 16810 of a bone fixation device with a non-threaded helical expandable segment with torsional engagement features 16803 employing length limiting dimensions or dimensional features and independent length limiting features 16804A and 16804B. FIG. 168 shows the cut slot pattern 16810 in a non-expanded state, and FIG. 168A shows the cut slot pattern 16810 in an expanded state. This embodiment is similar to that shown in FIG. 167 but the cut slot pattern 16810 further employs length deformation limiting features on the leading edge or face, similar to FIG. 152. The faces of the length limiting features 16804A and 16804B are angled to promote a sliding contact until the feature edges engage during length deformation. An opposite side or face of the torsional engagement features 16803 have a wedged shape or being sloped such that, upon axial deformation of the cut slot pattern 16810, the faces apply force for the engagement of the length limiting features 16804A and 16804B.

FIG. 168A depicts the construct in a tabular form deformed in a stretched or expanded state. The length limiting features 16804A and 16804B are shown in an engaged position. Corresponding opposing faces 16805A and 16805B of torsional engagement features 16803 engage or interact to generate a force vector that increases the force on the engagement of the length limiting features 16804A and 16804B. The interaction of faces 16805A and 16805B of torsional engagement features 16803 serve, in part, to increase not only the surface area of the interference but also define the geometry so that the axial and torsional forces generated are translated into forces that engage the entire cut slot pattern 16810. Accordingly, not only are the length limiting features 16804A and 16804B loaded, but the entire wrap member or strut 16810 is loaded. This dispersed or shared loading characteristic is similar for the embodiments shown in FIGS. 163-169 disclosed herein.

FIGS. 169 and 169A are partial side views scaled details of a portion of a cut slot pattern 16910 of a bone fixation device with a non-threaded helical expandable segment with torsional engagement features 16903 employing length limiting dimensions or dimensional features and independent length limiting features 16904A/16904B and 16905A/16905B on opposite sides or edges of the torsional engagement features 16903. FIG. 169 shows the cut slot pattern 16910 in a non-expanded state, and FIG. 169A shows the cut slot pattern 16910 in an expanded state. This embodiment is similar to that shown in FIG. 168 but further employs length deformation limiting features on the trailing edge or face similar to FIG. 160.

The faces or surfaces of the torsional engagement features 16903 forming length limiting features 16904A and 16904B are angled to promote a sliding contact until the length limiting features 16904A and 16904B engage during length deformation. Opposite faces or surfaces of the torsional engagement features 16903 forming length limiting features 16905A and 16905B engage upon axial deformation and also apply length deformation limiting engagement. The faces or surfaces of the torsional engagement features 16903 are angled so as to provide slidable engagement until the relatively perpendicular to a longitudinal central axis edges of the length limiting features 16904A/16904B and 16905A/16905B come into contact and effectively stop axial deformation. These length limiting engagement features, along with all others such features described herein, serve to not only limit the overall length of the construct but also to increase the axial tension force the construct can endure before permanent deformation.

FIG. 169A depicts the construct in tubular form deformed in the stretched or expanded state. The length limiting features 16804A/16804B and 16905A/16905B are shown in the engaged state. The feature faces have both slanted or angle surfaces to facilitate deformation and also have substantially perpendicular engagement surfaces to limit the length deformation. Both these features are on both leading and trailing sides of the torsional engagement features 16903. These deformation limiting features both enable the deformation in length and torsional directions, as well as limit the total deformation in both axial and rotational motion.

FIGS. 170 and 171 depict another embodiment of the invention in which the wrapped strut 17001 employs stepped or repeated step shaped torsional engagement features 17003 formed of a cut slot 17002. Alternatively stated, cut slot pattern 17010 employs torsional engagement features 17003 having a form or shape of a torsional engagement feature on a torsional engagement feature. Yet another way of describing cut slot pattern 17010 would be that the pattern employs both torsional engagement feature 17103A extending from trailing edge 17122 of the struts 17001 and torsional engagement feature 171038 extending from a leading edge 17121 of the struts 17001. A gap 17107 represents the cut slot pattern increasing in width near the ends of the pattern. This allows for strain relief of the construct as it transitions from a cut slot pattern into a solid, non-cut section or portion. This feature also allows for easier post processing such as electropolish, etching, and grit blasting.

The overall bending stiffness, axial stiffness and rotational stiffness properties of the cut slot pattern 17010 may be different than the other embodiments described herein. Each of the torsional engagement features 17003 can employ any and or all of the previously disclosed feature sets. FIG. 170 is a partial side view of a bone fixation device with a non-threaded expandable segment, in a non-expanded state. FIG. 171 is a partial side view of a portion of a cut slot pattern of a bone fixation device with a non-threaded expandable segment, in a non-expanded state.

The features depicted throughout this disclosure can be used together with features from any and all of the embodiments disclosed. The locking mechanisms or length engagement features, the torsional engagement features, and the helical patterns can all be used interchangeably, the figures are illustrative of possible embodiments and do not comprehensively encompass the scope of all variations of the invention.

FIGS. 172-175 illustrate other embodiments of the present invention. In these embodiments the deformable portions of the members are configured to not yield a rotation force.

With reference to FIGS. 172 and 173, cut pattern 17210 employs wrap members 17201 having a sinusoidal like path along a longitudinal axis of the pattern 17210 formed by cut slots 17202. The deflection of members 17201 work in concert to yield no net rotational moment. Optional perpendicular spline members 17223 placed at the apex of the peaks and valleys of the members 17201 act to limit the radial deforming forces imparted on members 17201.

Each section 17224 of wrap members 17201 between the spline members 17223 act like a beam in bending and thus a spring, lengthening as it is deformed into a straight or axial configuration. The number of wrap members 17201 can vary from 1 to 100 but is dependent on a width 17307 of the member 17201, a width of the cut slot 17202, an amplitude 17308 of deflection of wrap members 17201, and a diameter of a tubular form of the cut pattern 17210. The wrap members 17201 about the circumference of the tubular form of the construct act as springs in parallel, changing the spring constant accordingly.

In a substantially parallel arrangement as shown in FIGS. 172 and 173, the springs are set parallel to each other and the resulting spring constant is higher than if a single strut or spring having the width 17307 is employed throughout the length of the deformable portion. The bending pattern or profile of wrap members 17201 can vary to distribute the bending strain along the longitudinal axis in a desired manner. The width 17307 and length of sections 17224 of the wrap members 17201 can be the same or can vary about the circumference of the tubular form of the construct. FIG. 172 shows two spring mechanisms or sections 17224 in series, the number of these spring mechanisms is dependent on the overall length of the cut pattern 17210 but could vary from 1 to 100, changing the spring constant accordingly. For example, FIG. 173 shows four spring mechanisms or sections 17224 in series, each section 17224 having a different deformation than that shown in FIG. 172.

FIG. 172 is a partial side view of a tubular form of a cut pattern 17210 of a bone fixation device with a non-threaded sinusoidal expandable segment, in a non-expanded state. FIG. 173 is a partial side view of a bone fixation device with a non-threaded sinusoidal expandable segment in an expanded state.

FIGS. 174 and 175 show an alternative embodiment of the inventive concept described with regard to FIGS. 172 and 173. With reference to FIGS. 174 and 175, cut pattern 17410 employs wrap members 17401 having an angled path along a longitudinal axis of the pattern 17410 formed by cut slots 17402. The deflection of members 17401 work in concert to yield no net rotational moment. A longitudinal axis force indicated by arrows 17525 applied to the cut pattern 17410 yields reduction in a diameter 17526 relative to a diameter 17527 of a portion of the construct not employing cut pattern 17410, as depicted in FIG. 175. The strut members 17401 can be uniform or have different widths 17404.

FIG. 174 is a partial side view of a cut pattern 17410 of a bone fixation device with a non-threaded angled expandable segment, in a non-expanded state. FIG. 175 is a partial side view of a cut pattern 17410 of a bone fixation device with a non-threaded angled expandable segment, in an expanded state.

FIGS. 176 and 177 depict yet another embodiment of the present invention in which a cut pattern 17610 employs cut slots 17602 having a wave-like or chevron shape and struts 17601A and 17601B and joining portion 17604. A dimension 17703 between the similarly oriented cut slots 17602 increases as an axial load is applied to the cut pattern 17610. This deflection is controlled by several variables including the wall thickness of the tube; a width 17606 of the struts 17601A, 17601B; a length 17605 of the struts 17601A, 17601B; an angle of the struts 17601A, 17601B relative to a longitudinal central axis; an angle of the struts 17601A, 17601B relative to the adjacent struts 17601A, 17601B; the number of the struts 17601A, 17601B about the circumference; the number of the strut 17601A, 17601B along the axis of the construct; and the diameter of the tubular form of the cut pattern 17610.

The expanding section has the cut pattern 17610. The cut pattern 17610 having struts 17601A and 17601B in angles relative to the axis. The cut pattern 17610 struts 17601A and 17601B being shorter than the circumference of the body. The continuous body of the cut pattern 17610 having the angled struts 17601A and 17601B terminating at joining portion 17604. The angled struts 17601A and 17601B create the spring force for therapeutic effect. The angled struts 17601A and 17601B having alternating angles about the circumference of the body. The struts 17601A and 17601B are relatively parallel to each other axially, before axial load is applied. The relative angles of the struts 17601A and 17601B diverging from each other as the body or cut pattern 17610 is lengthened. The joining portions 17604 at the ends of the struts 17601A and 17601B increase in axial separation distance relative to each other during axial loading. The overall properties of bending, rotational, and axial stiffness may be different from the other embodiments disclosed herein. Variations on the cut pattern 17610 are considered included in this disclosure.

FIG. 176 is a partial side view of the cut pattern 17610 of a bone fixation device with a non-threaded expandable or deformable segment, in a non-expanded state. FIG. 177 is a partial enlarged detail side view of the cut pattern 17610 of a bone fixation device with a non-threaded expandable segment, in an expanded state.

FIG. 178 is a side view of a bone fixation device 17800, in a non-expanded state, inserted into two reduced bone segments 501A and 501B. This illustration is similar to that of FIG. 5 and the screw or joining member is similar to embodiment shown in FIGS. 139 and 140. A shaft of the member 17800 has a deformable portion 17606 off set to one end of the screw such that there remains a portion 17807 that is uncut and less flexible. The less flexible portion 17807 serves to interface with the bone segments 501A, 501B at the compression region 502. The less flexible portion 17807 can be threaded or unthreaded. The screw could employ any distal thread 17804 configuration appropriate for the type of tissue it is engaging with, such as cancellous or cortical thread types. The proximal head 17805 can also take on any feature set to optimize the clinical application such as headed, headless, threaded, self-tapping threaded, etc.

FIGS. 179-191 depict additional embodiments of the disclosed invention in which the therapeutic mechanism of action employs multiple components to obtain a drawbar spring assembly with the spring in compression instead of tension. Various compression spring designs can be used with these embodiments such as those depicted in FIGS. 186-191 including but not limited to compression springs, lock washers, spring washers, wave springs, Belleville annular rings of hollow truncated cone, springs of conical shape made of helically coiled wires, and others. The spring wire employed in certain of these embodiments could have any cross section; e.g. round, flat, rectangular, oval, square, etc. The end configurations can be plain, ground, varied pitch, wrapped, squared, or any other suitable configuration. The spring configuration can utilize any known configuration including but not limited to; constant pitch, conical, barrel, hourglass, or variable pitch. The springs can be made from wire wrapped and treated to maintain their profile. The springs can be cut or machined from rod stock or tubing. The outside diameter, inside diameter, mean diameter, wire diameter, free length, solid length, deflection, pitch, material, and material processing, are all variables that can be used to control the spring rate and stress concentrations in the design to achieve the desired force profile and geometric configuration.

Belleville annular rings of hollow truncated cone, may be advantageous in certain applications as they are able to absorb external axial forces counter-acting against each other. The spring member cross section is usually rectangular. Belleville springs are designed for higher loads with low deformations. They are used individually or in sets. When using springs in a set it is necessary to take account of friction effects. The springs could be configured into a serial arrangement, i.e. arranged against each other, the resulting spring constant of the set being lower than that of a single spring. Springs of conical shape made of helically coiled wires, with constant clearance between the active coils may be advantageous in certain applications as they are able to absorb external counter-acting forces applied against each other along their axis.

FIGS. 179-183 depict embodiments of the present invention in which bone segments 501A and 501B, with a compression zone 502, are brought together and compressed, both acutely and over time, with the inventive screw members.

FIG. 179 shows a spring or deformable portion 17906 of the member 17900 in a compressed/unexpanded/loaded state in which a compressive force is applied in directions indicated by arrows 505 to a compression zone 502 of bone segments 501A and 501B. A head of the screw 17907 transmits a compression force generated by the spring 17906 to the bone segments 501A and 501B in directions indicated by arrows 505 to the compression zone 502 through the engagement of a distal threaded section 17904 of the screw body 17900. The compression spring 17906 shown here is a beveled washer type spring, acting on the surface of the bone. The head 17907 of the screw 17900 and spring 17906 can remain on the surface of the bone segment 501B. The screws in FIGS. 179-185 could be cannulated or solid screws, and the screws could employ any distal thread 17904 configuration appropriate for the type of tissue it is engaging with, such as cancellous or cortical self-tapping thread types.

FIG. 180 is a side view of a bone fixation device 18000 inserted into two reduced bone segments 501A and 501B, in an expanded state. A helical conical spring 18006 interfaces with the head 18007 of the screw 18000 and a counter drilled feature 18008 in the bone 501B. This configuration allows the screw head 18007 and spring 18006 to reside tangent to and/or under the surface of the bone 501B within counter drilled features 18008. The use of a conical spring can minimize the height of the spring 18006 needed to yield the given force needed. FIG. 181 is a side view of a bone fixation device 18000 inserted into two reduced bone segments 501A and 501Bb, in a non-expanded state.

FIG. 182 is a side view of a bone fixation device 18200 inserted into two reduced bone segments 501A and 501B, in a compressed state. A spring element 18206 is positioned within a pocket washer 18209 sunken within a counter drilled bone feature 18208. A lip 18210 of the washer 18209 resides on a surface of the bone 501B. A head 18207 of the screw 18200 can be designed to reside inside of or tangent to a surface of the lip 18210 of the pocket washer 18209. The head 18207 of the screw 18200 can be flush with the lip 18210 of the washer 18209 (FIG. 182), on top of the lip 18210 of the washer 18209 (FIG. 183), or recessed within the pocket washer 18209. The spring 18206 and pocket washer 18209 can vary in diameter to accommodate a minimal or smaller diameter drill hole such as shown in FIG. 185. The amount of spring force needed can be met by varying the standard spring parameters, the length of compression, pitch, diameter, cross-section, material, shape and other parameters.

FIG. 183 is a side view of a bone fixation device 18300 inserted into two reduced bone segments 501A and 510B, in a compressed state. A spring element 18306 is positioned within a pocket washer 18309 sunken within a counter drill feature 18308. A lip 18310 of the washer 18309 resides on a surface of the bone 501B. A head 18307 of the screw 18300 can be designed to reside on a surface of the lip 18310 of the pocket washer 18209. The spring 18306 and pocket washer 18309 can vary in diameter to accommodate a minimal or smaller diameter drill hole such as shown in FIG. 185.

FIG. 184 is a side view of a bone fixation device 18400, in an expanded state, and FIG. 185 is a partial cross section, side view of the bone fixation device 18400, in an expanded state, in accordance with an aspect of the present invention.

A spring element 18406 is positioned within a pocket washer 18409 having a lip 18410. A head 18407 of the screw 18400 can be designed to reside within a recess 18409A of the pocket washer 18409. The head 18407 employs a tool interface 18503 for rotation of a member shaft 18501 having a lumen 18505. The spring 18406 and pocket washer 18409 can vary in diameter to accommodate a minimal or smaller diameter bone drill hole for the washer 18409 employing a stepped diameter as shown in FIG. 185. In an expanded state as shown in FIG. 185, the head 18407 may protrude above or from the lip 18410 of the washer 18409 by a length 18502. In a compressed or non-expanded state, the head 18407 is positioned within or substantially within the recess 18409A of washer 18409.

FIGS. 186-191 represent some of the types of spring mechanisms that can be used with the embodiments described herein. FIG. 186 is an isometric view of a bone fixation bevel washer with separated contact members on the outer diameter of the spring element. FIG. 187 is an isometric view of a bone fixation bevel washer with separate contact members on the inner diameter spring element device. FIG. 188 is an isometric view of a bone fixation bevel washer with separated contact members on the outer diameter with twisted orientation to aide rotational control and spin of the spring element device. FIG. 189 is an isometric view of a bone fixation wave spring element device. FIG. 190 is an isometric view of a bone fixation tapered helical wound flat element spring element device. FIG. 191 is an isometric view of a bone fixation helical wound round or oval wire element spring device.

FIGS. 192 and 193 depict embodiments of the present invention reduced to practice. FIG. 192 being similar to FIG. 140 and FIG. 193 similar to FIG. 165.

FIG. 194 is a graph comparing the loading and unloading force profile relative to distance displaced (not linear) of a device of the present invention relative to a standard bone screw. Line 19400 is the loading of the inventive screw during the deformable section deformation, line 19401 is the loading after the engagement features have limited the deformation and loading is continued. Line 19402 is the initial unloading of a deformable screw according to the present invention. Line 19403 is the unloading of a deformable screw during the recovery of the deformation of the deformable section. Dotted line 19404 is the loading and dotted line 19405 is the unloading of a standard non-expandable screw.

A standard screw loses compressive force in less than 1 millimeter of reduction of distance of substrates being compressed. The inventive deformable screw can maintain compressive loading of over 4 millimeters of distance or positional relaxation.

FIGS. 195-208 illustrate another aspect of certain embodiments of the present invention. FIGS. 195-208 show certain of the angles at which the cut slots forming above described features can be formed within a member. These cut slot angles can yield different behaviors in deformable portions employing otherwise similar cut patterns by changing the cross-sectional shape and area of the features. Different cut slot angles can also affect the embodiments by changing the interference, the surfaces that contact and the direction of load being applied to the surfaces. The following description will capture some of the features that different possible cut slot angle cutting enables.

FIG. 195 shows a cannulated screw or joining member 19500 that is similar to the embodiments shown in FIGS. 140-142. The member is shown with a partial axial cross section along surface 19531 and a partial transverse cross section along surface 19532 relative to a longitudinal central axis 19533. The surface 19531 transects a cut slot 19502 forming struts 19501. The surface 19532 transects the cut slot 19502 forming torsional engagement member 19503.

FIG. 196 shows a cross section view of a portion of a member 19600 employing a cannulated central helical expandable section 19610, similar to that shown in FIG. 138. The surface 19531 formed by axial cross section is the orientation of the image, i.e. is oriented perpendicular to the view. Struts 19601 are formed by a cut slot 19602 made through a side wall 19605 of the member 19600 at an angle that is approximately perpendicular to the longitudinal central axis 19533, i.e. 90 degrees or directly orthogonal to the central axis 19533.

FIG. 197 shows a cross section view of a portion of a member 19700 employing a cannulated central helical expandable section 19710. The surface 19531 formed by axial cross section is the orientation of the image, i.e. is oriented perpendicular to the viewer. Struts 19701 are formed by a cut slot 19702 made through a side wall 19705 of member 19700 at an angle 19734 relative to an orthogonal axis 19736. The angle 19734 can be approximately plus or minus 80 degrees. A line or plane between an exterior edge 19735 of the cut slot 19702 and an interior edge 19737 of the cut slot 19702 is not parallel to the orthogonal axis 19736. The angle 19734 is shown as being consistent or uniform throughout expandable section 19710.

FIG. 198 shows a cross section view of a portion of a member 19800 employing a cannulated central helical expandable section 19810. The surface 19531 formed by axial cross section is the orientation of the image, i.e. is oriented perpendicular to the viewer. Struts 19801 are formed by a cut slot 19802 made through a side wall 19805 of member 19800 at an angle 19834 relative to an orthogonal axis 19836. The angle 19834 can be approximately plus or minus 80 degrees. A line or plane between an exterior edge 19835 of the cut slot 19802 and an interior edge 19837 of the cut slot 19802 is not parallel to the orthogonal axis 19836. In the present embodiment, the angle 19834 is shown as varying along the axis 19533. For example, the cut slot 19802 can transition to a different angle 19834 yielding a cut slot 19802 in a different plane along the axis 19533. This angle change yields a different or variable cut slot pattern on the exterior and/or interior surface of the member 19800. This is because the cross-sectional area changes along the axis 19533 as this angle 19834 changes. The bending stiffness, rotational response, the diameter change, in response to torsional, axial, and bending loads is altered with these non-orthogonal cut angles.

The angle of the cut slot can also vary in other planes. FIGS. 199-203 are partial perspective views of deformable portions of bone fixation devices having a non-threaded deformable or expandable segment, in a non-expanded state, that depict cut angle variation shown on a cross-sectional plane 19502 which is approximately at an angle of a cut slot forming a strut of the deformable portion. FIGS. 204-208 are partial perspective views of deformable portions of bone fixation devices having a non-threaded deformable or expandable segment, in a non-expanded state, that depict cut angle variation shown on a cross-sectional plane that is orthogonal to a longitudinal central axis of the fixation device. Shown in FIGS. 199-208 are the cut angles of the cut slots forming the torsional engagement features of the devices.

FIGS. 199 and 204 show cross-sectional views through a torsional engagement feature 19903 of a deformable portion of a cannulated bone fixation member 19900. Sides of the torsional engagement feature 19903 are formed of a cut path 19944 and a cut path 19946 through a side wall 19931 of the member 19900. For the sake of clarity, in FIG. 204, the cut paths 19944 and 19946 are shown with lines or planes interposed therethrough and projecting therefrom. The cut paths 19944 and 19946 are formed orthogonal to a tangent of a circumference of the member 19900. Alternatively stated, lines or planes 20448 interposed through the cut paths 19944 and 19946 intersect at a longitudinal central axis 20433 of the member 19900.

FIGS. 200 and 205 show cross-sectional views through a torsional engagement feature 20003 of a deformable portion of a cannulated bone fixation member 20000. Sides of the torsional engagement feature 20003 are formed of a cut path 20044 and a cut path 20046 through a side wall 20031 of the member 20000. For the sake of clarity, in FIG. 205, the cut paths 20044 and 20046 are shown with lines or planes interposed therethrough and projecting therefrom. The cut paths 20044 and 20046 are formed asymmetrically and are formed non-orthogonal to a tangent of a circumference of the member 20000. The asymmetric cut paths 20044 and 20046 are each formed at different negative angles relative to a reference line or plane 20548 projecting or emanating radially from a longitudinal central axis 20533 of the member 20000.

FIGS. 201 and 206 show cross-sectional views through a torsional engagement feature 20103 of a deformable portion of a cannulated bone fixation member 20100. Sides of the torsional engagement feature 20103 are formed of a cut path 20144 and a cut path 20146 through a side wall 20131 of the member 20100. For the sake of clarity, in FIG. 206, the cut paths 20144 and 20146 are shown with lines or planes interposed therethrough and projecting therefrom. The cut paths 20144 and 20146 are formed symmetrically and are formed non-orthogonal to a tangent of a circumference of the member 20100. The cut path 20144 is formed at a negative angle relative to a reference line or plane 20648 projecting or emanating radially from a longitudinal central axis 20633 of the member 20100. The cut path 20146 is formed at a positive angle relative to the reference line or plane 20648 projecting or emanating radially from the longitudinal central axis 20633 of the member 20100. As shown in FIGS. 201 and 206, cut paths 20144 and 20146 are parallel to one another.

FIGS. 202 and 207 show cross-sectional views through a torsional engagement feature 20203 of a deformable portion of a cannulated bone fixation member 20200. Sides of the torsional engagement feature 20203 are formed of a cut path 20244 and a cut path 20246 through a side wall 20231 of the member 20200. For the sake of clarity, in FIG. 207, the cut paths 20244 and 20246 are shown with lines or planes interposed therethrough and projecting therefrom. The cut paths 20244 and 20246 are formed asymmetrically or symmetrically and are formed non-orthogonal to a tangent of a circumference of the member 20200. The cut path 20244 is formed at a negative angle relative to a reference line or plane 20748 projecting or emanating radially from a longitudinal central axis 20733 of the member 20200. The cut path 20246 is formed at a positive angle relative to the reference line or plane 20648 projecting or emanating radially from the longitudinal central axis 20633 of the member 20100. As shown in FIGS. 202 and 207, cut paths 20244 and 20246 are non-parallel to one another. Due to the orientations of the cut paths 20244 and 20246, the torsional engagement feature 20203 is limited in its ability to move in a radial direction away from the central axis 20733.

FIGS. 203 and 208 show cross-sectional views through a torsional engagement feature 20303 of a deformable portion of a cannulated bone fixation member 20300. Sides of the torsional engagement feature 20303 are formed of a cut path 20344 and a cut path 20346 through a side wall 20331 of the member 20300. For the sake of clarity, in FIG. 208, the cut paths 20344 and 20346 are shown with lines or planes interposed therethrough and projecting therefrom. The cut paths 20344 and 20346 are formed asymmetrically or symmetrically and are formed non-orthogonal to a tangent of a circumference of the member 20300. The cut path 20344 is formed at a positive angle relative to a reference line or plane 20848 projecting or emanating radially from a longitudinal central axis 20833 of the member 20300. The cut path 20346 is formed at a negative angle relative to the reference line or plane 20748 projecting or emanating radially from the longitudinal central axis 20833 of the member 20300. As shown in FIGS. 203 and 208, cut paths 20344 and 20346 are non-parallel to one another.

The methods described and shown with regard to FIGS. 209-211 are described as being performed in a progression or sequence of distinct steps only for the sake of clarity. It is understood and within the scope of the present invention that such steps be performed in alternate progressions or sequences and embodiments may omit steps shown and/or described in connection with the illustrative methods. Embodiments may include steps that are neither shown nor described in connection with the illustrative methods. Illustrative method steps may be combined. For example, one illustrative method may include steps shown in connection with another illustrative method.

FIGS. 209 and 210 are flow charts depicting methods and procedural progressions for insertion of a joining member of the present invention into bone tissue to facilitate a desired therapy. The progression starts with the inserting of a K-wire or guide pin into the desired location of placement, for example, transecting a fracture plane of the bone. Once the wire is placed, a measurement of the desired joining member length can be made utilizing the relative length of the wire and surface of the bone. Following this, a cannulated drill is inserted over the K-wire to increase the diameter of the hole and potentially facilitate a better mechanical fit between the bone and the joining member. Depending on the screw type and the desired position of the screw head one can countersink the bone tissue to accommodate for the head diameter, thereby helping to reduce the stress on the bone and/or adjusting the height of the exposed head of the screw above the bone tissue (FIG. 210).

The joining member can then be rotated into the bone over the K-wire. The end of the joining member can have self-cutting and self-tapping features that allow it to displace the bone tissue as it advances forward through the bone. As a head of the joining member engages the bone, an additional friction due to the increased size of the head and/or a differential pitch and/or starts of the head relative to a distal portion of the joining member will apply a compressive force to the bone segments across the fracture plane. This force will also be applied to an axial tension feature of the screw effectively elongating the joining member and storing potential energy into the axial tension. The member will stretch to a predetermined or designed length. After that length is obtained the continued rotation of the screw member will increase the loading or axial tension the member applies to the tissue. After insertion is complete, the bone will begin to remodel during the process of healing and depending on the stress state of any individual bone cell the bone growth process will either absorb or create more bone cells at that location. This process will continue until the bone has reached an acceptable stress level for the bone cells. This process can be aided by the stored axial tension energy continuing to apply force onto the bone across the fracture plane yielding a desired therapeutic beneficial pressure to aide healing.

FIG. 211 is a flow chart depicting a method and manufacturing progression for the construction of a joining member according to the present invention. From an ingot of metal such as Nitinol with an appropriate chemical structure, rod stock is drawn and cold worked to an appropriate diameter, and desired physical properties. The next step is to drill the central lumen and machine the desired outer profile of threads and features into the tubing material. This machining can be standard machining techniques, cryogenic machining, EDM (electrical discharge machining), grinding, or other techniques know to those in the art.

After the desired profile is obtained, the axial tension features are added to the construct. These features are obtained by removing the desired material by using methods understood by those in the industry such as laser cutting, EDM, chemically etching, and water jet machining. Great care being taken during all previous steps to assure minimal heating of the part, maintaining the transition temperature and mechanical properties of the material.

A final step is the finishing of the surface finish of the part. This could be done through a series of either chemically etching or mechanically etching of the heavy oxide surface from the part. Once the surface is relatively uniform, an electro-polishing process to both smooth the surface and establish roughly a 200-angstrom layer of titanium oxide is employed. These two process steps also serve to further remove any heat affected areas on the parts resulting from any of the machining or cutting processes. These steps also improve the biocompatibility, the corrosion resistance, and fatigue life of the construct. The parts at this point could enter a final cleaning process and then packaging. Sterilization of the screws could be done by the manufacturer or at the clinical site.

The load applied to bone through use of a standard compressive screw will increase rapidly after the bone segments come into contact with each other and the proximal engagement feature applies load to the bone segment. The load can easily exceed that of the holding force of the distal and proximal tissue engagement features. Additionally, the amount of remodeling needed to resolve that focal stress is minor and/or limited. The present invention is contrary to this effect in that the joining member of the present invention will continue to change in dimension as the bone remodels, thereby resulting in a compressive force that will continue over a longer period of time and or a greater distance of remodeling of bone tissue.

The loading profile of embodiment of the devices disclosed herein exhibit nonlinear behavior. A nonlinear spring has a nonlinear relationship between force and displacement. A graph showing force vs. displacement for a nonlinear spring will have a changing slope. The deformable elastic center section of the joining members of the present invention can be stretched while loading and follow a nonlinear profile similar to that of line 13602. When the spring mechanism has reached its maximum lengthening, the screw could then exhibit a profile similar to that of line 13603. The design could be such that the spring always stays in the nonlinear behavior. These properties of the springs or deformable portions of the inventive devices disclosed herein, that are based on strut or beam bending and on material properties of superelastic materials, produce forces that vary nonlinearly relative to their displacement. The apparatuses and methods of the present invention provide joining members that impart a compressive force on at least two tissue members through applying a stored axial tensile elastic potential energy that is released through a mechanism that uses beam bending and material properties of superelastic materials to produce forces that vary nonlinearly with displacement.

In certain embodiments of the present invention, any of the joining members herein disclosed are employed to secure or otherwise fix a rod and/or plate to tissue and/or bone. In certain embodiments of the present invention, the joining member employs a locking feature that corresponds to a feature on the rod and/or plate so as to lock or fix a portion of the joining member, e.g. a proximal head of the joining member, to the rod and/or plate, e.g. within an orifice or aperture of the rod and/or plate. In certain embodiments of the present invention, a position of a joining member is non-fixed or mobile within the rod and/or plate, e.g. within an orifice or aperture of the rod and/or plate. In certain embodiments of the present invention, the joining member and the rod and/or plate are cold welded to one another. In certain embodiments of the present invention, the joining member is employed to secure or otherwise fix a compressive rod and/or plate to tissue and/or bone. In certain embodiments of the present invention, the joining member is employed to secure or otherwise fix an active rod and/or plate to tissue and/or bone. In certain embodiments of the present invention, the joining member is employed to secure or otherwise fix a non-active rod and/or plate to tissue and/or bone.

In certain embodiments of the present invention, any of the joining members herein disclosed are provided with, treated with, or coated with a substance such as biologics, antibiotics, bone graft, BMP, bone cement, pharmaceuticals, or any other material used to help facilitate bone and/or tissue and combinations thereof. In certain embodiments, a coating of such substance is applied to all surfaces of the inventive device. In certain embodiments, a coating of such substance is applied to only an interior surface or only an exterior surface of the inventive device. In certain embodiments, a surface of the inventive device is provided with a surface texture and/or wells formed therein in which such substance or substances are deposited or coated. In certain embodiments of the present invention, the coating is a time-release substance.

It will be understood that while many of the embodiments disclosed above are described as providing a compressive force upon bone segments, depending upon the optimization of the cut slot features employed in the deformable portion of the joining member, all devices herein disclosed are also operable to provide tailored active axial, torsion, bending, radial, shear, and compression forces and combinations thereof to bone segments.

It will be understood that while the embodiments disclosed herein have been described as joining two bone segments, all devices herein disclosed are also operable to concurrently join more than two bone segments.

The above described embodiments of the present invention provide systems and methods for an active orthopedic screw system. Particularly, embodiments of the present invention are configured to provide tailored active axial, torsion, bending, radial, shear, and/or compression forces to a plurality of bone segments, thereby promoting bone growth. Consequently, the active orthopedic screw system of the present invention increases osteogenic stimulation as well as segment stabilization.

For the sake of providing a complete disclosure, the Applicants related U.S. Pat. No. 8,048,134 and International Application No. PCT/US2015.063472 are hereby incorporated herein by reference in their entirety.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof. In accordance with the standard practice in the industry, various features are not drawn to scale. The dimensions of the various features may be shown as arbitrarily increased or reduced for clarity of discussion. Some apparatuses may omit features shown and/or described in connection with illustrative apparatus. Embodiments may include features that are neither shown nor described in connection with the illustrative methods. Features of illustrative apparatus may be combined. For example, one illustrative embodiment may include features shown in connection with another illustrative embodiment.

What is claimed is:

1. An active compression bone screw apparatus for generating active compression of bone segments comprising:
   a distal bone engagement portion;
   a proximal bone engagement portion;
   a central portion configured to promote axial elongation and radial rotation of the apparatus during rotation of said apparatus into said bone segments;
   said central portion interposed between the proximal bone engagement portion and the distal bone engagement portion and having a perforation formed through a side wall of the central portion;
   a limiting feature formed by opposing sides of the perforation that constrains the axial elongation and the radial rotation of the apparatus;
   said limiting feature comprised of an asymmetric receiving portion and an asymmetric protruding portion.

2. The apparatus of claim 1 wherein the apparatus has a unitary contiguous structure.

3. The apparatus of claim 1 wherein the apparatus is cannulated.

4. The apparatus of claim 1 wherein the proximal bone engagement portion comprises threads having a pitch that are distinct from a pitch of threads of the distal bone engagement portion.

5. The apparatus of claim 1 wherein the distal bone engagement portion comprises threads.

6. The apparatus of claim 1 wherein the limiting feature also limits a change in a circumference of the apparatus.

7. The apparatus of claim 1 wherein the perforation comprises a helical form that defines a continuous helical strut.

8. The apparatus of claim 1 wherein the limiting feature has a stepped shape.

9. The apparatus of claim 1 wherein the perforation is formed through the sidewall perpendicular to a longitudinal central axis of a shaft of said apparatus and parallel to a radial direction of said shaft.

10. The apparatus of claim 1 wherein the active compression comprises active compression over a period of greater than 12 hours.

11. An active compression bone screw apparatus for generating active compression of bone segments comprising:
    a cannulated body having a compression preload feature;
    a perforation formed through a sidewall of the cannulated body; and
    said cannulated body configured to promote axial elongation and radial rotation upon deformation of the perforation through an activation of the compression preload feature during rotation of said cannulated body into said bone segments,
    the axial elongation and the radial rotation constrained by corresponding change limiting features formed in opposing sides of the perforation;
    said change limiting features comprised of a receiving portion having an asymmetric shape and a protruding portion having an asymmetric shape.

12. The apparatus of claim 11 wherein an exterior of the sidewall of the cannulated body comprises threads.

13. The apparatus of claim 11 wherein the compression preload feature comprises a plurality of threads having different pitches formed on an exterior of the sidewall of the cannulated body.

14. The apparatus of claim 11 wherein the activation of the compression preload feature comprises a rotation of the apparatus.

* * * * *